(12) United States Patent
Addis et al.

(10) Patent No.: US 12,037,379 B2
(45) Date of Patent: Jul. 16, 2024

(54) CD71 BINDING FIBRONECTIN TYPE III DOMAINS

(71) Applicant: ARO BIOTHERAPEUTICS COMPANY, Philadelphia, PA (US)

(72) Inventors: Russell C. Addis, Philadelphia, PA (US); Zhanna Druzina, Philadelphia, PA (US); Robert V. Kolakowski, Philadelphia, PA (US); Steven G. Nadler, Philadelphia, PA (US); Karyn T. O'Neil, Philadelphia, PA (US); Yao Xin, Philadelphia, PA (US)

(73) Assignee: ARO Biotherapeutics Company, Philadelphia, PA (US)

( * ) Notice: Subject to any disclaimer, the term of this patent is extended or adjusted under 35 U.S.C. 154(b) by 0 days.

(21) Appl. No.: 17/720,422

(22) Filed: Apr. 14, 2022

(65) Prior Publication Data
US 2022/0332795 A1 Oct. 20, 2022

Related U.S. Application Data

(60) Provisional application No. 63/324,431, filed on Mar. 28, 2022, provisional application No. 63/174,752, filed on Apr. 14, 2021.

(51) Int. Cl.
*C07K 14/78* (2006.01)
*A61K 31/7125* (2006.01)
*A61K 47/64* (2017.01)
*C12N 15/113* (2010.01)

(52) U.S. Cl.
CPC .......... *C07K 14/78* (2013.01); *A61K 31/7125* (2013.01); *A61K 47/6435* (2017.08); *C12N 15/113* (2013.01); *C12N 2310/11* (2013.01); *C12N 2310/14* (2013.01); *C12N 2310/3513* (2013.01); *C12N 2320/32* (2013.01)

(58) Field of Classification Search
CPC .............. C07K 14/78; C07K 14/70582; A61K 31/7125; A61K 47/6435; A61K 47/64; C12N 15/113; C12N 2310/11; C12N 2310/14; C12N 2310/3513; C12N 2320/32; C12N 2310/312; C12N 2310/315; C12N 2310/343; C12N 15/111
See application file for complete search history.

(56) References Cited

U.S. PATENT DOCUMENTS

| | | | |
|---|---|---|---|
| 4,281,061 A | 7/1981 | Zuk et al. | |
| 5,223,409 A | 6/1993 | Ladner et al. | |
| 5,643,763 A | 7/1997 | Dunn et al. | |
| 5,643,768 A | 7/1997 | Kawasaki | |
| 5,658,727 A | 8/1997 | Barbas et al. | |
| 5,691,157 A | 11/1997 | Gong et al. | |
| 5,846,456 A | 12/1998 | Liu | |
| 5,856,456 A | 1/1999 | Whitlow et al. | |
| 6,018,030 A | 1/2000 | Ferrari et al. | |
| 6,162,903 A | 12/2000 | Trowern et al. | |
| 6,172,197 B1 | 1/2001 | McCafferty et al. | |
| 6,355,776 B1 | 3/2002 | Ferrari et al. | |
| 6,462,189 B1 | 10/2002 | Koide | |
| 6,472,147 B1 | 10/2002 | Janda et al. | |
| 6,521,427 B1 | 2/2003 | Evans | |
| 6,582,915 B1 | 6/2003 | Griffiths et al. | |
| 6,670,127 B2 | 12/2003 | Evans | |
| 6,673,901 B2 | 1/2004 | Koide | |
| 6,703,199 B1 | 3/2004 | Koide | |
| 6,818,418 B1 | 11/2004 | Lipovsek et al. | |
| 6,846,655 B1 | 1/2005 | Wagner et al. | |
| 6,969,108 B2 | 11/2005 | Fukumoto et al. | |
| 7,078,490 B2 | 7/2006 | Koide | |
| 7,115,396 B2 | 10/2006 | Lipovsek et al. | |
| 7,119,171 B2 | 10/2006 | Koide | |
| 7,153,661 B2 | 12/2006 | Koide | |
| 7,288,638 B2 | 10/2007 | Jure-Kunkel et al. | |
| 7,427,672 B2 | 9/2008 | Imanishi et al. | |
| 7,709,214 B2 | 5/2010 | Freeman et al. | |
| 7,794,710 B2 | 9/2010 | Chen et al. | |
| 7,842,476 B2 | 11/2010 | McGregor et al. | |
| 7,943,743 B2 | 5/2011 | Korman et al. | |
| 8,217,149 B2 | 7/2012 | Irving et al. | |
| 8,278,419 B2 | 10/2012 | Jacobs et al. | |
| 8,293,482 B2 | 10/2012 | Jacobs et al. | |
| 8,552,154 B2 | 10/2013 | Freeman et al. | |
| 8,569,227 B2 | 10/2013 | Jacobs | |
| 8,741,295 B2 | 6/2014 | Olive | |
| 8,779,108 B2 | 7/2014 | Queva et al. | |

(Continued)

FOREIGN PATENT DOCUMENTS

CN 102076713 A 5/2011
CN 103827361 A 5/2014
(Continued)

OTHER PUBLICATIONS

Adjei et al., "Early Clinical Development of ARQ197, a Selective, Non-ADP-Competitive Inhibitor Targeting MET Tyrosine Kinase for the Treatment of Advanced Cancers," The Oncologist, vol. 16, pp. 788-799 {2011}.

(Continued)

*Primary Examiner* — Julie Ha
*Assistant Examiner* — Erinne R Dabkowski
(74) *Attorney, Agent, or Firm* — Goodwin Procter LLP

(57) ABSTRACT

The present disclosure relates to polypeptides, such as fibronectin type III (FN3) domains that can bind CD71, their conjugates, isolated nucleotides encoding the molecules, vectors, host-cells, as well as methods of making and using the same.

20 Claims, 6 Drawing Sheets

Specification includes a Sequence Listing.

(56) References Cited

U.S. PATENT DOCUMENTS

| | | |
|---|---|---|
| 8,981,063 B2 | 3/2015 | Chen |
| 9,156,887 B2 | 10/2015 | Jacobs |
| 9,175,082 B2 | 11/2015 | Zhou et al. |
| 9,200,273 B2 | 12/2015 | Diem et al. |
| 9,212,224 B2 | 12/2015 | Cogswell et al. |
| 9,326,941 B2 | 5/2016 | Chae et al. |
| 9,546,368 B2 | 1/2017 | Bennett et al. |
| 9,644,023 B2 | 5/2017 | Torres et al. |
| 9,695,228 B2 | 7/2017 | Mark et al. |
| 9,897,612 B2 | 2/2018 | Diem et al. |
| 10,196,446 B2 | 2/2019 | Goldberg et al. |
| 10,233,448 B2 | 3/2019 | Maier et al. |
| 10,597,438 B2 | 3/2020 | Diem et al. |
| 10,611,823 B2 | 4/2020 | Diem et al. |
| 10,626,165 B2 | 4/2020 | Hawkins et al. |
| 10,781,246 B2 | 9/2020 | Brezki et al. |
| 10,925,932 B2 | 2/2021 | Diem et al. |
| 11,628,222 B2 | 4/2023 | Addis et al. |
| 11,781,138 B2 | 10/2023 | Addis et al. |
| 2004/0197332 A1 | 10/2004 | Ullrich et al. |
| 2004/0259781 A1 | 12/2004 | Chiquet-Ehrismann et al. |
| 2005/0004029 A1 | 1/2005 | Garcia |
| 2005/0038229 A1 | 2/2005 | Lipovsek et al. |
| 2005/0255548 A1 | 11/2005 | Lipovsek et al. |
| 2005/0272083 A1 | 12/2005 | Seshagiri |
| 2006/0040278 A1 | 2/2006 | Cojocaru et al. |
| 2006/0246059 A1 | 11/2006 | Lipovsek et al. |
| 2006/0270604 A1 | 11/2006 | Lipovsek et al. |
| 2007/0148126 A1 | 6/2007 | Chen et al. |
| 2007/0160533 A1 | 7/2007 | Chen et al. |
| 2007/0184476 A1 | 8/2007 | Hsieh et al. |
| 2008/0015339 A1 | 1/2008 | Lipovsek et al. |
| 2008/0220049 A1 | 9/2008 | Chen et al. |
| 2008/0241159 A1 | 10/2008 | Gerritsen et al. |
| 2009/0042906 A1 | 2/2009 | Huang et al. |
| 2009/0176654 A1 | 7/2009 | Cappuccilli et al. |
| 2009/0274693 A1 | 11/2009 | Gilmer et al. |
| 2009/0299040 A1 | 12/2009 | Camphausen et al. |
| 2009/0311803 A1 | 12/2009 | Way et al. |
| 2010/0093662 A1 | 4/2010 | Defaye et al. |
| 2010/0136129 A1 | 6/2010 | Agueros Bazo et al. |
| 2010/0144601 A1 | 6/2010 | Jacobs et al. |
| 2010/0179094 A1 | 7/2010 | Emanuel et al. |
| 2010/0203142 A1 | 8/2010 | Zhang et al. |
| 2010/0216708 A1 | 8/2010 | Jacobs et al. |
| 2010/0221248 A1 | 9/2010 | Wittrup et al. |
| 2010/0254989 A1 | 10/2010 | Bossenmaier et al. |
| 2010/0255056 A1 | 10/2010 | Jacobs et al. |
| 2011/0021746 A1 | 1/2011 | Cappuccilli et al. |
| 2011/0038866 A1 | 2/2011 | Hastewell et al. |
| 2011/0053842 A1 | 3/2011 | Camphausen et al. |
| 2011/0081345 A1 | 4/2011 | Moore et al. |
| 2011/0118144 A1 | 5/2011 | Hyun et al. |
| 2011/0124527 A1 | 5/2011 | Cappuccilli et al. |
| 2011/0274623 A1 | 11/2011 | Jacobs |
| 2011/0287009 A1 | 11/2011 | Scheer et al. |
| 2012/0225870 A1 | 9/2012 | Janne et al. |
| 2012/0244164 A1 | 9/2012 | Beste et al. |
| 2012/0263723 A1 | 10/2012 | Davies et al. |
| 2012/0270797 A1 | 10/2012 | Wittrup et al. |
| 2012/0315639 A1 | 12/2012 | Deng et al. |
| 2012/0321666 A1 | 12/2012 | Cooper et al. |
| 2013/0012435 A1 | 1/2013 | Camphausen et al. |
| 2013/0039927 A1 | 2/2013 | Dewhurst et al. |
| 2013/0079243 A1 | 3/2013 | Diem et al. |
| 2013/0123342 A1 | 5/2013 | Brown |
| 2013/0130377 A1 | 5/2013 | Lee et al. |
| 2013/0184212 A1 | 7/2013 | Camphausen et al. |
| 2013/0226834 A1 | 8/2013 | Gannalo, II |
| 2013/0273561 A1 | 10/2013 | Walker et al. |
| 2014/0141000 A1 | 5/2014 | Chiu et al. |
| 2014/0155325 A1 | 6/2014 | Mark et al. |
| 2014/0155326 A1 | 6/2014 | Mark et al. |
| 2014/0255408 A1 | 9/2014 | Chiu et al. |
| 2014/0271467 A1 | 9/2014 | Hackel et al. |
| 2014/0341917 A1 | 11/2014 | Nastri et al. |
| 2014/0349929 A1 | 11/2014 | Camphausen et al. |
| 2014/0371296 A1 | 12/2014 | Bennett et al. |
| 2015/0005364 A1 | 1/2015 | Chae et al. |
| 2015/0104808 A1 | 4/2015 | Goldberg et al. |
| 2015/0118288 A1 | 4/2015 | Lee |
| 2015/0191543 A1 | 7/2015 | Wu et al. |
| 2015/0197571 A1 | 7/2015 | Freeman et al. |
| 2015/0203580 A1 | 7/2015 | Papadopoulos et al. |
| 2015/0210756 A1 | 7/2015 | Torres et al. |
| 2015/0252097 A1 | 9/2015 | Camphausen et al. |
| 2015/0274835 A1 | 10/2015 | Marasco et al. |
| 2015/0346208 A1 | 12/2015 | Couto et al. |
| 2015/0355184 A1 | 12/2015 | Pierce et al. |
| 2016/0041182 A1 | 2/2016 | Diem et al. |
| 2016/0303256 A1 | 10/2016 | Liu |
| 2016/0326232 A1 | 11/2016 | Rosa et al. |
| 2016/0347840 A1 | 12/2016 | Anderson et al. |
| 2016/0355599 A1 | 12/2016 | Sagert et al. |
| 2017/0174748 A1 | 6/2017 | Mitchell et al. |
| 2017/0258948 A1 | 9/2017 | Morin et al. |
| 2017/0281795 A1 | 10/2017 | Geall et al. |
| 2017/0348397 A1 | 12/2017 | Diem et al. |
| 2017/0362301 A1 | 12/2017 | Anderson et al. |
| 2018/0162929 A1 | 6/2018 | Diem et al. |
| 2019/0070322 A1 | 3/2019 | Bander |
| 2019/0127444 A1 | 5/2019 | Brezski et al. |
| 2019/0175651 A1 | 6/2019 | Lee et al. |
| 2019/0184018 A1 | 6/2019 | Manoharan et al. |
| 2019/0184028 A1 | 6/2019 | Dudkin et al. |
| 2019/0202927 A1 | 7/2019 | Sagert et al. |
| 2019/0256575 A1 | 8/2019 | Chen et al. |
| 2019/0263915 A1 | 8/2019 | Goldberg et al. |
| 2019/0330361 A1 | 10/2019 | Chin et al. |
| 2021/0108201 A1 | 4/2021 | Addis et al. |
| 2021/0145976 A1 | 5/2021 | Addis et al. |
| 2022/0370626 A1 | 11/2022 | Kulkarni et al. |
| 2023/0330246 A1 | 10/2023 | Marelius et al. |
| 2024/0043844 A1 | 2/2024 | Kulkarni et al. |

FOREIGN PATENT DOCUMENTS

| | | |
|---|---|---|
| CN | 105907719 A | 8/2016 |
| EP | 0985039 A2 | 3/2000 |
| EP | 1137941 A1 | 10/2001 |
| EP | 1210428 A1 | 6/2002 |
| EP | 1266025 A1 | 12/2002 |
| EP | 2935329 A1 | 10/2015 |
| EP | 3473270 A1 | 4/2019 |
| EP | 4146229 A1 | 3/2023 |
| JP | 2011507543 A | 3/2011 |
| JP | 2011517314 A | 6/2011 |
| JP | 2011520961 A | 7/2011 |
| JP | 2011522517 A | 8/2011 |
| JP | 2012507295 A | 3/2012 |
| JP | 2014530014 A | 11/2014 |
| JP | 2016504291 A | 2/2016 |
| KR | 10-2016-0067966 A | 6/2016 |
| WO | 9638557 A1 | 12/1996 |
| WO | 2001014557 A1 | 3/2001 |
| WO | 0164942 A1 | 9/2001 |
| WO | 0232925 A2 | 4/2002 |
| WO | 03104418 A2 | 12/2003 |
| WO | 2004029224 A2 | 4/2004 |
| WO | 2004058821 A2 | 7/2004 |
| WO | 2005018534 A2 | 3/2005 |
| WO | 2005042708 A2 | 5/2005 |
| WO | 2007000671 A2 | 1/2007 |
| WO | 2007047796 A2 | 4/2007 |
| WO | 2007085815 A2 | 8/2007 |
| WO | 2008066752 A2 | 6/2008 |
| WO | 2008079973 A2 | 7/2008 |
| WO | 2008127710 A2 | 10/2008 |
| WO | 2008156642 A1 | 12/2008 |
| WO | 2009023184 A2 | 2/2009 |
| WO | 2009058379 A2 | 5/2009 |
| WO | 2009083804 A2 | 7/2009 |
| WO | 2009085462 A1 | 7/2009 |
| WO | 2009086116 A2 | 7/2009 |

(56) References Cited

FOREIGN PATENT DOCUMENTS

| | | | |
|---|---|---|---|
| WO | 2009102421 | A2 | 8/2009 |
| WO | 2009111691 | A2 | 9/2009 |
| WO | 2009126834 | A2 | 10/2009 |
| WO | 2009133208 | A1 | 11/2009 |
| WO | 2009142773 | A2 | 11/2009 |
| WO | 2010037838 | A2 | 4/2010 |
| WO | 2010039248 | A1 | 4/2010 |
| WO | 2010051274 | A2 | 5/2010 |
| WO | 2010051310 | A2 | 5/2010 |
| WO | 2010060095 | A1 | 5/2010 |
| WO | 2010093627 | A2 | 8/2010 |
| WO | 2010115202 | A2 | 10/2010 |
| WO | 2010115551 | A1 | 10/2010 |
| WO | 2011005133 | A1 | 1/2011 |
| WO | 2011110642 | A2 | 9/2011 |
| WO | 2011130324 | A1 | 10/2011 |
| WO | 2011131746 | A2 | 10/2011 |
| WO | 2011137319 | A2 | 11/2011 |
| WO | 2011151412 | A1 | 12/2011 |
| WO | 2012016245 | A2 | 2/2012 |
| WO | 2012162418 | A1 | 11/2012 |
| WO | 2013049275 | A1 | 4/2013 |
| WO | 2014081944 | A2 | 5/2014 |
| WO | 2014081954 | A1 | 5/2014 |
| WO | 2014100079 | A1 | 6/2014 |
| WO | 2014165082 | A2 | 10/2014 |
| WO | 2014165093 | A2 | 10/2014 |
| WO | 2014189973 | A2 | 11/2014 |
| WO | 2014209804 | A1 | 12/2014 |
| WO | 2015057545 | A2 | 4/2015 |
| WO | 2015061668 | A1 | 4/2015 |
| WO | 2015089073 | A2 | 6/2015 |
| WO | 2015092393 | A2 | 6/2015 |
| WO | 2015109124 | A2 | 7/2015 |
| WO | 2015143199 | A1 | 9/2015 |
| WO | 2015195163 | A1 | 12/2015 |
| WO | 2016000619 | A1 | 1/2016 |
| WO | 20160004043 | A1 | 1/2016 |
| WO | 2016086021 | A1 | 6/2016 |
| WO | 2016086036 | | 6/2016 |
| WO | 2016179534 | | 11/2016 |
| WO | 2016197071 | A1 | 12/2016 |
| WO | 2017011618 | A1 | 1/2017 |
| WO | 2017223180 | A2 | 12/2017 |
| WO | 2018148501 | A1 | 8/2018 |
| WO | 2019217459 | A1 | 11/2019 |
| WO | 2021030763 | A1 | 2/2021 |
| WO | 2021030778 | A1 | 2/2021 |
| WO | 2021076546 | A1 | 4/2021 |
| WO | 2021076574 | A2 | 4/2021 |
| WO | 2021226107 | A1 | 11/2021 |
| WO | 2022198196 | A1 | 9/2022 |
| WO | 2022213118 | A1 | 10/2022 |
| WO | 2022221505 | A2 | 10/2022 |
| WO | 2022221550 | A1 | 10/2022 |
| WO | 2023201362 | A2 | 10/2023 |
| WO | 2023215880 | A2 | 11/2023 |

OTHER PUBLICATIONS

Alderson et al., "Molecular and Biological Characterization of Human 4-1 BB and its Ligand", Eur. J_ Immunol., vol. N, pp. 2219-2227, 1994.

Alfthan et al., "Properties of a single-chain antibody containing different linker peptides," Protein Engineering, vol. B, No. 7, pp. 725-731 (1995).

Anderson et al., "Towards next generation antisense oligonucleotides: mesylphosphoramidate modification improves therapeutic index and duration of effect of gapmer antisense oligonucleotides," Nucleic Acids Research, 2021, vol. 49, No. 16, Published online Aug. 20, 2021, https://doi.org/10.1093/nar/gkab718, pp. 9026-9041.

Attwood TK. Genomics. The Babel of bioinformatics. Science. 290(5491):471-473, 2000.

Basel GA et al., "Critical Update and Emerging Trends in Epidermal Growth Factor Receptor Targeting in Cancer," Journal of Clinical Oncology, vol. 23, No. 11, pp. 2445-2459 (2005).

Bass, et al., "Hormone Phage: An Enrichment Method for Variant Proteins with Altered Binding Properties," PROTEINS: Structure, Function, and Genetics, 8: 309-314 (1990).

Batley et al., "Inhibition of FGF-1 Receptor Tyrosine Kinase Activity By PD 161570, a New Protein-Tyrosine Kinase nhibitor," Life Sciences, vol. 62, No. 20, pp. 143-150 (1998).

Bean et al., "MET amplification occurs with or without T790M mutations in EGFR mutant lung tumors with acquired esistance to gefilinib or erlotinib," Proceedings of the National Academy of Science, vol. 104, No. 52, pp. ) 0932-20937 (2007).

Binz et al., "High-affinity binders selected from designed ankyrin repeat protein libraries," Nature Biotechnology, vol. e2, No. 5, pp. 575-582 (May 2004).

Binz, et al., "Engineered proteins as specific binding reagents," Current Opinion in Biotechnology, 16: 459-469 (2005).

Birtalan et al., "The Intrinsic Contributions of Tyrosine, Serine, Glycine and Arginine to the Affinity and Specificity of Antibodies," Journal of Molecular Biology, vol. 377, pp. 1518-1528 (2008).

Bork et al., "Proposed acquisition of an animal protein domain by bacteria," Proceedings of the National Academy of Science, USA, vol. 89, pp. 8990-8994 (1992).

Brown et al., "Tolerance of single, but not multiple, amino acid replacements in antibody VH CDR 2: a means of minimizing B cell wastage from somatic hypermutation", J. Immuno. (1996) pp. 3285-3291.

Burgess et al., "Possible dissociation of the heparin-binding and mitogenic activities of heparin-binding (acidic fibroblast) growth factor-1 from its receptor-binding activities by site-directed mutagenesis of a single lysine residue" J Cell Biol (1990) 111:pp. 2129-2138.

Burton Earle Barnett et al: "Disclosures", Blood, vol. 128, No. 22, Dec. 2, 2016 (Dec. 2, 2016), pp. 4557-4557, XP055711182, US ISSN: 0006-4971, doi: 10.1182/blood.V128.22.4557.4557 abstract.

C.N. Pace, "Determination and Analysis of Urea and Guanidine Hydrochloride Denaturation Curves," Methods in Enzymology, 131: 266-280 (1986).

Candelaria, Pierre V., et al, "Antibodies Targeting the Transferrin Receptor 1 (TfR1) as Direct Anti-Cancer Agents," Frontiers in Immunology (www.frontiersin.org), Mar. 2021, vol. 12, Article 607692.

Capellas, "Enzymatic Condensation of Cholecystokinin CCK-8 (4-6) and CCK-8 (7-8) Peptide Fragments in Organic Media", Biotechnology and Bioengineering (1997) vol. 56, No. 4, pp. 456-463.

Cappuzzo et al., "Epidermal Growth Factor Receptor Gene and Protein and Gefilinib Sensitivity in Non-small-Cell ung Cancer," Journal of the National Cancer Institute, vol. 97, pp. 643-655 (2005).

Chen et al., "Cell-Surface Display of Heterologous Proteins: From High-Throughput Screening to Environmental Applications", Biotechnology and Bioengineering, (2002) vol. 79, No. 5, pp. 496-503.

Chiba et al., Amyloid Fibril Formation in the Context of Full-length Protein Effects of Praline mutations on the Amyloid fibril formation of b2-Microglobulin, Journal of Biological Chemistry, vol. 278, No. 47, pp. 47016-47024, Nov. 2003.

Christensen et al., "c-Met as a target for human cancer and characterization of inhibitors for therapeutic ntervention," Cancer Letters, vol. 225, pp. 1-26 (2005).

Clarke, et al., "Folding and Stability of a Fibronectin Type III Domain of Human Tenascin," Journal of Molecular Biology, 270: 771-778 (1997).

Cooper et al., "4-1 BB (CD 137) controls the clonal expansion and survival of COB T cells in vivo but does not t: ontribute the development of cytotoxicity", Eur. J_ Immunol., vol. 32, pp. 521-529, 2002.

Cooper et al., "Molecular cloning of a new transforming gene from a chemically transformed human cell line," Nature, vol. 311, pp. 29-33 (1984).

Cota, et al., "Two Proteins with the Same Structure Respond very Differently to Mutation: The Role of Plasticity in Protein Stability", Journal of Molecular Biology, 302, 713-725 (2000).

(56) References Cited

OTHER PUBLICATIONS

DeBenedette et al., "Role of 4-1BB Ligand in Costimulation of T Lymphocyte Growth and its Upregulation on M12 B rymphomas by cAMP," J_ Exp_ Med., vol. 181, pp. 985-992 (1995).

Dehouck, et al., "Fast and accurate predictions of protein stability changes upon mutations using statistical potentials and neural networks: PoPMuSiC-2.0, Bioinformatics," 25(19): 2537-2543 (2009).

DeRoock et al., "Effects of KRAS, BRAF, NRAS, and PIK3CA mutations on the efficacy of cetuximab plus chemotherapy in chemotherapy-refractory metastatic colorectal cancer: a retrospective consortium analysis," Lancet Oncology, vol. 11, pp. 753-762 (2010).

Diem et al., "Selection of high-affinity Centyrin FN3 domains from a simply library diversified at a combination of strand and loop positions." Protein Engin Design (2014) Selection 27(10): 419-429.

Dineen, et al., "The Adnectin CT-322 is a novel VEGF receptor 2 inhibitor that decreases tumor burden in an orthotopic mouse model of pancreatic cancer," BMC Cancer, 8: 352-361 (2008).

Downward et al., "Autophosphorylation sites on the epidermal growth factor receptor," Nature, vol. 311, pp. 183-485 ( 1984).

Dutta, et al., "High-affinity fragment complementation of a fibronectin type III domain and its application to stability enhancement," Protein Science, 14: 2838-2848 (2005).

Engelman et al., "MET Amplification Leads to Gefitinib Resistance in Lung Cancer by Activating ERBB3 Signaling," Science, vol. 316, pp. 1039-1043 (2007).

Falvo, Elisabetta et al, "High Activity and Low Toxicity of a Novel CD71-Targetiong Nanotherapeutic Named The-0504 on Preclinical Models of Several Human Aggressive Tumors," Journal of Experimental Clinical Cancer Research, (2021) 40:63; https://doi.org/10.1186/s13046-021-01851-8, pp. 1-14.

Ferguson, Kathryn M., "Structure-Based View of Epidermal Growth Factor Receptor Regulation," Annual Review of Biophysics, vol. 37, pp. 535-373 (2008).

Final Office Action mailed on Jul. 10, 2020 in U.S. Appl. No. 15/637,276 (145965.00921).

Final Office Action mailed on Jul. 21, 2020 in U.S. Appl. No. 16/218,990 (145965.000701).

Garcia-Ibilcieta, et al., "Simple method for production of randomized human tenth fibronectin domain III libraries for use in combinatorial screening procedures," Bio Technologies, 44: 559-562 (2008).

Garon et al., "Pembrolizumab for the Treatment of Non-Small-Cell Lung Cancer," The New England Journal of Medicine, vol. 372, No. 21, pp. 2018-2028 (May 21, 2015).

Garrard, et al., "Selection of an anti-IGF-1 Fab from a Fab phage library created by mutagenesis of multiple CDR loops," Gene, 128: 103-109 (1993).

GenBank Accession No. NP 001120972.

GenBank Accession No. NP_002151.

Getmanova, et al., "Antagonists to Human and Mouse Vascular Endothelial Growth Factor Receptor 2 Generated by Directed Protein Evolution In Vitro," Chemistry & Biology, 13: 549-556 (2006).

Gill et al., "Monoclonal Anti-epidermal Growth Factor Receptor Antibodies Which Are Inhibitors of Epidermal Growth racier Binding and Antagonists of Epidermal Growth Factor-stimulated tyrosine Protein Kinase Activity, The Journal Jf Biological Chemistry," vol. 259, No. 12, pp. 7755-7760 (1984).

Goldberg et al., "Engineering a Targeted Delivery Platform using Centyrins" Protein Engineering, Design & selection, vol. 29, No. 12, pp. 563-572, 2016.

Goldstein et al., "Biological efficacy of a chimeric antibody to the epidermal growth factor receptor in a human umor kenografl model," Clinical Cancer Research, vol. 1, pp. 1311-1318 (1995).

Gramaglia et al., "Co-stimulation of antigen-specific CD4 T cells by 4-1BB ligand," Eur. J. Immunol., vol. 30, pp. ô €?92-402 (2000).

Grünwald et al., "Developing Inhibitors of the Epidermal Growth Factor Receptor for Cancer Treatment," Journal of he National Cancer Institute, vol. 95, No. 12, pp. 851-867 (2003).

Lohse et al., Fluorescein-Conjugated Lysine monomers for Solid Phase Synthesis of Fluorescent Peptides and PNA Pligomers Bioconjugate Chem, vol. 8, pp. 503-509, 1997 .pdf.

Ma et al., "c-Met: Structure, functions and potential for therapeutic inhibition," Cancer and Metastasis Reviews, vol. 22 pp. 309-325 (2003).

Makkouk Amani et al: "Rationale for anti-CD137 cancer immunotherapy", European Journal of Cancer, Elsevier, Amsterdam, NL, vol. 54, Jan. 2, 2016 (Jan. 2, 2016), pp. 112-119, XP029401784, ISSN: 0959-8049, DOI: 10.1016/j.ejca.2015.09.026 abstract p. 114, right-hand column, paragraph 4—p. 116, right-hand column, paragraph 1 table 1.

Mamluk et al., "Anti-tumor effect of CT-322 as an Adnectin inhibitor of vascular endothelial growth factor receptor-2", mAbs, 2(2), pp. 199-208, 2010.

Mattheakis et al., "An in vitro polysome display system for identifying ligands from very large peptide libraries", Proc. Natl. Acad. Sci. (1994) Vo .. 91, pp. 9022-9026.

Maus et al., Ex vivo expansion of polyclonal and antigen-specific cytotoxic T lymphocytes by artificial APCs Expressing ligands for the T-cell receptor, CD28 and 4-1BB Nature Biotechnology, vol. 20, pp. 143-148, Feb. 2002.

McCracken, "Non-invasive monitoring of hematopoietic reconstitution and immune cell function through Positron Emission Tomography" University of California, Los Angeles, Dissertaton ProQuest LLC (2014) pp. 1-202.

McLaughlin et al., "Quantitative Assessmenet of the Heterogeneity of PD-L 1 Expression in Non-small Cell Lung Cancer (NSCLC)," JAMA Oncol., vol. 2, No. 1, pp. 46-54, (Jan. 2016).

Meinke et al., "Cellulose-Binding Polypeptides from Cellulomonas fimi: Endoglucanase D (CenD), a Family A b-1,4-Glucanase," Journal of Bactenology, vol. 175, No. 7, pp. 1910-1918 (1993).

Mendelsohn et al., "Epidermal Growth Factor Receptor Targeting in Cancer," Seminars in Oncology, vol. 33, pp. 369-385 (2006).

Mendelsohn et al., "The EGF receptor family as targets for cancer therapy," Oncogene, vol. 19, pp. 6550-6565 2000).

Michel et al., "A soluble form of CD137 (ILA/4-1BB), a member of the TNF receptor family, is released by activated ymphocytes and is detectable in sera of patients with rheumatoid arthritis," Eur. J_ Immunol., vol. 28, pp. 290-295 1998).

Michel et al., "CD137-induced apoptosis is independent of CD95," Immunology, vol. 98, pp. 42-46 (1999).

Michel et al., "Expression of soluble CD137 correlates with activation-induced cell death of lymphocytes", Cytokine, vol. 12, No. 6, pp. 742-746, 2000.

Miller et al Ligand binding to proteins: the binding landscape model. Protein Sci. Oct. 1997;6(10):2166-79.

Määttä et al., "Proteolytic Cleavage and Phosphorylation of a Tumor-associated ErbB4 Isoform Promote Ligand-ndependent Survival and Cancer Cell Growth," Molecular Biology, vol. 17, pp. 67-79 (2006).

Natarajan, et al., "A Novel Engineered Anti-CD20 Tracer Enables Early Time PET Imaging in a Humanized Transgenic Mouse Model of B-cell Non-Hodgkins Lymphoma", Clin Cancer Res (2013) 19: pp. 6820-6829.

NCBI Reference Sequence NP _005219.2, "Epidermal Growth Factor Receptor Isoform a Precursor [*Homo sapiens*]," pp. 1-14 (May 18, 2014).

Non-Final Office Action dated Dec. 1, 2022, from U.S. Appl. No. 17/070,337 (145965.002301).

Non-Final Office Action dated Feb. 10, 2022 in U.S. Appl. No. 16/218,990 (145965.000701).

Non-Final Office Action for U.S. Appl. No. 17/070,337 dated Dec. 1, 2022.

Non-Final Office Action mailed on Feb. 3, 2021 in U.S. Appl. No. 16/218,990 (145965.00701).

Non-Final Office Action mailed on Jul. 9, 2021 in 16821064 (145965.001211).

Non-Final Office Action mailed on Aug. 18, 2021 in U.S. Appl. No. 16/801,787(145965.0001311).

Non-Final Office Action mailed on Sep. 24, 2021 in U.S. Appl. No. 16/820,844 (145965.001411).

(56) References Cited

OTHER PUBLICATIONS

Non-Final Office Action mailed on Feb. 4, 2022 in U.S. Appl. No. 16/801,787 (145965.001311).

Notice of Allowance dated Nov. 28, 2022 in U.S. Appl. No. 17/070,020 (145965.002101).

Notice of Allowance for U.S. Appl. No. 17/070,020 dated Nov. 28, 2022 and updated on Jan. 17, 2023 (145965.002101).

Notice of Allowance for U.S. Appl. No. 17/070,337 dated May 24, 2023.

Notice of Allowance mailed Mar. 3, 2020 in U.S. Appl. No. 15/840303 (145965.01401).

Odegrip et al., "CIS display: In vitro selection of peptides from libraries of protein-DNA complexes," Proceedings of he National Academy of Science USA, vol. 101, No. 9, pp. 2806-2810 (2004).

Olson et al., "Design, expression, and stability of a diverse protein library based on the human fibronectin type III ô €,?omain," Protein Science, vol. 16, pp. 476-484 (2007).

Olson, William C. et al., "Antibody-drug Conjugates Targeing Prostate-Specific Membrane Antigen," Frontiers in Bioscience (Landmark Edition) 19: pp. 12-33, Jan. 1, 2014.

Pace, "Determination and Analysis of Urea and Guanidine Hydrochloride Denaturation Curves", Methods in Enzymology (1986) vol. 131, pp. 266-280.

Panek et al., "In Vitro Pharmacological Characterization of PD 166285, a New Nanomolar Potent and Broadly Active Protein Tyrosine Kinase Inhibitor," The Journal of Pharmacology and Experimental Therapeutics, vol. 283, No. 3, pp. 1433-1444 (1997).

Parker, et al., "Antibody mimics based on human fibronectin type three domain engineered for thermostability and high-affinity binding to vascular endothelial growth factor receptor two," Protein Engineering, Design & Selection, 18(9): 435-444 (2005).

Pauly et al., CD137 is expressed by follicular dendritic cells and costimulates B lymphocyte activation in germinal t; enters, Journal of Leukocyte Biology, vol. 72, pp. 35-42, Jul. 2002.

Peters et al., "MET: a promising anticancer therapeutic target," Nature Reviews Clinical Oncology, vol. 9, pp. 314-326 (2012).

Prewett et al., "Mouse-Human chimeric Anti-Epidermal Growth Factor Receptor Antibody C225 Inhibits the Growth Jf Human Renal Cell Carcinoma Xenografls in Nude Mice," Clinical Cancer Research, vol. 4, pp. 2957-2966 (1998).

Reiss et al. Inhibition of platelet aggregation by grafting RGD and KGD sequences on the structural scaffold of small disulfide-rich proteins. Platelets 17(3):153-157, 2006.

Riel Yet al., "Clinical Course of Patients with Non-Small Cell Lung Cancer and Epidermal Growth Factor Receptor Exon 19 and Exon 21 Mutations Treated with Gefitinib or Erlotinib," Clinical Cancer Research, vol. 12, No. 3, pp. g39-844 (2006).

Roberts et al., "RNA-peptide fusions for the in vitro selection of peptides and proteins," Proceedings of the National Academy of Science USA, vol. 94, pp. 12297-12302 (1997).

Robinson et al., "Covalent Attachment of Arc Repressor Subunits by a Peptide Linker Enhances Affinity for Operator DNA," Biochemistry, vol. 35, pp. 109-116 (1996).

Rudikoff el al., "Single amino acid substitution altering antigenbinding specificity", Proc Natl Acad Sci (1982) 79(6): pp. 1979-1983.

Rybalov et al., "PSMA, EpCAM, VEGF and GRPR as Imaging Targets in Locally Recurrent Prostate Cancer after Radiotherapy", Int. J. Mol. Sci. (2014) 15, pp. 6046-6061.

Sakakura et al., "Gains, Losses, and Amplifications of Genomic Materials in Primary Gastric Cancers Analyzed by :; omparative Genomic Hybridization," Genes, Chromosomes & Cancer, vol. 24, pp. 299-305 (1999).

Schmidt et al., "Novel mutations of the MET proto-Oncogene in papillary rental carcinomas," Oncogene, vol. 18, pp. ]343-2350 (1999).

Schwarz et al., "ILA, a Member of the Human Nerve Growth FactorfTumor Necrosis Factor Receptor Family, Regulates T-Lymphocyte Proliferation and Survival," Blood, vol. 87, No. 7, pp. 2839-2845 (Apr. 1, 1996).

Shalom D. Goldberg et al: "Engineering a targeted delivery platform using Centyrins", Protein Engineering, Design and Selection, Oct. 13, 2016 (Oct. 13, 2016), XP055384705, GB ISSN: 1741-0126, DOI: 10.1093/protein/gzw054 abstract p. 564, left-hand column, paragraph 2—right-hand column, line 3 p. 567, right-hand column, paragraph 2 p. 568, right-hand column, paragraph 2—p. 569, left-hand column, paragraph 2 table I figure 1a.

Shuford et al., "4-18B Costimulatory Signals Preferentially Induce COB+ T Cell Proliferation and Lead to the amplification In Vivo of Cytotoxic T Cell Responses," J_ Exp_ Med., vol. 186, No. 1, pp. 47-55 (Jul. 7, 1997).

Siegfried et al., "The Clinical Significance of Hepatocyte Growth Factor for Non-Small Cell Lung Cancer," Annals of Thoracic Surgery, vol. 66, pp. 1915-1918 (1998).

Sierra et al., "c-MET as a potential therapeutic target and biomarker in cancer," Therapeutic Advances in Medical :: >ncology, vol. 3, No. 51, pp. 521-535 (2011).

Siggers et al. Conformational dynamics in loop swap mutants of homologous fibronectin type III domains. Biophys J. Oct. 1, 2007 ;93(7):2447-56.

Skerra, et al., "Engineered protein scaffolds for molecular recognition," Journal of Molecular Recognition, 13: 167-187 (2000).

Skolnick et al. From genes to protein structure and function: novel applications of computational approaches in the genomic era. Trends Biotechnol. 18(1 ):34-9, 2000.

Slonomics® Technology Website "https://www.morphosys.com/science/drug-development-capabilities/slonomics".

Smith, "Filamentous fusion phage: novel expression vectors that display cloned antigens on the virion surface.", Association of Science (1985) vol. 228, pp. 1315(3).

Song et al. Cancer stem cells—an old idea that's new again: implications for the diagnosis and treatment of breast cancer. Expert Opin Biol Ther 7:4):431-438, 2007.

Stamos et al., "Crystal structure of the HGF b-chain in complex with the Serna domain of the Met receptor," The EMBO Journal, vol. 23, pp. 2325-2335 (2004).

Steiner, et al., "Efficient Selection of DARPins with Sub-nonomolar Affinities using SRP Phage Display," Journal of Molecular Biology, 382: 1211-1227 (2008).

Strand et al., "Site-Specific Radioiodination of HER2-Targeting Affibody Molecules using 4-lodophenethylmaleimide Decreases Renal Uptake of Radioactivity"; Chemistry Open, vol. 4, pp. 174-182, 2015.

Strohl, William R., "Optimization of Fe-mediated effector functions of monoclonal antibodies," Current Opinion in Biotechnology, vol. 20, pp. 685-691 (2009).

SwissProt Accession No. P00533.2, "Epidermal Growth Factor Receptor," pp. 1-49 (Jun. 11, 2014).

Takahashi et al., "Cutting Edge: 4-1 BB Is a Bona Fide COB T Cell Survival Signal," J Immunol., vol. 162, pp. 0037-5040 (1999).

Tang et al, "Anti-Transferrin Receptor-Modified Amphotericin B-Loaded PLA-PEG Nanoparticles Cure Candidal Meningitis and Reduce Durg Toxicity," Oct. 5, 2015, International Journal of Medicine, 2015:10, pp. 6227-6241.

Tannock and Hill. The Basic Science of Oncology. 1998. New York: McGraw-Hill;; pp. 357-358.

Tie et al., "Safety and efficacy of nivolumab in the treatment of cancers: A meta-analysis of 27 prospective clinical rials," International Journal of Cancer, vol. 140, pp. 948-958, (2017).

Turke et al., "Preexistence and Clonal Selection of MET Amplification in EGFR Mutant NSCLC," Cancer Cell, vol. 17, pp. 77-88 (2010).

Ullrich et al., "Human epidermal growth factor receptor cDNA sequence and aberrant expression of the amplified Jene in A431 epiderrnoid carcinoma cells," Nature, vol. 309, pp. 418-425 (1984). UniProt Accession No. P10039.

Vajdos et al., "Comprehensive funtional maps of the antigenbinding site of an anti-ErbB2 antibody obtained with shotgun scanning mutagenisis", J. Mol. Biol. (2002) 32(2): pp. 415-428.

Van den Burg et al., "Selection of mutations for increased protein stability", Curr. Opin. Biotech. 13:333-337 (2002).

(56) References Cited

OTHER PUBLICATIONS

Wang et al., "VISTA, a novel mouse Ig superfamily ligand that negatively regulates T cell responses," Journal of Experimental Medicine, vol. 208, No. 3, pp. 577-592 (Mar. 14, 2011).
Watanabe et al., "Gene Cloning of Chitinase A1 from Bacillus circulans WL-12 Revealed Its Evolutionary Relationship to Serratia Chitinase and to the Type III Homology Units of Fibronectin," Journal of Biological Chemistry, vol. 265, pp. 15659-15665 (1990).
Wattanachaisaereekul, "Production of Polyketides by *Saccharomyces cerevisiae*", Ph.D. Thesis (2007) Center for Microbial Biotechnology, BioCentrum-DTU Technical University of Denmark, pp. 1-187.
Wu, Xiaoqiu, et als, "Elucidation and Structural Modeling of CD71 as a Molecular Target for Cell-Specific Aptamer Binding," J Am Chem Soc , Jul. 10, 2020; 141(27): 10760-10769. doi: 10.1021/jacs.9b0370.
Xu, et al., "Directed Evolution of High-Affinity Antibody Mimics Using mRNA Display,"Chemistry & Biology, 9: 933-942 (2002).
Yuyu Tan et al., "Selection of Transferrin Receptor-Specific Peptide for Recognition of Cancer Cell," China Science and Technology Papers Online, Apr. 30, 2017, pp. 1-10.
Zhang et al., "Complete disulfide bond assignment of a recombinant immunoglobulin G4 monoclonal antibody," Analytical Biochemistry, vol. 311, pp. 1-9 (2002).
Zhou et al., Characterization of human homologue of 4-1 BB and its ligand, Immunology Letters, vol. 45, pp. 7-73, 1995.
Zucali, et al., "Role of cMET expression in non-small-cell lung cancer patients treated with eGFR tyrosine kinase inhibitors", Annals of Anocology (2008) 19:: 1605-1612.
Hackel et al., "Use of 64Cu-Labeled Fibronectin Domain with EGFR-Overexpressing Tumor Xenograft: Molecular Imaging1", Radiology (2012) vol. 263:No. 1 pp. 179-188.
Hackel, et al., "Picomolar Affinity Fibronectin Domains Engineered Utilizing Loop Length Diversity, Recursive Mutagenesis, and Loop Shuffling," Journal of Molecular Biology, 381: 1238-1252 (2008).
Hackel, et al., "Stability and CDR Composition Biases Enrich Binder Functionality Landscapes," Journal of Molecular Biology, 401: 84-96 (2010).
Hallewell et al., "Genetically Engineered Polymers of Human CuZN Superoxide Dismutase," The Journal of Biological Chemistry, vol. 264, No. 9, pp. 5260-5268 (1989).
Hamill et al., "The Effect of Boundary Selection on the Stability and Folding of the Third Fibronectin Type III Domain from Human Tenascin", Biochemistry, 37: 8071-8079 (1998).
Hanes et al, "In vitro selection and evolution of functional proteins by using ribosome display," Proceedings of the National Academy of Sciences USA, vol. 94, pp. 4937-4942 (1997).
Helms et al. Destabilizing loop swaps in the CDRs of an immunoglobulin VL domain. Protein Science 4:2073-2081, 1995.
Hirsch et al, "Combination of EGFR gene copy number and protein expression predicts outcome for advanced non-, mall-cell lung cancer patients treated with gefitnib," Annals of Oncology, vol. 18, pp. 752-760 (2007).
Hoogenboom et al., "Natural and designer binding sites made by phage display technology" Immunology Today (2000) vol. 21, No. 8, pp. 371-378.
Hurtado et al., "Potential role of 4-1 BB in T cell Activation Comparison with the Costimulatory Molecule CD28", Journal of Immunology, vol. 155, pp. 3360-3367, 1995.
Hurtado et al., "Signals through 4-1BB are Costimulatory to previously activated splenic T cells and inhibit activation-induced cell death", Journal of Immunology, vol. 158, pp. 2600-2609, 1997.
Hylarides et al., "Preparation and in Vivo Evaluation of an N-9p-[125I]1odophenethyl) maleimide—Antibody Conjugate" Bioconjugate Chem., vol. 2, pp. 435-440, 1991.
Hynes et al., "ERBB Receptors and Cancer: the Complexity of Targeted Inhibitors," Nature Reviews, vol. 5, pp. 341-356 (2005).
Ichimura et al., "Expression of c-mel/HGF Receptor in Human Non-small Cell Lung Carcinomas in vitro and in vivo and Its Prognostic Significance," Japan Journal of Cancer Research, vol. 87. pp. 1063-1069 (1996).
International Preliminary Report on Patentability dated Apr. 19, 2022 from International Application No. PCT/US2020/055470, International Filing Date Oct. 14, 2020.
International Preliminary Report on Patentability dated Apr. 19, 2022 from International Application No. PCT/US2020/055509, International Filing Date Oct. 14, 2020.
International Search Report and Written Opinion dated Mar. 22, 2021 from International Application No. PCT/US2020/055509, International Filing Date Oct. 14, 2020.
International Search Report and Written Opinion dated Mar. 29, 2021 from International Application No. PCT/US2020/055470, International Filing Date Oct. 14, 2020.
International Search Report and Written Opinion dated Oct. 7, 2022 from International Application No. PCT/US22/24773 (145965.002002), International Filing Date Apr. 14, 2022.
International Search Report and Written Opinion dated Sep. 12, 2022 from International Application No. PCT/US2022024846, International Filing Date Apr. 14, 2022.
International Search Report and Written Opinion from International Application No. PCT/US2021/030863 dated Oct. 29, 2021, International Filing Date May 5, 2021 (145965.002502).
International Search Report and Written Opinion from PCT/US2022/024846 dated Sep. 12, 2022.
Itoh, et al., "Application of Inverse Substrates to Trypsin-Catalyzed Peptid Synthesis", Bioorganic Chemistry (1996) 24, 0007, pp. 59-68.
Jacobs et al., "Design of novel FN3 domains with high stability by a consensus sequence approach," Protein Engineering, Design & Selection, vol. 25, No. 3, pp. 107-117 (2012).
Jacobs et al., "FN3 Domain Engineering", Protein Engineering, pp. 145-162, 2012.
Jacobs et al., "Fusion to a highly stable consensus albumin binding domain allows for tunable pharmacokinetics", Protein Engineering, Design & Selection, vol. 28, No. 10, pp. 385-393, 2015.
Jänne et al., "Effect of Epidermal Growth Factor Receptor Tyrosine Kinase Domain Mutations on the Outcome of Patients with Non-small Cell Lung Cancer Treated with Epidermal Growth Factor Receptor Tyrosine Kinase Inhibitors," Clinical Cancer Research, vol. 12, No. 14 Suppl, pp. 4416s-4420s (2006).
Karatan, et al., "Molecular Recognition Properties of FN3 Mono bodies that Bind the Src SH3 Domain," Chemistry & Biology, 11: 835-844 (2004).
Klein et al. "Abstract LB-312: Bispecific Centyrin Simultaneously targeting EGFR and c—Met demonstrates improved ô €?'ctivity compared to the mixture of single agents", Cancer Research, 73 (8 Supplement), Abstract LB-312, Apr. 2013.
Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2002).
Koide et al., "High-affinity single-domain binding proteins with a binary-code interface," PNAS, vol. 104, No. 16, pp. 6632-6637(Apr. 17, 2017).
Koide, et al., Teaching an Old Scaffold New Tricks: Monobodies Constructed Using Alternative Surfaces of the FN3 Scaffold, Journal of Molecular Biology, 415: 393-405 (2012).
Koide, et al., "The Fibronectin Type III Domain as a Scaffold for Novel Binding Proteins," Journal of Molecular Biology, 284: 1141-1151 (1998).
Koivunen et al. Identification of Receptor Ligands with Phage Display Peptide Libraries J Nucl Med; 40:883-888, 1999.
Kumaran et al., "Confirmationally driven protease-catalyzed splicing of peptide segments: V8 protease-mediated syntheses of fragments derived from thermolysin and ribonuclease A", Protein Science, (1997) 6: pp. 2233-2241.
Kunkel et al., "Rapid and Efficient Site-Specific Mutagenesis without Phenotypic Selection", Methods In Enzymology, (1987) vol. 154 pp. 367-375.

(56) References Cited

OTHER PUBLICATIONS

Kuntz. Structure-based strategies for drug design and discovery. Science. 1992 257(5073):1078-1082.

Kwon et al., cDNA sequences of two inducible T-cell genes, Proc. Natl. Acad. Sci., vol. 86, pp. 1963-1967, Mar. 1989.

Langstein et al., "CD137 (ILA/4-1 BB), a Member of the TNF Receptor Family, Induces Monocyte Activation via Bidirectional Signaling," The Journal of Immunology, vol. 160, pp. 2488-2494 (1998).

Langstein et al., "CD137 Induces Proliferation and Endomitosis in Monocytes," Blood, vol. 94, No. 9, pp. 3161-3168 1999).

Langstein et al., Identification of CD137 as a potent monocyte survival factor, Journal of Leukocyte Biology, vol. 65, pp. 829-833, Jun. 1999.

Lazar et al., "Transforming growth factor alpha: mutation of aspartic acid 47 and leucie 48 results in different biological activities", Mol Cell Biol. (1988) 8: pp. 1247-1252.

Lee et al., "4-1BB Promotes the Survival of COB+ T Lymphocytes by Increasing Expression of Bcl-xL and Bfl-11," The Journal of Immunol., vol. 169, pp. 4882-4888 (2002).

Lee et al., "A Glu-ruea-Lys Ligand-conjugated Lipid nanoparticle/ siRNA System Inhibits Androgen Receptor Expression In Vivo", Molecular Therapy-Nucleic Acids (2016) 5, e348: pp. 1-11.

Lehmann et al., Engineering proteins for thermostability the use of sequence alignments versus rational design and directed evolution, Current Opinion in Biotechnology, vol. 12, pp. 371-375 (2001).

Lejon et al., "Structural basis for the binding of naproxen to human serum albumin in the presence of fatty acids and the GA module", Acta Cryst. (2008) F pp. 64-69.

Lepenies et al., "The Role of Negative Costimulators Dunng Parasitic Infections," Endocrine, Metabolic & Immune Disorders—Drug Targets, vol. 8, pp. 279-288 (2008).

Li et al., "Skin toxicities associated with epidermal growth factor receptor inhibitors," Target Oncology, vol. 4, pp. 107-119 (2009).

Linardou et al., "Somatic EGFR mutations and efficacy of tyrosine kinase inhibitors in NSCLC," National Review of :; linical Oncology, vol. 6, pp. 352-366 (2009).

Lipovsek, et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," Journal of Molecular Biology, 368: 1024-1041 (2007).

Brewer, et al., Cell Metabolism, "Targeting Pathogenic Lafora Bodies in Lafora Disease Using an Antibody-Enzyme Fusion", CellPress 30, 689-705, Oct. 1, 2019, https://doi.org/10.1016/j.cmet.2019.07.002.

Duran, et al., "Glycogen accumulation underlies neurodegeneration and autophagy impairment in Lafora disease", Human Molecular Genetics, 2014, vol. 23, No. 12 3147-3156 doi: 10.1093/hmg/ddu024; Advance Access published on Jan. 22, 2014.

Nitschke, et al., "An inducible glycogen synthase-1 knockout halts but does not reverse Lafora disease progression in mice", https://doi.org/10.1074/jbc.RA120.015773; American Society for Biochemistry and Molecular Biology, J. Biol. Chem. (2021) 296 100150.

Non-Final Office Action mailed on Oct. 18, 2023 in 17720996, 23 pages.

Soudah et al., "AntimiR-155 Cyclic Peptide-PNA Conjugate: Synthesis, Cellular Uptake, and Biological Activity", ACS Omega, 2019, 4(9): 13954-13961.

Varea, et al., "Suppression of glycogen synthesis as a treatment for Lafora disease: Establishing the window of opportunity", Neurobiology of Disease 147 (2021) 105173, https://doi.org/10.1016/j.nbd.2020.105173!.

ized and alter normal receptor trafficking so that instead of recycling, the receptor is targeted to the lysosome for degradation. In contrast, antibodies with low affinity for CD71 allow for receptor recycling and higher brain exposure.

CD71 BINDING FIBRONECTIN TYPE III DOMAINS

RELATED APPLICATIONS

The present application claims priority to U.S. Provisional Patent Application No. 63/174,752, filed Apr. 14, 2021, and U.S. Provisional Application No. 63/324,431, filed Mar. 28, 2022, which are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 17, 2022, is named 145965_002001_SL.txt and is 283,197 bytes in size.

FIELD

The present embodiments relate to fibronectin type III domains (FN3) that specifically bind cluster of differentiation 71 (CD71) and methods of making and using the molecules.

BACKGROUND

CD71, also known as transferrin receptor 1, is transmembrane that is essential for iron transport into cells. It is highly expressed on many tumor types and at the blood brain barrier, and has thus become an important target for drug delivery. Following binding to iron loaded transferrin, CD71 is rapidly endocytosed and efficiently recycled back to the cell surface. Studies with CD71 antibody drug conjugates suggest that targeting CD71 can improve specificity and selectivity of drug delivery and widen the therapeutic index. In addition, studies using anti-CD71 monoclonal antibodies indicate that binding affinity can play an important role in enabling tissue specific delivery including smooth or skeletal muscle delivery and blood brain barrier transcytosis. Antibodies with high affinity for CD71 are rapidly internalized and alter normal receptor trafficking so that instead of recycling, the receptor is targeted to the lysosome for degradation. In contrast, antibodies with low affinity for CD71 allow for receptor recycling and higher brain exposure.

While antibodies or antibody fragments are the most widely used class of therapeutic proteins when high affinity and specificity for a target molecule are desired, non-antibody proteins can be engineered to also bind such targets. These "alternative scaffold" proteins have advantages over traditional antibodies due to their small size, lack of disulphide bonds, high stability, ability to be expressed in prokaryotic hosts, easy purification, and they are easily conjugated to drugs/toxins, penetrate efficiently into tissues and are readily formatted into multispecific binders.

One such alternative scaffold is the immunoglobulin (Ig) fold. This fold is found in the variable regions of antibodies, as well as thousands of non-antibody proteins. It has been shown that one such Ig protein, the tenth fibronectin type III (FN3) repeat from human fibronectin, can tolerate a number of mutations in surface exposed loops while retaining the overall Ig-fold structure. Thus, what is needed is a FN3 domain that can specifically bind to CD71, and methods of using such molecules for novel therapeutics that enable intracellular access via receptor mediated internalization of CD71.

SUMMARY

In some embodiments, FN3 domains (e.g. polypeptides) that specifically bind CD71 protein are provided. In some embodiments, the FN3 domains are isolated. In some embodiments, the FN3 domains are recombinant. In some embodiments, the FN3 domains are non-naturally occurring.

In some embodiments, FN3 domains are provided that comprise the amino acid sequence of SEQ ID NOs: 1-7, 10, 12-219, 221-272, 292-299, or 304-306, 292-299, or 304-306, or 304-306. In some embodiments, the FN3 domains bind to CD71. In some embodiments, the FN3 domain binds to human CD71 at a site on CD71 that does not compete with transferrin binding to CD71. In some embodiments, the FN3 domains specifically bind to CD71. In some embodiments, the polypeptide is provided that comprises more than one FN3 domain connected by a linker, such as a flexible linker. In some embodiments, the polypeptide comprises 2, 3, or 4 FN3 domains that are connected to one another by one or more linkers between the domains.

In some embodiments, isolated polynucleotides encoding the FN3 domains described herein are provided.

In some embodiments, a vector comprising the polynucleotides described herein are provided.

In some embodiments, a host cell comprising the vectors described herein are provided.

In some embodiments, methods of producing the FN3 domains are provided. In some embodiments, the method comprises culturing a host cell comprising a vector encoding or expressing the FN3 domain. In some embodiments, the method further comprises purifying the FN3 domain. In some embodiments, the FN3 domain specifically binds CD71.

In some embodiments, pharmaceutical compositions comprising a FN3 domain that binds to CD71 and a pharmaceutically acceptable carrier are provided.

In some embodiments, anti-idiotypic antibodies that binds a FN3 domain that binds to CD71 are provided.

In some embodiments, kits comprising one or more of the FN3 domains are provided.

In some embodiments, methods of detecting CD71-expressing cancer cells in a tumor tissue are provided. In some embodiments, the method comprises obtaining a sample of the tumor tissue from a subject and detecting whether CD71 protein is expressed in the tumor tissue by contacting the sample of the tumor tissue with the FN3 domain that binds CD71 protein comprising the amino acid sequence of one of SEQ ID NOs: 1-7, 10, 12-219, 221-272, 292-299, or 304-306, or 304-306 and detecting the binding between CD71 protein and the FN3 domain.

In some embodiments, methods of isolating CD71 expressing cells are provided. In some embodiments, the method comprises obtaining a sample from a subject; contacting the sample with the FN3 domain that binds CD71 protein comprising the amino acid sequence of one of SEQ ID NOs: 1-7, 10, 12-219, 221-272, 292-299, or 304-306, or 304-306 and isolating the cells bound to the FN3 domains.

In some embodiments, methods of detecting CD71-expressing cancer cells in a tumor tissue are provided. In some embodiments, the method comprises conjugating the FN3 domain that binds CD71 protein comprising the amino acid sequence of one of SEQ ID NOs: 1-7, 10, 12-219, 221-272, 292-299, or 304-306, or 304-306 to a detectable label to form a conjugate; administering the conjugate to a subject; and visualizing the CD71 expressing cancer cells to which the conjugate is bound.

In some embodiments, methods of treating cancer in a subject in need thereof are provided. In some embodiments, the method comprises administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent.

In some embodiments, the polypeptide that binds to CD71 is directed to the central nervous system. In some embodiments, methods of treating a neurological condition and/or a brain tumor in a subject in need thereof are provided. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent. In some embodiments, the brain tumor is selected from the group consisting of non-malignant, benign, and malignant brain tumors. In some embodiments, the neurological condition is selected from the group consisting of Alzheimer's Disease, Amyotrophic Lateral Sclerosis, Parkinson's Disease, Lafora Disease, Pompe Disease, adult polyglucosan body disease, stroke, spinal cord injury, ataxia, Bell's Palsy, cerebral aneurysm, epilepsy, seizures, Guillain-Barre Syndrome, multiple sclerosis, muscular dystrophy, neurocutaneous syndromes, migraine, encephalitis, septicemia, and myasthenia gravis.

In some embodiments, the polypeptide that binds to CD71 is directed to a muscle cells. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent.

In some embodiments, methods of treating Pompe disease (GSD2, acid alpha-glucosidase (GAA) deficiency) in a subject in need thereof are provided. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent.

In some embodiments, methods of treating glycogen storage disease in a subject in need thereof, the method comprising administering a composition provided herein are provided. In some embodiments, the glycogen storage disease is selected from the group consisting of Cori's disease or Forbes' disease (GSD3, Glycogen debranching enzyme (AGL) deficiency), McArdle disease (GSD5, Muscle glycogen phosphorylase (PYGM) deficiency), type II Diabetes/diabetic nephropathy, Aldolase A Deficiency GSD12, Lafora Disease, hypoxia, Andersen disease (GSD4, Glycogen debranching enzyme (GBE1) deficiency), Tarui's Disease (GSD7, Muscle phosphofructokinase (PFKM) deficiency), and adult polyglucosan body disease. In some embodiments, the glycogen storage disease is selected from the group consisting of Glycogen synthase (GYS2) deficiency (GSD0), Glucose-6-phosphatase (G6PC/SLC37A4) deficiency (GSD1, von Gierke's disease), Hers' disease (GSD6, Liver glycogen phosphorylase (PYGL) or Muscle phosphoglycerate mutase (PGAM2) deficiency), Phosphorylase kinase (PHKA2/PHKB/PHKG2/PHKA1) deficiency (GSD9), Phosphoglycerate mutase (PGAM2) deficiency (GSD10), Muscle lactate dehydrogenase (LDHA) deficiency (GSD11), Fanconi-Bickel syndrome (GSD 11, Glucose transporter (GLUT2) deficiency, Aldolase A deficiency (GSD 12), β-enolase (ENO3) deficiency (GSD13), and Glycogenin-1 (GYG1) deficiency (GSD15).

In some embodiments, the polypeptide that binds to CD71 is directed to immune cells. In some embodiments, the polypeptide that binds to CD71 is directed to dendritic cells, T-cells, NK cells, or B-cells. In some embodiments, methods of treating an autoimmune disease in a subject in need thereof are provided. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent. In some embodiments, the autoimmune disease is selected from the group consisting of rheumatoid arthritis, Hashimoto's autoimmune thyroiditis, celiac disease, diabetes mellitus type 1, vitiligo, rheumatic fever, pernicious anemia/atrophic gastritis, alopecia areata, and immune thrombocytopenic purpura.

In some embodiments, methods of delivering an agent of interest to a CD71 positive cell are provided. In some embodiments, the methods comprise contacting a cell with the agent of interest coupled to a FN3 domain that binds to CD71, such as a polypeptide as provided herein. In some embodiments, the agent of interest is a chemotherapeutic agent, a drug, a growth inhibitory agent, a toxin, a radioactive isotope, an anti-tubulin agent, a polynucleotide, a siRNA molecule, an antisense molecule, a RNA molecule, a DNA molecule, DNA minor groove binders, DNA replication inhibitors, alkylating agents, antibiotics, antifolates, antimetabolites, chemotherapy sensitizers, topoisomerase inhibitors, or a vinca alkaloid.

In some embodiments, the FN3 domains provided for herein are conjugated to a polynucleotide, a siRNA molecule, an antisense molecule, a RNA molecule, or a DNA molecule.

In some embodiments, the polypeptide is a FN3 protein that binds to CD71 at a site that does not compete or inhibit transferrin binding to CD71.

In some embodiments, methods of identifying a FN3 protein that binds to CD71 at a site that does not compete or inhibit transferrin binding to CD71 are provided.

DETAILED DESCRIPTION OF THE DISCLOSURE

Figure 1:
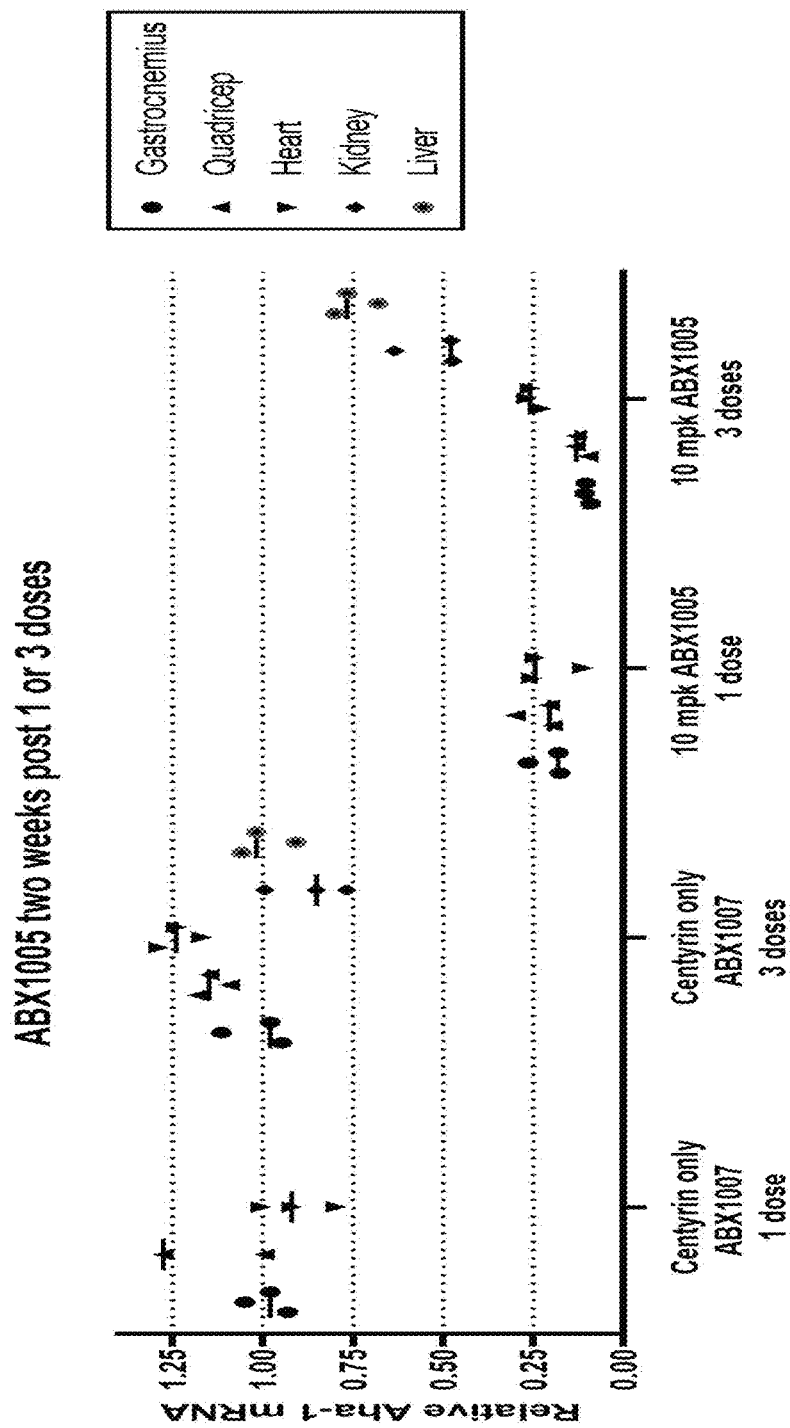
FIG. 1 illustrates quantification of AHA1 mRNA in various tissues of CD-1 mice following dosing of FN3 polypeptide (ABX1007) or FN3 polypeptide-siRNA conjugate (ABX1005).

As used in this specification and the appended claims, the singular forms "a," "an," and "the" include plural referents unless the content clearly dictates otherwise. Thus, for example, reference to "a cell" includes a combination of two or more cells, and the like.

"Fibronectin type III (FN3) domain" (FN3 domain) refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the $3^{rd}$ FN3 domain of tenascin (TN3), or the $10^{th}$ FN3 domain of fibronectin (FN10).

The term "capture agent" refers to substances that bind to a particular type of cells and enable the isolation of that cell from other cells. Exemplary capture agents are magnetic beads, ferrofluids, encapsulating reagents, molecules that bind the particular cell type and the like.

"Sample" refers to a collection of similar fluids, cells, or tissues isolated from a subject, as well as fluids, cells, or tissues present within a subject. Exemplary samples are tissue biopsies, fine needle aspirations, surgically resected tissue, organ cultures, cell cultures and biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium and lavage fluids and the like.

"Substituting" or "substituted" or "mutating" or "mutated" refers to altering, deleting of inserting one or more amino acids or nucleotides in a polypeptide or polynucleotide sequence to generate a variant of that sequence.

"Variant" refers to a polypeptide or a polynucleotide that differs from a reference polypeptide or a reference polynucleotide by one or more modifications for example, substitutions, insertions or deletions.

"Specifically binds" or "specific binding" refers to the ability of a FN3 domain to bind to its target, such as CD71, with a dissociation constant ($K_D$) of about $1 \times 10^{-6}$ M or less, for example about $1 \times 10^{-7}$ M or less, about $1 \times 10^{-8}$ M or less, about $1 \times 10^{-9}$ M or less, about $1 \times 10^{-10}$ M or less, about $1 \times 10^{-11}$ M or less, about $1 \times 10^{-12}$ M or less, or about $1 \times 10^{-13}$ M or less. Alternatively, "specific binding" refers to the ability of a FN3 domain to bind to its target (e.g. CD71) at least 5-fold above a negative control in standard solution ELISA assay. Specific binding can also be demonstrated using the proteome array as described herein and shown in FIG. 3. In some embodiments, a negative control is an FN3 domain that does not bind CD71. In some embodiment, an FN3 domain that specifically binds CD71 may have cross-reactivity to other related antigens, for example to the same predetermined antigen from other species (homologs), such as *Macaca fascicularis* (cynomolgus monkey, cyno) or *Pan troglodytes* (chimpanzee).

"Library" refers to a collection of variants. The library may be composed of polypeptide or polynucleotide variants.

"Stability" refers to the ability of a molecule to maintain a folded state under physiological conditions such that it retains at least one of its normal functional activities, for example, binding to a predetermined antigen such as CD71.

"CD71" refers to human CD71 protein having the amino acid sequence of SEQ ID NOs: 274 or 275. In some embodiments, SEQ ID NO: 274 is full length human CD71 protein. In some embodiments, SEQ ID NO: 275 is the extracellular domain of human CD71.

```
SEQ ID NO: 274 = human mature CD71
MTKEYQDLQHLDNEESDHHQLRKGPPPPQPLLQRLCSGPRLLLLSLGLSL

LLLVVVCVIGSQNSQLQEELRGLRETFSNFTASTEAQVKGLSTQGGNVGR

KMKSLESQLEKQQKDLSEDHSSLLLHVKQFVSDLRSLSCQMAALQGNGSE

RTCCPVNWVEHERSCYWFSRSGKAWADADNYCRLEDAHLVVVTSWEEQKF

VQHHIGPVNTWMGLHDQNGPWKWVDGTDYETGFKNWRPEQPDDWYGHGLG

GGEDCAHFTDDGRWNDDVCQRPYRWVCETELDKASQEPPLL

SEQ ID NO: 275 = human mature CD71 extracellular
domain
QNSQLQEELRGLRETFSNFTASTEAQVKGLSTQGGNVGRKMKSLESQLEK

QQKDLSEDHSSLLLHVKQFVSDLRSLSCQMAALQGNGSERTCCPVNWVEH

ERSCYWFSRSGKAWADADNYCRLEDAHLVVVTSWEEQKFVQHHIGPVNTW

MGLHDQNGPWKWVDGTDYETGFKNWRPEQPDDWYGHGLGGGEDCAHFTD

DGRWNDDVCQRPYRWVCETELDKASQEPPLL
```

"Tencon" refers to the synthetic fibronectin type III (FN3) domain having the sequence shown in SEQ ID NO: 276 and described in U.S. Pat. Publ. No. 2010/0216708.

```
SEQ ID NO: 276 = Original Tencon Sequence
LPAPKNLVVSEVTEDSLRLSWTAPDAAFDSFLIQYQESEKVGEAINLTVP

GSERSYDLTGLKPGTEYTVSIYGVKGGHRSNPLSAEFTT
```

A "cancer cell" or a "tumor cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

A "dendritic cell" refers to a type of antigen-presenting cell (APC) that form an important role in the adaptive immune system. The main function of dendritic cells is to present antigens. Dendritic cells have the capacity to induce a primary immune response in the inactive or resting naïve T lymphocytes.

An "immune cell" refers to the cells of the immune system categorized as lymphocytes (T-cells, B-cells and NK cells), neutrophils, or monocytes/macrophages. These are all types of white blood cells.

"Vector" refers to a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide. Small polypeptides of less than about 50 amino acids may be referred to as "peptides".

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Subject" includes any human or nonhuman animal. "Nonhuman animal" includes all vertebrates, e.g., mammals and non-mammals, such as nonhuman primates, sheep, dogs, cats, horses, cows chickens, amphibians, reptiles, etc. Except when noted, the terms "patient" or "subject" are used interchangeably.

"Isolated" refers to a homogenous population of molecules (such as synthetic polynucleotides or a polypeptide such as FN3 domains) which have been substantially separated and/or purified away from other components of the system the molecules are produced in, such as a recombinant cell, as well as a protein that has been subjected to at least one purification or isolation step. "Isolated FN3 domain" refers to an FN3 domain that is substantially free of other cellular material and/or chemicals and encompasses FN3 domains that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

Compositions of Matter

In some embodiments, proteins comprising a polypeptide comprising an amino acid sequence of SEQ ID NOs: 1-7, 10, 12-219, 221-272, 292-299, or 304-306 are provided.

In some embodiments, proteins comprising a polypeptide comprising an amino acid sequence of SEQ ID NO: 273. SEQ ID NO: 273 is a consensus sequence based on the sequences of SEQ ID NO: 288, SEQ ID NO: 289, SEQ ID NO: 290, and SEQ ID NO: 291.

The sequence of SEQ ID NO: 273 is:
MLPAPKNLVVSRVTEDSARLSWTAPDAAFDSFX$_1$IX$_2$YX$_3$EX$_4$X$_5$X$_6$X$_7$GEAIX$_8$LX$_9$VPGSERSYDLTGLKPGTEYX$_{10}$VX$_{11}$IX$_{12}$X$_{13}$VKGGX$_{14}$X$_{15}$SX$_{16}$PLX$_{17}$AX$_{18}$FTT wherein X$_8$, X$_9$, X$_{17}$, and X$_{18}$ are each, independently, any amino acid other than methionine or proline, and X$_1$ is selected from D, F, Y, or H,
X$_2$ is selected from Y, G, A, or V,
X$_3$ is selected from I, T, L, A, or H,
X$_4$ is selected from S, Y or P,
X$_5$ is selected from Y, G, Q, or R,
X$_6$ is selected from G or P,
X$_7$ is selected from A, Y, P, D, or S,
X$_{10}$ is selected from W, N, S, or E,
X$_{11}$ is selected from L, Y, or G,
X$_{12}$ is selected from D, Q, H, or V,
X$_{13}$ is selected from G or S,
X$_{14}$ is selected from R, G, F, L, or D,
X$_{15}$ is selected from W, S, P, or L, and
X$_{16}$ is selected from T, V, M, or S.

In some embodiments:
X$_1$ is selected from D, F, Y, or H,
X$_2$ is selected from G, A, or V,
X$_3$ is selected from T, L, A, or H,
X$_4$ is selected from Y or P,
X$_5$ is selected from G, Q, or R,
X$_6$ is selected from G or P,
X$_7$ is selected from Y, P, D, or S,
X$_{10}$ is selected from W, N, S, or E,
X$_{11}$ is selected from L, Y, or G,
X$_{12}$ is selected from Q, H, or V,
X$_{13}$ is selected from G or S,
X$_{14}$ is selected from G, F, L, or D,
X$_{15}$ is selected from S, P, or L, and
X$_{16}$ is selected from V, M, or S.

In some embodiments, X$_2$, X$_2$, X$_3$, X$_4$, X$_5$, X$_6$, X$_7$, X$_{10}$, X$_{11}$, X$_{12}$, X$_{13}$, X$_{14}$, X$_{15}$, and X$_{16}$ are as shown in the sequence of SEQ ID NO: 288. In some embodiments, X$_1$, X$_2$, X$_3$, X$_4$, X$_5$, X$_6$, X$_7$, X$_{10}$, X$_{11}$, X$_{12}$, X$_{13}$, X$_{14}$, X$_{15}$, and X$_{16}$ are as shown in the sequence of SEQ ID NO: 289. In some embodiments, X$_1$, X$_2$, X$_3$, X$_4$, X$_5$, X$_6$, X$_7$, X$_{10}$, X$_{11}$, X$_{12}$, X$_{13}$, X$_{14}$, X$_{15}$, and X$_{16}$ are as shown in the sequence of SEQ ID NO: 290. In some embodiments, X$_1$, X$_2$, X$_3$, X$_4$, X$_5$, X$_6$, X$_7$, X$_{10}$, X$_{11}$, X$_{12}$, X$_{13}$, X$_{14}$, X$_{15}$, and X$_{16}$ are as shown in the sequence of SEQ ID NO: 291.

In some embodiments, X8, X9, X17, and X18 is, independently, alanine, arginine, asparagine, aspartic acid, cysteine, glutamine, glutamic acid, glycine, histidine, isoleucine, leucine, lysine, phenylalanine, serine, threonine, tryptophan, tyrosine, or valine. In some embodiments, X8, X9, X17, and X18 is, independently, not alanine, arginine, asparagine, aspartic acid, cysteine, glutamine, glutamic acid, glycine, histidine, isoleucine, leucine, lysine, phenylalanine, serine, threonine, tryptophan, tyrosine, or valine. In some embodiments, X8, X9, X17, and X18 is, independently, alanine. In some embodiments, X8, X9, X17, and X18 is, independently, arginine. In some embodiments, X8, X9, X17, and X18 is, independently asparagine. In some embodiments, X8, X9, X17, and X18 is, independently, aspartic acid. In some embodiments, X8, X9, X17, and X18 is, independently, cysteine. In some embodiments, X8, X9, X17, and X18 is, independently, glutamine. In some embodiments, X8, X9, X17, and X18 is, independently, glutamic acid. In some embodiments, X8, X9, X17, and X18 is, independently, glycine. In some embodiments, X8, X9, X17, and X18 is, independently, histidine. In some embodiments, X8, X9, X17, and X18 is, independently, isoleucine. In some embodiments, X8, X9, X17, and X18 is, independently, leucine. In some embodiments, X8, X9, X17, and X18 is, independently, lysine. In some embodiments, X8, X9, X17, and X18 is, independently, phenylalanine. In some embodiments, X8, X9, X17, and X18 is, independently serine. In some embodiments, X8, X9, X17, and X18 is, independently, threonine. In some embodiments, X8, X9, X17, and X18 is, independently, tryptophan. In some embodiments, X8, X9, X17, and X18 is, independently, tyrosine. In some embodiments, X8, X9, X17, and X18 is, independently valine.

In some embodiments, the sequence is set forth as shown in in the sequence of SEQ ID NO: 288, except that the positions that correspond to the positions of X8, X9, X17, and X18 can be any other amino acid residue as set forth above, except that in some embodiments, X8 is not V, X9 is not T, X17 is not S, and X18 is not I.

In some embodiments, the sequence is set forth as shown in in the sequence of SEQ ID NO: 289, except that the positions that correspond to the positions of X8, X9, X17, and X18 can be any other amino acid residue as set forth above, except that in some embodiments, X8 is not V, X9 is not T, X17 is not S, and X18 is not I.

In some embodiments, the sequence is set forth as shown in in the sequence of SEQ ID NO: 290, except that the positions that correspond to the positions of X8, X9, X17, and X18 can be any other amino acid residue as set forth above, except that in some embodiments, X8 is not V, X9 is not T, X17 is not S, and X18 is not I.

In some embodiments, the sequence is set forth as shown in in the sequence of SEQ ID NO: 291, except that the positions that correspond to the positions of X8, X9, X17, and X18 can be any other amino acid residue as set forth above, except that in some embodiments, X8 is not V, X9 is not T, X17 is not S, and X18 is not I.

In some embodiments, proteins comprising a polypeptide comprising an amino acid sequence that is at least 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to a sequence of SEQ ID NO: 273. In some embodiments, the protein is at least 85%, 86%, 87%, 88%, 89%, 90%, 91%, 92%, 93%, 94%, 95%, 96%, 97%, 98% or 99% identical to a sequence of SEQ ID NO: 273. In some embodiments, the protein is at least 90%, 91%, 92%, 93%, 94%, 95%, 96%, 97%, 98% or 99% identical to a sequence of SEQ ID NO: 273. In some embodiments, the protein is at least 95%, 96%, 97%, 98% or 99% identical to a sequence of SEQ ID NO: 273. In some embodiments, the protein or polypeptide is at least 70%, 75%, 80%, 85%, or 90% identical to SEQ ID NO: 273.

Percent identity can be determined using the default parameters to align two sequences using BlastP available through the NCBI website.

The polypeptides provided herein can be part of a larger polypeptide and can be referred to as a domain. The homology or identity between two domains in different polypeptides is based on the domains that are similar as opposed to the overall polypeptide. For example, if a polypeptide comprises a polypeptide comprising a FN3 domain comprising SEQ ID NO: 1 and said domain is conjugated to a scFV antibody, another protein that has a domain that is similar but not identical to SEQ ID NO: 1 can be at least 90% identical even if the scFV shares no homology. Thus, the % identity can be based on the domain or on the entire length of the polypeptide. Methods of determining % identity are provided for herein or are known to one of skill in the art.

In some embodiments, fibronectin type III (FN3) domains that bind or specifically bind human CD71 protein (SEQ ID Nos: 274 or 275) are provided. As provided herein, the FN3 domains can bind to the CD71 protein. Also provided, even if not explicitly stated is that the domains can also specifically bind to the CD71 protein. Thus, for example, a FN3 domain that binds to CD71 would also encompass a FN3 domain protein that specifically binds to CD71. These molecules can be used, for example, in therapeutic and diagnostic applications and in imaging. In some embodiments, polynucleotides encoding the FN3 domains disclosed herein or complementary nucleic acids thereof, vectors, host cells, and methods of making and using them are provided.

In some embodiments, an isolated FN3 domain that binds or specifically binds CD71 is provided.

In some embodiments, the FN3 domain comprises two FN3 domains connected by a linker. The linker can be a flexible linker. The linker can be a short peptide sequence, such as those described herein. For example, the linker can be a G/S linker and the like.

In some embodiments, the FN3 domain comprising two FN3 domains connected by a linker, such as those provided for herein. Exemplary linker include, but are not limited to, (GS)2, (SEQ ID NO: 278), (GGGS)2 (SEQ ID NO: 279), (GGGGS)1-5 (SEQ ID NO: 280), (AP)1-20 (SEQ ID NO: 311); (AP)2 (SEQ ID NO: 281), (AP)5 (SEQ ID NO: 282), $(AP)_{10}$(SEQ ID NO: 283), $(AP)_{20}$ (SEQ ID NO: 284), $A(EAAAK)_5AAA$ (SEQ ID NO: 285), or $(EAAAK)_{1-5}$ (SEQ ID NO: 307). In some embodiments, the linker comprises or is an amino acid sequence of: EAAAKEAAAKEAAAKEAAAK (SEQ ID NO: 300); GGGGSGGGGSGGGGSGGGGS (SEQ ID NO: 301); APAPAPAPAP (SEQ ID NO: 302); or EAAAK (SEQ ID NO: 303).

In some embodiments, the polypeptide comprises an amino acid sequence of SEQ ID NO: 292. In some embodiments, the polypeptide comprises an amino acid sequence of SEQ ID NO: 293. In some embodiments, the polypeptide comprises an amino acid sequence of SEQ ID NO: 294. In some embodiments, the polypeptide comprises an amino acid sequence of SEQ ID NO: 295. In some embodiments, the polypeptide comprises an amino acid sequence of SEQ ID NO: 296. In some embodiments, the polypeptide comprises an amino acid sequence of SEQ ID NO: 297. In some embodiments, the polypeptide comprises an amino acid sequence of SEQ ID NO: 298. In some embodiments, the polypeptide comprises an amino acid sequence of SEQ ID NO: 299.

In some embodiments, the FN3 domain may bind CD71 with a dissociation constant (KD) of less than about 1×10-7 M, for example less than about 1×10-8 M, less than about 1×10-9 M, less than about 1×10-10 M, less than about 1×10-11 M, less than about 1×10-12 M, or less than about 1×10-13 M as determined by surface plasmon resonance or the Kinexa method, as practiced by those of skill in the art. The measured affinity of a particular FN3 domain-antigen interaction can vary if measured under different conditions (e.g., osmolarity, pH). Thus, measurements of affinity and other antigen-binding parameters (e.g., KD, Kon, Koff) are made with standardized solutions of protein scaffold and antigen, and a standardized buffer, such as the buffers described herein.

In some embodiments, the FN3 domain may bind CD71 at least 5-fold above the signal obtained for a negative control in a standard solution ELISA assay.

In some embodiments, the FN3 domain that binds or specifically binds CD71 comprises an initiator methionine (Met) linked to the N-terminus of the molecule. In some embodiments, the FN3 domain that binds or specifically binds CD71 comprises a cysteine (Cys) linked to a C-terminus of the FN3 domain. The addition of the N-terminal Met and/or the C-terminal Cys may facilitate expression and/or conjugation of half-life extending molecules.

The FN3 domain can also contain cysteine substitutions, such as those that are described in U.S. Pat. No. 10,196,446, which is hereby incorporated by reference in its entirety. Briefly, in some embodiments, the polypeptides provided herein can comprise at least one cysteine substitution at a position selected from the group consisting of residues 6, 8, 10, 11, 14, 15, 16, 20, 30, 34, 38, 40, 41, 45, 47, 48, 53, 54, 59, 60, 62, 64, 70, 88, 89, 90, 91, and 93 of the FN3 domain based on SEQ ID NO: 6 or SEQ ID NO: 1 of U.S. Pat. No. 10,196,446, and the equivalent positions in related FN3 domains. In some embodiments, the substitution is at residue 6. In some embodiments, the substitution is at residue 8. In some embodiments, the substitution is at residue 10. In some embodiments, the substitution is at residue 11. In some embodiments, the substitution is at residue 14. In some embodiments, the substitution is at residue 15. In some embodiments, the substitution is at residue 16. In some embodiments, the substitution is at residue 20. In some embodiments, the substitution is at residue 30. In some embodiments, the substitution is at residue 34. In some embodiments, the substitution is at residue 38. In some embodiments, the substitution is at residue 40. In some embodiments, the substitution is at residue 41. In some embodiments, the substitution is at residue 45. In some embodiments, the substitution is at residue 47. In some embodiments, the substitution is at residue 48. In some embodiments, the substitution is at residue 53. In some embodiments, the substitution is at residue 54. In some embodiments, the substitution is at residue 59. In some embodiments, the substitution is at residue 60. In some embodiments, the substitution is at residue 62. In some embodiments, the substitution is at residue 64. In some embodiments, the substitution is at residue 70. In some embodiments, the substitution is at residue 88. In some embodiments, the substitution is at residue 89. In some embodiments, the substitution is at residue 90. In some embodiments, the substitution is at residue 91. In some embodiments, the substitution is at residue 93.

A cysteine substitution at a position in the domain or protein comprises a replacement of the existing amino acid residue with a cysteine residue. Other examples of cysteine modifications can be found in, for example, U.S. Patent Application Publication No. 20170362301, which is hereby incorporated by reference in its entirety. The alignment of the sequences can be performed using BlastP using the default parameters at, for example, the NCBI website.

In some embodiments, the FN3 domain that binds CD71 is internalized into a cell. In some embodiments, internalization of the FN3 domain may facilitate delivery of a detectable label or therapeutic into a cell. In some embodiments, internalization of the FN3 domain may facilitate delivery of a cytotoxic agent into a cell. The cytotoxic agent can act as a therapeutic agent. In some embodiments, internalization of the FN3 domain may facilitate the delivery of any detectable label, therapeutic, and/or cytotoxic agent disclosed herein into a cell. In some embodiments, the cell is a tumor cell. In some embodiments, the cell is a liver cell. In some embodiments, the cell is a muscle cell. In some embodiments, the cell is an immune cell. In some embodiments, the cell is a dendritic cell. In some embodiments, the cell is a T-cell. In some embodiments, the cell is a NK cells. In some embodiments, the cell is a B-cell. In some embodiments, the cell is a cell of the central nervous system.

In some embodiments, the FN3 domain that binds CD71 is based on Tencon sequence of SEQ ID NO: 276 or Tencon 27 sequence of SEQ ID NO: 277, optionally having substitutions at residues positions 11, 14, 17, 37, 46, 73, or 86 (residue numbering corresponding to SEQ ID NO: 277).

```
SEQ ID NO: 276 = Original Tencon Sequence
LPAPKNLVVSEVTEDSLRLSWTAPDAAFDSFLIQYQESEKVGEAINLTVP

GSERSYDLTGLKPGTEYTVSIYGVKGGHRSNPLSAEFTT

SEQ ID NO: 277 = Stabilized Tencon (Tencon27)
LPAPKNLVVSRVTEDSARLSWTAPDAAFDSFLIQYQESEKVGEAIVLTVP

GSERSYDLTGLKPGTEYTVSIYGVKGGHRSNPLSAIFTT
```

In some embodiments, an isolated FN3 domain that binds CD71 comprises the amino acid sequence of SEQ ID Nos: 1-7, 10, 12-219, 221-272, 292-299, or 304-306.

In some embodiments, an isolated FN3 domain that binds CD71 comprises the amino acid sequence of SEQ ID NO: 1. In some embodiments, an isolated FN3 domain that binds CD71 comprises the amino acid sequence of SEQ ID NO: 2. In some embodiments, an isolated FN3 domain that binds CD71 comprises the amino acid sequence of SEQ ID NO: 3. In some embodiments, an isolated FN3 domain that binds CD71 comprises the amino acid sequence of SEQ ID NO: 4. In some embodiments, an isolated FN3 domain that binds CD71 comprises the amino acid sequence of SEQ ID NO: 5. In some embodiments, an isolated FN3 domain that binds CD71 comprises the amino acid sequence of SEQ ID NO: 6. In some embodiments, an isolated FN3 domain that binds CD71 comprises the amino acid sequence of SEQ ID NO: 7. In some embodiments, an isolated FN3 domain that binds CD71 comprises the amino acid sequence of SEQ ID NO: 10. In some embodiments, an isolated FN3 domain that binds CD71 comprises the amino acid sequence of SEQ ID NO: 12. In some embodiments, an isolated FN3 domain that binds CD71 comprises the amino acid sequence of SEQ ID NO: 13. In some embodiments, an isolated FN3 domain that binds CD71 comprises the amino acid sequence of SEQ ID NO: 14. In some embodiments, an isolated FN3 domain that binds CD71 comprises the amino acid sequence of SEQ ID NO: 15. In some embodiments, an isolated FN3 domain that binds CD71 comprises the amino acid sequence of SEQ ID NO: 16. In some embodiments, an isolated FN3 domain that binds CD71 comprises the amino acid sequence of SEQ ID NO: 17. In some embodiments, an isolated FN3 domain that binds CD71 comprises the amino acid sequence of SEQ ID NO: 18. In some embodiments, an isolated FN3 domain that binds CD71 comprises the amino acid sequence of SEQ ID NO: 19. In some embodiments, an isolated FN3 domain that binds CD71 comprises the amino acid sequence of SEQ ID NO: 20. In some embodiments, an isolated FN3 domain that binds CD71 comprises the amino acid sequence of SEQ ID NO: 21. In some embodiments, an isolated FN3 domain that binds CD71 comprises the amino acid sequence of SEQ ID NO: 22. In some embodiments, an isolated FN3 domain that binds CD71 comprises the amino acid sequence of SEQ ID NO: 23. In some embodiments, an isolated FN3 domain that binds CD71 comprises the amino acid sequence of SEQ ID NO: 24. In some embodiments, an isolated FN3 domain that binds CD71 comprises the amino acid sequence of SEQ ID NO: 25. In some embodiments, an isolated FN3 domain that binds CD71 comprises the amino acid sequence of SEQ ID NO: 26. In some embodiments, an isolated FN3 domain that binds CD71 comprises the amino acid sequence of SEQ ID NO: 27. In some embodiments, an isolated FN3 domain that binds CD71 comprises the amino acid sequence of SEQ ID NO: 28. In some embodiments, an isolated FN3 domain that binds CD71 comprises the amino acid sequence of SEQ ID NO: 29. In some embodiments, an isolated FN3 domain that binds CD71 comprises the amino acid sequence of SEQ ID NO: 30. In some embodiments, an isolated FN3 domain that binds CD71 comprises the amino acid sequence of SEQ ID NO: 31. In some embodiments, an isolated FN3 domain that binds CD71 comprises the amino acid sequence of SEQ ID NO: 32. In some embodiments, an isolated FN3 domain that binds CD71 comprises the amino acid sequence of SEQ ID NO: 33. In some embodiments, an isolated FN3 domain that binds CD71 comprises the amino acid sequence of SEQ ID NO: 34. In some embodiments, an isolated FN3 domain that binds CD71 comprises the amino acid sequence of SEQ ID NO: 35. In some embodiments, an isolated FN3 domain that binds CD71 comprises the amino acid sequence of SEQ ID NO: 36. In some embodiments, an isolated FN3 domain that binds CD71 comprises the amino acid sequence of SEQ ID NO: 37. In some embodiments, an isolated FN3 domain that binds CD71 comprises the amino acid sequence of SEQ ID NO: 38. In some embodiments, an isolated FN3 domain that binds CD71 comprises the amino acid sequence of SEQ ID NO: 39. In some embodiments, an isolated FN3 domain that binds CD71 comprises the amino acid sequence of SEQ ID NO: 40. In some embodiments, an isolated FN3 domain that binds CD71 comprises the amino acid sequence of SEQ ID NO: 41. In some embodiments, an isolated FN3 domain that binds CD71 comprises the amino acid sequence of SEQ ID NO: 42. In some embodiments, an isolated FN3 domain that binds CD71 comprises the amino acid sequence of SEQ ID NO: 43. In some embodiments, an isolated FN3 domain that binds CD71 comprises the amino acid sequence of SEQ ID NO: 44. In some embodiments, an isolated FN3 domain that binds CD71 comprises the amino acid sequence of SEQ ID NO: 45. In some embodiments, an isolated FN3 domain that binds CD71 comprises the amino acid sequence of SEQ ID NO: 46. In some embodiments, an isolated FN3 domain that binds CD71 comprises the amino acid sequence of SEQ ID NO: 47. In some embodiments, an isolated FN3 domain that binds CD71 comprises the amino acid sequence of SEQ ID NO: 48. In some embodiments, an isolated FN3 domain that binds CD71 comprises the amino acid sequence of SEQ ID NO: 49. In some embodiments, an isolated FN3 domain that binds CD71 comprises the amino acid sequence of SEQ ID NO: 50. In some embodiments, an isolated FN3 domain that binds CD71 comprises the amino acid sequence of SEQ ID NO: 51. In some embodiments, an isolated FN3 domain that binds CD71 comprises the amino acid sequence of SEQ ID NO: 52. In some embodiments, an isolated FN3 domain that binds CD71 comprises the amino acid sequence of SEQ ID NO: 53. In some embodiments, an isolated FN3 domain that binds CD71 comprises the amino acid sequence of SEQ ID NO: 54. In some embodiments, an isolated FN3 domain that binds CD71 comprises the amino acid sequence of SEQ ID NO: 55. In some embodiments, an isolated FN3 domain that binds CD71 comprises the amino acid sequence of SEQ ID NO: 56. In some embodiments, an isolated FN3 domain that binds CD71 comprises the amino acid sequence of SEQ ID NO: 57. In some embodiments, an isolated FN3 domain that binds CD71 comprises the amino acid sequence of SEQ ID NO: 58. In some embodiments, an isolated FN3 domain that binds CD71 comprises the amino acid sequence of SEQ ID NO: 59. In some embodiments, an isolated FN3 domain that binds CD71 comprises the amino acid sequence of SEQ ID NO: 60. In some embodiments, an isolated FN3 domain that binds CD71 comprises the amino acid sequence of SEQ ID NO: 61. In some embodiments, an isolated FN3 domain that binds CD71 comprises the amino acid sequence of SEQ ID NO: 62. In some embodiments, an isolated FN3 domain that binds CD71 comprises the amino acid sequence of SEQ ID NO: 63. In some embodiments, an isolated FN3 domain that binds CD71 comprises the amino acid sequence of SEQ ID NO: 64. In some embodiments, an isolated FN3 domain that binds CD71 comprises the amino acid sequence of SEQ ID NO: 65. In some embodiments, an isolated FN3 domain that binds CD71 comprises the amino acid sequence of SEQ ID NO: 66. In some embodiments, an isolated FN3 domain that binds CD71 comprises the amino acid sequence of SEQ ID NO: 67. In some embodiments, an isolated FN3 domain that binds CD71 comprises the amino acid sequence of SEQ ID NO: 68. In some embodiments, an isolated FN3 domain that binds CD71 comprises the amino acid sequence of SEQ ID NO: 69. In some embodiments, an isolated FN3 domain that binds CD71 comprises the amino acid sequence of SEQ ID NO: 70. In some embodiments, an isolated FN3 domain that binds CD71 comprises the amino acid sequence of SEQ ID NO: 71. In some embodiments, an isolated FN3 domain that binds CD71 comprises the amino acid sequence of SEQ ID NO: 72. In some embodiments, an isolated FN3 domain that binds CD71 comprises the amino acid sequence of SEQ ID NO: 73. In some embodiments, an isolated FN3 domain that binds CD71 comprises the amino acid sequence of SEQ ID NO: 74. In some embodiments, an isolated FN3 domain that binds CD71 comprises the amino acid sequence of SEQ ID NO: 75. In some embodiments, an isolated FN3 domain that binds CD71 comprises the amino acid sequence of SEQ ID NO: 76. In some embodiments, an isolated FN3 domain that binds CD71 comprises the amino acid sequence of SEQ ID NO: 77. In some embodiments, an isolated FN3 domain that binds CD71 comprises the amino acid sequence of SEQ ID NO: 78. In some embodiments, an isolated FN3 domain that binds CD71 comprises the amino acid sequence of SEQ ID NO: 79. In some embodiments, an isolated FN3 domain that binds CD71 comprises the amino acid sequence of SEQ ID NO: 80. In some embodiments, an isolated FN3 domain that binds CD71 comprises the amino acid sequence of SEQ ID NO: 81. In some embodiments, an isolated FN3 domain that binds CD71 comprises the amino acid sequence of SEQ ID NO: 82. In some embodiments, an isolated FN3 domain that binds CD71 comprises the amino acid sequence of SEQ ID NO: 83. In some embodiments, an isolated FN3 domain that binds CD71 comprises the amino acid sequence of SEQ ID NO: 84. In some embodiments, an isolated FN3 domain that binds CD71 comprises the amino acid sequence of SEQ ID NO: 85. In some embodiments, an isolated FN3 domain that binds CD71 comprises the amino acid sequence of SEQ ID NO: 86. In some embodiments, an isolated FN3 domain that binds CD71 comprises the amino acid sequence of SEQ ID NO: 87. In some embodiments, an isolated FN3 domain that binds CD71 comprises the amino acid sequence of SEQ ID NO: 88. In some embodiments, an isolated FN3 domain that binds CD71 comprises the amino acid sequence of SEQ ID NO: 89. In some embodiments, an isolated FN3 domain that binds CD71 comprises the amino acid sequence of SEQ ID NO: 90. In some embodiments, an isolated FN3 domain that binds CD71 comprises the amino acid sequence of SEQ ID NO: 91. In some embodiments, an isolated FN3 domain that binds CD71 comprises the amino acid sequence of SEQ ID NO: 92. In some embodiments, an isolated FN3 domain that binds CD71 comprises the amino acid sequence of SEQ ID NO: 93. In some embodiments, an isolated FN3 domain that binds CD71 comprises the amino acid sequence of SEQ ID NO: 94. In some embodiments, an isolated FN3 domain that binds CD71 comprises the amino acid sequence of SEQ ID NO: 95. In some embodiments, an isolated FN3 domain that binds CD71 comprises the amino acid sequence of SEQ ID NO: 96. In some embodiments, an isolated FN3 domain that binds CD71 comprises the amino acid sequence of SEQ ID NO: 97. In some embodiments, an isolated FN3 domain that binds CD71 comprises the amino acid sequence of SEQ ID NO: 98. In some embodiments, an isolated FN3 domain that binds CD71 comprises the amino acid sequence of SEQ ID NO: 99. In some embodiments, an isolated FN3 domain that binds CD71 comprises the amino acid sequence of SEQ ID NO: 100. In some embodiments, an isolated FN3 domain that binds CD71 comprises the amino acid sequence of SEQ ID NO: 101. In some embodiments, an isolated FN3 domain that binds CD71 comprises the amino acid sequence of SEQ ID NO: 102. In some embodiments, an isolated FN3 domain that binds CD71 comprises the amino acid sequence of SEQ ID NO: 103. In some embodiments, an isolated FN3 domain that binds CD71 comprises the amino acid sequence of SEQ ID NO: 104. In some embodiments, an isolated FN3 domain that binds CD71 comprises the amino acid sequence of SEQ ID NO: 105. In some embodiments, an isolated FN3 domain that binds CD71 comprises the amino acid sequence of SEQ ID NO: 106. In some embodiments, an isolated FN3 domain that binds CD71 comprises the amino acid sequence of SEQ ID NO: 107. In some embodiments, an isolated FN3 domain that binds CD71 comprises the amino acid sequence of SEQ ID NO: 108. In some embodiments, an isolated FN3 domain that binds CD71 comprises the amino acid sequence of SEQ ID NO: 109. In some embodiments, an isolated FN3 domain that binds CD71 comprises the amino acid sequence of SEQ ID NO: 110. In some embodiments, an isolated FN3 domain that binds CD71 comprises the amino acid sequence of SEQ ID NO: 111. In some embodiments, an isolated FN3 domain that binds CD71 comprises the amino acid sequence of SEQ ID NO: 112. In some embodiments, an isolated FN3 domain that binds CD71 comprises the amino acid sequence of SEQ ID NO: 113. In some embodiments, an isolated FN3 domain that binds CD71 comprises the amino acid sequence of SEQ ID NO: 114. In some embodiments, an isolated FN3 domain that binds CD71 comprises the amino acid sequence of SEQ ID NO: 115. In some embodiments, an isolated FN3 domain that binds CD71 comprises the amino acid sequence of SEQ ID NO: 116. In some embodiments, an isolated FN3 domain that binds CD71 comprises the amino acid sequence of SEQ ID NO: 117. In some embodiments, an isolated FN3 domain that binds CD71 comprises the amino acid sequence of SEQ ID NO: 118. In some embodiments, an isolated FN3 domain that binds CD71 comprises the amino acid sequence of SEQ ID NO: 119. In some embodiments, an isolated FN3 domain that binds CD71 comprises the amino acid sequence of SEQ ID NO: 120. In some embodiments, an isolated FN3 domain that binds CD71 comprises the amino acid sequence of SEQ ID NO: 121. In some embodiments, an isolated FN3 domain that binds CD71 comprises the amino acid sequence of SEQ ID NO: 122. In some embodiments, an isolated FN3 domain that binds CD71 comprises the amino acid sequence of SEQ ID NO: 123. In some embodiments, an isolated FN3 domain that binds CD71 comprises the amino acid sequence of SEQ ID NO: 124. In some embodiments, an isolated FN3 domain that binds CD71 comprises the amino acid sequence of SEQ ID NO: 125. In some embodiments, an isolated FN3 domain that binds CD71 comprises the amino acid sequence of SEQ ID NO: 126. In some embodiments, an isolated FN3 domain that binds CD71 comprises the amino acid sequence of SEQ ID NO: 127. In some embodiments, an isolated FN3 domain that binds CD71 comprises the amino acid sequence of SEQ ID NO: 128. In some embodiments, an isolated FN3 domain that binds CD71 comprises the amino acid sequence of SEQ ID NO: 129. In some embodiments, an isolated FN3 domain that binds CD71 comprises the amino acid sequence of SEQ ID NO: 130. In some embodiments, an isolated FN3 domain that binds CD71 comprises the amino acid sequence of SEQ ID NO: 131. In some embodiments, an isolated FN3 domain that binds CD71 comprises the amino acid sequence of SEQ ID NO: 132. In some embodiments, an isolated FN3 domain that binds CD71 comprises the amino acid sequence of SEQ ID NO: 133. In some embodiments, an isolated FN3 domain that binds CD71 comprises the amino acid sequence of SEQ ID NO: 134. In some embodiments, an isolated FN3 domain that binds CD71 comprises the amino acid sequence of SEQ ID NO: 135. In some embodiments, an isolated FN3 domain that binds CD71 comprises the amino acid sequence of SEQ ID NO: 136. In some embodiments, an isolated FN3 domain that binds CD71 comprises the amino acid sequence of SEQ ID NO: 137. In some embodiments, an isolated FN3 domain that binds CD71 comprises the amino acid sequence of SEQ ID NO: 138. In some embodiments, an isolated FN3 domain that binds CD71 comprises the amino acid sequence of SEQ ID NO: 139. In some embodiments, an isolated FN3 domain that binds CD71 comprises the amino acid sequence of SEQ ID NO: 140. In some embodiments, an isolated FN3 domain that binds CD71 comprises the amino acid sequence of SEQ ID NO: 141. In some embodiments, an isolated FN3 domain that binds CD71 comprises the amino acid sequence of SEQ ID NO: 142. In some embodiments, an isolated FN3 domain that binds CD71 comprises the amino acid sequence of SEQ ID NO: 143. In some embodiments, an isolated FN3 domain that binds CD71 comprises the amino acid sequence of SEQ ID NO: 144. In some embodiments, an isolated FN3 domain that binds CD71 comprises the amino acid sequence of SEQ ID NO: 145. In some embodiments, an isolated FN3 domain that binds CD71 comprises the amino acid sequence of SEQ ID NO: 146. In some embodiments, an isolated FN3 domain that binds CD71 comprises the amino acid sequence of SEQ ID NO: 147. In some embodiments, an isolated FN3 domain that binds CD71 comprises the amino acid sequence of SEQ ID NO: 148. In some embodiments, an isolated FN3 domain that binds CD71 comprises the amino acid sequence of SEQ ID NO: 149. In some embodiments, an isolated FN3 domain that binds CD71 comprises the amino acid sequence of SEQ ID NO: 150. In some embodiments, an isolated FN3 domain that binds CD71 comprises the amino acid sequence of SEQ ID NO: 151. In some embodiments, an isolated FN3 domain that binds CD71 comprises the amino acid sequence of SEQ ID NO: 152. In some embodiments, an isolated FN3 domain that binds CD71 comprises the amino acid sequence of SEQ ID NO: 153. In some embodiments, an isolated FN3 domain that binds CD71 comprises the amino acid sequence of SEQ ID NO: 154. In some embodiments, an isolated FN3 domain that binds CD71 comprises the amino acid sequence of SEQ ID NO: 155. In some embodiments, an isolated FN3 domain that binds CD71 comprises the amino acid sequence of SEQ ID NO: 156. In some embodiments, an isolated FN3 domain that binds CD71 comprises the amino acid sequence of SEQ ID NO: 157. In some embodiments, an isolated FN3 domain that binds CD71 comprises the amino acid sequence of SEQ ID NO: 158. In some embodiments, an isolated FN3 domain that binds CD71 comprises the amino acid sequence of SEQ ID NO: 159. In some embodiments, an isolated FN3 domain that binds CD71 comprises the amino acid sequence of SEQ ID NO: 160. In some embodiments, an isolated FN3 domain that binds CD71 comprises the amino acid sequence of SEQ ID NO: 161. In some embodiments, an isolated FN3 domain that binds CD71 comprises the amino acid sequence of SEQ ID NO: 162. In some embodiments, an isolated FN3 domain that binds CD71 comprises the amino acid sequence of SEQ ID NO: 163. In some embodiments, an isolated FN3 domain that binds CD71 comprises the amino acid sequence of SEQ ID NO: 164. In some embodiments, an isolated FN3 domain that binds CD71 comprises the amino acid sequence of SEQ ID NO: 165. In some embodiments, an isolated FN3 domain that binds CD71 comprises the amino acid sequence of SEQ ID NO: 166. In some embodiments, an isolated FN3 domain that binds CD71 comprises the amino acid sequence of SEQ ID NO: 167. In some embodiments, an isolated FN3 domain that binds CD71 comprises the amino acid sequence of SEQ ID NO: 168. In some embodiments, an isolated FN3 domain that binds CD71 comprises the amino acid sequence of SEQ ID NO: 169. In some embodiments, an isolated FN3 domain that binds CD71 comprises the amino acid sequence of SEQ ID NO: 170. In some embodiments, an isolated FN3 domain that binds CD71 comprises the amino acid sequence of SEQ ID NO: 171. In some embodiments, an isolated FN3 domain that binds CD71 comprises the amino acid sequence of SEQ ID NO: 172. In some embodiments, an isolated FN3 domain that binds CD71 comprises the amino acid sequence of SEQ ID NO: 173. In some embodiments, an isolated FN3 domain that binds CD71 comprises the amino acid sequence of SEQ ID NO: 174. In some embodiments, an isolated FN3 domain that binds CD71 comprises the amino acid sequence of SEQ ID NO: 175. In some embodiments, an isolated FN3 domain that binds CD71 comprises the amino acid sequence of SEQ ID NO: 176. In some embodiments, an isolated FN3 domain that binds CD71 comprises the amino acid sequence of SEQ ID NO: 177. In some embodiments, an isolated FN3 domain that binds CD71 comprises the amino acid sequence of SEQ ID NO: 178. In some embodiments, an isolated FN3 domain that binds CD71 comprises the amino acid sequence of SEQ ID NO: 179. In some embodiments, an isolated FN3 domain that binds CD71 comprises the amino acid sequence of SEQ ID NO: 180. In some embodiments, an isolated FN3 domain that binds CD71 comprises the amino acid sequence of SEQ ID NO: 181. In some embodiments, an isolated FN3 domain that binds CD71 comprises the amino acid sequence of SEQ ID NO: 182. In some embodiments, an isolated FN3 domain that binds CD71 comprises the amino acid sequence of SEQ ID NO: 183. In some embodiments, an isolated FN3 domain that binds CD71 comprises the amino acid sequence of SEQ ID NO: 184. In some embodiments, an isolated FN3 domain that binds CD71 comprises the amino acid sequence of SEQ ID NO: 185. In some embodiments, an isolated FN3 domain that binds CD71 comprises the amino acid sequence of SEQ ID NO: 186. In some embodiments, an isolated FN3 domain that binds CD71 comprises the amino acid sequence of SEQ ID NO: 187. In some embodiments, an isolated FN3 domain that binds CD71 comprises the amino acid sequence of SEQ ID NO: 188. In some embodiments, an isolated FN3 domain that binds CD71 comprises the amino acid sequence of SEQ ID NO: 189. In some embodiments, an isolated FN3 domain that binds CD71 comprises the amino acid sequence of SEQ ID NO: 190. In some embodiments, an isolated FN3 domain that binds CD71 comprises the amino acid sequence of SEQ ID NO: 191. In some embodiments, an isolated FN3 domain that binds CD71 comprises the amino acid sequence of SEQ ID NO: 192. In some embodiments, an isolated FN3 domain that binds CD71 comprises the amino acid sequence of SEQ ID NO: 193. In some embodiments, an isolated FN3 domain that binds CD71 comprises the amino acid sequence of SEQ ID NO: 194. In some embodiments, an isolated FN3 domain that binds CD71 comprises the amino acid sequence of SEQ ID NO: 195. In some embodiments, an isolated FN3 domain that binds CD71 comprises the amino acid sequence of SEQ ID NO: 196. In some embodiments, an isolated FN3 domain that binds CD71 comprises the amino acid sequence of SEQ ID NO: 197. In some embodiments, an isolated FN3 domain that binds CD71 comprises the amino acid sequence of SEQ ID NO: 198. In some embodiments, an isolated FN3 domain that binds CD71 comprises the amino acid sequence of SEQ ID NO: 199. In some embodiments, an isolated FN3 domain that binds CD71 comprises the amino acid sequence of SEQ ID NO: 200. In some embodiments, an isolated FN3 domain that binds CD71 comprises the amino acid sequence of SEQ ID NO: 201. In some embodiments, an isolated FN3 domain that binds CD71 comprises the amino acid sequence of SEQ ID NO: 202. In some embodiments, an isolated FN3 domain that binds CD71 comprises the amino acid sequence of SEQ ID NO: 203. In some embodiments, an isolated FN3 domain that binds CD71 comprises the amino acid sequence of SEQ ID NO: 204. In some embodiments, an isolated FN3 domain that binds CD71 comprises the amino acid sequence of SEQ ID NO: 205. In some embodiments, an isolated FN3 domain that binds CD71 comprises the amino acid sequence of SEQ ID NO: 206. In some embodiments, an isolated FN3 domain that binds CD71 comprises the amino acid sequence of SEQ ID NO: 207. In some embodiments, an isolated FN3 domain that binds CD71 comprises the amino acid sequence of SEQ ID NO: 208. In some embodiments, an isolated FN3 domain that binds CD71 comprises the amino acid sequence of SEQ ID NO: 209. In some embodiments, an isolated FN3 domain that binds CD71 comprises the amino acid sequence of SEQ ID NO: 210. In some embodiments, an isolated FN3 domain that binds CD71 comprises the amino acid sequence of SEQ ID NO: 211. In some embodiments, an isolated FN3 domain that binds CD71 comprises the amino acid sequence of SEQ ID NO: 212. In some embodiments, an isolated FN3 domain that binds CD71 comprises the amino acid sequence of SEQ ID NO: 213. In some embodiments, an isolated FN3 domain that binds CD71 comprises the amino acid sequence of SEQ ID NO: 214. In some embodiments, an isolated FN3 domain that binds CD71 comprises the amino acid sequence of SEQ ID NO: 215. In some embodiments, an isolated FN3 domain that binds CD71 comprises the amino acid sequence of SEQ ID NO: 216. In some embodiments, an isolated FN3 domain that binds CD71 comprises the amino acid sequence of SEQ ID NO: 217. In some embodiments, an isolated FN3 domain that binds CD71 comprises the amino acid sequence of SEQ ID NO: 218. In some embodiments, an isolated FN3 domain that binds CD71 comprises the amino acid sequence of SEQ ID NO: 219. In some embodiments, an isolated FN3 domain that binds CD71 comprises the amino acid sequence of SEQ ID NO: 221. In some embodiments, an isolated FN3 domain that binds CD71 comprises the amino acid sequence of SEQ ID NO: 222. In some embodiments, an isolated FN3 domain that binds CD71 comprises the amino acid sequence of SEQ ID NO: 223. In some embodiments, an isolated FN3 domain that binds CD71 comprises the amino acid sequence of SEQ ID NO: 224. In some embodiments, an isolated FN3 domain that binds CD71 comprises the amino acid sequence of SEQ ID NO: 225. In some embodiments, an isolated FN3 domain that binds CD71 comprises the amino acid sequence of SEQ ID NO: 226. In some embodiments, an isolated FN3 domain that binds CD71 comprises the amino acid sequence of SEQ ID NO: 227. In some embodiments, an isolated FN3 domain that binds CD71 comprises the amino acid sequence of SEQ ID NO: 228. In some embodiments, an isolated FN3 domain that binds CD71 comprises the amino acid sequence of SEQ ID NO: 229. In some embodiments, an isolated FN3 domain that binds CD71 comprises the amino acid sequence of SEQ ID NO: 230. In some embodiments, an isolated FN3 domain that binds CD71 comprises the amino acid sequence of SEQ ID NO: 231. In some embodiments, an isolated FN3 domain that binds CD71 comprises the amino acid sequence of SEQ ID NO: 232. In some embodiments, an isolated FN3 domain that binds CD71 comprises the amino acid sequence of SEQ ID NO: 233. In some embodiments, an isolated FN3 domain that binds CD71 comprises the amino acid sequence of SEQ ID NO: 234. In some embodiments, an isolated FN3 domain that binds CD71 comprises the amino acid sequence of SEQ ID NO: 235. In some embodiments, an isolated FN3 domain that binds CD71 comprises the amino acid sequence of SEQ ID NO: 236. In some embodiments, an isolated FN3 domain that binds CD71 comprises the amino acid sequence of SEQ ID NO: 237. In some embodiments, an isolated FN3 domain that binds CD71 comprises the amino acid sequence of SEQ ID NO: 238. In some embodiments, an isolated FN3 domain that binds CD71 comprises the amino acid sequence of SEQ ID NO: 239. In some embodiments, an isolated FN3 domain that binds CD71 comprises the amino acid sequence of SEQ ID NO: 240. In some embodiments, an isolated FN3 domain that binds CD71 comprises the amino acid sequence of SEQ ID NO: 241. In some embodiments, an isolated FN3 domain that binds CD71 comprises the amino acid sequence of SEQ ID NO: 242. In some embodiments, an isolated FN3 domain that binds CD71 comprises the amino acid sequence of SEQ ID NO: 243. In some embodiments, an isolated FN3 domain that binds CD71 comprises the amino acid sequence of SEQ ID NO: 244. In some embodiments, an isolated FN3 domain that binds CD71 comprises the amino acid sequence of SEQ ID NO: 245. In some embodiments, an isolated FN3 domain that binds CD71 comprises the amino acid sequence of SEQ ID NO: 246. In some embodiments, an isolated FN3 domain that binds CD71 comprises the amino acid sequence of SEQ ID NO: 247. In some embodiments, an isolated FN3 domain that binds CD71 comprises the amino acid sequence of SEQ ID NO: 248. In some embodiments, an isolated FN3 domain that binds CD71 comprises the amino acid sequence of SEQ ID NO: 249. In some embodiments, an isolated FN3 domain that binds CD71 comprises the amino acid sequence of SEQ ID NO: 250. In some embodiments, an isolated FN3 domain that binds CD71 comprises the amino acid sequence of SEQ ID NO: 251. In some embodiments, an isolated FN3 domain that binds CD71 comprises the amino acid sequence of SEQ ID NO: 252. In some embodiments, an isolated FN3 domain that binds CD71 comprises the amino acid sequence of SEQ ID NO: 253. In some embodiments, an isolated FN3 domain that binds CD71 comprises the amino acid sequence of SEQ ID NO: 254. In some embodiments, an isolated FN3 domain that binds CD71 comprises the amino acid sequence of SEQ ID NO: 255. In some embodiments, an isolated FN3 domain that binds CD71 comprises the amino acid sequence of SEQ ID NO: 256. In some embodiments, an isolated FN3 domain that binds CD71 comprises the amino acid sequence of SEQ ID NO: 257. In some embodiments, an isolated FN3 domain that binds CD71 comprises the amino acid sequence of SEQ ID NO: 258. In some embodiments, an isolated FN3 domain that binds CD71 comprises the amino acid sequence of SEQ ID NO: 259. In some embodiments, an isolated FN3 domain that binds CD71 comprises the amino acid sequence of SEQ ID NO: 260. In some embodiments, an isolated FN3 domain that binds CD71 comprises the amino acid sequence of SEQ ID NO: 261. In some embodiments, an isolated FN3 domain that binds CD71 comprises the amino acid sequence of SEQ ID NO: 262. In some embodiments, an isolated FN3 domain that binds CD71 comprises the amino acid sequence of SEQ ID NO: 263. In some embodiments, an isolated FN3 domain that binds CD71 comprises the amino acid sequence of SEQ ID NO: 264. In some embodiments, an isolated FN3 domain that binds CD71 comprises the amino acid sequence of SEQ ID NO: 265. In some embodiments, an isolated FN3 domain that binds CD71 comprises the amino acid sequence of SEQ ID NO: 266. In some embodiments, an isolated FN3 domain that binds CD71 comprises the amino acid sequence of SEQ ID NO: 267. In some embodiments, an isolated FN3 domain that binds CD71 comprises the amino acid sequence of SEQ ID NO: 268. In some embodiments, an isolated FN3 domain that binds CD71 comprises the amino acid sequence of SEQ ID NO: 269. In some embodiments, an isolated FN3 domain that binds CD71 comprises the amino acid sequence of SEQ ID NO: 270. In some embodiments, an isolated FN3 domain that binds CD71 comprises the amino acid sequence of SEQ ID NO: 271. In some embodiments, an isolated FN3 domain that binds CD71 comprises the amino acid sequence of SEQ ID NO: 272. In some embodiments, an isolated FN3 domain that binds CD71 comprises the amino acid sequence of SEQ ID NO: 304. In some embodiments, an isolated FN3 domain that binds CD71 comprises the amino acid sequence of SEQ ID NO: 305. In some embodiments, an isolated FN3 domain that binds CD71 comprises the amino acid sequence of SEQ ID NO: 306.

In some embodiments, the FN3 domain binds to human CD71 at site on CD71 that does not compete with transferrin binding to CD71. In some embodiments, the FN3 domain comprises a sequence of SEQ ID NO: 1-7, 10, 12-219, 221-272, 292-299, or 304-306.

In some embodiments, the isolated FN3 domain that binds CD71 comprises an initiator methionine (Met) linked to the N-terminus of the molecule.

Conjugates of the FN3 Domains That Bind CD71
of the Disclosure

In some embodiments, an isolated FN3 domain that binds CD71 conjugated to a heterologous molecule(s) is provided.

In some embodiments, the FN3 domain is conjugated to an oligonucleotide. For example, the oligonucleotide can be used for inhibiting the expression of a gene or mRNA transcript. The oligonucleotide can be a siRNA, miRNA, antisense oligonucleotide, and the like. Accordingly, in some embodiments, the FN3 domain can be conjugated to a polynucleotide, such as, but not limited to, a siRNA molecule, an antisense molecule, a RNA molecule, or a DNA molecule. In some embodiments, FN3 domain that binds CD71 is conjugated to an siRNA molecule using a linker as described herein. In some embodiments, the linker is a chemical linker.

In some embodiments, a composition comprising a polypeptide, such as a polypeptide comprising a FN3 domain, linked to a nucleic acid molecule are provided. The nucleic acid molecule can be, for example, a siRNA molecule.

Accordingly, in some embodiments, the siRNA is a double-stranded RNAi (dsRNA) agent capable of inhibiting the expression of a target gene. The dsRNA agent comprises a sense strand and an antisense strand. In some embodiments, each strand of the dsRNA agent can range from 12-40 nucleotides in length. For example, each strand can be from 14-40 nucleotides in length, 17-37 nucleotides in length, 25-37 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

In some embodiments, the sense strand and antisense strand typically form a duplex dsRNA. The duplex region of a dsRNA agent may be from 12-40 nucleotide pairs in length. For example, the duplex region can be from 14-40 nucleotide pairs in length, 17-30 nucleotide pairs in length, 25-35 nucleotides in length, 27-35 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotide pairs in length.

In some embodiments, the dsRNA comprises one or more overhang regions and/or capping groups of dsRNA agent at the 3'-end, or 5'-end or both ends of a strand. The overhang can be 1-10 nucleotides in length, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

In some embodiments, the nucleotides in the overhang region of the dsRNA agent can each independently be a modified or unmodified nucleotide including, but not limited to 2'-sugar modified, such as, 2-F 2'-Omethyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be other sequence.

The 5'- or 3'-overhangs at the sense strand, antisense strand or both strands of the dsRNA agent may be phosphorylated. In some embodiments, the overhang region contains two nucleotides having a phosphorothioate between the two nucleotides, where the two nucleotides can be the same or different. In one embodiment, the overhang is present at the 3'-end of the sense strand, antisense strand or both strands. In one embodiment, this 3'-overhang is present in the antisense strand. In one embodiment, this 3'-overhang is present in the sense strand.

The dsRNA agent may comprise only a single overhang, which can strengthen the interference activity of the dsRNA, without affecting its overall stability. For example, the single-stranded overhang is located at the 3'-terminal end of the sense strand or, alternatively, at the 3'-terminal end of the antisense strand. The dsRNA may also have a blunt end, located at the 5'-end of the antisense strand (or the 3'-end of the sense strand) or vice versa. Generally, the antisense strand of the dsRNA has a nucleotide overhang at the 3'-end, and the 5'-end is blunt. While not bound by theory, the asymmetric blunt end at the 5'-end of the antisense strand and 3'-end overhang of the antisense strand favor the guide strand loading into RISC process. For example the single overhang comprises at least two, three, four, five, six, seven, eight, nine, or ten nucleotides in length. In some embodiments, the dsRNA agent may also have two blunt ends, at both ends of the dsRNA duplex.

In some embodiments, every nucleotide in the sense strand and antisense strand of the dsRNA agent may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2 hydroxyl on the ribose sugar; wholesale replacement of the phosphate moiety with "dephospho" linkers; modification or replacement of a naturally occurring base; and replacement or modification of the ribose-phosphate backbone.

In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, HNA, CeNA, 2'-methoxyethyl, 2'-O-methyl, 2'-O-allyl, 2'-C-allyl, 2'-deoxy, or 2'-fluoro. The strands can contain more than one modification. In one embodiment, each residue of the sense strand and antisense strand is independently modified with 2'-O-methyl or 2'-fluoro.

In some embodiments, at least two different modifications are typically present on the sense strand and antisense strand. Those two modifications may be the 2'-deoxy, 2'-O-methyl or 2'-fluoro modifications, acyclic nucleotides or others.

In one embodiment, the sense strand and antisense strand each comprises two differently modified nucleotides selected from 2'-fluoro, 2'-O-methyl or 2'-deoxy.

The dsRNA agent may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand and/or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA agent comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. In some embodiments, these terminal three nucleotides may be at the 3'-end of the antisense strand.

In some embodiments, the dsRNA composition is linked by a modified base or nucleoside analogue as described in U.S. Pat. No. 7,427,672, which is incorporated herein by reference.

In some embodiments, the linker can be used to link the FN3 domain as described herein to the sense strand has a formula of I:

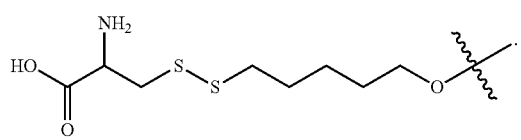 [SMILES: *OCCCCCSSCC(N)C(=O)O]

In some embodiments, the linker can be used to link the FN3 domain as described herein to the antisense strand has a formula of II:

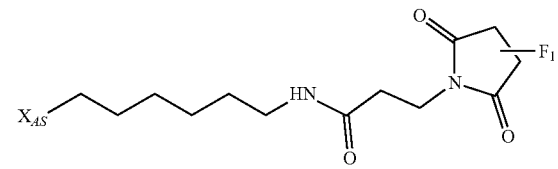

wherein $X_{AS}$ represents the antisense strand and $F_1$ represents a FN3 domain as described herein.

In some embodiments, the linker is covalently attached to F1 through a cysteine residue present on F1, which can be illustrated as follows:

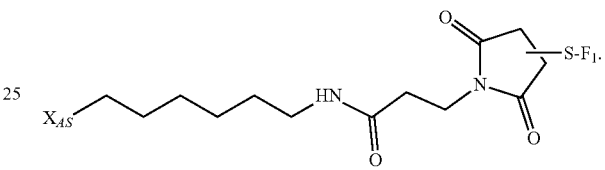

In some embodiments, the linked ds RNA and FN3 domain as described herein has a formula of III:

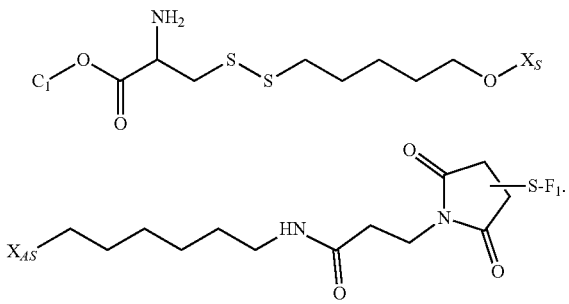

wherein C1 represents the same or different FN3 domain as described herein.

In some embodiments, A1-B 1 has a formula of:

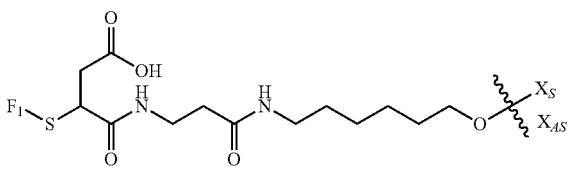

wherein $F_1$ is a polypeptide comprising at least one FN3 domain and is conjugated to $L_1$, $CL_1$ is linked to $X_s$, wherein $X_s$ is a 5' to 3' oligonucleotide sense strand of a double stranded siRNA molecule and $X_{AS}$ is a 3' to 5' oligonucleotide antisense strand of a double stranded siRNA molecule; and wherein $X_s$ and $X_{AS}$ form a double stranded siRNA molecule.

Structures of additional linkers are as follows:
mal-C$_2$H$_4$C(O)(NH)—(CH$_2$)$_6$— is

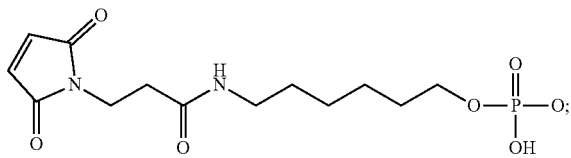

(Mal-(PEG)$_{12}$)(NH)CH$_2$)$_6$) is

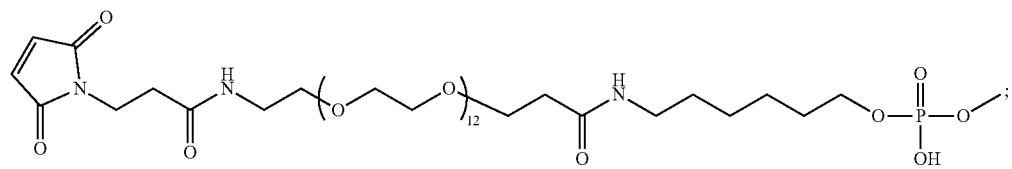

Mal-NH—(CH$_2$)$_{6-}$, which can also be referred to as aminohexyl linker—(CH$_2$)$_{6-}$, is

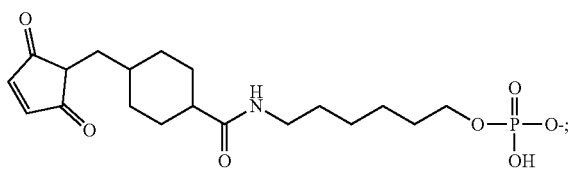

and
Val-Cit Paba, which has the structure:

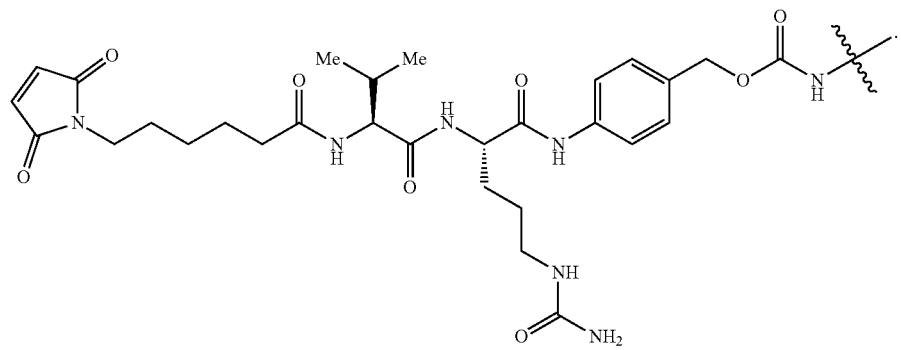 [SMILES: *NC(=O)OCc1ccc(NC(=O)[C@H](CCCNC(N)=O)NC(=O)[C@@H](NC(=O)CCCCCN2C(=O)C=CC2=O)C(C)C)cc1]

As described herein, in some embodiments, the nucleic acid molecules can be modified to include a linker at the 5' end of the of the sense strand of the dsRNA. In some embodiments, the nucleic acid molecules can be modified to include a vinyl phosphonate at the 5' end of the of the anti-sense strand of the dsRNA. In some embodiments, the nucleic acid molecules can be modified to include a linker at the 3' end of the of the sense strand of the dsRNA. In some embodiments, the nucleic acid molecules can be modified to include a vinyl phosphonate at the 3' end of the of the anti-sense strand of the dsRNA. The linker can be used to link the dsRNA to the FN3 domain. The linker can covalently attach, for example, to a cysteine residue on the FN3 domain that is there naturally or that has been substituted as described herein, and for example, in U.S. Pat. No. 10,196,446, which is hereby incorporated by reference in its entirety.

In some embodiments, the peptide is conjugated to a lipid nanoparticle, which can be used, for example, for cell-specific targeting.

In some embodiments, the protein is conjugated to a binding moiety that targets CD71 or another protein for protein degradation. For example, the protein can be conjugated to a PROTACS (binding moieties for an E3 ubiquitin ligase) and thus deliver the protein to the E3 ligase. These can linked through a linker, such as a glycine-serine linker and the like.

The FN3 domain that binds to CD71 can also be conjugated or linked to another FN3 domain that binds to a different target, other than CD71. This would enable the peptide to be multi-specific (e.g. bi-specific, tri-specific, etc.), such that it binds to CD71 and another, for example, protein. In some embodiments, the CD71 FN3 binding domain is linked to another FN3 domain that binds to an antigen expressed by a tumor cell (tumor antigen).

In some embodiments, FN3 domains can be linked together by a linker to form a bivalent FN3 domain. The linker can be a flexible linker. In some embodiments, the linker is a G/S linker. In some embodiments the linker has 1, 2, 3, or 4 G/S repeats. A G/S repeat unit is four glycines followed by a serine, e.g. GGGGS (SEQ ID NO: 308). In some embodiments, the FN3 domain comprising two FN3 domains connected by a linker, such as those provided for herein. Exemplary linker include, but are not limited to, (GS)2, (SEQ ID NO: 278), (GGGS)2 (SEQ ID NO: 279), (GGGGS)1-5 (SEQ ID NO: 280), (AP)1-20 (SEQ ID NO: 311); (AP)2 (SEQ ID NO: 281), (AP)5 (SEQ ID NO: 282), (AP)10 (SEQ ID NO: 283), (AP)20 (SEQ ID NO: 284), A(EAAAK)SAAA (SEQ ID NO: 285), or (EAAAK)1-5 (SEQ ID NO: 307). In some embodiments, the linker comprises or is an amino acid sequence of:

EAAAKEAAAKEAAAKEAAAK (SEQ ID NO: 300); GGGGSGGGGSGGGGSGGGGS (SEQ ID NO: 301); APAPAPAP (SEQ ID NO: 302); or EAAAK (SEQ ID NO: 303).

In some embodiments, the heterologous molecule is a detectable label or a therapeutic agent, such as, but not limited to a cytotoxic agent.

In some embodiments, an FN3 domain that binds CD71 conjugated to a detectable label is provided. Non-limiting examples of detectable labels are provided for herein.

In some embodiments, an FN3 domain that binds CD71 conjugated to a therapeutic agent is provided. Non-limiting examples of therapeutic agents, such as, but not limited to, cytotoxic agents, are provided for herein.

The FN3 domains that bind CD71 conjugated to a detectable label can be used to evaluate expression of CD71 on samples such as tumor tissue in vivo or in vitro. The FN3 domains that bind CD71 conjugated to a detectable label can be used to evaluate expression of CD71 on samples blood, immune cells, or dendritic cells in vivo or in vitro.

Detectable labels include compositions that when conjugated to the FN3 domains that bind CD71 renders CD71 detectable, via spectroscopic, photochemical, biochemical, immunochemical, or other chemical methods.

Exemplary detectable labels include, but are not limited to, radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, cintillants, avidin, streptavidin, protein A, protein G, antibodies or fragments thereof, polyhistidine, Ni2+, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In some embodiments, the detectable label emits a signal as a result of being stimulated by an external stimulus, such as a magnetic or electric, or electromagnetic field.

Exemplary radioactive isotopes may be γ-emitting, Auger-emitting, (β-emitting, an alpha-emitting or positron-emitting radioactive isotope. Exemplary radioactive isotopes include 3H, 11C, 13C, 15N, 18F, 19F, 55Co, 57Co, 60Co, 61Cu, 62Cu, 64Cu, 67Cu, 68Ga, 72As, 75Br, 86Y, 89Zr, 90Sr, 94mTc, 99mTc, 115In, 123I, 124I, 125I, 131I, 211At, 212Bi, 213Bi, 223Ra, 226Ra, 225Ac and 227Ac.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e., iodine) to 83 (i.e., bismuth).

In some embodiments, the metal atoms may be atoms suitable for magnetic resonance imaging.

The metal atoms may be metal ions in the form of +1, +2, or +3 oxidation states, such as Ba2+, Bi3+, Cs+, Ca2+, Cr2+, Cr3+, Cr6+, Co2+, Co3+, Cu+, Cu2+, Cu3+, Ga3+, Gd3+, Au+, Au3+, Fe2+, Fe3+, F3+, Pb2+, Mn2+, Mn3+, Mn4+, Mn7+, Hg2+, Ni2+, Ni3+, Ag+, Sr2+, Sn2+, Sn4+, and Zn2+. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The FN3 domains that specifically bind CD71 conjugated to a detectable label may be used, for example, as an imaging agent to evaluate tumor distribution, diagnosis for the presence of tumor cells and/or, recurrence of tumor. The FN3 domains that specifically bind CD71 conjugated to a detectable label may be used, for example, as an imaging agent to evaluate the presence of CD71 positive cells in a variety of tissues in the body, including but not limited to dendritic cells, T-cells, NK cells, B-cells immune cells, muscle cells, and cells of the central nervous system.

In some embodiments, the FN3 domains that specifically bind CD71 are conjugated to a therapeutic agent, such as, but not limited to, a cytotoxic agent.

In some embodiments, the therapeutic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The FN3 domains that bind CD71 conjugated to a therapeutic agent disclosed herein may be used in the targeted delivery of the therapeutic agent to CD71 expressing cells (e.g. tumor cells, dendritic cells, T-cells, NK cells, B-cells immune cells, cells of the central nervous system), and intracellular accumulation therein. Although not bound to any particular theory, this type of delivery can be helpful where systemic administration of these unconjugated agents may result in unacceptable levels of toxicity to normal cells.

In some embodiments, the therapeutic agent can elicit their cytotoxic and/or cytostatic effects by mechanisms such as, but not limited to, tubulin binding, DNA binding, topoisomerase inhibition, DNA cross linking, chelation, spliceosome inhibition, NAMPT inhibition, and HDAC inhibition.

In some embodiments, the therapeutic agent is a spliceosome inhibitor, a NAMPT inhibitor, or a HDAC inhibitor. In some embodiments, the agent is an immune system agonist, for example, TLR7,8,9, RIG-I (dsRNA), and STING (CpG) agonists. In some embodiments, the agent is daunomycin, doxorubicin, methotrexate, vindesine, bacterial toxins such as diphtheria toxin, ricin, geldanamycin, maytansinoids or calicheamicin.

In some embodiments, the therapeutic agent is an enzymatically active toxin such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, or the tricothecenes.

In some embodiments, the therapeutic agent is a radionuclide, such as 212Bi, 131I, 131In, 90Y, or 186Re.

In some embodiments, the therapeutic agent is dolastatin or dolostatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancer and antifungal activity. The dolastatin or auristatin drug moiety may be attached to the FN3 domain through the N (amino) terminus or the C (carboxyl) terminus of the peptidic drug moiety (WO 02/088172), or via any cysteine engineered into the FN3 domain.

In some embodiments, therapeutic agent can be, for example, auristatins, camptothecins, duocarmycins, etoposides, maytansines and maytansinoids, taxanes, benzodiazepines or benzodiazepine containing drugs (e.g., pyrrolo[1, 41-benzodiazepines (PBDs), indolinobenzodiazepines, and oxazolidinobenzodiazepines) or vinca alkaloids.

The FN3 domains that specifically bind CD71 may be conjugated to a detectable label using known methods.

In some embodiments, the detectable label is complexed with a chelating agent.

In some embodiments, the detectable label is conjugated to the FN3 domain that binds CD71 via a linker as described above.

The detectable label, therapeutic compound, or the cytotoxic compound may be linked directly, or indirectly, to the FN3 domain that binds CD71 using known methods. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HC1), active esters (such as disuccinimidyl suberate), aldehydes (such as glutaraldehyde), bis-azido compounds (such as bis(p-azidobenzoyl)hexanediamine), bis-diazonium derivatives (such as bis(p-diazoniumbenzoyl)ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

In some embodiment, the FN3 domain that binds CD71 is removed from the blood via renal clearance.

Isolation of CD71 Binding FN3 Domains from a Library Based on Tencon Sequence

Tencon (SEQ ID NO: 276) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, may be randomized in order to construct libraries of fibronectin type III (FN3) domains that may be used to select novel molecules that bind CD71. Table 1 shows positions and sequences of each loop and beta-strand in Tencon (SEQ ID NO: 276).

TABLE 1

| Tencon topology | |
|---|---|
| FN3 domain | Tencon (SEQ ID NO: 276) |
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is described in U.S. Pat. Publ. No. 2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 276), and which variants display improve thermal stability. Exemplary Tencon variants are described in US Pat. Publ. No. 2011/0274623, and include Tencon27 (SEQ ID NO: 277) having substitutions E11R, L17A, N46V and E86I when compared to Tencon of SEQ ID NO: 276.

Tencon and other FN3 sequence based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http:_// www_sloning_com). This technology uses a library of premade double stranded triplets that act as universal building blocks sufficient for thousands of gene synthesis processes. The triplet library represents all possible sequence combinations necessary to build any desired DNA molecule. The codon designations are according to the well-known IUB code.

The FN3 domains that specifically bind CD71 may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., Proc Natl Acad Sci U.S.A 101, 2806-2810, 2004), and assaying the library for specific binding to PSMA by any method known in the art and described in the Example. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains that specifically bind CD71 are further characterized for their binding to CD71, modulation of CD71 activity, internalization, stability, and other desired characteristics.

The FN3 domains that specifically bind CD71 may be generated using any FN3 domain as a template to generate a library and screening the library for molecules specifically binding CD71 using methods provided within. Exemplar FN3 domains that may be used are the 3rd FN3 domain of tenascin C (TN3), Fibcon, and the 10$^{th}$ FN3 domain of fibronectin (FN10). Accordingly, PCT applications WO 2010/051274, WO 2011/137319, and WO 2013/049275 are incorporated herein in their entirety. Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak, Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. W02009/085462; U.S. Pat. Nos. 6,969,108; 6,172,197; 5,223,409; 6,582,915; 6,472,147).

In some embodiments. the FN3 domain that binds CD71 is based on Tencon sequence of SEQ ID NO: 276 or Tencon27 sequence of SEQ ID NO: 277, the SEQ ID NO: 276 or the SEQ ID NO: 277, optionally having substitutions at residues positions 11, 14, 17, 37, 46, 73, and/or 86.

In some embodiments, the FN3 protein or polypeptide is one that binds to human CD71 at a site on CD71 that does not compete with transferrin binding to CD71. As used herein, a site on CD71 that does not compete with transferrin binding to CD71 refers to an epitope or part of CD71 where the binding of the FN3 protein does not compete or inhibit the binding of transferrin to CD71. The competition, or lack thereof, can be complete or partial. In some embodiments, the binding also does not inhibit the internalization of transferrin into the cell through its interaction with CD71.

In some embodiments, methods for identifying a FN3 protein that binds to CD71 at a site that does not compete or inhibit transferrin binding to CD71 are provided. In some embodiments, the methods comprise contacting CD71 in the presence of transferrin or an agent that binds to the CD71 transferrin binding site with a test FN3 protein; and identifying a test FN3 protein that binds to CD71 in the presence of transferrin or an agent that binds to the CD71 transferrin binding site. In some embodiments, the method comprises isolating the test FN3 protein that binds to CD71 in the presence of transferrin or an agent that binds to the CD71 transferrin binding site. In some embodiments, the methods comprise sequencing the test FN3 protein that binds to CD71 in the presence of transferrin or an agent that binds to the CD71 transferrin binding site. In some embodiments, the methods comprise preparing or obtaining a nucleic acid sequence encoding the test FN3 protein that binds to CD71 in the presence of transferrin or an agent that binds to the CD71 transferrin binding site. In some embodiments, the methods comprise expressing the test FN3 protein that binds to CD71 in the presence of transferrin or an agent that binds to the CD71 transferrin binding site from a nucleic acid sequence encoding the test FN3 protein that binds to CD71 in the presence of transferrin or an agent that binds to the CD71 transferrin binding site. In some embodiments, the test FN3 protein is expressed in a cell. In some embodiments, the methods comprise isolating and/or purifying the expressed test FN3 protein.

In some embodiments a FN3 protein is provided, wherein the FN3 protein is identified according to any method provided herein.

The FN3 domains that specifically bind CD71 may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr. Opin. Biotechnol., 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO: 276) are residue positions 11, 14, 17, 37, 46, 73, or 86, and are described in US Pat. Publ. No. 2011/0274623. Substitutions corresponding to these residues may be incorporated to the FN3 domain containing molecules disclosed herein.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("$T_m$") temperature, the temperature in ° Celsius (° C.) at which half of the molecules become unfolded, using standard methods. Typically, the higher the $T_m$, the more stable the molecule. In addition to heat, the chemical environment also changes the ability of the protein to maintain a particular three dimensional structure.

In some embodiments, the FN3 domain that binds CD71 may exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the Tm.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HC1), acetic acid ($CH_3COOH$), halogenated acetic acids), hydrophobic molecules (e.g. phospholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FN3 domain that binds CD71 may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include, but are not limited to GS)2, (SEQ ID NO: 278), (GGGS)2 (SEQ ID NO: 279), (GGGGS)1-5 (SEQ ID NO: 280), (AP)1-20 (SEQ ID NO: 311); (AP)2 (SEQ ID NO: 281), (AP)5 (SEQ ID NO: 282), (AP)10 (SEQ ID NO: 283), (AP)20 (SEQ ID NO: 284), A(EAAAK)SAAA (SEQ ID NO: 285), or (EAAAK) 1-5 (SEQ ID NO: 307). In some embodiments, the linker is an amino acid sequence of: EAAAKEAAAKEAAAKEAAAK (SEQ ID NO: 300); GGGGSGGGGSGGGGSGGGGS (SEQ ID NO: 301); APAPAPAPAP(SEQ ID NO: 302); or EAAAK (SEQ ID NO: 303).

The dimers and multimers may be linked to each other in a N-to C-direction. The use of naturally occurring as well as artificial peptide linkers to connect polypeptides into novel linked fusion polypeptides is well known in the literature (Hallewell et al., J Biol Chem 264, 5260-5268, 1989; Alfthan et al., Protein Eng. 8, 725-731, 1995; Robinson & Sauer, Biochemistry 35, 109-116, 1996; U.S. Pat. No. 5,856, 456).

Half-Life Extending Moieties

The FN3 domains that specifically bind CD71 may incorporate other subunits for example via covalent interaction. In some embodiments, the FN3 domains that specifically bind CD71 further comprise a half-life extending moiety. Exemplary half-life extending moieties are albumin, albumin variants, albumin-binding proteins and/or domains, transferrin and fragments and analogues thereof, and Fc regions Amino acid sequences of the human Fc regions are well known, and include IgG1, IgG2, IgG3, IgG4, IgM, IgA and IgE Fc regions. In some embodiments, the FN3 domains that specifically bind CD71 may incorporate a second FN3 domain that binds to a molecule that extends the half-life of the entire molecule, such as, but not limited to, any of the half-life extending moieties described herein. In some embodiments, the second FN3 domain binds to albumin, albumin variants, albumin-binding proteins and/or domains, and fragments and analogues thereof.

All or a portion of an antibody constant region may be attached to the FN3 domain that binds CD71 to impart antibody-like properties, especially those properties associated with the Fc region, such as Fc effector functions such as C1q binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and may be further modified by modifying residues in the Fc responsible for these activities (for review; see Strohl, Curr Opin Biotechnol. 20, 685-691, 2009).

Additional moieties may be incorporated into the FN3 domains that specifically bind CD71 such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules disclosed herein.

A pegyl moiety may for example be added to the FN3 domain that binds CD71 by incorporating a cysteine residue to the C-terminus of the molecule, or engineering cysteines into residue positions that face away from the CD71 binding face of the molecule, and attaching a pegyl group to the cysteine using well known methods.

FN3 domains that specifically bind CD71 incorporating additional moieties may be compared for functionality by several well-known assays. For example, altered properties due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating pharmacokinetic properties of the molecules disclosed herein in in vivo models.

Polynucleotides, Vectors, Host Cells

In some embodiments, nucleic acids encoding the FN3 domains specifically binding CD71 as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof are provided. Certain exemplary polynucleotides are disclosed herein, however, other polynucleotides which, given the degeneracy of the genetic code or codon preferences in a given expression system, encode the FN3 domains disclosed herein are also within the scope of the disclosure.

In some embodiments, an isolated polynucleotide encodes the FN3 domain specifically binding CD71 comprising the amino acid sequence of SEQ ID Nos: 1-7, 10, 12-219, 221-272, 292-299, or 304-306.

The polynucleotides disclosed herein may be produced by chemical synthesis such as solid phase polynucleotide synthesis on an automated polynucleotide synthesizer and assembled into complete single or double stranded molecules. Alternatively, the polynucleotides disclosed herein may be produced by other techniques such as PCR followed by routine cloning. Techniques for producing or obtaining polynucleotides of a given known sequence are well known in the art.

The polynucleotides disclosed herein may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

In some embodiments, a vector comprising at least one polynucleotide disclosed herein is provided. Such vectors may be plasmid vectors, viral vectors, vectors for baculovirus expression, transposon based vectors or any other vector suitable for introduction of the polynucleotides disclosed herein into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

In some embodiments, a host cell comprising the vector is provided. The FN3 domain that specifically bind CD71 may be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, 2$^{nd}$ Edition, Cold Spring Harbor, NY (1989); Harlow and Lane, Antibodies, a Laboratory Manual, Cold Spring Harbor, NY (1989); Colligan, et al., eds., Current Protocols in Immunology, John Wiley & Sons, Inc., N.Y. (1994-2001); Colligan et al., Current Protocols in Protein Science, John Wiley & Sons, NY, NY, (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

In some embodiments, a method of producing the isolated FN3 domain that binds CD71, comprising culturing the isolated host cell under conditions such that the isolated FN3 domain that binds CD71 is expressed, and purifying the FN3 domain.

The FN3 domains that bind CD71 may be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography, or high performance liquid chromatography (HPLC).

In some embodiments, the FN3 domain specifically binding CD71 comprises the amino acid sequence of SEQ ID Nos: 1-7, 10, 12-219, 221-272, 292-299, or 304-306, wherein a histidine tag has been appended to the N-terminal or C-terminal end of the polypeptide for ease of purification. In some embodiments, the histidine tag (His-tag) comprises six histidine residues (SEQ ID NO: 309). In further embodiments, the His-tag to connected to the FN3 domain by at least one glycine residue or about 2 to about 4 glycine residues. Accordingly, after purification of the FN3 domain and cleavage of the His-tag from the polypeptide one or more glycine may be left on the N-terminus or C-terminus. In some embodiments, if the His-tag is removed from the N-terminus all of the glycines are removed. In some embodiments, if the His-tag is removed from the C-terminus one or more of the glycines are retained.

In some embodiments, the FN3 domain specifically binding CD71 comprises the amino acid sequence of SEQ ID Nos: 1-7, 10, 12-219, 221-272, 292-299, or 304-306, wherein the N-terminal methionine is retained after purification of the FN3 domain.

Kits

In some embodiments, a kit comprising the FN3 domain that binds CD71 is provided.

The kit may be used for therapeutic uses and as a diagnostic kit.

In some embodiments, the kit comprises the FN3 domain that binds CD71 and reagents for detecting the FN3 domain. In some embodiments, the kit comprises a bivalent FN3 domain. The kit can include one or more other elements including: instructions for use; other reagents, e.g., a label, an agent useful for chelating, or otherwise coupling, a radioprotective composition; devices or other materials for preparing the FN3 domain that binds CD71 for administration for imaging, diagnostic or therapeutic purpose; pharmaceutically acceptable carriers; and devices or other materials for administration to a subject.

In some embodiments, the kit comprises the FN3 domain that binds CD71 comprising the amino acid sequences of one of SEQ ID Nos: 1-7, 10, 12-219, 221-272, 292-299, or 304-306.

Uses of CD71 Binding FN3 Domains

The FN3 domains that specifically bind CD71 or conjugates thereof may be used to diagnose, monitor, modulate, treat, alleviate, help prevent the incidence of, or reduce the symptoms of human disease or specific pathologies in cells, tissues, organs, fluid, or, generally, a host.

In some embodiments, the FN3 domain can facilitate delivery into CD71 positive tissues (eg. Skeletal muscle, smooth muscle) for treatment of muscle diseases.

In some embodiments, the FN3 domain can facilitate delivery to activated lymphocytes, dendritic cells, T-cells, NK cells and B-cells, or other immune cells for treatment of immunological diseases.

In some embodiments, the FN3 domains that specifically bind CD71 or conjugates thereof may also be used in imaging CD71 positive tumor tissue in a subject. The methods disclosed herein may be used with an animal patient belonging to any classification. Examples of such animals include mammals such as humans, rodents, dogs, cats and farm animals.

In some embodiments, a method of diagnosing a subject having, or who is likely to develop cancer of a tissue based on the expression of CD71 by cells of the cancer tissue, methods of predicting success of immunotherapy, methods of prognosis, and methods of treatment are provided.

In some embodiments, a method of detecting CD71-expressing cancer cells in a tumor tissue is provided, the method comprising: obtaining a sample of the tumor tissue from a subject; detecting whether CD71 is expressed in the tumor tissue by contacting toe sample of the tumor tissue with the FN3 domain that binds CD71 comprising the amino acid sequence of one of SEQ ID Nos: 1-7, 10, 12-219, 221-272, 292-299, or 304-306, and detecting the binding between CD71 and the FN3 domain. In some embodiments, methods of treating cancer in a subject in need thereof are provided. In some embodiments, the method comprises administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent.

In some embodiments, the CD71 cell is a cell involved in a CNS diseases, inflammatory/immune diseases, such as MS & infectious diseases of the brain. In some embodiments, the polypeptide that binds to CD71 is directed to the central nervous system. In some embodiments, methods of treating a neurological condition and/or a brain tumor in a subject in need thereof are provided. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent. In some embodiments, the brain tumor is selected from the group consisting of nonmalignant, benign, and malignant brain tumors. In some embodiments, the neurological condition is selected from the group consisting of Alzheimer's Disease, Amyotrophic Lateral Sclerosis, Parkinson's Disease, Lafora Disease, Pompe Disease, adult polyglucosan body disease, stroke, spinal cord injury, ataxia, Bell's Palsy, cerebral aneurysm, epilepsy, seizures, Guillain-Barre Syndrome, multiple sclerosis, muscular dystrophy, neurocutaneous syndromes, migraine, encephalitis, septicemia, and myasthenia gravis.

In some embodiments, the polypeptide that binds to CD71 is directed to muscle cells. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent.

In some embodiments, methods of treating Pompe disease (GSD2, acid alpha-glucosidase (GAA) deficiency) in a subject in need thereof are provided. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent.

In some embodiments, methods of treating glycogen storage disease in a subject in need thereof, the method comprising administering a composition provided herein are provided. In some embodiments, the glycogen storage disease is selected from the group consisting of Cori's disease or Forbes' disease (GSD3, Glycogen debranching enzyme (AGL) deficiency), McArdle disease (GSD5, Muscle glycogen phosphorylase (PYGM) deficiency), type II Diabetes/diabetic nephropathy, Aldolase A Deficiency GSD12, Lafora Disease, hypoxia, Andersen disease (GSD4, Glycogen debranching enzyme (GBE1) deficiency), Tarui's Disease (GSD7, Muscle phosphofructokinase (PFKM) deficiency), and adult polyglucosan body disease. In some embodiments, the glycogen storage disease is selected from the group consisting of Glycogen synthase (GYS2) deficiency (GSD0), Glucose-6-phosphatase (G6PC/SLC37A4) deficiency (GSD1, von Gierke's disease), Hers' disease (GSD6, Liver glycogen phosphorylase (PYGL) or Muscle phosphoglycerate mutase (PGAM2) deficiency), Phosphorylase kinase (PHKA2/PHKB/PHKG2/PHKA1) deficiency (GSD9), Phosphoglycerate mutase (PGAM2) deficiency (GSD10), Muscle lactate dehydrogenase (LDHA) deficiency (GSD11), Fanconi-Bickel syndrome (GSD 11, Glucose transporter (GLUT2) deficiency, Aldolase A deficiency (GSD 12), β-enolase (ENO3) deficiency (GSD13), and Glycogenin-1 (GYG1) deficiency (GSD15).

In some embodiments, the polypeptide that binds to CD71 is directed to immune cells. In some embodiments, the polypeptide that binds to CD71 is directed to dendritic cells, T-cells, NK cells, or B-cells. In some embodiments, methods of treating an autoimmune disease in a subject in need thereof are provided. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent. In some embodiments, the autoimmune disease is selected from the group consisting of rheumatoid arthritis, Hashimoto's autoimmune thyroiditis, celiac disease, diabetes mellitus type 1, vitiligo, rheumatic fever, pernicious anemia/ atrophic gastritis, alopecia areata, and immune thrombocytopenic purpura.

In some embodiments, the tissue can be tissue of any organ or anatomical system, that expresses CD71.

In some embodiments, CD71 expression may be evaluated using known methods, such as immunohistochemistry or ELISA.

In some embodiments, a method of isolating CD71 expressing cells is provided, the method comprising: obtaining a sample from a subject; contacting the sample with the FN3 domain that binds CD71 comprising the amino acid sequence of one of SEQ ID Nos: 1-7, 10, 12-219, 221-272, 292-299, or 304-306, and isolating the cells bound to the FN3 domains.

In some embodiments, a method of detecting CD71-expressing cancer cells in a tumor tissue is provided, the method comprising: conjugating the FN3 domain that binds CD71 comprising the amino acid sequence of one of SEQ ID Nos: 1-7, 10, 12-219, 221-272, 292-299, or 304-306 to a detectable label to form a conjugate; administering the conjugate to a subject; and visualizing the CD71 expressing cancer cells to which the conjugate is bound.

In some embodiments, methods of treating cancer in a subject in need thereof are provided. In some embodiments, the method comprises administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent. In some embodiments, a method of treating a subject having cancer is provided, the method comprising administering to the subject a FN3 domain that binds CD71. In some embodiments, the FN3 domain is conjugated to a therapeutic agent (e.g. cytotoxic agent, an oligonucleotide, such as a siRNA, antisense, and the like, a FN3 domain that binds to another target, and the like).

In some embodiments, the subject has a solid tumor.

In some embodiments, the solid tumor is a melanoma.

In some embodiments, the solid tumor is a lung cancer. In some embodiments, the solid tumor is a non-small cell lung cancer (NSCLC). In some embodiments, the solid tumor is a squamous non-small cell lung cancer (NSCLC). In some embodiments, the solid tumor is a non-squamous NSCLC. In some embodiments, the solid tumor is a lung adenocarcinoma.

In some embodiments, the solid tumor is a renal cell carcinoma (RCC).

In some embodiments, the solid tumor is a mesothelioma.

In some embodiments, the solid tumor is a nasopharyngeal carcinoma (NPC).

In some embodiments, the solid tumor is a colorectal cancer.

In some embodiments, the solid tumor is a prostate cancer. In some embodiments, the solid tumor is castration-resistant prostate cancer.

In some embodiments, the solid tumor is a stomach cancer.

In some embodiments, the solid tumor is an ovarian cancer.

In some embodiments, the solid tumor is a gastric cancer.

In some embodiments, the solid tumor is a liver cancer.

In some embodiments, the solid tumor is pancreatic cancer.

In some embodiments, the solid tumor is a thyroid cancer.

In some embodiments, the solid tumor is a squamous cell carcinoma of the head and neck.

In some embodiments, the solid tumor is a carcinomas of the esophagus or gastrointestinal tract.

In some embodiments, the solid tumor is a breast cancer.

In some embodiments, the solid tumor is a fallopian tube cancer.

In some embodiments, the solid tumor is a brain cancer.

In some embodiments, the solid tumor is an urethral cancer.

In some embodiments, the solid tumor is a genitourinary cancer.

In some embodiments, the solid tumor is an endometriosis.

In some embodiments, the solid tumor is a cervical cancer.

In some embodiments, the solid tumor is a metastatic lesion of the cancer.

In some embodiments, the subject has a hematological malignancy. In some embodiments, the hematological malignancy is a lymphoma, a myeloma or a leukemia. In some embodiments, the hematological malignancy is a B cell lymphoma. In some embodiments, the hematological malignancy is Burkitt's lymphoma. In some embodiments, the hematological malignancy is Hodgkin's lymphoma. In some embodiments, the hematological malignancy is a non-Hodgkin's lymphoma.

In some embodiments, the hematological malignancy is a myelodysplastic syndrome.

In some embodiments, the hematological malignancy is an acute myeloid leukemia (AML). In some embodiments, the hematological malignancy is a chronic myeloid leukemia (CML). In some embodiments, the hematological malignancy is a chronic myelomoncytic leukemia (CMML).

In some embodiments, the hematological malignancy is a multiple myeloma (MM).

In some embodiments, the hematological malignancy is a plasmacytoma.

In some embodiments, the compositions or pharmaceutical compositions provided herein may be administered alone or in combination with other therapeutics, that is, simultaneously or sequentially. In some embodiments, the other or additional therapeutics are other anti-tumor agent or therapeutics. Different tumor types and stages of tumors can require the use of various auxiliary compounds useful for treatment of cancer. For example, the compositions provided herein can be used in combination with various chemotherapeutics such as taxol, tyrosine kinase inhibitors, leucovorin, fluorouracil, irinotecan, phosphatase inhibitors, MEK inhibitors, among others. The composition may also be used in combination with drugs which modulate the immune response to the tumor such as anti-PD-1 or anti-CTLA-4, among others. Additional treatments can be agents that modulate the immune system, such antibodies that target PD-1 or PD-L1.

In some embodiments, the polypeptide that binds to CD71 is directed to the central nervous system. In some embodiments, methods of treating a neurological condition and/or a brain tumor in a subject in need thereof are provided. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent. In some embodiments, the brain tumor is selected from the group consisting of non-malignant, benign, and malignant brain tumors. In some embodiments, the neurological condition is selected from the group consisting of Alzheimer's Disease, Amyotrophic Lateral Sclerosis, Parkinson's Disease, Lafora Disease, Pompe Disease, adult polyglucosan body disease, stroke, spinal cord injury, ataxia, Bell's Palsy, cerebral aneurysm, epilepsy, seizures, Guillain-Barre Syndrome, multiple sclerosis, muscular dystrophy, neurocutaneous syndromes, migraine, encephalitis, septicemia, and myasthenia gravis. In some embodiments, a method of treating a neurological condition and/or a brain tumor in a subject, the method comprising administering to the subject a FN3 domain that binds CD71 and the FN3 domain is conjugated to a therapeutic agent (e.g. cytotoxic agent, an oligonucleotide, such as a siRNA, antisense, and the like, a FN3 domain that binds to another target, and the like).

In some embodiments, methods of treating Pompe disease (GSD2, acid alpha-glucosidase (GAA) deficiency) in a subject in need thereof are provided. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent. In some embodiments, a method of treating a Pompe disease (GSD2, acid alpha-glucosidase (GAA) deficiency) in a subject, the method comprising administering to the subject a FN3 domain that binds CD71 and the FN3 domain is conjugated to a therapeutic agent (e.g. cytotoxic agent, an oligonucleotide, such as a siRNA, antisense, and the like, a FN3 domain that binds to another target, and the like).

In some embodiments, the polypeptide that binds to CD71 is directed to immune cells. In some embodiments, the polypeptide that binds to CD71 is directed to dendritic cells. In some embodiments, methods of treating an autoimmune disease in a subject in need thereof are provided. In some embodiments, the methods comprise administering to the subject a polypeptide or the pharmaceutical composition that binds to CD71. In some embodiments, that the polypeptide is a FN3 domain that binds to CD71. In some embodiments, the polypeptide comprises a sequence such as SEQ ID Nos: 1-7, 10, 12-219, 221-272, 292-299, or 304-306, or a polypeptide as provided herein that is linked to or conjugated to a therapeutic agent. In some embodiments, the autoimmune disease is selected from the group consisting of rheumatoid arthritis, Hashimoto's autoimmune thyroiditis, celiac disease, diabetes mellitus type 1, vitiligo, rheumatic fever, pernicious anemia/atrophic gastritis, alopecia areata, and immune thrombocytopenic purpura. In some embodiments, a method of treating an autoimmune disease in a subject, the method comprising administering to the subject a FN3 domain that binds CD71 and the FN3 domain is conjugated to a therapeutic agent (e.g. cytotoxic agent, an oligonucleotide, such as a siRNA, antisense, and the like, a FN3 domain that binds to another target, and the like).

In some embodiments, the FN3 domains that specifically bind CD71 or conjugates thereof that may be used to diagnose, monitor, modulate, treat, alleviate, help prevent the incidence of, or reduce the symptoms of human disease or specific pathologies in cells, tissues, organs, fluid, or, generally, a host, also exhibit the property of being able to cross the blood brain barrier. The blood-brain barrier (BBB) prevents most macromolecules (e.g., DNA, RNA, and polypeptides) and many small molecules from entering the brain. The BBB is principally composed of specialized endothelial cells with highly restrictive tight junctions, consequently, passage of substances, small and large, from the blood into the central nervous system is controlled by the BBB. This structure makes treatment and management of patients with neurological diseases and disorders (e.g., brain cancer) difficult as many therapeutic agents cannot be delivered across the BBB with desirable efficiency. Additional conditions that involve disruptions of the BBB include: stroke, diabetes, seizures, hypertensive encephalopathy, acquired immunodeficiency syndrome, traumatic brain injuries, multiple sclerosis, Parkinson's disease (PD) and Alzheimer disease. This ability is especially useful for treating brain cancers including for example: astrocytoma, medulloblastoma, glioma, ependymoma, germinoma (pinealoma), glioblastoma multiform, oligodendroglioma, schwannoma, retinoblastoma, and congenital tumors; or a cancer of the spinal cord, e.g., neurofibroma, meningioma, glioma, and sarcoma. In certain embodiments, the FN3 domains that specifically bind CD71 comprising the amino acid sequence of one of SEQ ID Nos: 1-7, 10, 12-219, 221-272, 292-299, or 304-306 or conjugates thereof, are useful to deliver a therapeutic or cytotoxic agent, for example, across the blood brain barrier.

In some embodiments, the polypeptide that can facilitates the transport of a therapeutic across the BBB is a protein comprising a sequence of SEQ ID NO: 1-7, 10, 12-219, 221-272, 292-299, or 304-306.

"Treat" or "treatment" refers to the therapeutic treatment and prophylactic measures, wherein the object is to prevent or slow down (lessen) an undesired physiological change or disorder, such as the development or spread of cancer. In some embodiments, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "therapeutically effective amount" refers to an amount effective, at dosages and for periods of time necessary, to achieve a desired therapeutic result. A therapeutically effective amount of the FN3 domains that specifically bind CD71 may vary according to factors such as the disease state, age, sex, and weight of the individual. Exemplary indicators of an effective FN3 domain that binds CD71 is improved well-being of the patient, decrease or shrinkage of the size of a tumor, arrested or slowed growth of a tumor, and/or absence of metastasis of cancer cells to other locations in the body.

Administration/Pharmaceutical Compositions

In some embodiments, pharmaceutical compositions of the FN3 domains that specifically bind CD71, optionally conjugated to a detectable label, therapeutic, or a cytotoxic agent disclosed herein and a pharmaceutically acceptable carrier, are provided. For therapeutic use, the FN3 domains that specifically bind CD71 may be prepared as pharmaceutical compositions containing an effective amount of the domain or molecule as an active ingredient in a pharmaceutically acceptable carrier. "Carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules disclosed herein in such pharmaceutical formulation can vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21" Edition, Troy, D. B. ed., Lipincott Williams and Wilkins, Philadelphia, PA 2006, Part 5, Pharmaceutical Manufacturing pp 691-1092, See especially pp. 958-989.

The mode of administration for therapeutic use of the FN3 domains disclosed herein may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intra-articular, intrabronchial, intra-abdominal, intracapsular, intracartilaginous, intracavitary, intracelial, intracerebellar, intracerebroventricular, intracolic, intracervical, intragastric, intrahepatic, intracardial, intraosteal, intrapelvic, intraperi-cardial, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

EXAMPLES

The following examples are illustrative of the embodiments disclosed herein. These examples are provided for the purpose of illustration only and the embodiments should in no way be construed as being limited to these examples, but rather should be construed to encompass any and all variations which become evidence as a result of the teaching provided herein. Those of skill in the art will readily recognize a variety of non-critical parameters that could be changed or modified to yield essentially similar results.

Example 1. Construction of Tencon Libraries With Randomized Loops

Tencon (SEQ ID NO: 276) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. No. 8,278,419). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets. Various libraries were generated using the Tencon scaffold and various design strategies. In general, libraries TCL1 and TCL2 produced good binders. Generation of TCL1 and TCL2 libraries are described in detail in Int. Pat. Publ. No. WO/2014081944A2.

Example 2: Generation of Tencon Libraries Having Alternative Binding Surfaces

The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc. Natl. Acad. Sci. USA 104: 6632-6637, 2007). In contrast, an ankyrin repeat scaffold protein that was selected to bind to MBP was found to have a much more planar interaction surface and to bind to the outer surface of MBP distant from the active (Binz et al., Nat. Biotechnol. 22: 575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

A full description of the methods used to construct this library is described in US. Pat. Publ. No. 2013/0226834.

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL14 design due to the larger theoretical size of the library if all 22 residues were randomized Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL14 design, they could be included in subsequent library designs to provide additional diversity for de novo selection or for example for an affinity maturation library on a select TCL14 target specific hit.

Subsequent to the production of TCL14, 3 additional Tencon libraries of similar design were produced. These two libraries, TCL19, TCL21 and TCL23, are randomized at the same positions as TCL14 (see above) however the distribution of amino acids occurring at these positions is altered. TCL19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J. Mol. Biol. 377: 1518-1528, 2008). As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and I86 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21.

Generation of TCL21, TCL23, and TCL24 Libraries

The TCL21 library was generated using Colibra library technology (Isogenica) in order to control amino acid distributions. TCL19, TCL23, and TCL24 gene fragments were generated using Slonomics technology (Morphosys) to control amino acid distributions. PCR was used to amplify each library following initial synthesis followed by ligation to the gene for RepA in order to be used in selections using the CIS-display system (Odegrip et al., Proc. Natl. Acad. Sci. USA 101: 2806-2810, 2004) as described above for the loop libraries.

Example 3: Selection of Fibronectin Type III (FN3) Domains that Bind CD71

Panning and Biochemical Screening

FN3 domains specific for human CD71 were selected via CIS-Display (Odegrip et al 2004) using recombinant biotinylated CD71 extracellular domain (Sino Biologics) with an N-terminal 6His tag (SEQ ID NO: 309). For in vitro transcription and translation (ITT), 3 µg of DNA from FN3 domain libraries TCL18, TCL19, TCL21, TCL23, and TCL24 were used, with unbound library members removed by washing. DNA was eluted from the target protein by heating and amplified by PCR using KOD polymerase for further rounds of panning High affinity binders were isolated by successively lowering the concentration of target CD71 during each round from 400 nM to 100 nM and increasing the washing stringency. Outputs from the fifth round panning were subjected to four additional rounds of off-rate selection. The biotinylated target antigen concentration was reduced from 25 nM in rounds 6 and 7 to 2.5 nM in rounds 8 and 9.

Following panning, genes encoding the selected FN3 domains were amplified by PCR, subcloned into a pET vector modified to include a ligase independent cloning site, and transformed into BL21 (DE3) (Stratagene) cells for soluble expression in E. coli using standard molecular biology techniques. A gene sequence encoding a C-terminal poly-histidine tag was added to each FN3 domain to enable purification and detection.

To screen for FN3 domains that specifically bind CD71, streptavidin-coated Maxisorp plates (Nunc catalog 436110) were blocked for 1 hour in Starting Block T20 (Pierce) and then coated with biotinylated CD71 (using same antigen as in panning) or negative controls (an unrelated Fc-fused recombinant protein and human serum albumin) for 1 hour. Plates were rinsed with TBST and diluted lysate was applied to plates for 1 hour. Following additional rinses, wells were treated with HRP-conjugated anti-V5 tag antibody (Abcam, ab1325), for 1 hour and then assayed with POD Roche, 11582950001). The DNA from FN3 domain lysates with signals at least 10-fold ELISA signal above that of streptavidin controls were sequenced resulting in 23 unique, readable FN3 domain sequences isolated from Round 9 screening.

Size Exclusion Chromatography Analysis

Size exclusion chromatography was used to determine the aggregation state of anti-CD71 FN3 domains. Aliquots (10 µL) of each purified FN3 domain were injected onto a Superdex 75 5/150 column (GE Healthcare) at a flow rate of 0.3 mL/min in a mobile phase of PBS pH 7.4. Elution from the column was monitored by absorbance at 280 nm. Tencon protein was included in each run as a control. Agilent ChemStation software was used to analyze the elution profiles.

High-Throughput Expression and Conjugation

Clones identified were grown in duplicate 5 mL cultures in 24 well deep block plates. Briefly, 5 mL/well of TB media supplemented with 50 µg/mL Kanamycin was seeded with 150 µL of overnight culture and grown for about 3 hours at 37° C. with shaking at 220 rpm (OD600~1). Cultures were induced with IPTG to a final concentration of 1 mM for an additional 4 hours at 37° C., 220 rpm. Bacterial pellets were recovered by centrifugation at 2250×g for 15 minutes. 600 µL/well BugBuster HT (Novagen) supplemented with lysozyme (Sigma) at 0.2 mg/mL was added to each well; pellets were dissociated by pipette and then shaken vigorously on a platform shake for about 30 minutes until pellets were lysed. Plates were spun at 2250×g for 15 minutes to clarify lysates and the 2 600-µL aliquots for each sample were combined. His-tagged FN3 domains were purified on His Trap plates (GE) according to the manufacturer's instructions followed by buffer exchange into TBS using Zeba Spin 7K desalt plates (Thermo Scientific). Protein concentrations were assessed by Nanodrop. For conjugation to GlyGly-VC-MMAF (SEQ ID NO: 310), FN3 domain (30 µM) was mixed with 150 µM GlyGlyVC-MMAF (SEQ ID NO: 310) (Concords) and 1 µM Sortase A in a total volume of 200 µL. Conjugations were allowed to proceed for 1.5 hours at room temperature and purified again using a 96 well His Multitrap HP plate from GE Healthcare according to the manufacturer's instructions. Buffer exchange into PBS was achieved using Zeba desalt plates followed by sterile filtering using Multiscreen HTS GV plates (Durapore) with centrifugation at 3000×g for 2 mins. Concentrations were assessed by Nanodrop.

CD71 Mediated SK-BR3 Cell Killing Assay.

Cell killing was assessed by measuring viability of the CD71-overexpressing human tumor cell line H1573 w/SKBR3 following exposure to the cysteine variant-cytotoxin conjugates. Cells were plated in black-well, clear bottomed, tissue culture-treated plates (Falcon 353219) at 7000/well in 100 µL/well of phenol red free RPMI media (Gibco11835-030) with 5% fetal bovine serum (Gibco). Cells were allowed to attach overnight at 37° C. in a humidified 5% CO2 atmosphere. Medium was aspirated from 96-well plate and cells were treated with 50 µL of fresh media and 50 µL of 2X inhibitor made up in fresh media. Cell viability was determined by an endpoint assay with Cell TiterGlo (Promega) at 70 hours. IC50 values were determined by fitting data to the equation for a sigmoidal dose response with variable slope using GraphPad Prism 5 (GraphPad Software).

Binding of Selected Clones by Dose-Response ELISA

Selected clones are analyzed by ELISA to determine EC50 values for binding. Briefly, Maxisorb plates are coated with streptavidin at 5 µg/ml overnight at 4C. Plates were then blocked with StartingBlock (ThermoFisher) at room temperature for 1 hour and then washed with TBS-Tween. Biotinylated CD71 (2 µg/ml) was captured onto the streptavidin plates and serially diluted FN3 proteins were added to appropriate wells for 1 hour at room temperature. After washing, bound FN3 proteins was detected with anti-V5 tag antibody, which is conjugated to HRP and POD substrate and a luminescence plate reader. Luminescence values are plotted as a function of concentration and fit to a dose response using PRISM to determine EC50 values for binding.

Identification of internalizing FN3 domains via toxin conjugates. The FN3 domains were conjugated to the cytotoxic tubulin inhibitor momomethyl auristatin F (MMAF) via an enzyme-cleavable Val-Cit linker or a non-cleavable PEG4 linker (VC-MMAF) using the methodology described for the NEM conjugation. Cell killing was assessed by measuring viability of the SKBR-3 cells following exposure to the cysteine variant-cytotoxin conjugates. Cells are plated in white-well, opaque bottomed, tissue culture-treated plates (Fisher, PI15042) at 3000/well in 50 µL/well of phenol red RPMI media (Gibco, 11875093) with 10% fetal bovine serum (Gibco). Cells are allowed to attach overnight at 37° C. in a humidified 5% CO2 atmosphere. Cells are treated with 25 uL of fresh media and 25 uL of 4× inhibitor made up in fresh media. Cell viability is determined by an endpoint assay with Cell TiterGlo (Promega) at 72 hours. IC50 values are determined by fitting data to the equation for a sigmoidal dose response with variable slope using GraphPad Prism (GraphPad Software).

Bivalent FN3 Protein

A bivalent FN3 protein is produced using two FN3 domains connected by a 4 repeat G/S linker or other appropriate polypeptide linker. The bivalent FN3 protein is conjugated to VC-MMAF as described and assessed for cytotoxicity in SK-BR3 cells. The IC50 value for bivalent molecule is often found to be better than the monovalent version.

Competition for Transferrin Binding and Internalization

FN3 domain vcMMAF conjugates were screened for competition with human transferrin using the cytotoxicity assay described above. FN3 domains were screened in the absence or presence of 0.6 uM holo-human transferrin (T0665-100MG).

pHrodo-Tf Assay

CD71-targeting Centyrins were evaluated for their ability to compete with transferrin for binding to the transferrin receptor. Cells are treated with transferrin that is directly conjugated to pHrodo-Red, a dye that fluoresces in acidic compartments and is therefore visible upon cellular uptake into endosomal and lysosomal compartments. Imaging of pHrodo-transferrin (pHrodo-Tf) is performed on an Incucyte, allowing real-time measurement of Tf uptake. When cells are incubated with pHrodo-Tf and a molecule that competes with Tf for CD71 binding, the pHrodo signal is reduced or eliminated. Centyrins that do not compete with Tf for CD71 binding have no impact on the pHrodo signal.

Example 4: Selection of Fibronectin Type III (FN3) Domains That Bind CD71 and are not Competitive with Transferrin To identify CD71 binding FN3 domains that were either not competitive or minimally competitive with transferrin a biased CIS-display strategy was designed. In short, using the output recovered after 5 rounds of panning on the ECD of human CD71 (Example 3), additional rounds of off-rate selection were performed as described in Example 3 with the addition of either 1) a wash step with human holo transferrin to elute FN3 proteins that bound at the same site as transferrin before the final elution step or 2) elution of FN3 domain binders with monoclonal antibody OKT9. FN3 domains recovered from the transferrin wash strategy and the OKT9 elution strategy were PCR amplified and cloned into pET vector as previously described (Example 3). 228 FN3 domains that specifically bound huCD71 were confirmed by solution ELISA for binding to huCD71 ECD. A subset of the unique binders was analyzed by SEC, conjugated to MMAF and assessed for internalization via cell viability assay in SKBR-3 cells+/−holo human transferrin. The polypeptides were found to be internalized by the receptor. Integral Molecular performed Membrane Proteome Array (MPA) assay to profile the specificity of ABX1198 (SEQ ID NO: 209), ABX1142 (SEQ ID NO: 209 plus a His-tag) and ABX1100 (SEQ ID NO: 209 plus siRNA pair with linker) against the library of human membrane proteins. The MPA library contains over 6000 human membrane proteins, including 94% of all single-pass, multi-pass and GPI anchored proteins including GPCRs, ion channels and transporters with each membrane protein uniquely expressed in an avian QT6 cell background. Flow cytometry is used to directly detect ligand (FN3 domain) binding to membrane proteins individually expressed in unfixed cells.

ABX1198 (SEQ ID NO: 209), ABX1142 (SEQ ID NO: 209 plus a His-tag) and ABX1100 (SEQ ID NO: 209 plus siRNA pair with linker) were screened at the concentration with optimal signal/background noise ratio, 1.25 ug/ml, 1.25 ug/ml and 0.31 ug/ml respectively, against the MPA. Membrane protein targets identified in screening were followed up in validation procedure using ligand serial dilution and cells individually transfected with identified targets.

Example 5. Knockdown of mRNA in Muscle Cells Using CD71 FN3 Domain-Oligonucleotide Conjugates muCD71 binding FN3 domains are conjugated to siRNA oligonucleotides or antisense oligonucleotides (ASOs) using maleimide chemistry via a cysteine that is uniquely engineered into the FN3 domain. The cysteine substitutions can be one such as those provided for herein and also as provided for in U.S. Patent Application Publication No. 20150104808, which is hereby incorporated by reference in its entirety. siRNAs or ASOs are modified with standard chemical modifications and confirmed to enable knockdown of the targeted mRNA in vitro. FN3 domain-oligonucleotide conjugates are dosed intravenously in mice at doses up to 10 mg/kg oligonucleotide payload. At various time points following dosing, mice are sacrificed; skeletal muscle, heart muscle and various other tissues will be recovered and stored in RNAlater™(Sigma Aldrich) until needed. Target gene knockdown is assessed using standard qPCR $AAC_T$ methods and primers specific for the target gene and a control gene. The target gene is found to be knock downed in the muscles and such knockdown is enhanced by conjugating the siRNA or ASO to the CD71 FN3 binding domain.

Example 6. Affinity Maturation Panning 4 sequences (A, B, C, and D) that demonstrated selective CD71 apical domain binding were the basis of affinity maturation library. In each sequence, 4 amino acids (double underlined), part of extended sheet library, were randomized to 18 amino acids (alanine, arginine, asparagine, aspartic acid, cysteine, glutamine, glutamic acid, glycine, histidine, isoleucine, leucine, lysine, phenylalanine, serine, threonine, tryptophan, tyrosine, or valine, not including proline, methionine). The new libraries underwent selection against 4 rounds of a) Transferrin wash; b) OKT9 elution; c) Apical domain selection; d) Apical domain, CD71_ECD selection. See sequences SEQ ID NOL 288-291 below.

| SEQ ID NO: | SEQUENCE |
|---|---|
| 288 | MLPAPKNLVVSRVTEDSARLSWTAPDAAFDSFYIAYAEPRPDGEAI VLTVPGSERSYDLTGLKPGTEYSVLIHGVKGGLLSSPLSAIFTT |
| 289 | MLPAPKNLVVSRVTEDSARLSWTAPDAAFDSFFIGYLEPQPPGEAI VLTVPGSERSYDLTGLKPGTEYNVTIQGVKGGFPSMPLSAIFTT |
| 290 | MLPAPKNLVVSRVTEDSARLSWTAPDAAFDSFHIVYHEPRPSGEAI VLTVPGSERSYDLTGLKPGTEYEVGIVSVKGGDLSVPLSAIFTT |
| 291 | MLPAPKNLVVSRVTEDSARLSWTAPDAAFDSFDIGYTEYGGYGEAI VLTVPGSERSYDLTGLKPGTEYWVLIQGVKGGGSSVPLSAIFTT |

TABLE 2

Summary of Screening Hits from the Apical domain Panning: Primary Solution Elisa Screen

| hCD71, RLU | HSA, RLU | hCD71:HSA | SEQ ID |
|---|---|---|---|
| 1513450 | 15750 | 96 | 1 |
| 382750 | 28350 | 14 | 2 |
| 687350 | 9950 | 69 | 3 |
| 2097500 | 173650 | 12 | 4 |
| 1731850 | 44950 | 39 | 5 |
| 314750 | 7300 | 43 | 6 |
| 761250 | 26100 | 29 | 7 |
| 788350 | 29300 | 27 | 10 |
| 1243750 | 48950 | 25 | 12 |
| 1728000 | 24650 | 70 | 13 |
| 1404200 | 1100 | 1277 | 14 |
| 512000 | 14450 | 35 | 15 |
| 656900 | 6900 | 95 | 16 |
| 221400 | 3650 | 61 | 17 |
| 827750 | 10450 | 79 | 18 |
| 955800 | 17900 | 53 | 19 |
| 791200 | 18450 | 43 | 20 |
| 578950 | 6850 | 85 | 21 |
| 3153600 | 29950 | 105 | 22 |
| 1392100 | 12650 | 110 | 23 |
| 2452600 | 6550 | 374 | 24 |
| 221700 | 3850 | 58 | 25 |
| 460800 | 20750 | 22 | 26 |
| 297350 | 2350 | 127 | 27 |
| 382600 | 13900 | 28 | 28 |
| 2174900 | 3750 | 580 | 29 |
| 204900 | 4450 | 46 | 30 |
| 642000 | 4650 | 138 | 31 |
| 341550 | 4550 | 75 | 32 |
| 271350 | 2050 | 132 | 33 |
| 1575900 | 8100 | 195 | 34 |
| 1987300 | 18800 | 106 | 35 |
| 288400 | 4800 | 60 | 36 |
| 2946550 | 28600 | 103 | 37 |
| 517500 | 8150 | 63 | 38 |
| 1476450 | 51100 | 29 | 39 |
| 223200 | 13550 | 16 | 40 |
| 1374450 | 115000 | 12 | 41 |
| 586300 | 1000 | 586 | 42 |
| 772450 | 21500 | 36 | 43 |
| 714900 | 56650 | 13 | 44 |
| 393800 | 18450 | 21 | 45 |
| 1037700 | 8150 | 127 | 46 |
| 1986900 | 20350 | 98 | 47 |
| 3039800 | 114750 | 26 | 48 |
| 968550 | 13750 | 70 | 49 |
| 320700 | 15950 | 20 | 50 |
| 469100 | 41600 | 11 | 51 |
| 888200 | 15200 | 58 | 52 |
| 1271750 | 32050 | 40 | 53 |
| 578800 | 11700 | 49 | 54 |
| 670750 | 6800 | 99 | 55 |
| 1919800 | 19450 | 99 | 56 |
| 1115450 | 38800 | 29 | 57 |
| 1035000 | 10200 | 101 | 58 |
| 1111700 | 16450 | 68 | 59 |
| 472400 | 11650 | 41 | 60 |
| 252200 | 13550 | 19 | 61 |
| 229400 | 8100 | 28 | 62 |
| 4707950 | 5700 | 826 | 63 |
| 1310850 | 6000 | 218 | 64 |
| 959100 | 16050 | 60 | 65 |

TABLE 2-continued

Summary of Screening Hits from the Apical domain Panning: Primary Solution Elisa Screen

| hCD71, RLU | HSA, RLU | hCD71:HSA | SEQ ID |
|---|---|---|---|
| 232350 | 8100 | 29 | 66 |
| 1854450 | 14200 | 131 | 67 |
| 521350 | 38400 | 14 | 68 |
| 3170900 | 2700 | 1174 | 69 |
| 991450 | 94800 | 10 | 70 |
| 2643400 | 27500 | 96 | 71 |
| 338100 | 8950 | 38 | 72 |
| 1472250 | 20250 | 73 | 73 |
| 824500 | 14650 | 56 | 74 |
| 529750 | 3700 | 143 | 75 |
| 673950 | 16300 | 41 | 76 |
| 738800 | 10400 | 71 | 77 |
| 270900 | 9350 | 29 | 78 |
| 273400 | 6000 | 46 | 79 |
| 844350 | 33650 | 25 | 80 |
| 863750 | 9850 | 88 | 81 |
| 1555100 | 14850 | 105 | 82 |
| 3258100 | 110750 | 29 | 83 |
| 3526900 | 127150 | 28 | 84 |
| 210150 | 6350 | 33 | 85 |
| 624700 | 46500 | 13 | 86 |
| 281700 | 3650 | 77 | 87 |
| 515200 | 24150 | 21 | 88 |
| 918850 | 6500 | 141 | 89 |
| 564250 | 12350 | 46 | 90 |
| 491000 | 6600 | 74 | 91 |
| 528200 | 9850 | 54 | 92 |
| 430000 | 4750 | 91 | 93 |
| 1020750 | 87200 | 12 | 94 |
| 667050 | 40750 | 16 | 95 |
| 726000 | 15150 | 48 | 96 |
| 956900 | 6500 | 147 | 97 |
| 1305450 | 11200 | 117 | 98 |
| 440250 | 9850 | 45 | 99 |
| 408450 | 5150 | 79 | 100 |
| 335900 | 4600 | 73 | 101 |
| 443800 | 39700 | 11 | 102 |

TABLE 3

Summary of Screening Hits from the Affinity Maturation Panning: Primary Solution Elisa Screen against CD71 and Apical Domain

| hCD71, RLU | Apical domain, RLU | HAS, RLU | hCD71:HSA | apical domain:HSA | SEQ ID |
|---|---|---|---|---|---|
| 817750 | 4141100 | 28950 | 28.2 | 143.0 | 103 |
| 947400 | 5902000 | 10550 | 89.8 | 559.4 | 104 |
| 2434450 | 6785550 | 17100 | 142.4 | 396.8 | 105 |
| 4966400 | 7370750 | 42000 | 118.2 | 175.5 | 106 |
| 1364850 | 5990050 | 62550 | 21.8 | 95.8 | 107 |
| 932300 | 2444500 | 13400 | 69.6 | 182.4 | 108 |
| 5327200 | 28300 | 38500 | 138.4 | 0.7 | 109 |
| 635550 | 802950 | 10600 | 60.0 | 75.8 | 110 |
| 2410700 | 112700 | 134450 | 17.9 | 0.8 | 111 |
| 4482200 | 7695300 | 10850 | 413.1 | 709.2 | 112 |
| 1266250 | 5832750 | 29700 | 42.6 | 196.4 | 113 |
| 2600900 | 6219500 | 21550 | 120.7 | 288.6 | 114 |
| 3470900 | 150050 | 172450 | 20.1 | 0.9 | 115 |
| 428500 | 4933450 | 11550 | 37.1 | 427.1 | 116 |
| 1296850 | 5357550 | 17200 | 75.4 | 311.5 | 117 |
| 1727250 | 6583250 | 14350 | 120.4 | 458.8 | 118 |
| 1246900 | 4926450 | 21650 | 57.6 | 227.5 | 119 |
| 501100 | 5745200 | 11800 | 42.5 | 486.9 | 120 |
| 4769200 | 6177350 | 17750 | 268.7 | 348.0 | 121 |
| 4769950 | 8057250 | 13600 | 350.7 | 592.4 | 122 |
| 1250400 | 4778850 | 29300 | 42.7 | 163.1 | 123 |
| 1539000 | 5460950 | 24400 | 63.1 | 223.8 | 124 |
| 1226400 | 5261600 | 16100 | 76.2 | 326.8 | 125 |
| 2735400 | 4416650 | 32200 | 85.0 | 137.2 | 126 |
| 1414600 | 6242100 | 21350 | 66.3 | 292.4 | 127 |

TABLE 3-continued

Summary of Screening Hits from the Affinity Maturation Panning: Primary Solution Elisa Screen against CD71 and Apical Domain

| hCD71, RLU | Apical domain, RLU | HAS, RLU | hCD71:HSA | apical domain:HSA | SEQ ID |
|---|---|---|---|---|---|
| 4308600 | 7406800 | 35500 | 121.4 | 208.6 | 128 |
| 218650 | 4179150 | 15850 | 13.8 | 263.7 | 129 |
| 1610200 | 105950 | 121850 | 13.2 | 0.9 | 130 |
| 203050 | 5277600 | 19650 | 10.3 | 268.6 | 131 |
| 1781950 | 7429250 | 41250 | 43.2 | 180.1 | 132 |
| 1044600 | 4739150 | 25500 | 41.0 | 185.8 | 133 |
| 639900 | 5387400 | 17450 | 36.7 | 308.7 | 134 |
| 967300 | 6048000 | 23000 | 42.1 | 263.0 | 135 |
| 3685900 | 4773100 | 23750 | 155.2 | 201.0 | 136 |
| 5108650 | 7866150 | 19100 | 267.5 | 411.8 | 137 |
| 1077450 | 5345250 | 14500 | 74.3 | 368.6 | 138 |
| 1133300 | 1860500 | 15350 | 73.8 | 121.2 | 139 |
| 603150 | 317150 | 21650 | 27.9 | 14.6 | 140 |
| 965000 | 4963650 | 26050 | 37.0 | 190.5 | 141 |
| 2965700 | 4364600 | 24100 | 123.1 | 181.1 | 142 |
| 3249450 | 7509300 | 20700 | 157.0 | 362.8 | 143 |
| 516500 | 3913550 | 16750 | 30.8 | 233.6 | 144 |
| 6196350 | 8295250 | 17800 | 348.1 | 466.0 | 145 |
| 1079650 | 5718700 | 16950 | 63.7 | 337.4 | 146 |
| 2939600 | 6887450 | 14400 | 204.1 | 478.3 | 147 |
| 289900 | 3411200 | 13750 | 21.1 | 248.1 | 148 |
| 1555800 | 6157400 | 17050 | 91.2 | 361.1 | 149 |
| 1300500 | 3157650 | 102550 | 12.7 | 30.8 | 150 |
| 1227350 | 4044500 | 27150 | 45.2 | 149.0 | 151 |
| 764200 | 4957500 | 13800 | 55.4 | 359.2 | 152 |
| 339200 | 3960750 | 21250 | 16.0 | 186.4 | 153 |
| 779200 | 5542450 | 23150 | 33.7 | 239.4 | 154 |
| 513250 | 4862050 | 18500 | 27.7 | 262.8 | 155 |
| 2455450 | 6708400 | 23500 | 104.5 | 285.5 | 156 |
| 3614600 | 7390500 | 38100 | 94.9 | 194.0 | 157 |
| 4992950 | 8005250 | 16000 | 312.1 | 500.3 | 158 |
| 185400 | 4433850 | 12850 | 14.4 | 345.0 | 159 |
| 4464400 | 8309700 | 22000 | 202.9 | 377.7 | 160 |
| 2632900 | 7310900 | 24650 | 106.8 | 296.6 | 161 |
| 638100 | 93100 | 37500 | 17.0 | 2.5 | 162 |
| 312700 | 74500 | 27150 | 11.5 | 2.7 | 163 |
| 3781250 | 8417150 | 25650 | 147.4 | 328.2 | 164 |
| 4906500 | 8370450 | 28000 | 175.2 | 298.9 | 165 |
| 1220000 | 6080200 | 35850 | 34.0 | 169.6 | 166 |
| 4173000 | 128250 | 179800 | 23.2 | 0.7 | 167 |
| 3972000 | 6860300 | 14650 | 271.1 | 468.3 | 168 |
| 4136300 | 7211350 | 17150 | 241.2 | 420.5 | 169 |
| 813500 | 4861500 | 41400 | 19.6 | 117.4 | 170 |
| 653400 | 5475650 | 18500 | 35.3 | 296.0 | 171 |
| 376600 | 353200 | 28200 | 13.4 | 12.5 | 172 |
| 1486150 | 1796200 | 22350 | 66.5 | 80.4 | 173 |
| 1899250 | 4829350 | 30800 | 61.7 | 156.8 | 174 |
| 4321900 | 7163900 | 13800 | 313.2 | 519.1 | 175 |
| 730600 | 5926750 | 9500 | 76.9 | 623.9 | 176 |
| 2796650 | 7737350 | 34850 | 80.2 | 222.0 | 177 |
| 865300 | 4948100 | 19250 | 45.0 | 257.0 | 178 |
| 3679650 | 7294100 | 28900 | 127.3 | 252.4 | 179 |
| 652900 | 3879150 | 10600 | 61.6 | 366.0 | 180 |
| 942200 | 6151700 | 15200 | 62.0 | 404.7 | 181 |
| 197350 | 2843300 | 13600 | 14.5 | 209.1 | 182 |
| 1128400 | 6952050 | 22450 | 50.3 | 309.7 | 183 |
| 4040600 | 119550 | 145000 | 27.9 | 0.8 | 184 |
| 651650 | 5458200 | 14800 | 44.0 | 368.8 | 185 |
| 844300 | 5382550 | 16700 | 50.6 | 322.3 | 186 |
| 796500 | 77900 | 73100 | 10.9 | 1.1 | 187 |
| 357550 | 5244350 | 26950 | 13.3 | 194.6 | 188 |
| 2567500 | 98900 | 119150 | 21.5 | 0.8 | 189 |
| 384850 | 4892250 | 23500 | 16.4 | 208.2 | 190 |
| 3864050 | 4656300 | 32500 | 118.9 | 143.3 | 191 |
| 1769550 | 7584950 | 22150 | 79.9 | 342.4 | 192 |
| 1711550 | 6118550 | 27950 | 61.2 | 218.9 | 193 |
| 682500 | 4781900 | 17500 | 39.0 | 273.3 | 194 |
| 4265600 | 7351800 | 41550 | 102.7 | 176.9 | 195 |
| 2133100 | 5927950 | 25200 | 84.6 | 235.2 | 196 |
| 1395000 | 6777950 | 47200 | 29.6 | 143.6 | 197 |
| 3905250 | 7195200 | 21050 | 185.5 | 341.8 | 198 |
| 416250 | 5555950 | 17150 | 24.3 | 324.0 | 199 |
| 929650 | 6103250 | 18000 | 51.6 | 339.1 | 200 |

TABLE 3-continued

Summary of Screening Hits from the Affinity Maturation Panning: Primary Solution Elisa Screen against CD71 and Apical Domain

| hCD71, RLU | Apical domain, RLU | HAS, RLU | hCD71:HSA | apical domain:HSA | SEQ ID |
|---|---|---|---|---|---|
| 3249150 | 7496450 | 232850 | 14.0 | 32.2 | 201 |
| 1508700 | 5468850 | 25750 | 58.6 | 212.4 | 202 |
| 2378300 | 5694300 | 25950 | 91.6 | 219.4 | 203 |
| 3285350 | 6352000 | 20050 | 163.9 | 316.8 | 204 |
| 2805100 | 150050 | 155300 | 18.1 | 1.0 | 205 |
| 827850 | 5220700 | 14000 | 59.1 | 372.9 | 206 |
| 2735800 | 7111400 | 120850 | 22.6 | 58.8 | 207 |
| 3001350 | 3698200 | 16350 | 183.6 | 226.2 | 208 |
| 6196350 | 8295200 | 17800 | 348.1 | 466.0 | 209 |
| 2411400 | 4124450 | 48550 | 49.7 | 85.0 | 210 |
| 660100 | 4739550 | 13050 | 50.6 | 363.2 | 211 |
| 466900 | 5090650 | 17450 | 26.8 | 291.7 | 212 |
| 1727000 | 2030750 | 70300 | 24.6 | 28.9 | 213 |
| 393150 | 4299750 | 30150 | 13.0 | 142.6 | 214 |
| 2020450 | 5842350 | 22350 | 90.4 | 261.4 | 215 |
| 4147550 | 141900 | 191700 | 21.6 | 0.7 | 216 |
| 3475050 | 6812350 | 16200 | 214.5 | 420.5 | 217 |
| 143600 | 2845650 | 14100 | 10.2 | 201.8 | 218 |
| 459750 | 4948500 | 11850 | 38.8 | 417.6 | 219 |
| 965600 | 31750 | 58950 | 16.4 | 0.5 | 221 |
| 1468850 | 1073450 | 15550 | 94.5 | 69.0 | 222 |
| 1929050 | 3597800 | 18300 | 105.4 | 196.6 | 223 |
| 3547950 | 6822800 | 26150 | 135.7 | 260.9 | 224 |
| 4057750 | 7377100 | 16950 | 239.4 | 435.2 | 225 |
| 2154200 | 6376550 | 15950 | 135.1 | 399.8 | 226 |
| 634750 | 4992500 | 28200 | 22.5 | 177.0 | 227 |
| 3881750 | 7042200 | 29550 | 131.4 | 238.3 | 228 |
| 1443150 | 5772800 | 15450 | 93.4 | 373.6 | 229 |
| 1100650 | 6105450 | 32000 | 34.4 | 190.8 | 230 |
| 2322100 | 6834550 | 20650 | 112.5 | 331.0 | 231 |
| 1079350 | 95450 | 75400 | 14.3 | 1.3 | 232 |
| 771600 | 5605650 | 22000 | 35.1 | 254.8 | 233 |
| 4506100 | 7037650 | 20850 | 216.1 | 337.5 | 234 |
| 943050 | 1672000 | 23850 | 39.5 | 70.1 | 235 |
| 4071550 | 7411950 | 15550 | 261.8 | 476.7 | 236 |
| 4576600 | 7006350 | 27700 | 165.2 | 252.9 | 237 |
| 3069350 | 111900 | 98950 | 31.0 | 1.1 | 238 |
| 559400 | 4653950 | 21100 | 26.5 | 220.6 | 239 |
| 610150 | 5256450 | 18000 | 33.9 | 292.0 | 240 |
| 3100050 | 5054100 | 26550 | 116.8 | 190.4 | 241 |
| 648150 | 4898500 | 20350 | 31.9 | 240.7 | 242 |
| 1972450 | 3193200 | 30900 | 63.8 | 103.3 | 243 |
| 1747650 | 5926450 | 18000 | 97.1 | 329.2 | 244 |
| 773800 | 4773600 | 18450 | 41.9 | 258.7 | 245 |
| 548350 | 47500 | 25750 | 21.3 | 1.8 | 246 |
| 4298600 | 7512300 | 19050 | 225.6 | 394.3 | 247 |
| 755550 | 5450050 | 34000 | 22.2 | 160.3 | 248 |
| 4935550 | 7432850 | 24100 | 204.8 | 308.4 | 249 |
| 724450 | 5544450 | 48550 | 15.0 | 114.4 | 250 |
| 2508550 | 5734450 | 26100 | 96.1 | 219.7 | 251 |
| 4344000 | 7572700 | 72850 | 59.6 | 103.9 | 252 |
| 3469100 | 7212700 | 37700 | 92.0 | 191.3 | 253 |
| 2239400 | 6619100 | 21500 | 104.2 | 307.9 | 254 |
| 5021750 | 7080200 | 102200 | 49.1 | 69.3 | 255 |
| 2071450 | 5839450 | 76100 | 27.2 | 76.7 | 256 |
| 802300 | 4835650 | 29800 | 26.9 | 162.3 | 257 |
| 5396000 | 7340850 | 26500 | 203.6 | 277.0 | 258 |
| 1259150 | 5961350 | 25350 | 49.7 | 235.2 | 259 |
| 4875150 | 7054650 | 33400 | 146.0 | 211.2 | 260 |
| 2393600 | 93150 | 174150 | 13.7 | 0.5 | 261 |
| 3941300 | 7126200 | 30900 | 127.6 | 230.6 | 262 |
| 584250 | 4370450 | 23800 | 24.5 | 183.6 | 263 |
| 368350 | 4322150 | 24400 | 15.1 | 177.1 | 264 |
| 5772300 | 7208200 | 30700 | 188.0 | 234.8 | 265 |
| 418150 | 4232150 | 36150 | 11.6 | 117.1 | 266 |
| 573450 | 5545650 | 29850 | 19.2 | 185.8 | 267 |
| 2767600 | 94850 | 117300 | 23.6 | 0.8 | 268 |
| 812000 | 5559700 | 19900 | 40.8 | 279.4 | 269 |
| 3320500 | 6487650 | 64350 | 51.6 | 100.8 | 270 |

TABLE 4

Summary of Size Exclusion Chromatography Analysis of Hits from the Apical domain panning

| SEQ ID | RT (min) | Height (mAU) | Y/N |
|---|---|---|---|
| 1 | 4.85 | 1276 | N |
| 2 | 6.18 | 5190 | Y |
| 3 | 4.49 | 12962 | N |
| 4 | 4.94 | 4430 | N |
| 5 | 5.76 | 72277 | Y |
| 6 | 4.42 | 9816 | N |
| 7 | 5.80 | 6831 | N |
| 10 | 4.42 | 13626 | N |
| 12 | 5.19 | 17868 | N |
| 13 | 5.02 | 7274 | Y |
| 14 | 5.83 | 49446 | Y |
| 15 | 4.43 | 16661 | N |
| 16 | 4.42 | 14549 | N |
| 17 | 4.47 | 12403 | N |
| 18 | 4.41 | 11175 | N |
| 19 | 4.43 | 12918 | N |
| 20 | 4.41 | 31082 | N |
| 21 | 5.75 | 50073 | Y |
| 22 | 6.02 | 24897 | Y |
| 23 | 4.42 | 12349 | N |
| 24 | 5.35 | 12795 | N |
| 25 | 4.45 | 14147 | Y |
| 26 | 5.81 | 11762 | N |
| 27 | 4.41 | 12376 | N |
| 28 | 5.79 | 6468 | N |
| 29 | 4.42 | 14375 | N |
| 30 | 5.90 | 31537 | N |
| 31 | 5.78 | 64734 | Y |
| 32 | 4.48 | 11824 | N |
| 33 | 4.43 | 14874 | N |
| 34 | 4.40 | 16722 | N |
| 35 | 4.43 | 30118 | N |
| 36 | 4.43 | 10366 | N |
| 37 | 5.91 | 10078 | N |
| 38 | 5.77 | 65938 | Y |
| 39 | 5.73 | 21308 | N |
| 40 | 5.78 | 9542 | N |
| 41 | 5.84 | 51999 | Y |
| 42 | 5.99 | 68358 | Y |
| 43 | 4.85 | 103763 | N |
| 44 | 6.11 | 39261 | N |
| 45 | 6.04 | 107908 | Y |
| 46 | 4.89 | 6108 | Y |
| 47 | 5.97 | 4414 | N |
| 48 | 6.16 | 40159 | Y |
| 49 | 6.04 | 95232 | Y |
| 50 | 4.49 | 10016 | N |
| 51 | 5.82 | 9242 | N |
| 52 | 4.48 | 15396 | N |
| 53 | 4.47 | 11234 | N |
| 54 | 4.43 | 15089 | N |
| 55 | 5.93 | 45271 | Y |
| 56 | 4.43 | 21968 | N |
| 57 | 4.48 | 9865 | N |
| 58 | 5.84 | 27831 | N |
| 59 | 4.49 | 15581 | N |
| 60 | 4.44 | 15771 | N |
| 61 | 4.44 | 16491 | N |
| 62 | 4.46 | 12971 | N |
| 63 | 5.84 | 55413 | Y |
| 64 | 5.76 | 66310 | Y |
| 65 | 5.74 | 13334 | N |
| 66 | 5.74 | 31088 | N |
| 67 | 4.43 | 24872 | N |
| 68 | 5.85 | 68979 | Y |
| 69 | 5.76 | 54708 | Y |
| 70 | 5.85 | 57285 | Y |
| 71 | 4.45 | 11624 | N |
| 72 | 4.47 | 17529 | N |
| 73 | 5.89 | 115880 | Y |
| 74 | 4.50 | 11311 | N |
| 75 | 5.84 | 33371 | Y |
| 76 | 4.49 | 19602 | N |
| 77 | 5.74 | 61741 | Y |
| 78 | 5.81 | 51210 | Y |

TABLE 4-continued

Summary of Size Exclusion Chromatography Analysis of Hits from the Apical domain panning

| SEQ ID | RT (min) | Height (mAU) | Y/N |
|---|---|---|---|
| 79 | 4.48 | 14307 | N |
| 80 | 5.87 | 82953 | Y |
| 81 | 4.49 | 11000 | N |
| 82 | 4.50 | 9074 | N |
| 83 | 5.73 | 27551 | N |
| 84 | 5.86 | 108824 | Y |
| 85 | 5.82 | 70054 | Y |
| 86 | 5.80 | 7988 | N |
| 87 | 4.47 | 12777 | N |
| 88 | 5.80 | 88617 | Y |
| 89 | 5.80 | 14227 | N |
| 90 | — | — | N |
| 91 | 4.45 | 19485 | N |
| 92 | 5.85 | 15361 | N |
| 93 | 5.994 | 7470 | Y |
| 94 | 6.045 | 4967 | N |
| 95 | 6.011 | 2105 | N |
| 96 | 4.694 | 2993 | N |
| 97 | 5.982 | 5411 | N |
| 98 | 6.086 | 15055 | Y |
| 99 | 6.127 | 5459 | Y |
| 100 | 4.764 | 1593 | N |
| 101 | 4.799 | 1552 | N |
| 102 | 5.971 | 1289 | N |

TABLE 5

Summary of Size Exclusion Chromatography Analysis of Hits from the Affinity Maturation panning

| SEQ ID | RT (min) | Height (mAU) | Y/N |
|---|---|---|---|
| 103 | 5.88 | 138095 | Y |
| 104 | 5.89 | 130922 | Y |
| 105 | 5.81 | 89766 | Y |
| 106 | 5.80 | 176348 | Y |
| 107 | 5.91 | 101236 | Y |
| 108 | 5.75 | 115796 | Y |
| 109 | 5.83 | 142833 | Y |
| 110 | 5.78 | 94728 | Y |
| 111 | 5.12 | 35930 | N |
| 112 | 5.81 | 109962 | Y |
| 113 | 5.09 | 106964 | Y |
| 114 | 5.84 | 104762 | Y |
| 115 | 5.81 | 38373 | N |
| 116 | 5.81 | 104287 | Y |
| 117 | 5.76 | 115912 | Y |
| 118 | 5.87 | 138528 | Y |
| 119 | 5.74 | 119491 | Y |
| 120 | 5.82 | 105691 | Y |
| 121 | 5.78 | 110048 | Y |
| 122 | 5.83 | 158539 | Y |
| 123 | 5.74 | 111953 | Y |
| 124 | 5.94 | 114526 | Y |
| 125 | 5.92 | 137742 | Y |
| 126 | 5.79 | 112960 | Y |
| 127 | 5.86 | 110390 | Y |
| 128 | 5.90 | 120352 | Y |
| 129 | 5.89 | 134927 | Y |
| 130 | 5.81 | 118419 | Y |
| 131 | 5.91 | 166662 | Y |
| 132 | 5.88 | 119689 | Y |
| 133 | 5.82 | 132427 | Y |
| 134 | 5.83 | 114205 | Y |
| 135 | 5.92 | 103105 | Y |
| 136 | 5.71 | 98649 | Y |
| 137 | 5.75 | 117138 | Y |
| 138 | 5.91 | 106938 | Y |
| 139 | 5.77 | 86558 | Y |
| 140 | 5.74 | 96522 | Y |
| 141 | 5.78 | 95668 | Y |
| 142 | 5.88 | 73328 | Y |

TABLE 5-continued

Summary of Size Exclusion Chromatography Analysis of Hits from the Affinity Maturation panning

| SEQ ID | RT (min) | Height (mAU) | Y/N |
|---|---|---|---|
| 143 | 6.00 | 83733 | Y |
| 144 | 5.87 | 100941 | Y |
| 145 | 5.82 | 109668 | Y |
| 146 | 5.87 | 99569 | Y |
| 147 | 5.75 | 120095 | Y |
| 148 | 5.83 | 129029 | Y |
| 149 | 5.91 | 130589 | Y |
| 150 | 4.91 | 30926 | N |
| 151 | 5.81 | 95796 | Y |
| 152 | 5.85 | 141203 | Y |
| 153 | 5.93 | 106098 | Y |
| 154 | 5.94 | 160425 | Y |
| 155 | 5.90 | 143145 | Y |
| 156 | 5.86 | 115893 | Y |
| 157 | 5.85 | 100355 | Y |
| 158 | 5.83 | 126349 | Y |
| 159 | 5.84 | 158223 | Y |
| 160 | 5.84 | 148628 | Y |
| 161 | 5.82 | 138546 | Y |
| 162 | 5.73 | 57532 | N |
| 163 | 5.82 | 39335 | N |
| 164 | 5.84 | 117968 | Y |
| 165 | 5.84 | 149834 | Y |
| 166 | 5.89 | 114338 | Y |
| 167 | 5.17 | 30228 | N |
| 168 | 5.77 | 127513 | Y |
| 169 | 5.82 | 100417 | Y |
| 170 | 5.92 | 132112 | Y |
| 171 | 5.89 | 67901 | N |
| 172 | 5.78 | 86348 | Y |
| 173 | 5.81 | 119484 | Y |
| 174 | 5.83 | 80373 | Y |
| 175 | 5.84 | 128180 | Y |
| 176 | 5.90 | 163155 | Y |
| 177 | 5.84 | 43159 | Y |
| 178 | 5.83 | 125240 | Y |
| 179 | 5.77 | 119270 | Y |
| 180 | 5.95 | 110362 | Y |
| 181 | 4.81 | 190088 | Y |
| 182 | 5.81 | 151104 | Y |
| 183 | 5.77 | 143551 | Y |
| 184 | 4.94 | 40376 | N |
| 185 | 5.90 | 117671 | Y |
| 186 | 5.80 | 119592 | Y |
| 187 | 4.91 | 59493 | N |
| 188 | 5.80 | 126167 | Y |
| 189 | 5.83 | 173711 | Y |
| 190 | 5.75 | 132569 | Y |
| 191 | 5.82 | 129102 | Y |
| 192 | 5.86 | 185255 | Y |
| 193 | 5.82 | 110511 | Y |
| 194 | 5.94 | 101317 | Y |
| 195 | 5.77 | 117916 | Y |
| 196 | 5.88 | 122474 | Y |
| 197 | 5.84 | 103601 | Y |
| 198 | 5.81 | 132253 | Y |
| 199 | 5.89 | 118621 | Y |
| 200 | 5.84 | 179035 | Y |
| 201 | 5.90 | 162216 | Y |
| 202 | 6.04 | 41767 | Y |
| 203 | 6.02 | 14216 | Y |
| 204 | 5.21 | 10597 | N |
| 205 | 5.27 | 4282 | N |
| 206 | 6.06 | 14434 | Y |
| 207 | 6.07 | 16590 | Y |
| 208 | 5.05 | 14071 | Y |
| 209 | 5.82 | 109668 | Y |
| 210 | 5.97 | 15408 | Y |
| 211 | 6.17 | 13650 | Y |
| 212 | 6.10 | 22359 | Y |
| 213 | 5.92 | 3377 | N |
| 214 | 6.07 | 20042 | Y |
| 215 | 6.14 | 20768 | Y |
| 216 | 5.25 | 5654 | N |
| 217 | 5.98 | 20229 | Y |

TABLE 5-continued

Summary of Size Exclusion Chromatography Analysis of Hits from the Affinity Maturation panning

| SEQ ID | RT (min) | Height (mAU) | Y/N |
|---|---|---|---|
| 218 | 6.00 | 14717 | Y |
| 219 | 6.00 | 13928 | Y |
| 221 | 5.20 | 9340 | N |
| 222 | 5.98 | 15512 | Y |
| 223 | 6.01 | 12837 | Y |
| 224 | 6.13 | 12868 | Y |
| 225 | 6.02 | 18790 | Y |
| 226 | 6.13 | 15649 | Y |
| 227 | 6.14 | 13107 | Y |
| 228 | 6.05 | 18737 | Y |
| 229 | 6.17 | 15369 | Y |
| 230 | 6.11 | 26740 | Y |
| 231 | 5.99 | 14844 | Y |
| 232 | 5.19 | 9635 | N |
| 233 | 6.10 | 22603 | Y |
| 234 | 6.04 | 15360 | Y |
| 235 | 5.95 | 12764 | Y |
| 236 | 5.99 | 16948 | Y |
| 237 | 6.05 | 17113 | Y |
| 238 | 5.22 | 9826 | N |
| 239 | 6.05 | 19054 | Y |
| 240 | 5.99 | 11335 | Y |
| 241 | 6.02 | 12881 | Y |
| 242 | 6.15 | 15577 | Y |
| 243 | 5.98 | 11788 | Y |
| 244 | — | — | N |
| 245 | 6.15 | 17079 | Y |
| 246 | 6.14 | 113391 | Y |
| 247 | 6.02 | 13674 | Y |
| 248 | 6.10 | 19453 | Y |
| 249 | 5.98 | 17677 | Y |
| 250 | 6.07 | 13344 | Y |
| 251 | 6.13 | 16320 | Y |
| 252 | 6.05 | 14756 | Y |
| 253 | 6.05 | 16634 | Y |
| 254 | 6.02 | 14227 | Y |
| 255 | 6.03 | 12605 | Y |
| 256 | 6.03 | 16075 | Y |
| 257 | 6.02 | 16086 | Y |
| 258 | 6.02 | 15720 | Y |
| 259 | 6.03 | 12004 | Y |
| 260 | 5.99 | 14310 | Y |
| 261 | 5.99 | 6832 | Y |
| 262 | 6.04 | 13901 | Y |
| 263 | 6.03 | 15172 | Y |
| 264 | 6.00 | 13075 | Y |
| 265 | 5.97 | 10535 | Y |
| 266 | 5.98 | 12563 | Y |
| 267 | 6.17 | 18078 | Y |
| 268 | 6.05 | 9392 | N |
| 269 | — | — | N |
| 270 | 4.78 | 2974 | N |

Sequences of Hits from the Apical Domain Panning

| SEQ ID | Amino Acid sequence of FN3 domains that bind to CD71 |
|---|---|
| 1 | MLPAPKNLVVSRVTEDSARLSWTAPDAAFDSFPITYIEAVVLGEAIVLTVPGSER SYDLTGLKPGTEYPVGISGVKGGHNSMPLSAIFTT |
| 2 | MLPAPKNLVVSEVTEDSARLSWQGVARAFDSFMINYSELFWMGEAIVLTVPGS ERSYDLTGLKPGTEYVVRIKGVKGGKGSWPLHAHFTT |
| 3 | MLPAPKNLVVSRVTEDSARLSWTAPDAAFDSFNIEYAETRWYGEAIVLTVPGSE RSYDLTGLKPGTEYVVPIDGVKGGIASKPLSAIFTT |
| 4 | MLPAPKNLVVSEVTEDSARLSWQGVARAFDSFLITYRDQIFAGEVIVLTVPGSE RSYDLTGLKPGTEYPVWIQGVKGGSPSAPLSAESTT |
| 5 | MLPAPKNLVVSEVTEDSARLSWQGVARAFDSFLITYREQIFAGEVIVLTVPGSER SYDLTGLKPGTEYWVYIWGVKGGKPSFPLRAGFTT |
| 6 | MLPAPKNLVVSRVTEDSARLSWTAPDAAFDSFPIIYMETFSRGEAIVLTVPGSER SYDLTGLKPGTEYRVPIGGVKGGSSSCPLSAIFTT |
| 7 | MLPAPKNLVVSDVTEDSARLSWQGVARAFDSFLITYREQIFAGEVIVLTVPGSE RSYDLTGLKPGTEYPVWIQGVKGGSPSAPLSAEFTT |
| 10 | MLPAPKNLVVSRVTEDSARLSWTAPDAAFDSFKIAYIETATRGEAIVLTVPGSER SYDLTGLKPGTEYVVPIPGVKGGNTSSPLSAIFTT |
| 12 | MLPAPKNLVVSRVTEDSARLSWTAPDAAFDSFFIPYAEPSPTGEAIVLTVPGSER SYDLTGLKPGTEYSVLIHGVKGGHLSDPLSAISTT |
| 13 | MLPAPKNLVVSRVTEDSARLSWTAPDAAFDSFLIAYPEDGFRGEAIVLTVPGSE RSYDLTGLKPGTEYPVPILGVKGGGGSGPLSAIFTT |
| 14 | MLPAPKNLVVSRVTEDSARLSWTAPDAAFDSFPIYYVENVWGEAIVLTVPGSE RSYDLTGLKPGTEYWEVIIGVKGGQCSRPLSAIFTT |
| 15 | MLPAPKNLVVSRVTEDSARLSWQGVARAFDSFLITYREQIFAGEVIVLTVPGSER SYDLTGLKPGTECPVWIQGVKGGSPSAPLSAEFTT |
| 16 | MLPAPKNLVVSRVTEDSARLSWTAPDAAFDSFGIAYREFRPSGEAIVLTVPGSER SYDLTVETGYRNEVVICGVKGGPWSGPLSAIFTT |

-continued

Sequences of Hits from the Apical Domain Panning

| SEQ ID | Amino Acid sequence of FN3 domains that bind to CD71 |
|---|---|
| 17 | MLPAPKNLVVSRVTEDSARLSWTAPDAAFDSFPILYTECVYRGEAIVLTVPGSE RSYDLTGLKPGTEYHVPITGVKGGGGSWPLSAIFTT |
| 18 | MLPAPKNLVVSRVTEDSARLSWTAPDAAFDSFNIMYHEIIYVGEAIVLTVPGSER SYDLTGLKPGTEYPVPIEGVKGGGTSGPLSAIFTT |
| 19 | MLPAPKNLVVSRVTEDSARLSWTAPDAAFDSFAITYTEAALCGEAIVLTVPGSE RSYDLTGLKPGTEYPVPINGVKGGGTSGPLSAIFTT |
| 20 | MLPAPKNLVVARVTEDSARLSWTAPDAAIDSFPIDYSEYWWGGEAIVLTVPGSE RSYDLTGLKPGTEYPVLITGVKGGYRSGPLSAIFTT |
| 21 | MLPAPKNLVVSRVTEDSARLSWTAPDAAFDSFSIRYNEFIVAGEAIVLTVPGSER SYDLTGLKPGTEYDVPIAGVKGGASWPLSAIVTT |
| 22 | MLPAPKNLVVSRVTEDSARLSWTAPDAAFDSFWYLELQFAGEAIVLTVPGSERS YDLTGLKPGTEYNVPITGVKGGIISFPLSAIFTT |
| 23 | MLPAPKNLVVSRVTEDSARLSWTAPDAAFDSFAIWYHEWYGDEAIVLTVPGS ERSYDLTGPKPGTEYRVRISGVKGGFESGPLSAIFTT |
| 24 | MLPAPKNLVVSRVTEDSARLSWTAPDAAFDSFMIRYQEGTRWGEAIVLTVPGS ERSYDLTGLKPGTEYIVMIAGVKGGQISLPLSAIFTT |
| 25 | MLPAPKNLVVSRVTEDSARLSWTAPDAAFDSFPIWYLEKSYQGEAIVLTVPGSE RSYDLTGLKPGTEYVVPIIGVKGGRDSCPLSAIFTT |
| 26 | MLPAPKNLVVSEVTEDSARLSWQGVARAFDSFLITYREQIFAGEVIVLTVPGSER SYDLTGLKPGTEYPVWIQGVKGGSPSAPLSAEFTT |
| 27 | MLPAPKNLVVSRVTEDSARLSWTAPDAAFDSFRISYAETVRQGEAIVLTVPGSE RSYDLTVETGYRNWVMILGVKGGPGSLPLSAIFTT |
| 28 | MLPAPKNLVVSEVTEDSARLSWQGVVRAFDSFLITYREQIFAGEVIVLTVPGSER SYDLTGLKPGTEYPVWIQGVKGGSPSAPLSAEFTT |
| 29 | MLPAPKNLVVSRVTEDSARLSWTAPDAAFDSFWIEYWEAVGFGEAIVLTVPGS ERSYDLTGLKPGTEYFVGIYGVKGGYLSAPLSAIFTT |
| 30 | MLPAPKNLVVSRVTEDSARLSWTAPDAAFDSFIIHYVEQQLIGEAIVLTVPGSER SYDLTGLKPGTEYPVPITGVKGGACSWPLSAIFTT |
| 31 | MLPAPKNLVVSRVTEDSARLSWTAPDAAFDSFTIEYSEHPIDGEAIPLFVPGSERS YDLTGLKPGTEYYVRIHGVKGGWFSHPLWAFFTT |
| 32 | MLPAPKNLVVSRVTEDSARLSWQGVARAFDSFLITYREQIFAGEVIVLTVPGSER SYDLTGLKPGTEYGVTIAGVKGGWRSKPLNAESTT |
| 33 | MLPAPKNLVVSRVTEDSARLSWTAPDAAFDSFGIAYVESYWYGEAIVLTVPGSE RSYDLTGLKPGTEYNVPIYGVKGGDGSGPLSAIFTT |
| 34 | MLPAPKNLVVSRVTEDSARLSWTAPDAAFDSFYITYVELNLAGEAIVLTVPGSE RSYDLTGLKPGTEYPVPILGVKGGSLSQPLSAIFTT |
| 35 | MLPAPKNLVVSRVTEDSARLSWTAPDAAFDSFPISYIESIADGEAIVLTVPGSERS YDLTGLKPGTEYWVAIVGVKGGPFSWSLSAIVTT |
| 36 | MLPAPKNLVVSEVTEDSARLSWQGVARAFDSFLITYREQIFAGEVIVPTVPGSER SYDLTGLKPGTEYPVPIAGVKGGGPSAPLSAIFTT |
| 37 | MLPAPKNLVVSRVTEDSARLSWTTPDAAFDSFPIYYWEVTITGEAIYLSVPGSER SYDLTGLKPGTEYPVDIPGVKGGAASPPLSAIFTT |
| 38 | MLPAPKNLVVSRVTEDSARLSWTAPDAAFDSFPILYLEHTVRSEAIVLTVPGSER SYDLTDLKPGTEYCVPIDGVKGGLRSRPLSAIFTT |
| 39 | MLPAPKNLVVSRVTEDSARLSWTAPDAAFDSFPIPYTEPPDPGEAIVLTVPGSER SYDLTGLKPGTEYLVTILGVKGGSMSVPLSAIFTT |
| 40 | MLPAPKNLVVSRVTEDSARLSWTAPDAAFDSFTIDYWENRCPGEAIVLTVPGSE RSYDLTGLKPGTEYCVWISGVKGGYSSWPLSAIFTT |
| 41 | MLPAPKNLVVSRVTEDSARLSWQGVARAFDSFLITYREQIFAGEVIVLTVPGSER SYDLTGLKPGTEYPVWIQGVKGGHLSDPLSAIVTT |

Sequences of Hits from the Apical Domain Panning

SEQ ID Amino Acid sequence of FN3 domains that bind to CD71

42  MLPAPKNLVVSRVTEDSARLSWTAPDAAFDSFLIPYAETSPSGEAIVLTVPGSER
    SYDLTGLKPGTEYSVLIHGVKGGDYSEPLSAIFTT

43  MLPAPKNLVVSRVTEDSARLSWTAPDAAFDSFMIVYYEYTRFGEAIVLTVPGSE
    RSYDLTGLKPGTEYTVPIDGVKGGRSSPLSAIFTT

44  MLPAPKNLVVSRVTEDSARLSWTAPDAAFDSFFIPYAEPSPTGEAIVLTVPGSER
    SYDLTGLKPGTEYSVLIHGVKGGHLSDPLSAIVTT

45  MLPAPKNLVVSEVTEDSARLSWQGVARAFDSFLITYREQIFAGEVIVLTVPGSER
    SYDLTGLKPGTEYPVWIQGVKGGSPSAPLSAEFTT

46  MLPAPKNLVVSRVTEDSARLSWTAPDAAFDSFIIPYAEVRPDGEAIVLTVPGSER
    SYDLTGLKPGTEYSVLIHGVKGGKLSLPLSAIFTT

47  MLPAPKNLVVSRVTEDSARLSWTAPDAAFDSFGIVYLEMMVTGEAIVLTVPGS
    ERSYDLTGLKPGTEYDVPILGVKGGTRSVPLSAIFTT

48  MLPAPKNLVVSRVTEDSARLSWTAPDAAFDSFLIYYEEGYLEYYYSGEAIVLTV
    PGSERS YDLTGLKPGTEYYVGIVGVKGGGLSGPLSAISTT

49  MLPAPKNLVVSRVTEDSARLSWTAPDAAFDSFPIAYAEPRPDGEAIVLTVPGSE
    RSYDLTGLKPGTEYSVLIHGVKGGDWSLPLSAIFTT

50  MSLPAPKNLVVSRVTEDSARLSWTAPDAAFDSFTIHYREFQLSGEAIVLTVPGSE
    RSYDLTGLKPGTEYDVPIEGVKGGPGSRPLSAIFTT

51  MLPAPKNLVVSEVTEDSARLSWQGVARAFDSFLITYREQIFAGEVIVLTVPGSEC
    SYDLTGLKPGTEYPVWIQGVKGGSPSAPLSAEFTT

52  MLPAPKNLVVSRVTEDSARLSWTAPDAAFDSFEIDYDELAIYGEAIVLTVPGSER
    SYDLTGLKPGTEYGVRIPGVKGGMPSLPLSAIVTT

53  MLPAPENLVVSEVTEDSARLSWQGVARAFDSFLITYREQIFAGEVIVLTVPGSER
    SYDLTGLKPGTEYPVWIQGVKGGSPSAPLSAESTT

54  MLPAPKNLVVSRVTEDSARLSWTAPDAAFDSFAIAYGEHIVIGEAIVLTVPGSER
    SYDLTGLKPGTEYMVPIAGVKGGPISLPLSAIFTT

55  MLPAPKNLVVSRVTEDSARLSWTAPDAAFDSFFIPYAEPSPTGEAIVLTVPGSER
    SYDLTGLKPGTEYSVLIHGVKGGHLSDPLSAIFTT

56  MLPAPKNLVVSRVTEDSARLSWTAPDAAFDSFSIGYVELVLLGEAIVLTVPGSE
    RSYDLTGLKPGTEYDVLIPGVKGGSLSRPLSAIFTT

57  MLPAPKNLVVSRVTEDSARLSWTAPDAAFDSFAIPYAELSRNGEAIVLTVPGSE
    RSYDLTGLKPGTEYTVLIHGVKGGCLSDPLSAIFTT

58  MLPAPKNLVVSRVTEDSARLSWTAPDAAFDSFHIEYLELSRHGEAIVLTVPGSE
    RSYDLTGLKPGTEYWVMIFGVKGGGPSKPLSAIFTT

59  MLPAPKNLVVSRVTEDSARLSWTAPDAAFDSFVYNEVHWIGEAIVLTVPGSERS
    YDLTGLKPGTEYFVGIYGVKGGHWSKPLSAIFTT

60  MLPAPKNLVVSRVTEDSARLSWTAPDAAFDSFEIDYDELAIYGEAIVLTVPGSER
    SYDLTGLKPGTEYGVRIPGVKGGMPSLPLSAIVTT

61  MLPAPKNLVVSRVTEDSARLSWTAPDAAFDSFQIVYSELWIKGEAIVLTVPGSE
    RSYDLTGLKPGTEYQVPIPGVKGGRNSFPLSAIFTT

62  MLPAPKNLVVSRVTEDSARLSWTAPDAAFDSFKIRYTETRSIGEAIVLTVPGSER
    SYDLTGLKPGTEYCVPIGGVKGGDSSWPLSAISTT

63  MLPAPKNLVVSRVTEDSARLSWTAPDAAFDSFCISYYERMGRGEAIVLTVPGSE
    RSYDLTGLKPGTEYMVYIFGVKGGLNSLPLSAIFTT

64  MLPAPKNLVVSRVTEDSARLSWTAPDAAFDSFYIVYAEPIPNGEAIVLTVPGSER
    SYDLTGLKPGTEYSVLIHGVKGGRNSDPLSAIFTT

65  MLPAPKNLVVSRVTKDSARLSWTAPDAAFDSFPIAYAEPRPDGEAIVLTVPGSE
    RSYDLTGLKPGTEYSVLIHGVKGGLLSSPLSAIFTT

Sequences of Hits from the Apical Domain Panning

| SEQ ID | Amino Acid sequence of FN3 domains that bind to CD71 |
|---|---|
| 66 | MLPAPKNLVVSRVTEDSARLSWTAPDAAFDSFTIDYDEPRSPGEAIVLTVPGSERSYDLTGLKPGTEYRVFIWGIKGGDTSFPLSAIFTT |
| 67 | MLPAPKNLVVSRVTEDSARLSWTAPDAAFDSFTILYAEQAQFGEAIVLTVPGSERSYDLTGLKPGTEYPITGVKGGTRSGPLSAISTT |
| 68 | MLPAPKNLVVSRVTEDSARLSWTAPDAAFDSFIIPYAEVRPDGEAIVLTVPGSERSYDLTGLKPGTEYSVLIHGVKGGHLSDPLSAISTT |
| 69 | MLPAPKNLVVSRVTEDSARLSWTAPDAAFDSFHIAYEETATSGEAIYLRVPGSERSYDLTGLKPGTEYGVEIEGVKGGARSRPLYADFTT |
| 70 | MLPAPKNLVVSRVTEDSARLSWQGVARAFDSFLITYREQIFAGEVIVLTVPGSERSYDLTGLKPGTEYPVWIQGVKGGDLSNPLSAIFTT |
| 71 | MLPAPKNLVVSRVTEDSARLSWTAPDAAFDSFPISYLELSLYGEAIVLTVPGSERSYDLTGLKPGTEYPVGIAGVKGGVVSRPLSAIFTT |
| 72 | MLPAPKNLVVSRVTEDSARLSWTAPDAAFDSFTIGYREWYWYGEAIVLTVPGSERSYDLTGLKPGTEYNVPISGVKGGLDSFPLSAIFTT |
| 73 | MLPAPKNLVVSEVTEDSARLSWQGVARAFDSFLITYREQIFAGEVIVLTVPGSERSYDLTGLKPGTEYPVWIQGVKGGSPSAPLSAESTT |
| 74 | MLPAPKNLVVSRVTEDSARLSWTAPDAAFDSFSITYLEWWNLGEAIVLTVPGSERSYDLTGLKPGTEYMVTIPGVKGGMSSYPLSAIFTT |
| 75 | MLPAPKNLVVSRVTEDSARLSWTAPDAAFDSFTISYGEEALIGEAIYLRVPGSERSYDLTGLKPGTEYYVHIEGVKGGSWSQPLAAAFTT |
| 76 | MLPAPKNLVVSRVTEDSARLSWTAPDAAFDSFTIEYYENIGIGEAIVLTVPGSERSYDLTGLKPGTEYSVPIVGVKGGPYSHPLSAIFTT |
| 77 | MLPAPKNLVVSRVTEDSARLSWTAPDAAFDSFPIAYAEPRPDGEAIVLTVPGSERSYDLTGLKPGTEYSVLIHGVKGGLLSSPLSAIFTT |
| 78 | MLPAPKNLVVSRVTEDSARLSWTAPDAAFDSFGIGYYEHKRFGEAIQLSVPGSERSYDLTGLKPGTEYEVDIEGVKGGVLSWPLFAEFTT |
| 79 | MLPAPKNLVVSRVTEDSARLSWTAPDAAFDSFVIEYTERFWSGEAIVLTVPGSERSYDLTGLKPGTEYSVPIDGVKGGQCSTPLSAIFTT |
| 80 | MLPAPKNLVVSRVTEDSARLSWTAPDAAFDSFWIDYEEEGVIGEAIYLHVPGSERSYDLTGLKPGTEYVVKIHGVKGGHPSHPLVAVFTT |
| 81 | MLPAPKNLVVSRVTEDSARLSWQGVARAFDSFLITYVELRHLGEAIVLTVPGSERSYDLTGLKPGTEYPVWIQGVKGGSPSAPLSAEFTT |
| 82 | MLPAPKNLVVSRVTEDSARLSWTAPDAAFDSFLIPYAETSPSGEAIVLTVPGSERSYDLTGLKPGTEYSVLIHGVKGGDYSSPLSAIFTT |
| 83 | MLPAPKNLVVSRVTEDSARLSWTAPDAAFDSFPIAYAEPRPDGEAIVLTVPGSERSYDLTGLKPGTEYSVLIHGVKGGLLSSPLSAISTT |
| 84 | MLPAPKNLVVSRVTEDSARLSWQGVARAFDSFSILYLELTPKGEAIVLTVPGSERSYDLTGLKPGTEYPVWIQGVKGGSPSAPLSAEFTT |
| 85 | MLPAPKNLVVSRVTEDSARLSWTAPDAAFDSFIIEYFEPIPIGEAIVLTVPGSERSYDLTGLKPGTEYAVNIYGVKGGYLSHPLSAIFTT |
| 86 | MLPAPKNLVVSEVTEDSARLSWQGVARAFDSFLITYREQIFAGEVIVLTVPGSECSYDLTGLKPGTEYPVWIQGVKGGSPSAPLSAEFTT |
| 87 | MLPAPKNLVVSRVTEDSARLSWTAPDAAFDSFAIEYTEFLYSGEAIVLTVPGSERSYDLTGLKPGTEYGVPINGVKGGFVSPPLSAIVTT |
| 88 | MLPAPKNLVVSRVTEDSARLSWTAPDAAFDSFPIKYREVLRCGEAIVLTVPGSERSYDLTGLKPGTEYTVPITGVKGGFGSSPLSAIFTT |
| 89 | MLPAPENLVVSRVTEDSARLSWTAPDAAFDSFWIEYYEGVIQGEAIVLTVPGSERSYDLTGLKPGTEYFVAIWGVKGGKWSVPLSAIFTT |

-continued

Sequences of Hits from the Apical Domain Panning

| SEQ ID | Amino Acid sequence of FN3 domains that bind to CD71 |
|---|---|
| 90 | MLPAPKNLVVSRVTEDSARLSWQGVARAFDSFLITYREQIFAGEVIVLTVPGSERSYDLTGLKPGTEYPVWIQGVKGGSPSAEFTT |
| 91 | MLPAPKNLVVSRVTEDSARLSWTAPDAAFDSFQIHYWETQGFGEAIVLTVPGSERSYDLTGLKPGTEYPVLIPGVKGGPSSLPLSAIFTT |
| 92 | MLPAPKNLVVSRVTEDSARLSWTAPDAAFDSFFIPYAEPSPTGEAIVLTVPGSERSYDLTGLKPGTEYSVLIHGVKGGHLSDPLSAIFTT |
| 93 | MLPAPKNLVVSRVTEDSARLSWTAPDAAFDSFAIEYYEPVPAGEAIYLDVPGSERSYDLTGLKPGTEYDVTIYGVKGGYYSHPLFASFTT |
| 94 | MLPAPKNLVVSEVTEDSARLSWQGVARAFDSFLITYREQIFAGEVIVLTVPGSERSYDLTGLKPGTEYPVWIQGVKGGSPSAPLSAIFTT |
| 95 | MLPAPKNLVVSEVTEDSARLSWQGVARAFDSFLITYREQIFAGEVIVLTVPGSERSYDLTGLKPGTEYPVWIQGVKGGSPSAPLSAEFTT |
| 96 | MSLPAPKNLVVSRVTEDSARLSWTAPDAAFDSFPIAYLEVFYEGEAIVLTVPGSERSYDLTGLKPGTEYQVPIEGVKGGAMSLPLSAIFTT |
| 97 | MLPAPKNLVVSRVTEDSARLSWTAPDAAFDSFHIWYEEETTIGEAIYLHVPGSERSYDLTGLKPGTEYEVHITGVKGGPYSRPLFANFTT |
| 98 | MLPAPKNLVVSRVTEDSARLSWTAPDAAFDSFGIAYDEWPEFGEAIVLTVPGSERSYDLTGLKPDTEYIVEIYGVKGGWFSWPLSAIFTT |
| 99 | MLPAPKNLVVSRVTEDSARLSWTAPDAAFDSFFIPYAEPSPTGEAIVLTVPGSERSYDLTGLKPGTEYSVLIHGVKGGHLSDPLSVIFTT |
| 100 | MLPAPKNLVVSRVTEDSARLSWTAPDAAFDSFYIWYEEVMYLGEAIVLTVPGSERSYDLTGLKPGTEYNVPIPGVKGGHSSPPLSAIFTT |
| 101 | MLPAPKNLVVSRVTEDSARLSWTAPDAAFDSFHILYEELFLVGEAIVLTVPGSERSYDLTGLKPGTEYKVPISGVKGGPVSRPLSAIFTT |
| 102 | MLPAPKNLVVSRVTEDSARLSWQGVARAFDSFLITYREQIFAGEVIVLTVPGSERSYDLTGLKPGTEYPVWIQGVKGGSPSAPLSAEFTT |

Sequences of Hits from the Affinity Maturation Panning

| SEQ ID | Amino Acid sequence of FN3 domains that bind to CD71 |
|---|---|
| 103 | MLPAPKNLVVSRVTEDSARLSWTAPDAAFDSFHIVYHEPRPSGEAIWLHVPGSERSYDLTGLKPGTEYEVGIVSVKGGDLSVPLVAFFTT |
| 104 | MLPAPKNLVVSRVTEDSARLSWTAPDAAFDSFYIAYAEPRPDGEAISLLVPGSERSYDLTGLKPGTEYSVLIHGVKGGLLSSPLYAVFTT |
| 105 | MLPAPKNLVVSRVTEDSARLSWTAPDAAFDSFYIAYAEPRPDGEAIFLVVPGSERSYDLTGLKPGTEYSVLIHGVKGGLLSSPLHANFTT |
| 106 | MLPAPKNLVVSRVTEDSARLSWTAPDAAFDSFYIAYAEPRPDGEAILLDVPGSERSYDLTGLKPGTEYSVLIHGVKGGLLSSPLYASFTT |
| 107 | MSLPAPKNLVVSRVTEDSARLSWTAPDAAFDSFYIAYAEPRPDGEAISLYVPGSERSYDLTGLKPGTEYSVLIHGVKGGLLSSPLSAISTT |
| 108 | MLPAPKNLVVSRVTEDSARLSWTAPDAAFDSFFIGYLEPQPPGEAIQLRVPGSERSYDLTGLKPGTEYNVTIQGVKGGFPSMPLSAIFTT |
| 109 | MLPAPKNLVVSRVTEDSARLSWTAPDAAFDSFHISYEEDYTFGEAIYLRVPGSERSYDLTGLKPGTEYRVVIGGVKGGWFSEPLLAAFTT |
| 110 | MLPAPKNLVVSRVTEDSARLSWTAPDAAFDSFFIGYLEPQPPGEAIYLTVPGSERSYDLTGLKPGTEYNVTIQGVKGGFPSYPLDASFTT |
| 111 | MLPAPKNLVVSRVTEDSARLSWTAPDAAFDSFFIGYLEPQPPGEAIDLGVPGSERSYDLTGLKPGTEYNVTIQGVKGGFPSMPLDPLEAYFTT |

-continued

Sequences of Hits from the Affinity Maturation Panning

| SEQ ID | Amino Acid sequence of FN3 domains that bind to CD71 |
|---|---|
| 112 | MLPAPKNLVVSRVTEDSARLSWTAPDAAFDSFYIAYAEPRPDGEAILLLVPGSERS YDLTGLKPGTEYSVLIHGVKGGLLSSPLSAIFTT |
| 113 | MLPAPKNLVVSRVTEDSARLSWTAPDAAFDSFYIAYAEPRPDGEAINLQVPGSER SYDLTGLKPGTEYSVLIHGVKGGLLSSPLVAFFTT |
| 114 | MLPAPKNLVVSRVTEDSARLSWTTPDAAFDSFFIGYLEPQPPGEAISLQVPGSERS YDLTGLKPGTEYNVTIQGVKGGFPSSPLFAVFTT |
| 115 | MLPAPKNLVVSRVTEDSARLSWTAPDAAFDSFYIAYAEPRPDGEAIELHVPGSER SYDLTGLKPGTEYSVLIHGVKGGLLSSPLFTT |
| 116 | MLPAPKNLVVSRVTEDSARLSWTAPDAAFDSFYIAYAEPRPDGEAIQLVVPGSER SYDLTGLKPGTEYSVLIHGVKGGLLSSPLSAIFTT |
| 117 | MLPAPKNLVVSRVTEDSARLSWTAPDAAFDSFYIAYAEPRPDGEAITLDVPGSER SYDLTGLKPGTEYSVLIHGVKGGLLSSPLSAIFTT |
| 118 | MLPAPKNLVVSRVTEDSARLSWTAPDAAFDSFYIAYAEPRPDGEAIWLVVPGSER SYDLTGLKPGTEYSVLIHGVKGGLLSSPLVASFTT |
| 119 | MLPAPKNLVVSRVTEDSARLSWTAPDAAFDSFYIAYAEPRPDGEAINLDVPGSER SYDLTGLKPGTEYSVLIHGVKGGLLSSPLVAEFTT |
| 120 | MLPAPKNLVVSRVTEDSARLSWTAPDAAFDSFYIAYAEPRPDGEAIHLSVPGSERS YDLTGLKPGTEYSVLIHGVKGGLLSSPLVAIFTT |
| 121 | MLPAPKNLVVSRVTEDSARLSWTAPDAAFDSFFIGYLEPQPPGEAIALWVPGSERS YDLTGLKPGTEYNVTIQGVKGGFPSMPLSAIFTT |
| 122 | MLPAPKNLVVSRVTEDSARLSWTAPDAAFDSFYIAYAEPRPDGEAIILVVPGSERS YDLTGLKPGTEYSVLIHGVKGGLLSSPLSAHFTT |
| 123 | MLPAPKNLVVSRVTEDSARLSWTAPDAAFDSFFIGYLEPQPPGEAIQLWVPGSERS YDLTGLKPGTEYNVTIQGVKGGFPSHPLGAVFTT |
| 124 | MLPAPKNLVVSRVTEDSARLSWTAPDAAFDSFYIAYAEPRPDGEAIQLHVPGSER SYDLTGLKPGTEYSVLIHGVKGGLLSSPLLASFTT |
| 125 | MLPAPKNLVVSRVTEDSARLSWTAPDAAFDSFYIAYAEPRPDGEAIALHVPGSER SYDLTGLKPGTEYSVLIHGVKGGLLSSPLVAFFTT |
| 126 | MLPAPKNLVVSRVTEDSARLSWTAPDAAFDSFFIGYLEPQPPGEAIHLHVPGSERS YDLTGLKPGTEYNVTIQGVKGGFPSIPLHANFTT |
| 127 | MLPAPKNLVVSRVTEDSARLSWTAPDAAFDSFYIAYAEPRPDGEAIFLGVPGSERS YDLTGLKPGTEYSVLIHGVKGGLLSSPLSAIFTT |
| 128 | MLPAPKNLVVSRVTEDSARLSWTAPDAAFDSFYIAYAEPRPDGEAIVLRVPGSER SYDLTGLKPGTEYSVLIHGVKGGLLSSPLIASFTT |
| 129 | MLPAPKNLVVSRVTEDSARLSWTAPDAAFDSFYIAYAEPRPDGEAINLWVPGSER SYDLTGLKPGTEYSVLIHGVKGGLLSSPLDASFTT |
| 130 | MLPAPKNLVVSRVTEDSARLSWTAPDAAFDSFVIEYFEWTLNGEAIVLTVPGSER SYDLTGLKPGTEYSVQIYGVKGGCLSRPLSAIFTT |
| 131 | MLPAPKNLVVSRVTEDSARLSWTAPDAAFDSFYIAYAEPRPDGEAIHLWVPGSER SYDLTGLKPGTEYSVLIHGVKGGLLSSPLIAHFTT |
| 132 | MLPAPKNLVVSRVTEDSARLSWTAPDAAFDSFFIPYAEPSPTGEAIVLTVPGSERS YDLTGLKPGTEYSVLIHGVKGGLLSSPLSAHFTT |
| 133 | MLPAPKNLVVSRVTEDSARLSWTAPDAAFDSFYIAYAEPRPDGEAIYLVVPGSER SYDLTGLKPGTEYSVLIHGVKGGLLSSPLDAFFTT |
| 134 | MLPAPKNLVVSRVTEDSARLSWTAPDAAFDSFYIAYAEPRPDGEAIGLQVPGSER SYDLTGLKPGTEYSVLIHGVKGGLLSSPLSAIFTT |
| 135 | MLPAPKNLVVSRVTEDSARLSWTAPDAAFDSFYIAYAEPRPDGEAIQLAVPGSER SYDLTGLKPGTEYSVLIHGVKGGLLSSPLHAFFTT |

Sequences of Hits from the Affinity Maturation Panning

SEQ ID Amino Acid sequence of FN3 domains that bind to CD71

136 MLPAPKNLVVSRVTEDSARLSWTAPDAAFDSFFIGYLEPQPPGEAIWLHVPGSERS
    YDLTGLKPGTEYNVTIQGVKGGFPSIPLIAIFTT

137 MLPAPKNLVVSRVTEDSARLSWTAPDAAFDSFYIAYAEPRPDGEAIVLDVPGSER
    SYDLTGLKPGTEYSVLIHGVKGGLLSSPLVAEFTT

138 MLPTPKNLVVSRVTEDSARLSWTAPDAAFDSFYIAYAEPRPDGEAIQLRVPGSERS
    YDLTGLKPGTEYSVLIHGVKGGLLSSPLHASFTT

139 MLPAPKNLVVSRVTEDSARLSWTAPDAAFDSFFIGYLEPQPPGEAIQLGVPGSERS
    YDLTGLKPGTEYNVTIQGVKGGFPSHPLNANFTT

140 MLPAPKNLVVSRVTEDSARLSWTAPDAAFDSFFIGYLEPQPPGEAIQLEVPGSERS
    YDLTGLKPGTEYNVTIQGVKGGFPSMPLSAIFTT

141 MLPAPKNLVVSRVTEDSARLSWTAPDAAFDSFYIAYAEPRPDGEAIFLGVPGSERS
    YDLTGLKPGTEYSVLIHGVKGGLLSSPLIAFFTT

142 MLPAPKNLVVSRVTEDSARLSWTAPDAAFDSFFIGYLEPQPPGEAIGLQVPGSERS
    YDLTGLKPGTEYNVTIQGVKGGFPSHPLKAQFTT

143 MLPAPKNLVVSRVTEDSARLSWTAPDAAFDSFYIAYAEPRPDGEAILLFVPGSERS
    YDLTGLKPGTEYSVLIHGVKGGLLSSPLVAHFTT

144 MLPAPKNLVVSRVTEDSARLSWTAPDAAFDSFYIAYAEPRPDGEAIGLYVPGSER
    SYDLTGLKPGTEYSVLIHGVKGGLLSSPLGAFFTT

145 MLPAPKNLVVSRVTEDSARLSWTAPDAAFDSFYIAYAEPRPDGEAILLQVPGSER
    SYDLTGLKPGTEYSVLIHGVKGGLLSSPLTAIFTT

146 MLPAPKNLVVSRVTEDSARLSWTAPDAAFDSFYIAYAEPRPDGEAITLHVPGSER
    SYDLTGLKPGTEYSVLIHGVKGGLLSSPLSAIFTT

147 MLPAPKNLVVSRVTEDSARLSWTAPDAAFDSFYIAYAEPRPDGEAIVLEVPGSER
    SYDLTGLKPGTEYSVLIHGVKGGLLSSPLDAHFTT

148 MLPAPKNLVVSRVTEDSARLSWTAPDAAFDSFYIAYAEPRPDGEAIALHVPGSER
    SYDLTGLKPGTEYSVLIHGVKGGLLSSPLRAVFTT

149 MLPAPKNLVVSRVTEDSARLSWTAPDAAFDSFYIAYAEPRPDGEAIQLWVPGSER
    SYDLTGLKPGTEYSVLIHGVKGGLLSSPLSAIFTT

150 MLPAPKNLVVSRVTEDSARLSRTAPDAAFDSFYIAYAEPRPDGEAIVLIVPGSERS
    YDLTGLKPGTEYSVLIHGVKGGLLSSPLSAIFTT

151 MLPAPKNLVVSRVTEDSARLSWTAPDAAFDSFFIGYLEPQPPGEAIQLWVPGSERS
    YDLTGLKPGTEYNVTIQGVKGGFPSRPLQAHFTT

152 MLPAPKNLVVSRVTEDSARLSWTAPDAAFDSFYIAYAEPRPDGEAITLDVPGSER
    SYDLTGLKPGTEYSVLIHGVKGGLLSSPLYAFFTT

153 MLPAPKNLVVSRVTEDSARLSWTAPDAAFDSFYIAYAEPRPDGEAIALHVPGSER
    SYDLTGLKPGTEYSVLIHGVKGGLLSSPLSAIFTT

154 MLPAPKNLVVSRVTEDSARLSWTAPDAAFDSFYIAYAEPRPDGEAIGLWVPGSER
    SYDLTGLKPGTEYSVLIHGVKGGLLSSPLIAHFTT

155 MLPAPKNLVVSRVTEDSARLSWTAPDAAFDSFYIAYAEPRPDGEAIWLVVPGSER
    SYDLTGLKPGTEYSVLIHGVKGGLLSSPLHARFTT

156 MLPAPKNLVVSRVTEDSARLSWTAPDAAFDSFYIAYAEPRPDGEAIFLQVPGSERS
    YDLTGLKPGTEYSVLIHGVKGGLLSSPLAAVFTT

157 MLPAPKNLVVSRVTEDSARLSWTAPDAAFDSFYIAYAEPRPDGEAILLHVPGSER
    SYDLTGLKPGTEYSVLIHGVKGGLLSSPLSAISTT

158 MLPAPKNLVVSRVTEDSARLSWTAPDAAFDSFYIAYAEPRPDGEAIILQVPGSERS
    YDLTGLKPGTEYSVLIHGVKGGLLSSPLSAVFTT

159 MLPAPKNLVVSRVTEDSARLSWTAPDAAFDSFYIAYAEPRPDGEAIYLKVPGSER
    SYDLTGLKPGTEYSVLIHGVKGGLLSSPLVAHFTT

Sequences of Hits from the Affinity Maturation Panning

SEQ ID Amino Acid sequence of FN3 domains that bind to CD71

160 MLPAPKNLVVSRVTEDSARLSWTAPDAAFDSFYIAYAEPRPDGEAIVLTVPGSER
SYDLTGLKPGTEYSVLIHGVKGGLLSSPLLAYFTT

161 MLPAPKNLVVSRVTEDSARLSWTAPDAAFDSFYIAYAEPRPDGEAIILHVPGSERS
YDLTGLKPGTEYSVLIHGVKGGLLSSPLEAKFTT

162 MLPAPKNLVVSRVTEDSARLSWTAPDAAFDSFYIAYAEPRPDGEAIKLEVPGSER
SYDLTGLKPGTEYSVLIHGVKGGLLSSPLAIFTT

163 MLPAPKNLVVSRVTEDSARLSWTAPDAAFDSFFIGYLEPQPPGEAIYLEVPGSERS
YDLTGLKPGTEYNVTIQGVKGGFPSFPLKAAFTT

164 MLPAPKNLVVSRVTEDSARLSWTAPDAAFDSFYIAYAEPRPDGEAIILRVPGSERS
YDLTGLKPGTEYSVLIHGVKGGLLSSPLVAIFTT

165 MLPAPKNLVVSRVTEDSARLSWTAPDAAFDSFYIAYAEPRPDGEAIVLQVPGSER
SYDLTGLKPGTEYSVLIHGVKGGLLSSPLAAWFTT

166 MLPAPKNLVVSRVTEDSARLSWTAPDAAFDSFYIAYAEPRPDGEAIFLQVPGSERS
YDLTGLKPGTEYSVLIHGVKGGLLSSPLNAFFTT

167 MLPAPKNLVVSRVTEDSARLSWTAPDAAFDSFFIGYLEPQPPGEAIILGVPGSERS
YDLTGLKPGTEYSVLIHGVKGGLLSSPLHAYSTT

168 MLPAPKNLVVSRVTEDSARLSWTAPDAAFDSFYIAYAEPRPDGEAILLDVPGSER
SYDLTGLKPGTEYSVLIHGVKGGLLSSPLSAIFTT

169 MLPAPKNLVVSRVTEDSARLSWTAPDAAFDSFYIAYAEPRPDGEAILLLVPGSERS
YDLTGLKPGTEYSVLIHGVKGGLLSSPLSAVFTT

170 MLPAPKNLVVSRVTEDSARLSWTAPDAAFDSFYIAYAEPRPDGEAIHLLVPGSER
SYDLTGLKPGTEYSVLIHGVKGGLLSSPLLAHFTT

171 MLPAPKNLVVSRVTEDSARLSWTAPDAAFDSFYIAYAEPRPDGEAIQLWVPGSER
SYDLTGLKPGTEYSVLIHGVKGGLLSSPLDAYFTT

172 MLPAPKNLVVSRVTEDSARLSWTAPDAAFDSFFIGYLEPQPPGEAIVLTVPGSERS
YDLTGLKPGTEYNVTIQGVKGGFPSMPLASFTT

173 MLPAPKNLVVSRVTEDSARLSWTAPDAAFDSFHIVYHEPRPSGEAIHLQVPGSERS
YDLTGLKPGTEYNVTIQGVKGGFPSYPLSAFFTT

174 MLPAPKNLVVSRVTEDSARLSWTAPDAAFDSFFIGYLEPQPPGEAIQLWVPGSERS
YDLTGLKPGTEYNVTIQGVKGGFPSMPLSAIFTT

175 MLPAPKNLVVSRVTEDSARLSWTAPDAAFDSFRISYCETFYHGEAIVLTVPGSERS
YDLTGLKPGTEYSVLIHGVKGGLLSSPLIAKFTT

176 MLPAPKNLVVSRVTEDSARLSWTAPDAAFDSFYIAYAEPRPDGEAIWLKVPGSER
SYDLTGLKPGTEYSVLIHGVKGGLLSSPLQANFTT

177 MLPAPKNLVVSRVTEDSARLSWTAPDAAFDSFYIAYAEPRPDGEAIWLKVPGSER
SYDLTGLKPGTEYSVLIHGVKGGLLSSPLQANFTT

178 MLPAPKNLVVSRVTEDSARLSWTAPDAAFDSFYIAYAEPRPDGEAIQLQVPGSER
SYDLTGLKPGTEYSVLIHGVKGGLLSSPLSAIVTT

179 MLPAPKNLVVSRVTEDSARLSWTAPDAAFDSFPIAYAEPRPDGEAIVLTVPGSER
SYDLTGLKPGTEYSVLIHGVKGGLLSSPLSAFFTT

180 MLPAPKNLVVSRVTEDSARLSWTAPDAAFDSFYIAYAEPRPDGEAIALLVPGSER
SYDLTGLKPGTEYSVLIHGVKGGLLSSPLVAQFTT

181 MLPAPKNLVVSRVTEDSARLSWTAPDAAFDSFYIAYAEPRPDGEAIILHVPGSERS
YDLTGLKPGTEYSVLIHGVKGGLLSSPLEAKFTT

182 MLPAPKNLVVSRVTEDSARLSWTAPDAAFDSFYIAYAEPRPDGEAIDLHVPGSER
SYDLTGLKPGTEYSVLIHGVKGGLLSSPLHALFTT

183 MLPAPKNLVVSRVTEDSARLSWTAPDAAFDSFYIAYAEPRPDGEAILLDVPGSER
SYDLTGLKPGTEYSVLIHGVKGGFPSMPLSAIFTT

184 MLPAPKNLVVSRVTEDSARLSWTAPDAAFDSFFIGYLEPQPPGEAIDLAVPGSERS
YDLTGLKPGTEYSVLIHGVKGGLLSSPLSFTT

Sequences of Hits from the Affinity Maturation Panning

SEQ ID  Amino Acid sequence of FN3 domains that bind to CD71

185 MLPAPKNLVVSRVTEDSARLSWTAPDAAFDSFYIAYAEPRPDGEAIYLGVPGSER
    SYDLTGLKPGTEYSVLIHGVKGGLLSSPLRAKFTT

186 MLPAPKNLVVSRVTEDSARLSWTAPDAAFDSFYIAYAEPRPDGEAIQLGVPGSER
    SYDLTGLKPGTEYSVLIHGVKGGLLSSPLSAIFTT

187 MLPAPKNLVVSRVTEDSARLSWTAPDAAFDSFFIGYLEPQPPGEAISLLVPDSERS
    YDLTGLKPGTEYNVTIQGVKGGFPSMPLKFTT

188 MLPAPKNLVVSRVTEDSARLSWTAPDAAFDSFYIAYAEPRPDGEAIGLGVPGSER
    SYDLTGLKPGTEYSVLIHGVKGGLLSSPLDASFTT

189 MLPAPKNLVVSRVTEDSARLSWTAPDAAFDSFYIAYAEPRPDGEAIQLTVPGSER
    SYDLTGPKPGTEYWVLIQGVKGGGSSVPLVAYFTT

190 MLPAPKNLVVSRVTEDSARLSWTAPDAAFDSFYIAYAEPRPDGEAISLDVPGSERS
    YDLTGLKPGTEYSVLIHGVKGGLLSSPLEASFTT

191 MLPAPKNLVVSRVTEDSARLSWTAPDAAFDSFFIGYLEPQPPGEAIILAVPGSERS
    YDLTGLKPGTEYNVTIQGVKGGFPSLPLVASFTT

192 MLPAPKNLVVSRVTEDSARLSWTAPDAAFDSFDIGYTEYGGYGEAIYLSVPGSER
    SYDLTGLKPGTEYWVLIQGVKGGGSSVPLSAIFTT

193 MLPAPKNLVVSRVTEDSARLSWTAPDAAFDSFYIAYAEPRPDGEAISLSVPGSERS
    YDLTGLKPGTEYSVLIHGVKGGLLSSPLIANFTT

194 MLPAPKNLVVSRVTEDSARLSWTAPDAAFDSFYIAYAEPRPDGEAIALLVPGSER
    SYDLTGLKPGTEYSVLIHGVKGGLLSSPLSAIVTT

195 MLPAPKNLVVSRVTEDSARLSWTAPDAAFDSFYIAYAEPRPDGEAIILDVPGSERS
    YDLTGLKPGTEYSVLIHGVKGGLLSSPLSSIFTT

196 MLPAPKNLVVSRVTEDSARLSWTAPDAAFDSFYIAYAEPRPDGEAIVLWVPGSER
    SYDLTGLKPGTEYSVLIHGVKGGLLSSPLRASFTT

197 MLPAPKNLVVSRVTEDSARLSWTAPDAAFDSFYIAYAEPRPDGEAIKLDVPGSER
    SYDLTGLKPGTEYSVLIHGVKGGLLSSPLVAFFTT

198 MLPAPKNLVVSRVTEDSARLSWTAPDAAFDSFYIAYAEPRPDGEAIILEVPGSERS
    YDLTGLKPGTEYSVLIHGVKGGLLSSPLVAYFTT

199 MLPAPKNLVVSRVTEDSARLSWTAPDAAFDSFYIAYAEPRPDGEAIHLWVPGSER
    SYDLTGLKPGTEYSVLIHGVKGGLLSSPLHADFTT

200 MLPAPKNLVVSRVTEDSARLSWTAPDAAFDSFYIAYAEPRPDGEAIWLEVPGSER
    SYDLTGLKPGTEYSVLIHGVKGGLLSSPLVADFTT

201 MLPAPKNLVVSRVTEDSARLSWTAPDAAFDSFYIAYAEPRPDGEAISLWVPGSER
    SYDLTGLKPGTEYSVLIHGVKGGLLSSPLLAHFTT

202 MLPAPKNLVVSRVTEDSARLSWTAPDAAFDSFDIGYTEYGGYGEAILHVPGSERS
    YDLTGLKPGTEYWVLIQGVKGGGSSVPLSAIFTT

203 MLPAPKNLVVSRVTEDSARLSWTAPDAAFDSFFIGYLEPQPPGEAIVLLVPGSERS
    YDLTGLKPGTEYNVTIQGVKGGFPSVPLAAFFTT

204 MLPAPKNLVVSRVTEDSARLSWTAPDAAFDSFFIGYLEPQPPGEAILLWVPGSERS
    YDLTGLKPGTEYNVTIQGVKGGFPSQFTT

205 MLPAPKNLVVSRVTEDSARLSWTAPDAAFDSFFIGYLEPQPPGEAILLGVPGSERS
    YDLTGLKPGTEYNVTIQGVKGGFPSMPLHPLVALFTT

206 MLPAPKNLVVSRVTEDSARLSWTAPDAAFDSFYIAYAEPRPDGEAIGLDVPGSER
    SYDLTGLKPGTEYSVLIHGVKGGLLSSPLSAIFTT

207 MLPAPKNLVVSRVTEDSARLSWTAPDAAFDSFYIAYAEPRPDGEAIHLSVPGSERS
    YDLTGLKPGTEYSVLIHGVKGGLLSSPLAAYFTT

208 MLPAPKNLVVSRVTEDSARLSWTAPDAAFDSFFIGYLEPQPPGEAIVLAVPGSERS
    YDLTGLKPGTEYNVTIQGVKGGFPSYPLVAAFTT

-continued

Sequences of Hits from the Affinity Maturation Panning

| SEQ ID | Amino Acid sequence of FN3 domains that bind to CD71 |
|---|---|
| 209 | MLPAPKNLVVSRVTEDSARLSWTAPDAAFDSFYIAYAEPRPDGEAILLQVPGSCRSYDLTGLKPGTEYSVLIHGVKGGLLSSPLTAIFTT |
| 210 | MLPAPKNLVVSRVTEDSARLSWTAPDAAFDSFFIGYLEPQPPGEAINLQVPGSERSYDLTGLKPGTEYNVTIQGVKGGFPSFPLSAVFTT |
| 211 | MLPAPKNLVVSRVTEDSARLSWTAPDAAFDSFYIAYAEPRPDGEAIQLHVPGSERSYDLTGLKPGTEYSVLIHGVKGGLLSSPLVAIFTT |
| 212 | MLPAPKNLVVSRVTEDSARLSWTAPDAAFDSFYIAYAEPRPDGEAIWLAVPGSERSYDLTGLKPGTEYSVLIHGVKGGLLSSPLHAQFTT |
| 213 | MLPAPKNLVVSRVTEDSARLSWTAPDAAFDSFYIAYAEPRPDGEAILLGVPGSERSYDLTGLKPGTEYSVLIHGVKGGLLSSPLFTT |
| 214 | MLPAPKNLVVSRVTEDSARLSWTAPDAAFDSFYIAYAEPRPDGEAIGLQVPGSERSYDLTGLKPGTEYSVLIHGVKGGLLSSPLCAEFTT |
| 215 | MLPAPKNLVVSRVTEDSARLSWTAPDAAFDSFYIAYAEPRPDGEAIVLWVPGSERSYDLTGLKPGTEYSVLIHGVKGGLLSSPLIAEFTT |
| 216 | MLPAPKNLVVSRVTEDSARLSWTAPDAAFDSFYIAYAEPRPDGEAISLSVPGSERSYDLTGLKPGTEYSVLIHGVKGGLLSSPPKFTT |
| 217 | MLPAPKNLVVSRVTEDSARLSWTAPDAAFDSFYIAYAEPRPDGEAIILEVPGSERSYDLTGLKPGTEYSVLIHGVKGGLLSSPLRAVFTT |
| 218 | MLPAPKNLVVSRVTEDSARLSWTAPDAAFDSFYIAYAEPRPDGEAIHLVVPGSERSYDLTGLKPGTEYSVLIHGVKGGLLSSPLSAIFTT |
| 219 | MLPAPKNLVVSRVTEDSARLSWTAPDAAFDSFYIAYAEPRPDGEAISLKVPGSERSYDLTGLKPGTEYSVLIHGVKGGLLSSPLEAIFTT |
| 220 | MLPAPKNPVVSRVTEDSARLSWTAPDAAFDSFYIAYAEPRPDGEAIHLLVPGSERSYDLTGLKPGTEYSVLIHGVKGGLLSSPLKRLSPPVVTITITMAVCRKPVAENLSQTLS |
| 221 | MLPAPKNLVVSRVTEDSARLSWTAPDAAFDSFFIGYLEPQPPGEAIFLDVPGSERSYDLTGLKPGTEYNVTIQGVKGGFPSPLTAFFTT |
| 222 | MLPAPKNLVVSRVTEDSARLSWTAPDAAFDSFFIGYLEPQPPGEAIVLDVPGSERSYDLTGLKPGTEYNVTIQGVKGGFPSHPLAAAFTT |
| 223 | MLPAPKNLVVSRVTEDSARLSWTAPDAAFDSFFIGYLEPQPPGEAIGLAVPGSERSYDLTGLKPGTEYNVTIQGVKGGFPSVPLQANFTT |
| 224 | MLPAPKNLVVSRVTEDSARLSWTAPDAAFDSFYIAYAEPRPDGEAILLRVPGSERSYDLTGLKPGTEYSVLIHGVKGGLLSSPLVAEFTT |
| 225 | MLPAPKNLVVSRVTEDSARLSWTAPDAAFDSFYIAYAEPRPDGEAILLQVPGSERSYDLTGLKPGTEYSVLIHGVKGGLLSSPLSASFTT |
| 226 | MLPAPKNLVVSRVTEDSARLSWTAPDAAFDSFYIAYAEPRPDGEAIGLHVPGSERSYDLTGLKPGTEYSVLIHGVKGGLLSSPLTASFTT |
| 227 | MLPAPKNLVVSRVTEDSARLSWTAPDAAFDSFYIAYAEPRPDGEAIGLRVPGSERSYDLTGLKPGTEYSVLIHGVKGGLLSSPLSAIFTT |
| 228 | MLPAPKNLVVSRVTEDSARLSWTAPDAAFDSFYIAYAEPRPDGEAIVLRVPGSERSYDLTGLKPGTEYSVLIHGVKGGLLSSPLAASFTT |
| 229 | MLPAPKNLVVSRVTEDSARLSWTAPDAAFDSFYIAYAEPRPDGEAIQLLVPGSERSYDLTGLKPGTEYSVLIHGVKGGLLSSPLVAHFTT |
| 230 | MLPAPKNLVVSRVTEDSARLSWTAPDAAFDSFYIAYAEPRPDGEAIWLLVPGSERSYDLTGLKPGTEYSVLIHGVKGGLLSSPLVAFFTT |
| 231 | MLPAPKNLVVSRVTEDSARLSWTAPDAAFDSFFIGYLEPQPPGEAIHLYVPGSERSYDLTGLKPGTEYNVTIQGVKGGFPSDPLDAVFTT |
| 232 | MLPAPKNLVVSRVTEDSARLSWTAPDAAFDSFFIGYLEPQPPGEAIYLDVPGSERSYDLTGLKPGTEYNVTIQGVKGGFPSTFTT |

-continued

Sequences of Hits from the Affinity Maturation Panning

| SEQ ID | Amino Acid sequence of FN3 domains that bind to CD71 |
|---|---|
| 233 | MLPAPKNLVVSRVTEDSARLSWTAPDAAFDSFYIAYAEPRPDGEAIQLFVPGSERSYDLTGLKPGTEYSVLIHGVKGGLLSSPLKAYFTT |
| 234 | MLPAPKNLVVSRVTEDSARLSWTAPDAAFDSFYIAYAEPRPDGEAIVLVVPGSERSYDLTGLKPGTEYSVLIHGVKGGLLSSPLSAIFTT |
| 235 | MLPAPKNLVVSRVTEDSARLSWTAPDAAFDSFFIGYLEPQPPGEAIQLTVPGSERSYDLTGLKPGTEYNVTIQGVKGGFPSLPLSADFTT |
| 236 | MLPAPKNLVVSRVTEDSARLSWTAPDAAFDSFYIAYAEPRPDGEAILLQVPGSERSYDLTGLKPGTEYSVLIHGVKGGLLSSPLDAEFTT |
| 237 | MLPAPKNLVVSRVTEDSARLSWTAPDAAFDSFYIAYAEPRPDGEAIVLAVPGSERSYDLTGLKPGTEYSVLIHGVKGGLLSSPLYASFTT |
| 238 | MLPAPKNLVVSRVTEDSARLSWTTPDAAFDSFYIAYAEPRPDGEAIRLQVPGSERSYDLTGLKPGTEYSVLIHGVKGGLLSSPLGFTT |
| 239 | MLPAPKNLVVSRVTEDSARLSWTAPDAAFDSFYIAYAEPRPDGEAIQLVVPGSERSYDLTGLKPGTEYSVLIHGVKGGLLSSPLYAIFTT |
| 240 | MLPAPKNLVVSRVTEDSARLSWTAPDAAFDSFYIAYAEPRPDGEAISLSVPGSERSYDLTGLKPGTEYSVLIHGVKGGLLSSPLHAKFTT |
| 241 | MLPAPKNLVVSRVTEDSARLSWTAPDAAFDSFFIGYLEPQPPGEAIHLGVPGSERSYDLTGLKPGTEYNVTIQGVKGGFPSIPLFASFTT |
| 242 | MLPAPKNLVVSRVTEDSARLSWTAPDAAFDSFYIAYAEPRPDGEAIQLLVPGSERSYDLTGLKPGTEYSVLIHGVKGGLLSSPLYAAFTT |
| 243 | MLPAPKNLVVSRVTEDSARLSWTAPDAAFDSFFIGYLEPQPPGEAIHLAVPGSERSYDLTGLKPGTEYNVTIQGVKGGFPSVPLAAVFTT |
| 244 | MLPAPKNLVVSRVTEDSARLSWTAPDAAFDSFYIAYAEPRPDGEAISLQVPGSERSYDLTGLKPGTEYSVLIHGVKGGLLSSPLGAHFTT |
| 245 | MLPAPKNLVVSRVTEDSARLSWTAPDAAFDSFYIAYAEPRPDGEAIALWVPGSERSYDLTGLKPGTEYSVLIHGVKGGLLSSPLVASFTT |
| 246 | MLPAPKNLVVSRVTEDSARLSWTAPDAAFDSFYIAYAEPRPDGEAIQLHVPGSERSYDLTGLKPGTEYSVLIHGVKGGLLSSPLYAFFTT |
| 247 | MLPAPKNLVVSRVTEDSARLSWTAPDAAFDSFYIAYAEPRPDGEAILLHVPGSERSYDLTGLKPGTEYSVLIHGVKGGLLSSPLRASFTT |
| 248 | MLPAPKNLVVSRVTEDSARLSWTAPDAAFDSFYIAYAEPRPDGEAIWLGVPGSERSYDLTGLKPGTEYSVLIHGVKGGLLSSPLHATFTT |
| 249 | MLPAPKNLVVSRVTEDSARLSWTAPDAAFDSFYIAYAEPRPDGEAIVLEVPGSERSYDLTGLKPGTEYSVLIHGVKGGLLSSPLHANFTT |
| 250 | MLPAPKNLVVSRVTEDSARLSWTAPDAAFDSFYIAYAEPRPDGEAILLRVPGSERSYDLTGLKPGTEYSVLIHGVKGGLLSSPLYAKFTT |
| 251 | MLPAPKNLVVSRVTEDSARLSWTAPDAAFDSFFIGYLEPQPPGEAIGLWVPGSERSYDLTGLKPGTEYNVTIQGVKGGFPSDPLQAVFTT |
| 252 | MLPAPKNLVVSRVTEDSARLSWTAPDAAFDSFYIAYAEPRPDGEAIVLHVPGSERSYDLTGLKPGTEYSVLIHGVKGGLLSSPLDAFFTT |
| 253 | MLPAPKNLVVSRVTEDSARLSWTAPDAAFDSFYIAYAEPRPDGEAIILHVPGSERSYDLTGLKPGTEYSVLIHGVKGGLLSSPLDAYFTT |
| 254 | MLPAPKNLVVSRVTEDSARLSWTAPDAAFDSFYIAYAEPRPDGEAILLAVPGSERSYDLTGLKPGTEYSVLIHGVKGGLLSSPLSAKFTT |
| 255 | MLPAPKNLVVSRVTEDSARLSWTAPDAAFDSFFIGYLEPQPPGEAILLFVPGSERSYDLTGLKPGTEYNVTIQGVKGGFPSTPLSASFTT |
| 256 | MLPAPKNLVVSRVTEDSARLSWTAPDAAFDSFYIAYAEPRPDGEAIQLTVPGSERSYDLTGLKPGTEYSVLIHGVKGGLLSSPLHAYFTT |
| 257 | MLPAPKNLVVSRVTEDSARLSWTAPDAAFDSFYIAYAEPRPDGEAIQLGVPGSERSYDLTGLKPGTEYSVLIHGVKGGLLSSPLRAYFTT |

Sequences of Hits from the Affinity Maturation Panning

| SEQ ID | Amino Acid sequence of FN3 domains that bind to CD71 |
|---|---|
| 258 | MLPAPKNLVVSRVTEDSARLSWTAPDAAFDSFYIAYAEPRPDGEAILLEVPGSERS YDLTGLKPGTEYSVLIHGVKGGLLSSPLVAFFTT |
| 259 | MLPAPKNLVVSRVTEDSARLSWTAPDAAFDSYIAYAEPRPDGEAIQLGVPGSER SYDLTGLKPGTEYSVLIHGVKGGLLSSPLLAVFTT |
| 260 | MLPAPKNLVVSRVTEDSARLSWTAPDAAFDSFYIAYAEPRPDGEAIHLRVPGSER SYDLTGLKPGTEYNVTIQGVKGGFPSMPLSAIFTT |
| 261 | MLPAPKNLVVSRVTEDSARLSWTAPDAAFDSFYIAYAEPRPDGEAILLQVPGSER SYDLTGLKPGTEYSVLIHGVKGGLLSSPLIAKFTT |
| 262 | MLPAPKNLVVSRVTEDSARLSWTAPDAAFDSFYIAYAEPRPDGEAIVLHVPGSER SYDLTGLKPGTEYSVLIHGVKGGLLSSPLQAIFTT |
| 263 | MLPAPKNLVVSRVTEDSARLSWTAPDAAFDS FYIAYAEPRPDGEAIALVVPGSER SYDLTGLKPGTEYSVLIHGVKGGLLSSPLAANFTT |
| 264 | MLPAPKNLVVSRVTEDSARLSWTAPDAAFDSFYIAYAEPRPDGEAINLSVPGSERS YDLTGLKPGTEYSVLIHGVKGGLLSSPLDAYFTT |
| 265 | MLPAPKNLVVSRVTEDSARLSWTAPDAAFDSFYIAYAEPRPDGEAIVLEVPGSER SYDLTGLKPGTEYSVLIHGVKGGLLSSPLTASFTT |
| 266 | MLPAPKNLVVSRVTEDSARLSWTAPDAAFDSFYIAYAEPRPDGEAIRLQVPGSER SYDLTGLKPGTEYSVLIHGVKGGLLSSPLGASFTT |
| 267 | MLPAPKNLVVSRVTEDSARLSWTAPDAAFDSFYIAYAEPRPDGEAIGLWVPGSER SYDLTGLKPGTEYSVLIHGVKGGLLSSPLVAYFTT |
| 268 | MLPAPKNLVVSRVTEDSARLSWTAPDAAFDSFYIAYAEPRPDGEAIYLEVPGSER SYDLTGLKPGTEYSVLIHGVKGGLLSSPLFTT |
| 269 | MLPAPKNLVVSRVTEDSARLSWTAPDAAFDSFYIAYAEPRPDGEAIWLDVPGSER SYDLTGLKPGTEYSVLIHGVKGGLLSSPLDAYFTT |
| 270 | MLPAPKNLVVSRVTEDSARLSWTAPDAAFDSFAIEYCETKMCGEAIVLTVPGSER SYDLTGLKPGTEYRVPIPGVKGGTASLPLSAIFTT |
| 271 | MLPAPKNLVVSRVTEDSARLSWTAPDAAFDSFFIYYIESYPAGEAIVLTVPGSERS YDLTGLKPGTEYWVGIDGVKGGRWSTPLSAIFTT |
| 272 | MLPAPKNLVVSRVTEDSARLSWTAPDAAFDSFFIYYIESYPAGEAIVLTVPGSCRS YDLTGLKPGTEYWVGIDGVKGGRWSTPLSAIFTT |
| 292 | MLPAPKNLVVSRVTEDSARLSWTAPDAAFDSFAIVYHEPRPDGEAIVLTVPGSCR SYDLTGLKPGTEYEVVILGVKGGVHSYPLSAIFTTAPAPAPAPAPLPAPKNLVVSR VTEDSARLSWTAPDAAFDSFAIVYHEPRPDGEAIVLTVPGSERSYDLTGLKPGTEY EVVILGVKGGVHSYPLSAIFTT |
| 293 | MLPAPKNLVVSRVTEDSARLSWTAPDAAFDSFAIVYHEPRPDGEAIVLTVPGSCR SYDLTGLKPGTEYEVVILGVKGGVHSYPLSAIFTTGGGGSGGGGSGGGGSGGGGS LPAPKNLVVSRVTEDSARLSWTAPDAAFDSFAIVYHEPRPDGEAIVLTVPGSERSY DLTGLKPGTEYEVVILGVKGGVHSYPLSAIFTT |
| 294 | MLPAPKNLVVSRVTEDSARLSWTAPDAAFDSFAIVYHEPRPDGEAIVLTVPGSCR SYDLTGLKPGTEYEVVILGVKGGVHSYPLSAIFTTEAAAKEAAAKEAAAKEAAA KLPAPKNLVVSRVTEDSARLSWTAPDAAFDSFAIVYHEPRPDGEAIVLTVPGSERS YDLTGLKPGTEYEVVILGVKGGVHSYPLSAIFTT |
| 295 | MLPAPKNLVVSRVTEDSARLSWTAPDAAFDSFAIVYHEPRPDGEAIVLTVPGSCR SYDLTGLKPGTEYEVVILGVKGGVHSYPLSAIFTTEAAAKLPAPKNLVVSRVTED SARLSWTAPDAAFDSFAIVYHEPRPDGEAIVLTVPGSERSYDLTGLKPGTEYEVVI LGVKGGVHSYPLSAIFTT |
| 296 | MLPAPKNLVVSRVTEDSARLSWTAPDAAFDSFKIEYFEYVGYGEAIVLTVPGSCR SYDLTGLKPGTEYYVAIYGVKGGWYSRPLSAIFTTAPAPAPAPAPLPAPKNLVVS RVTEDSARLSWTAPDAAFDSFKIEYFEYVGYGEAIVLTVPGSERSYDLTGLKPGTE YYVAIYGVKGGWYSRPLSAIFTT |

-continued

Sequences of Hits from the Affinity Maturation Panning

| SEQ ID | Amino Acid sequence of FN3 domains that bind to CD71 |
|---|---|
| 297 | MLPAPKNLVVSRVTEDSARLSWTAPDAAFDSFKIEYFEYVGYGEAIVLTVPGSCR<br>SYDLTGLKPGTEYYVAIYGVKGGWYSRPLSAIFTTGGGSGGGGSGGGGSGGGG<br>SLPAPKNLVVSRVTEDSARLSWTAPDAAFDSFKIEYFEYVGYGEAIVLTVPGSERS<br>YDLTGLKPGTEYYVAIYGVKGGWYSRPLSAIFTT |
| 298 | MLPAPKNLVVSRVTEDSARLSWTAPDAAFDSFKIEYFEYVGYGEAIVLTVPGSCR<br>SYDLTGLKPGTEYYVAIYGVKGGWYSRPLSAIFTTEAAAKEAAAKEAAAKEAAA<br>KLPAPKNLVVSRVTEDSARLSWTAPDAAFDSFKIEYFEYVGYGEAIVLTVPGSERS<br>YDLTGLKPGTEYYVAIYGVKGGWYSRPLSAIFTT |
| 299 | MLPAPKNLVVSRVTEDSARLSWTAPDAAFDSFKIEYFEYVGYGEAIVLTVPGSCR<br>SYDLTGLKPGTEYYVAIYGVKGGWYSRPLSAIFTTEAAAKLPAPKNLVVSRVTED<br>SARLSWTAPDAAFDSFKIEYFEYVGYGEAIVLTVPGSERSYDLTGLKPGTEYYVAI<br>YGVKGGWYSRPLSAIFTT |
| 304 | MLPAPKNLVVSRVTEDSARLSWTAPDAAFDSFAIVYHEPRPDGEAIVLTVPGSCR<br>SYDLTGLKPGTEYEVVILGVKGGVHSYPLSAIFTT |
| 305 | MLPAPKNLVVSRVTEDSARLSWTAPDAAFDSFAIVYHEPRPDGEAIVLTVPGSER<br>SYDLTGLKPGTEYEVVILGVKGGVHSYPLSAIFTT |
| 306 | MLPAPKNLVVSRVTEDSARLSWTAPDAAFDSFFIGYLEPQPPGEAIHLGVPGSCRS<br>YDLTGLKPGTEYNVTIQGVKGGFPSIPLFASFTT |

Example 7: FN3-siRNA Conjugation and Purification

ABX1005 was prepared by conjugation of cysteine modified FN3 CD71-49 (SEQ ID: 272) to ABX0214 (Table 6) via cysteine-specific chemistry using maleimide modified siRNA. For cysteine-maleimide conjugation, cysteine-containing FN3 domains in PBS at 50-200 µM were reduced with 10 mM tris(2-carboxyethyl)phosphine (TCEP) at room temperature (30 mins) to yield a free thiol. To remove the TCEP, the FN3 protein was precipitated with saturated ammonium sulfate solution and then mixed with maleimide-modified siRNA duplex dissolved in water immediately prior at a molar ratio of ~1.5:1 FN3-protein:siRNA. After 1 hr incubation at RT or 37° C., reaction was quenched with N-ethyl maleimide (1 mM final NEM concentration in the reaction mixture).

FN3-siRNA conjugates were purified in two steps using IMAC chromatography (HisTrap HP) to remove unreacted siRNA linker, and anion exchange chromatography-Capto-DEAE; to remove unreacted FN3 proteins. FN3-protein-siRNA conjugates were characterized by PAGE, analytical size exclusion chromatography and LC/MS. Concentration of conjugate was calculated based on absorbance of conjugate solution at 260 using a Nanodrop.

FN3-siRNA In Vivo Activity in Mice

Male CD-1 mice were treated with either one or three intravenous doses of ABX1005 (CD71 FN3 domain conjugated to siRNA) at 10 mpk siRNA or ABX1007 (FN3-only control) at an equimolar dose. Tissues were collected two weeks after the final dose and were processed for AHA-1 knockdown analysis by quantitative reverse transcription polymerase chain reaction (RT-PCR). 18S ribosomal RNA was used as the RT-PCR endogenous control gene. Levels of knockdown are compared to vehicle-treated mice. siRNA-mediated knockdown of AHA-1 was observed in all muscle groups analyzed in this study (gastrocnemius, quadriceps, heart) (FIG. 1).

Figure 2:
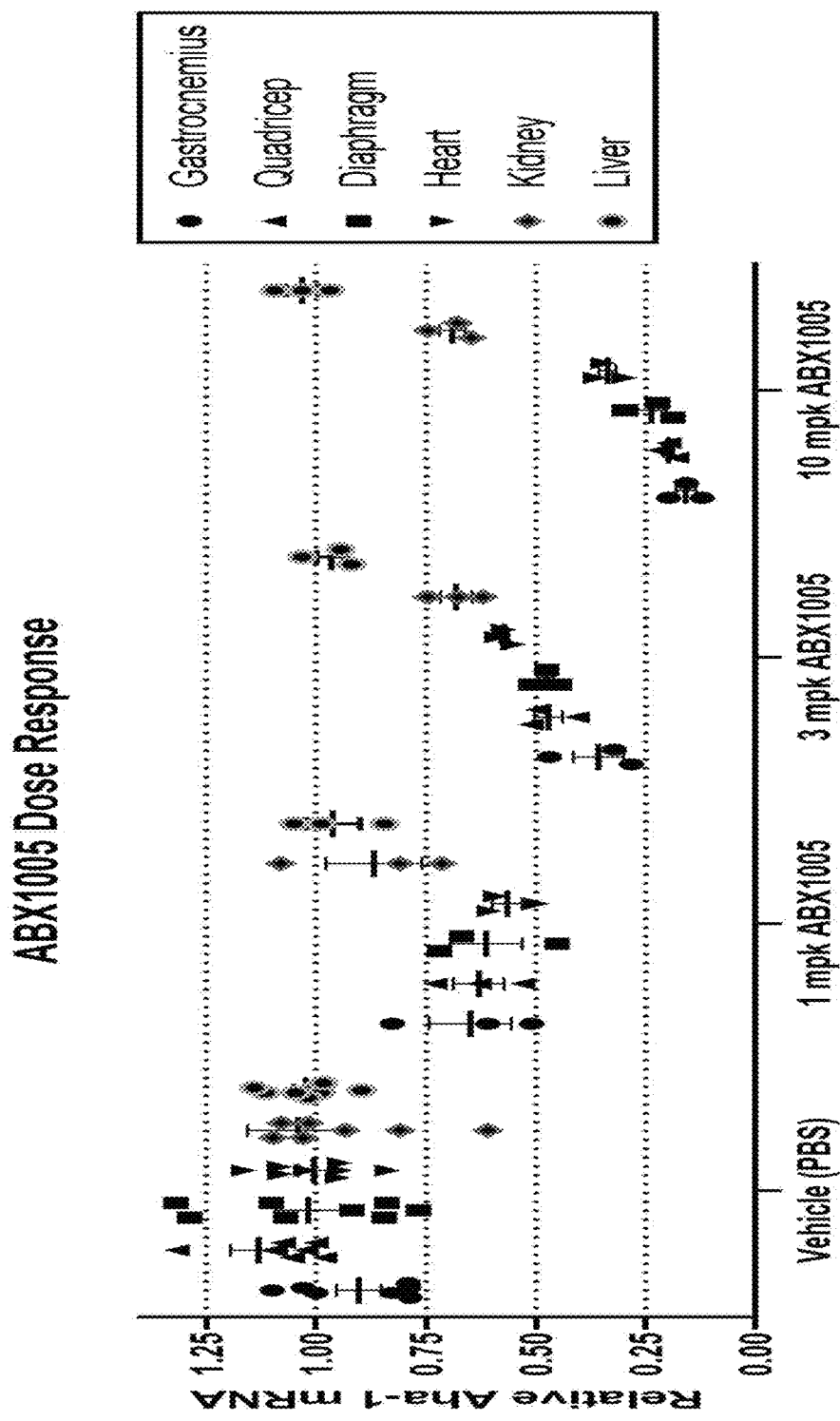
FIG. 2 illustrates dose dependent quantification of AHA1 mRNA in various tissues of C57BL6 mice following dosing of FN3-siRNA conjugate (ABX1005).

Male C57/BL6 mice were treated with a single intravenous dose of ABX1005 at 10mpk, 3mpk, or 1mpk siRNA. Tissues were collected two weeks after a single dose and were processed for AHA-1 knockdown analysis by quantitative reverse transcription polymerase chain reaction (RT-PCR). 18S ribosomal RNA was used as the RT-PCR endogenous control gene. Levels of knockdown are compared to vehicle-treated mice. A dose-dependent knockdown of AHA-1 was observed in all muscle groups analyzed in this study (gastrocnemius, quadriceps, diaphragm, heart) (FIG. 2).

These examples demonstrate that siRNA molecules conjugated to the FN3 domains, such as the FN3 domains that bind to CD71 provided for herein can be used to deliver

TABLE 6

AHA1 siRNA design

| siRNA Pair | SEQ ID NO: | Sense 5-3 | SEQ ID NO: | Antisense 5-3 | Linker |
|---|---|---|---|---|---|
| ABXO 214 | 286 | [mU][*mC][*fU][mC][fG][mU][fG]<br>[mG][fC][mC][fU][mU][fA][mA]<br>[fU][mG][fA][mA][fA]-L | 287 | [VP][*fU][*mU][fC][mA][fU][mU]<br>[fA][mA][fG][mG][fC][mC][fA]<br>[mC][fG][mA][fG][mA][*mU][*mU] | Mal-<br>$C_2H_4C(O)(NH)—(CH_2)_6$ |

Abbreviations Key: (n/N = any nucleotide) mN = 2'-O-methyl residues, fN = 2'-F residues, *= phosphorothioate and (idt) = inverted DT, (VP) 2'-O methyl vinylyl phosphonate uridine siRNA molecules, as well as other active moieties to specific tissues and regulate the expression of a specific target.

Example 8: CD71 FN3 domain siRNA Conjugate Binding Specificity

Figure 3:
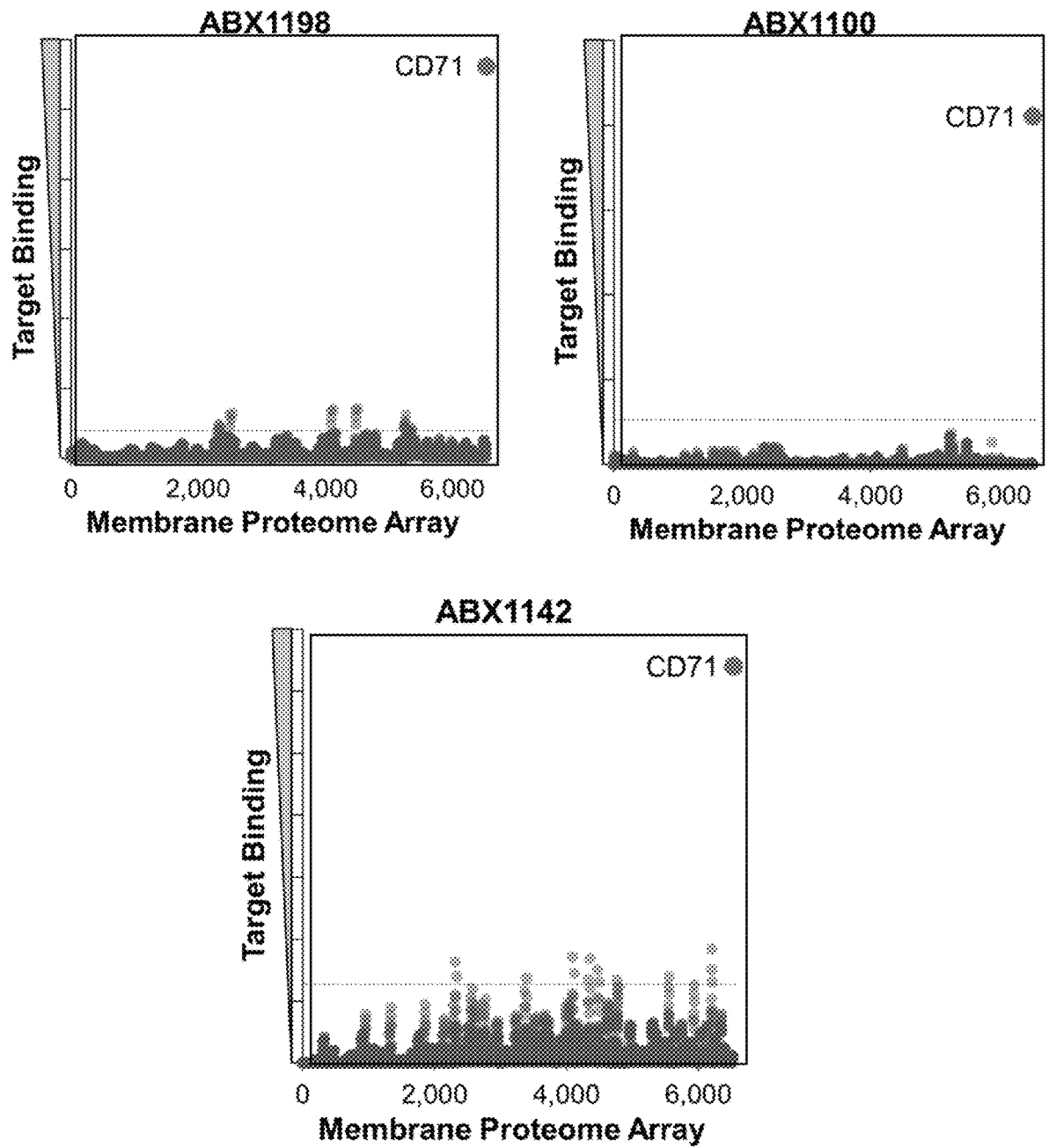
FIG. 3 provides the results of a target binding assay using over 6,000 receptors in the proteome array, wherein the data demonstrates that CD71 is the exclusive binding target of the FN3 domain.

Integral Molecular (www.integralmolecular.com) performed their proprietary Membrane Proteome Array (MPA) assay to profile the specificity of CD71 FN3 domain and CD71 FN3 domain siRNA conjugate against the library of human membrane proteins (FIG. 3). The MPA contains over 6000 human membrane proteins, covering 94% of all single-pass, multi-pass and GPI anchored proteins including GPCRs, ion channels and transporters with each membrane protein uniquely expressed in an avian QT6 cell background. Flow cytometry was used to directly detect FN3 domain binding to membrane proteins individually expressed in unfixed cells.

FN3 domain and FN3 domain-siRNA conjugate were screened at the concentration with optimal signal/background noise ratio, 1.25 ug/ml or 0.31 ug/ml respectively, against the MPA. Membrane protein targets identified in screening were validated using ligand serial dilution on cells uniquely expressing the identified targets.

Example 9: In Vivo Comparison of CD71 Centyrin Conjugate and CD71 Monoclonal Antibody Conjugate Our objective in this study is to determine the duration of pharmacodynamic activity of the tool centyrin-AHA1 conjugate in comparison to a monoclonal antibody R17 conjugated with AHA1 siRNA. In C57BL6/J male mice, a single intravenous bolus of 17.9 mg tool centyrin-AHA1 siRNA conjugate containing 10 mg AHA1 siRNA or 120 mg monoclonal antibody R17 conjugated with AHA1 siRNA containing 10 mg AHA1 siRNA was administered. Gastrocnemius muscle tissue not exceeding 0.5 cm in any direction was collected at time points 2,4 and 8 weeks post dose (N=3/time point) in RNA later to ensure good penetration of RNA later and stored at 4C for 24 hours before storing them at −80C. Total RNA was isolated from the gastrocnemius using Qiagen's RNeasy Fibrous Tissue kit. Using real-time, quantitative PCR, the expression levels of the target AHA1 and the endogenous control, Pgkl were measured. Data were analyzed using the AACt method normalized to control animals dosed with vehicles alone. Gene expression levels of AHA1 and Pgkl for each animal in the treatment groups were presented relative to an average of the 3-vehicle controls. The percentage knockdown of AHA1 mRNA in the tool AHA1-siRNA conjugate treatment groups and in the monoclonal antibody R17 conjugated with AHA1 siRNA treatment groups were measured by subtracting the percentage remaining AHA1 mRNA levels by 100.

Figure 4:
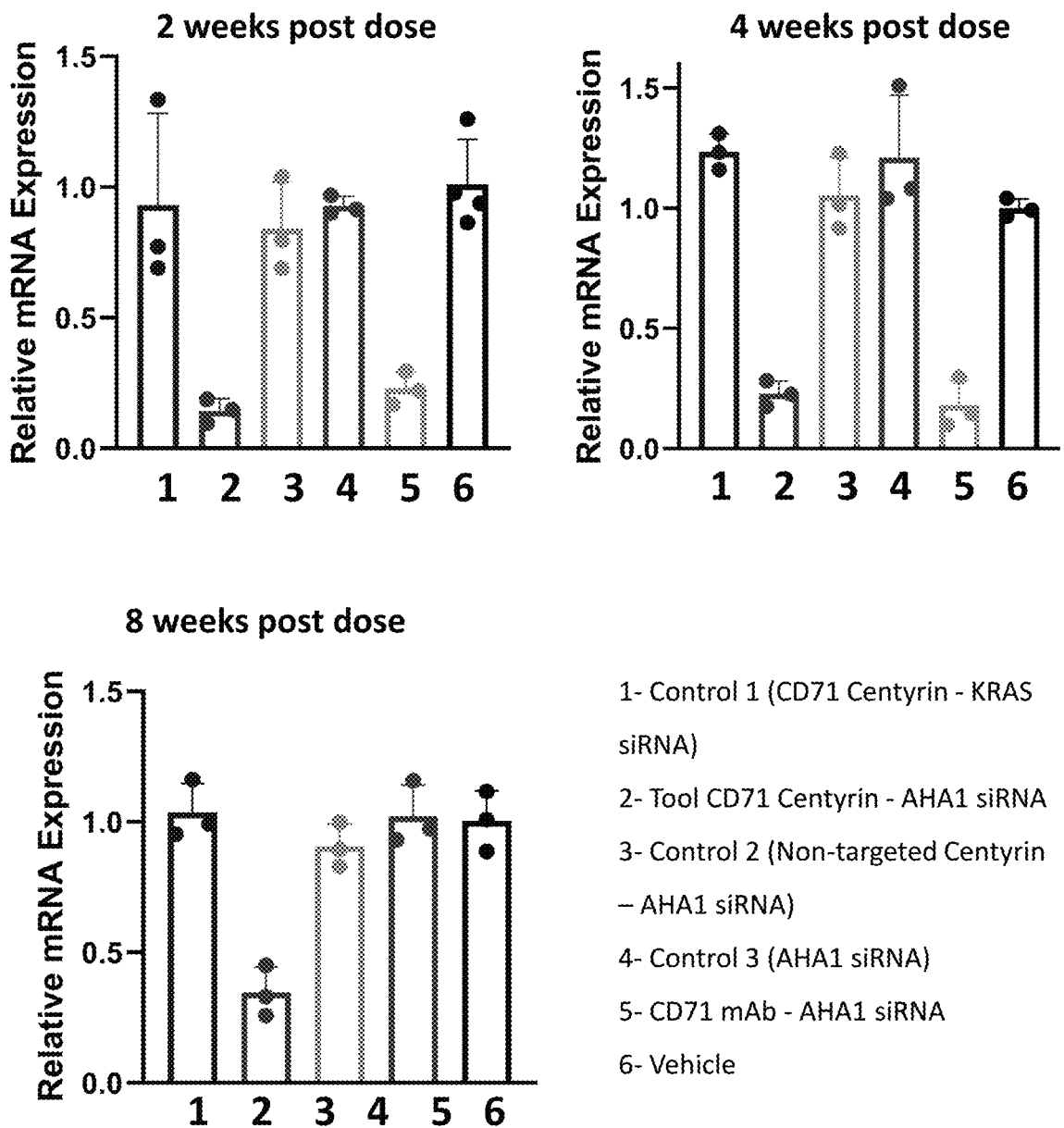
FIG. 4 provides data to demonstrate CD71 Centyrin conjugate drives sustained gene knockdown compared with mAb conjugate at 2 weeks, 4 weeks and 8 weeks post dose.

CD71 Centyrin conjugate drives sustained gene knockdown at fraction of mAb conjugate dose. C57/B6 mice received a single dose (10 mg/kg siRNA) of test conjugate. Relative RNA expression of AHA1 was measured in the gastrocnemius muscle at 2 weeks post dose, 4 weeks post dose and 8 weeks post dose. FIG. 4 and Table 7 present the data demonstrating equivalent activity for the mRNA knockdown in muscle however the CD71 Centyrin conjugate requires far less conjugate dose.

TABLE 7

| | Centyrin - siRNA conjugate | mAb - siRNA conjugate |
|---|---|---|
| AHA knockdown wk 2 | 86% | 77% |
| AHA knockdown wk 4 | 77% | 82% |
| siRNA dose (mg/kg) | 10 mg/kg | 10 mg/kg |
| Conjugate dose (mg/kg) | 18 mg/kg | 120 mg/kg |

Figure 5:
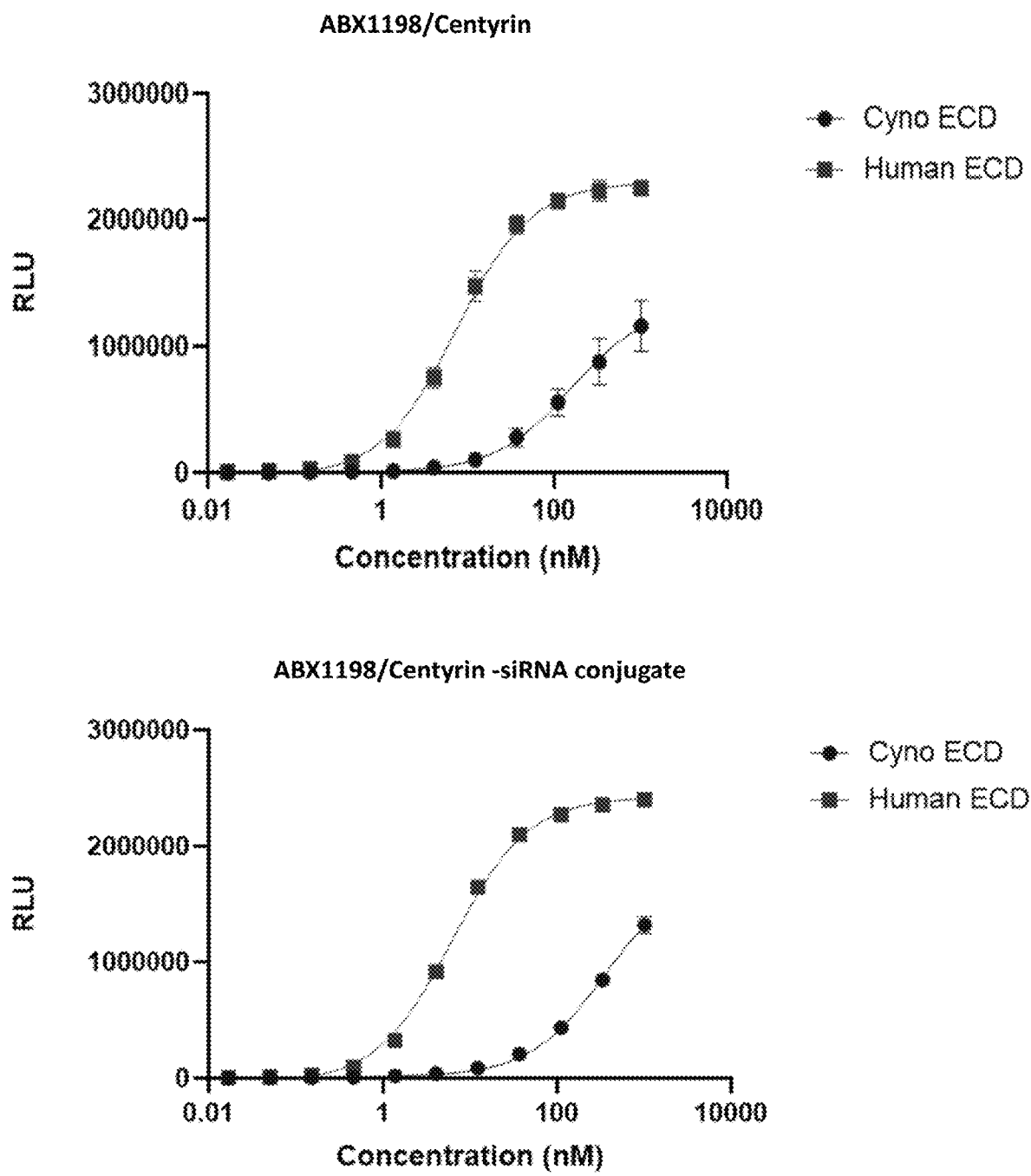
FIG. 5 provides ELISA data demonstrating that Centyrin and Centyrin conjugate actively bind human and cynomolgus monkey CD71.

Example 10: Centyrin-siRNA Conjugates are Active in Cynomolgus Monkey (Macaca fascicularis) Skeletal Muscles and Heart NeutrAvidin coated 96-well plates (Pierce, 15116) were washed with PBS-Tween (0.05%), and blocked for 30 minutes with blocking buffer (Starting Block T20, ThermoFisher 37539). Biotinylated antigen (human CD71-ECD [Acro Biosystems TFR-H8243] or cyno CD71-ECD [Acro Biosystems TFR-C82491]) was immobilized on blocked plates at a concentration of 20 nM, incubated for 1 hour at room temperature. Centyrin samples were diluted in blocking buffer, titrated from 1000 nM to 0.0169 nM, and incubated for 2 hours at room temperature. The plates were washed with PBS-Tween. Anti-Centyrin antibody prepared at 1:2500 in blocking buffer, added to plates, and incubated for 1 hour. The plates were washed with PBS-Tween. Anti-rabbit HRP antibody was prepared at 1:2500 in blocking buffer, added to plates, and incubated for 1 hour. The plates were washed and read-out with ELISA substrate (Roche, 11582950001) on SpectraMax Paradigm. FIG. 5 and Table 8 present the data demonstrating CD71 Centyrin as well as the CD71 Centyrin conjugate effectively bind both human and cyno CD71 and the siRNA conjugate does not interfere with CD71 Centyrin binding.

TABLE 8

| Domain | Centyrin EC50 (nM) | Conjugate EC50 (nM) |
|---|---|---|
| Hu CD71 ECD | 7.4 | 6.3 |
| Cyno CD71 ECD | >150 | >150 |

The purpose of the present study was to determine the pharmacodynamic (PD) activity of centyrin-AHA1 siRNA conjugate in the cynomolgus monkey model. Two male cynomolgus monkeys were treated with either 17.12 mpk centyrin-AHA1 siRNA conjugate containing 10mpk AHA1 siRNA (N=2) or vehicle (N=2) via IV bolus once a week on the right saphenous vein for three weeks. Four weeks post the last dose, skeletal muscle tissues (left and right gastrocnemius, left and right quadriceps, diaphragm, left and right biceps, soleus), smooth muscle tissue (jejunum), left and right heart and non-skeletal muscle tissues (skin, liver and kidney) were harvested and stored in RNA later to ensure good penetration of RNA later and stored at 4C for 24 hours. Total RNA was isolated from these tissues using Qiagen's RNeasy Fibrous Tissue kit. The expression levels of the target AHA1 and endogenous controls (ARL1, ARFGAP2, HPRT1, GAPDH, Gysl) were measured by real-time, quantitative PCR. Data were analyzed using the ΔΔCt method normalized to control animals dosed with vehicles alone. The average of 2 samples (1 biopsy from each side of the tissue) or 1 sample (1 biopsy) was taken for analysis. The percentage knockdown of AHA1 mRNA in the centyrin-AHA1 siRNA conjugate treatment group and in the vehicle group were measured by subtracting the percentage remaining AHA1 mRNA levels by 100. In each tissue, the percentage of AHA1 knockdown is shown in order from the highest to the least amount of AHA1 knockdown.

Figure 6:
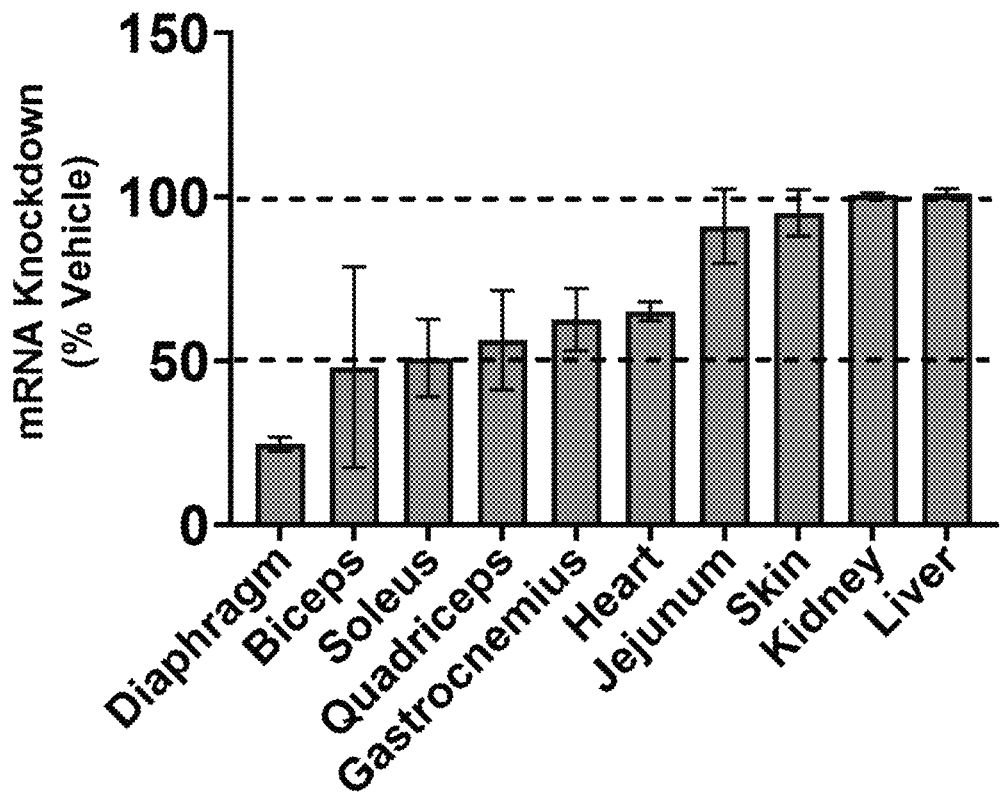
FIG. 6 provides data demonstrating the ability of Centryin-siRNA AHA1 conjugate to effectively knockdown mRNA levels in vivo in cynomolgus monkey muscles and heart.

Centryin-siRNA AHA1 conjugate effectively knockeddown mRNA levels in vivo in cynomolgus monkey muscles and heart, see FIG. 6. Monkeys were dosed at 10 mg/kg siRNA 3 times per week. mRNA levels were assessed at day 28 post three doses.

GENERAL METHODS

Standard methods in molecular biology are described Sambrook, Fritsch and Maniatis (1982 & 1989 2nd Edition, 2001 $3^{rd}$ Edition) *Molecular Cloning, A Laboratory Manual*, Cold Spring Harbor Laboratory Press, Cold Spring Harbor, NY; Sambrook and Russell (2001) *Molecular Cloning, $3^{rd}$ ed.*, Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology*, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17; Sigma-Aldrich, CO (2001) Products for Life Science Research, St. Louis, MO; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, NY; Harlow and Lane, supra). Standard techniques for characterizing ligand/receptor interactions are available (see, e.g., Coligan, et al. (2001) Current Protocols in Immunology, Vol. 4, John Wiley, Inc., New York).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications of the embodiments in addition to those described herein will become apparent to those skilled in the art from the foregoing description. Such modifications are intended to fall within the scope of the appended claims.

The foregoing written specification is considered to be sufficient to enable one skilled in the art to practice the embodiments. Various modifications of the embodiments in addition to those shown and described herein will become apparent to those skilled in the art from the foregoing description and fall within the scope of the appended claims.

What is claimed:

1. A polypeptide comprising the amino acid sequence of SEQ ID NO: 209.

2. The polypeptide of claim 1, wherein the polypeptide is conjugated to a therapeutic agent.

3. The polypeptide of claim 2, wherein the therapeutic agent is a chemotherapeutic agent, a drug, an antibody, a growth inhibitory agent, a toxin, a radioactive isotope, an anti-tubulin agent, a polynucleotide, an siRNA molecule, or sense or antisense strand thereof, an antisense molecule, or a strand thereof, an RNA molecule, a DNA molecule, DNA minor groove binders, DNA replication inhibitors, alkylating agents, antibiotics, antifolates, antimetabolites, chemotherapy sensitizers, topoisomerase inhibitors, or a vinca alkaloid.

4. The polypeptide of claim 2, wherein the therapeutic agent can elicit one or more cytotoxic effects by modulating gene expression, RNA expression or levels, tubulin binding, DNA binding, topoisomerase inhibition, DNA cross linking, chelation, spliceosome inhibition, nicotinamide phosphoribosyltransferase (NAMPT) inhibition, or histone deacetylase (HDAC) inhibition.

5. The polypeptide of claim 1, wherein the polypeptide is coupled to a half-life extending moiety.

6. The polypeptide of claim 5, wherein the half-life extending moiety is an albumin binding molecule, a polyethylene glycol (PEG), albumin, albumin variant, or an Fc region of an immunoglobulin or a fragment thereof.

7. A pharmaceutical composition comprising the polypeptide of claim 1 and a pharmaceutically acceptable carrier.

8. The polypeptide of claim 1, wherein the polypeptide is coupled to an oligonucleotide.

9. A pharmaceutical composition comprising the polypeptide of claim 8 and a pharmaceutically acceptable carrier.

10. The polypeptide of claim 1, wherein the polypeptide is coupled to an siRNA molecule, wherein the siRNA molecule comprises a sense strand and an antisense strand.

11. A pharmaceutical composition comprising the polypeptide of claim 10 and a pharmaceutically acceptable carrier.

12. The polypeptide of claim 10, wherein the polypeptide is coupled to the sense strand of the siRNA molecule.

13. The polypeptide of claim 12, wherein the polypeptide is coupled to the 3' end of the sense strand of the siRNA molecule.

14. A pharmaceutical composition comprising the polypeptide of claim 13 and a pharmaceutically acceptable carrier.

15. The polypeptide of claim 12, wherein the polypeptide is coupled to the 5' end of the sense strand of the siRNA molecule.

16. A pharmaceutical composition comprising the polypeptide of claim 15 and a pharmaceutically acceptable carrier.

17. A pharmaceutical composition comprising the polypeptide of claim 12 and a pharmaceutically acceptable carrier.

18. The polypeptide of claim 1, wherein the polypeptide is coupled to an antisense molecule.

19. A pharmaceutical composition comprising the polypeptide of claim 18 and a pharmaceutically acceptable carrier.

20. The polypeptide of claim 1, wherein the polypeptide is coupled to a DNA molecule.

* * * * *

SEQUENCE LISTING

```
<160> NUMBER OF SEQ ID NOS: 311

<210> SEQ ID NO 1
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Thr Tyr Ile Glu Ala Val Val Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Gly Ile Ser Gly Val Lys Gly Gly His Asn
```

```
                65                  70                  75                  80
Ser Met Pro Leu Ser Ala Ile Phe Thr Thr
                85                  90

<210> SEQ ID NO 2
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
                20                  25                  30

Met Ile Asn Tyr Ser Glu Leu Phe Trp Met Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Val Val Arg Ile Lys Gly Val Lys Gly Gly Lys Gly
65                  70                  75                  80

Ser Trp Pro Leu His Ala His Phe Thr Thr
                85                  90

<210> SEQ ID NO 3
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asn Ile Glu Tyr Ala Glu Thr Arg Trp Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Val Val Pro Ile Asp Gly Val Lys Gly Gly Ile Ala
65                  70                  75                  80

Ser Lys Pro Leu Ser Ala Ile Phe Thr Thr
                85                  90

<210> SEQ ID NO 4
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
                20                  25                  30
```

```
Leu Ile Thr Tyr Arg Asp Gln Ile Phe Ala Gly Glu Val Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Pro Val Trp Ile Gln Gly Val Lys Gly Gly Ser Pro
65                  70                  75                  80

Ser Ala Pro Leu Ser Ala Glu Ser Thr Thr
                85                  90

<210> SEQ ID NO 5
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Trp Val Tyr Ile Trp Gly Val Lys Gly Gly Lys Pro
65                  70                  75                  80

Ser Phe Pro Leu Arg Ala Gly Phe Thr Thr
                85                  90

<210> SEQ ID NO 6
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Ile Tyr Met Glu Thr Phe Ser Arg Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Arg Val Pro Ile Gly Gly Val Lys Gly Gly Ser Ser
65                  70                  75                  80

Ser Cys Pro Leu Ser Ala Ile Phe Thr Thr
                85                  90

<210> SEQ ID NO 7
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 7

Met Leu Pro Ala Pro Lys Asn Leu Val Val Ser Asp Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Trp Ile Gln Gly Val Lys Gly Gly Ser Pro
65                  70                  75                  80

Ser Ala Pro Leu Ser Ala Glu Phe Thr Thr
                85                  90

<210> SEQ ID NO 8

<400> SEQUENCE: 8

000

<210> SEQ ID NO 9

<400> SEQUENCE: 9

000

<210> SEQ ID NO 10
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Lys Ile Ala Tyr Ile Glu Thr Ala Thr Arg Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Val Val Pro Ile Pro Gly Val Lys Gly Gly Asn Thr
65                  70                  75                  80

Ser Ser Pro Leu Ser Ala Ile Phe Thr Thr
                85                  90

<210> SEQ ID NO 11

<400> SEQUENCE: 11

000

<210> SEQ ID NO 12
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Pro Tyr Ala Glu Pro Ser Pro Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly His Leu
65                  70                  75                  80

Ser Asp Pro Leu Ser Ala Ile Ser Thr Thr
                85                  90

<210> SEQ ID NO 13
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Ala Tyr Pro Glu Asp Gly Phe Arg Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Pro Ile Leu Gly Val Lys Gly Gly Gly Gly
65                  70                  75                  80

Ser Gly Pro Leu Ser Ala Ile Phe Thr Thr
                85                  90

<210> SEQ ID NO 14
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Tyr Tyr Val Glu Asn Val Trp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Glu Val Ile Ile Gly Val Lys Gly Gly Gln Cys
65                  70                  75                  80

Ser Arg Pro Leu Ser Ala Ile Phe Thr Thr
                85                  90

<210> SEQ ID NO 15
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Leu Pro Ala Pro Lys Asn Leu Val Val Ser Arg Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Leu
        35                  40                  45

Thr Val Pro Gly Ser Glu Arg Ser Tyr Asp Leu Thr Gly Leu Lys Pro
    50                  55                  60

Gly Thr Glu Cys Pro Val Trp Ile Gln Gly Val Lys Gly Gly Ser Pro
65                  70                  75                  80

Ser Ala Pro Leu Ser Ala Glu Phe Thr Thr
                85                  90

<210> SEQ ID NO 16
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gly Ile Ala Tyr Arg Glu Phe Arg Pro Ser Gly Glu Ala Ile Val Leu
        35                  40                  45

Thr Val Pro Gly Ser Glu Arg Ser Tyr Asp Leu Thr Val Glu Thr Gly
    50                  55                  60

Tyr Arg Asn Glu Val Val Ile Cys Gly Val Lys Gly Gly Pro Trp Ser
65                  70                  75                  80

Gly Pro Leu Ser Ala Ile Phe Thr Thr
                85

<210> SEQ ID NO 17
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Leu Tyr Thr Glu Cys Val Tyr Arg Gly Glu Ala Ile Val Leu
        35                  40                  45

Thr Val Pro Gly Ser Glu Arg Ser Tyr Asp Leu Thr Gly Leu Lys Pro

```
                50                  55                  60
Gly Thr Glu Tyr His Val Pro Ile Thr Gly Val Lys Gly Gly Gly
 65                  70                  75                  80

Ser Trp Pro Leu Ser Ala Ile Phe Thr Thr
                 85                  90

<210> SEQ ID NO 18
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Asn Ile Met Tyr His Glu Ile Ile Tyr Val Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Pro Val Pro Ile Glu Gly Val Lys Gly Gly Gly Thr
 65                  70                  75                  80

Ser Gly Pro Leu Ser Ala Ile Phe Thr Thr
                 85                  90

<210> SEQ ID NO 19
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Ala Ile Thr Tyr Thr Glu Ala Ala Leu Cys Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Pro Val Pro Ile Asn Gly Val Lys Gly Gly Gly Thr
 65                  70                  75                  80

Ser Gly Pro Leu Ser Ala Ile Phe Thr Thr
                 85                  90

<210> SEQ ID NO 20
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Leu Pro Ala Pro Lys Asn Leu Val Val Ala Arg Val Thr Glu Asp
  1               5                  10                  15
```

Ser Ala Arg Leu Ser Trp Thr Ala Pro Asp Ala Ala Ile Asp Ser Phe
            20                  25                  30

Pro Ile Asp Tyr Ser Glu Tyr Trp Gly Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Pro Val Leu Ile Thr Gly Val Lys Gly Gly Tyr Arg
 65                  70                  75                  80

Ser Gly Pro Leu Ser Ala Ile Phe Thr Thr
                 85                  90

<210> SEQ ID NO 21
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
            20                  25                  30

Ser Ile Arg Tyr Asn Glu Phe Ile Val Ala Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Asp Val Pro Ile Ala Gly Val Lys Gly Gly Gly Ala
 65                  70                  75                  80

Ser Trp Pro Leu Ser Ala Ile Val Thr Thr
                 85                  90

<210> SEQ ID NO 22
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
            20                  25                  30

Trp Tyr Leu Glu Leu Gln Phe Ala Gly Glu Ala Ile Val Leu Thr Val
            35                  40                  45

Pro Gly Ser Glu Arg Ser Tyr Asp Leu Thr Gly Leu Lys Pro Gly Thr
 50                  55                  60

Glu Tyr Asn Val Pro Ile Thr Gly Val Lys Gly Gly Ile Ile Ser Phe
 65                  70                  75                  80

Pro Leu Ser Ala Ile Phe Thr Thr
                 85

<210> SEQ ID NO 23
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Leu Pro Ala Pro Lys Asn Leu Val Val Ser Arg Val Thr Glu Asp

Ala Ile Trp Tyr His Glu Trp Tyr Gly Asp Gly Glu Ala Ile Val Leu
            35                  40                  45

Thr Val Pro Gly Ser Glu Arg Ser Tyr Asp Leu Thr Gly Pro Lys Pro
    50                  55                  60

Gly Thr Glu Tyr Arg Val Arg Ile Ser Gly Val Lys Gly Gly Phe Glu
65                  70                  75                  80

Ser Gly Pro Leu Ser Ala Ile Phe Thr Thr
                85                  90

<210> SEQ ID NO 24
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Met Ile Arg Tyr Gln Glu Gly Thr Arg Trp Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Ile Val Met Ile Ala Gly Val Lys Gly Gly Gln Ile
65                  70                  75                  80

Ser Leu Pro Leu Ser Ala Ile Phe Thr Thr
                85                  90

<210> SEQ ID NO 25
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Trp Tyr Leu Glu Lys Ser Tyr Gln Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Val Val Pro Ile Ile Gly Val Lys Gly Gly Arg Asp
65                  70                  75                  80

Ser Cys Pro Leu Ser Ala Ile Phe Thr Thr
                85                  90

<210> SEQ ID NO 26
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
                20                  25                  30

Leu Ile Thr Tyr Arg Glu Gln Ile Phe Ala Gly Glu Val Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Val Trp Ile Gln Gly Val Lys Gly Gly Ser Pro
65                  70                  75                  80

Ser Ala Pro Leu Ser Ala Glu Phe Thr Thr
                85                  90

<210> SEQ ID NO 27
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Arg Ile Ser Tyr Ala Glu Thr Val Arg Gln Gly Glu Ala Ile Val Leu
            35                  40                  45

Thr Val Pro Gly Ser Glu Arg Ser Tyr Asp Leu Thr Val Glu Thr Gly
        50                  55                  60

Tyr Arg Asn Trp Val Met Ile Leu Gly Val Lys Gly Pro Gly Ser
65                  70                  75                  80

Leu Pro Leu Ser Ala Ile Phe Thr Thr
                85

<210> SEQ ID NO 28
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Leu Pro Ala Pro Lys Asn Leu Val Val Ser Glu Val Thr Glu Asp
1               5                   10                  15

Ser Ala Arg Leu Ser Trp Gln Gly Val Val Arg Ala Phe Asp Ser Phe
                20                  25                  30

Leu Ile Thr Tyr Arg Glu Gln Ile Phe Ala Gly Glu Val Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Val Trp Ile Gln Gly Val Lys Gly Gly Ser Pro
65                  70                  75                  80

Ser Ala Pro Leu Ser Ala Glu Phe Thr Thr
                85                  90

```
<210> SEQ ID NO 29
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Glu Tyr Trp Glu Ala Val Gly Phe Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Gly Ile Tyr Gly Val Lys Gly Gly Tyr Leu
65                  70                  75                  80

Ser Ala Pro Leu Ser Ala Ile Phe Thr Thr
                85                  90

<210> SEQ ID NO 30
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ile Ile His Tyr Val Glu Gln Gln Leu Ile Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Pro Ile Thr Gly Val Lys Gly Gly Ala Cys
65                  70                  75                  80

Ser Trp Pro Leu Ser Ala Ile Phe Thr Thr
                85                  90

<210> SEQ ID NO 31
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Glu Tyr Ser Glu His Pro Ile Asp Gly Glu Ala Ile Pro Leu
        35                  40                  45

Phe Val Pro Gly Ser Glu Arg Ser Tyr Asp Leu Thr Gly Leu Lys Pro
```

```
                    50                  55                  60
Gly Thr Glu Tyr Tyr Val Arg Ile His Gly Val Lys Gly Gly Trp Phe
 65                  70                  75                  80

Ser His Pro Leu Trp Ala Phe Phe Thr Thr
                     85                  90

<210> SEQ ID NO 32
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Leu Pro Ala Pro Lys Asn Leu Val Val Ser Arg Val Thr Glu Asp
  1               5                  10                  15

Ser Ala Arg Leu Ser Trp Gln Gly Val Ala Arg Ala Phe Asp Ser Phe
                 20                  25                  30

Leu Ile Thr Tyr Arg Glu Gln Ile Phe Ala Gly Glu Val Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Gly Val Thr Ile Ala Gly Val Lys Gly Gly Trp Arg
 65                  70                  75                  80

Ser Lys Pro Leu Asn Ala Glu Ser Thr Thr
                     85                  90

<210> SEQ ID NO 33
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Gly Ile Ala Tyr Val Glu Ser Tyr Trp Tyr Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Asn Val Pro Ile Tyr Gly Val Lys Gly Gly Asp Gly
 65                  70                  75                  80

Ser Gly Pro Leu Ser Ala Ile Phe Thr Thr
                     85                  90

<210> SEQ ID NO 34
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Leu Pro Ala Pro Lys Asn Leu Val Val Ser Arg Val Thr Glu Asp
  1               5                  10                  15
```

```
Ser Ala Arg Leu Ser Trp Thr Ala Pro Asp Ala Ala Phe Asp Ser Phe
            20                  25                  30

Tyr Ile Thr Tyr Val Glu Leu Asn Leu Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Pro Ile Leu Gly Val Lys Gly Gly Ser Leu
65                  70                  75                  80

Ser Gln Pro Leu Ser Ala Ile Phe Thr Thr
                85                  90

<210> SEQ ID NO 35
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Ser Tyr Ile Glu Ser Ile Ala Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Ala Ile Val Gly Val Lys Gly Gly Pro Phe
65                  70                  75                  80

Ser Trp Ser Leu Ser Ala Ile Val Thr Thr
                85                  90

<210> SEQ ID NO 36
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Pro
        35                  40                  45

Thr Val Pro Gly Ser Glu Arg Ser Tyr Asp Leu Thr Gly Leu Lys Pro
    50                  55                  60

Gly Thr Glu Tyr Pro Val Pro Ile Ala Gly Val Lys Gly Gly Gly Pro
65                  70                  75                  80

Ser Ala Pro Leu Ser Ala Ile Phe Thr Thr
                85                  90

<210> SEQ ID NO 37
<211> LENGTH: 90
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 37

Met Leu Pro Ala Pro Lys Asn Leu Val Val Ser Arg Val Thr Glu Asp
1               5                   10                  15

Ser Ala Arg Leu Ser Trp Thr Thr Pro Asp Ala Ala Phe Asp Ser Phe
            20                  25                  30

Pro Ile Tyr Tyr Trp Glu Val Thr Ile Thr Gly Glu Ala Ile Tyr Leu
        35                  40                  45

Ser Val Pro Gly Ser Glu Arg Ser Tyr Asp Leu Thr Gly Leu Lys Pro
    50                  55                  60

Gly Thr Glu Tyr Pro Val Asp Ile Pro Gly Val Lys Gly Gly Ala Ala
65                  70                  75                  80

Ser Pro Pro Leu Ser Ala Ile Phe Thr Thr
                85                  90

<210> SEQ ID NO 38
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Leu Tyr Leu Glu His Thr Val Arg Ser Glu Ala Ile Val Leu
        35                  40                  45

Thr Val Pro Gly Ser Glu Arg Ser Tyr Asp Leu Thr Asp Leu Lys Pro
    50                  55                  60

Gly Thr Glu Tyr Cys Val Pro Ile Asp Gly Val Lys Gly Gly Leu Arg
65                  70                  75                  80

Ser Arg Pro Leu Ser Ala Ile Phe Thr Thr
                85                  90

<210> SEQ ID NO 39
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Pro Tyr Thr Glu Pro Pro Asp Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Leu Val Thr Ile Leu Gly Val Lys Gly Gly Ser Met
65                  70                  75                  80
```

-continued

Ser Val Pro Leu Ser Ala Ile Phe Thr Thr
                85                  90

<210> SEQ ID NO 40
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Asp Tyr Trp Glu Asn Arg Cys Pro Gly Glu Ala Ile Val Leu
                35                  40                  45

Thr Val Pro Gly Ser Glu Arg Ser Tyr Asp Leu Thr Gly Leu Lys Pro
            50                  55                  60

Gly Thr Glu Tyr Cys Val Trp Ile Ser Gly Val Lys Gly Tyr Ser
65              70                  75                  80

Ser Trp Pro Leu Ser Ala Ile Phe Thr Thr
                85                  90

<210> SEQ ID NO 41
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Leu Pro Ala Pro Lys Asn Leu Val Val Ser Arg Val Thr Glu Asp
1               5                   10                  15

Ser Ala Arg Leu Ser Trp Gln Gly Val Ala Arg Ala Phe Asp Ser Phe
                20                  25                  30

Leu Ile Thr Tyr Arg Glu Gln Ile Phe Ala Gly Glu Val Ile Val Leu
                35                  40                  45

Thr Val Pro Gly Ser Glu Arg Ser Tyr Asp Leu Thr Gly Leu Lys Pro
            50                  55                  60

Gly Thr Glu Tyr Pro Val Trp Ile Gln Gly Val Lys Gly Gly His Leu
65              70                  75                  80

Ser Asp Pro Leu Ser Ala Ile Val Thr Thr
                85                  90

<210> SEQ ID NO 42
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Leu Ile Pro Tyr Ala Glu Thr Ser Pro Ser Gly Glu Ala Ile Val Leu

```
                35                  40                  45
Thr Val Pro Gly Ser Glu Arg Ser Tyr Asp Leu Thr Gly Leu Lys Pro
 50                  55                  60
Gly Thr Glu Tyr Ser Val Leu Ile His Gly Val Lys Gly Gly Asp Tyr
65                  70                  75                  80
Ser Glu Pro Leu Ser Ala Ile Phe Thr Thr
                85                  90

<210> SEQ ID NO 43
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Leu Pro Ala Pro Lys Asn Leu Val Val Ser Arg Val Thr Glu Asp
1               5                   10                  15
Ser Ala Arg Leu Ser Trp Thr Ala Pro Asp Ala Ala Phe Asp Ser Phe
                20                  25                  30
Met Ile Val Tyr Glu Tyr Thr Arg Phe Gly Glu Ala Ile Val Leu
                35                  40                  45
Thr Val Pro Gly Ser Glu Arg Ser Tyr Asp Leu Thr Gly Leu Lys Pro
 50                  55                  60
Gly Thr Glu Tyr Thr Val Pro Ile Asp Gly Val Lys Gly Gly Gly Arg
65                  70                  75                  80
Ser Ser Pro Leu Ser Ala Ile Phe Thr Thr
                85                  90

<210> SEQ ID NO 44
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Leu Pro Ala Pro Lys Asn Leu Val Val Ser Arg Val Thr Glu Asp
1               5                   10                  15
Ser Ala Arg Leu Ser Trp Thr Ala Pro Asp Ala Ala Phe Asp Ser Phe
                20                  25                  30
Phe Ile Pro Tyr Ala Glu Pro Ser Pro Thr Gly Glu Ala Ile Val Leu
                35                  40                  45
Thr Val Pro Gly Ser Glu Arg Ser Tyr Asp Leu Thr Gly Leu Lys Pro
 50                  55                  60
Gly Thr Glu Tyr Ser Val Leu Ile His Gly Val Lys Gly Gly His Leu
65                  70                  75                  80
Ser Asp Pro Leu Ser Ala Ile Val Thr Thr
                85                  90

<210> SEQ ID NO 45
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
                20                  25                  30

Leu Ile Thr Tyr Arg Glu Gln Ile Phe Ala Gly Glu Val Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Val Trp Ile Gln Gly Val Lys Gly Gly Ser Pro
65                  70                  75                  80

Ser Ala Pro Leu Ser Ala Glu Phe Thr Thr
                85                  90

<210> SEQ ID NO 46
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ile Ile Pro Tyr Ala Glu Val Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Lys Leu
65                  70                  75                  80

Ser Leu Pro Leu Ser Ala Ile Phe Thr Thr
                85                  90

<210> SEQ ID NO 47
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Gly Ile Val Tyr Leu Glu Met Met Val Thr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asp Val Pro Ile Leu Gly Val Lys Gly Gly Thr Arg
65                  70                  75                  80

Ser Val Pro Leu Ser Ala Ile Phe Thr Thr
                85                  90

<210> SEQ ID NO 48

<211> LENGTH: 94
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 48

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Tyr Tyr Glu Glu Gly Tyr Leu Glu Tyr Tyr Ser Gly Glu
        35                  40                  45

Ala Ile Val Leu Thr Val Pro Gly Ser Glu Arg Ser Tyr Asp Leu Thr
50                  55                  60

Gly Leu Lys Pro Gly Thr Glu Tyr Tyr Val Gly Ile Val Gly Val Lys
65                  70                  75                  80

Gly Gly Gly Leu Ser Gly Pro Leu Ser Ala Ile Ser Thr Thr
                85                  90

<210> SEQ ID NO 49
<211> LENGTH: 90
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 49

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Ala Tyr Ala Glu Pro Arg Pro Asp Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Ser Val Leu Ile His Gly Val Lys Gly Gly Asp Trp
65                  70                  75                  80

Ser Leu Pro Leu Ser Ala Ile Phe Thr Thr
                85                  90

<210> SEQ ID NO 50
<211> LENGTH: 91
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 50

Met Ser Leu Pro Ala Pro Lys Asn Leu Val Val Ser Arg Val Thr Glu
1               5                   10                  15

Asp Ser Ala Arg Leu Ser Trp Thr Ala Pro Asp Ala Ala Phe Asp Ser
            20                  25                  30

Phe Thr Ile His Tyr Arg Glu Phe Gln Leu Ser Gly Glu Ala Ile Val
        35                  40                  45

Leu Thr Val Pro Gly Ser Glu Arg Ser Tyr Asp Leu Thr Gly Leu Lys
50                  55                  60

Pro Gly Thr Glu Tyr Asp Val Pro Ile Glu Gly Val Lys Gly Gly Pro
65                  70                  75                  80

Gly Ser Arg Pro Leu Ser Ala Ile Phe Thr Thr
                85                  90

<210> SEQ ID NO 51
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Leu
        35                  40                  45

Thr Val Pro Gly Ser Glu Cys Ser Tyr Asp Leu Thr Gly Leu Lys Pro
    50                  55                  60

Gly Thr Glu Tyr Pro Val Trp Ile Gln Gly Val Lys Gly Gly Ser Pro
65                  70                  75                  80

Ser Ala Pro Leu Ser Ala Glu Phe Thr Thr
                85                  90

<210> SEQ ID NO 52
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Asp Tyr Asp Glu Leu Ala Ile Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Arg Ile Pro Gly Val Lys Gly Gly Met Pro
65                  70                  75                  80

Ser Leu Pro Leu Ser Ala Ile Val Thr Thr
                85                  90

<210> SEQ ID NO 53
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Leu Pro Ala Pro Glu Asn Leu Val Val Ser Glu Val Thr Glu Asp
1               5                   10                  15

Ser Ala Arg Leu Ser Trp Gln Gly Val Ala Arg Ala Phe Asp Ser Phe

```
                    20                  25                  30

Leu Ile Thr Tyr Arg Glu Gln Ile Phe Ala Gly Glu Val Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Val Trp Ile Gln Gly Val Lys Gly Gly Ser Pro
65                  70                  75                  80

Ser Ala Pro Leu Ser Ala Glu Ser Thr Thr
                85                  90

<210> SEQ ID NO 54
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Ala Tyr Gly Glu His Ile Val Ile Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Met Val Pro Ile Ala Gly Val Lys Gly Gly Pro Ile
65                  70                  75                  80

Ser Leu Pro Leu Ser Ala Ile Phe Thr Thr
                85                  90

<210> SEQ ID NO 55
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Pro Tyr Ala Glu Pro Ser Pro Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly His Leu
65                  70                  75                  80

Ser Asp Pro Leu Ser Ala Ile Phe Thr Thr
                85                  90

<210> SEQ ID NO 56
<211> LENGTH: 90
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 56

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Gly Tyr Val Glu Leu Val Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Leu Ile Pro Gly Val Lys Gly Gly Ser Leu
65                  70                  75                  80

Ser Arg Pro Leu Ser Ala Ile Phe Thr Thr
                85                  90

<210> SEQ ID NO 57
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Pro Tyr Ala Glu Leu Ser Arg Asn Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Leu Ile His Gly Val Lys Gly Gly Cys Leu
65                  70                  75                  80

Ser Asp Pro Leu Ser Ala Ile Phe Thr Thr
                85                  90

<210> SEQ ID NO 58
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Glu Tyr Leu Glu Leu Ser Arg His Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Met Ile Phe Gly Val Lys Gly Gly Gly Pro
65                  70                  75                  80

Ser Lys Pro Leu Ser Ala Ile Phe Thr Thr
                85                  90

<210> SEQ ID NO 59
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Tyr Asn Glu Val His Trp Ile Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Phe Val Gly Ile Tyr Gly Val Lys Gly His Trp Ser Lys
65                  70                  75                  80

Pro Leu Ser Ala Ile Phe Thr Thr
                85

<210> SEQ ID NO 60
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Asp Tyr Asp Glu Leu Ala Ile Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Arg Ile Pro Gly Val Lys Gly Gly Met Pro
65                  70                  75                  80

Ser Leu Pro Leu Ser Ala Ile Val Thr Thr
                85                  90

<210> SEQ ID NO 61
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gln Ile Val Tyr Ser Glu Leu Trp Ile Lys Gly Glu Ala Ile Val Leu
        35                  40                  45

```
Thr Val Pro Gly Ser Glu Arg Ser Tyr Asp Leu Thr Gly Leu Lys Pro
    50                  55                  60
Gly Thr Glu Tyr Gln Val Pro Ile Pro Gly Val Lys Gly Gly Arg Asn
 65                  70                  75                  80
Ser Phe Pro Leu Ser Ala Ile Phe Thr Thr
                85                  90

<210> SEQ ID NO 62
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Leu Pro Ala Pro Lys Asn Leu Val Val Ser Arg Val Thr Glu Asp
 1               5                  10                  15
Ser Ala Arg Leu Ser Trp Thr Ala Pro Asp Ala Ala Phe Asp Ser Phe
                20                  25                  30
Lys Ile Arg Tyr Thr Glu Thr Arg Ser Ile Gly Glu Ala Ile Val Leu
            35                  40                  45
Thr Val Pro Gly Ser Glu Arg Ser Tyr Asp Leu Thr Gly Leu Lys Pro
    50                  55                  60
Gly Thr Glu Tyr Cys Val Pro Ile Gly Gly Val Lys Gly Gly Asp Ser
 65                  70                  75                  80
Ser Trp Pro Leu Ser Ala Ile Ser Thr Thr
                85                  90

<210> SEQ ID NO 63
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Leu Pro Ala Pro Lys Asn Leu Val Val Ser Arg Val Thr Glu Asp
 1               5                  10                  15
Ser Ala Arg Leu Ser Trp Thr Ala Pro Asp Ala Ala Phe Asp Ser Phe
                20                  25                  30
Cys Ile Ser Tyr Tyr Glu Arg Met Gly Arg Gly Glu Ala Ile Val Leu
            35                  40                  45
Thr Val Pro Gly Ser Glu Arg Ser Tyr Asp Leu Thr Gly Leu Lys Pro
    50                  55                  60
Gly Thr Glu Tyr Met Val Tyr Ile Phe Gly Val Lys Gly Gly Leu Asn
 65                  70                  75                  80
Ser Leu Pro Leu Ser Ala Ile Phe Thr Thr
                85                  90

<210> SEQ ID NO 64
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Leu Pro Ala Pro Lys Asn Leu Val Val Ser Arg Val Thr Glu Asp
```

```
                1               5                  10                  15
Ser Ala Arg Leu Ser Trp Thr Ala Pro Asp Ala Ala Phe Asp Ser Phe
                20                  25                  30

Tyr Ile Val Tyr Ala Glu Pro Ile Pro Asn Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Arg Asn
65                  70                  75                  80

Ser Asp Pro Leu Ser Ala Ile Phe Thr Thr
                85                  90
```

<210> SEQ ID NO 65
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Met Leu Pro Ala Pro Lys Asn Leu Val Val Ser Arg Val Thr Lys Asp
1               5                   10                  15

Ser Ala Arg Leu Ser Trp Thr Ala Pro Asp Ala Ala Phe Asp Ser Phe
                20                  25                  30

Pro Ile Ala Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90
```

<210> SEQ ID NO 66
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Asp Tyr Asp Glu Pro Arg Ser Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Arg Val Phe Ile Trp Gly Ile Lys Gly Gly Asp Thr
65                  70                  75                  80

Ser Phe Pro Leu Ser Ala Ile Phe Thr Thr
                85                  90
```

<210> SEQ ID NO 67
<211> LENGTH: 88
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 67

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Leu Tyr Ala Glu Gln Ala Gln Phe Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Ile Thr Gly Val Lys Gly Gly Thr Arg Ser Gly
65                  70                  75                  80

Pro Leu Ser Ala Ile Ser Thr Thr
                85

<210> SEQ ID NO 68
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ile Ile Pro Tyr Ala Glu Val Arg Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly His Leu
65                  70                  75                  80

Ser Asp Pro Leu Ser Ala Ile Ser Thr Thr
                85                  90

<210> SEQ ID NO 69
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ala Tyr Glu Glu Thr Ala Thr Ser Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Gly Val Glu Ile Glu Gly Val Lys Gly Gly Ala Arg
65                  70                  75                  80
```

```
Ser Arg Pro Leu Tyr Ala Asp Phe Thr Thr
                85                  90

<210> SEQ ID NO 70
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Leu Pro Ala Pro Lys Asn Leu Val Val Ser Arg Val Thr Glu Asp
1               5                   10                  15

Ser Ala Arg Leu Ser Trp Gln Gly Val Ala Arg Ala Phe Asp Ser Phe
                20                  25                  30

Leu Ile Thr Tyr Arg Glu Gln Ile Phe Ala Gly Glu Val Ile Val Leu
                35                  40                  45

Thr Val Pro Gly Ser Glu Arg Ser Tyr Asp Leu Thr Gly Leu Lys Pro
        50                  55                  60

Gly Thr Glu Tyr Pro Val Trp Ile Gln Gly Val Lys Gly Gly Asp Leu
65                  70                  75                  80

Ser Asn Pro Leu Ser Ala Ile Phe Thr Thr
                85                  90

<210> SEQ ID NO 71
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Ser Tyr Leu Glu Leu Ser Leu Tyr Gly Glu Ala Ile Val Leu
                35                  40                  45

Thr Val Pro Gly Ser Glu Arg Ser Tyr Asp Leu Thr Gly Leu Lys Pro
        50                  55                  60

Gly Thr Glu Tyr Pro Val Gly Ile Ala Gly Val Lys Gly Gly Val Val
65                  70                  75                  80

Ser Arg Pro Leu Ser Ala Ile Phe Thr Thr
                85                  90

<210> SEQ ID NO 72
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30
```

```
Thr Ile Gly Tyr Arg Glu Trp Tyr Trp Tyr Gly Glu Ala Ile Val Leu
            35                  40                  45

Thr Val Pro Gly Ser Glu Arg Ser Tyr Asp Leu Thr Gly Leu Lys Pro
     50                  55                  60

Gly Thr Glu Tyr Asn Val Pro Ile Ser Gly Val Lys Gly Gly Leu Asp
 65                  70                  75                  80

Ser Phe Pro Leu Ser Ala Ile Phe Thr Thr
                 85                  90

<210> SEQ ID NO 73
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Leu Pro Ala Pro Lys Asn Leu Val Val Ser Glu Val Thr Glu Asp
  1               5                  10                  15

Ser Ala Arg Leu Ser Trp Gln Gly Val Ala Arg Ala Phe Asp Ser Phe
             20                  25                  30

Leu Ile Thr Tyr Arg Glu Gln Ile Phe Ala Gly Glu Val Ile Val Leu
            35                  40                  45

Thr Val Pro Gly Ser Glu Arg Ser Tyr Asp Leu Thr Gly Leu Lys Pro
     50                  55                  60

Gly Thr Glu Tyr Pro Val Trp Ile Gln Gly Val Lys Gly Gly Ser Pro
 65                  70                  75                  80

Ser Ala Pro Leu Ser Ala Glu Ser Thr Thr
                 85                  90

<210> SEQ ID NO 74
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
             20                  25                  30

Ser Ile Thr Tyr Leu Glu Trp Trp Asn Leu Gly Glu Ala Ile Val Leu
            35                  40                  45

Thr Val Pro Gly Ser Glu Arg Ser Tyr Asp Leu Thr Gly Leu Lys Pro
     50                  55                  60

Gly Thr Glu Tyr Met Val Thr Ile Pro Gly Val Lys Gly Gly Met Ser
 65                  70                  75                  80

Ser Tyr Pro Leu Ser Ala Ile Phe Thr Thr
                 85                  90

<210> SEQ ID NO 75
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 75

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Ser Tyr Gly Glu Glu Ala Leu Ile Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Tyr Val His Ile Glu Gly Val Lys Gly Gly Ser Trp
65                  70                  75                  80

Ser Gln Pro Leu Ala Ala Ala Phe Thr Thr
                85                  90

<210> SEQ ID NO 76
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Glu Tyr Tyr Glu Asn Ile Gly Ile Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Pro Ile Val Gly Val Lys Gly Gly Pro Tyr
65                  70                  75                  80

Ser His Pro Leu Ser Ala Ile Phe Thr Thr
                85                  90

<210> SEQ ID NO 77
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Ala Tyr Ala Glu Pro Arg Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

```
<210> SEQ ID NO 78
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Gly Ile Gly Tyr Tyr Glu His Lys Arg Phe Gly Glu Ala Ile Gln Leu
            35                  40                  45

Ser Val Pro Gly Ser Glu Arg Ser Tyr Asp Leu Thr Gly Leu Lys Pro
        50                  55                  60

Gly Thr Glu Tyr Glu Val Asp Ile Glu Gly Val Lys Gly Gly Val Leu
65                  70                  75                  80

Ser Trp Pro Leu Phe Ala Glu Phe Thr Thr
                85                  90

<210> SEQ ID NO 79
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Val Ile Glu Tyr Thr Glu Arg Phe Trp Ser Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Pro Ile Asp Gly Val Lys Gly Gly Gln Cys
65                  70                  75                  80

Ser Thr Pro Leu Ser Ala Ile Phe Thr Thr
                85                  90

<210> SEQ ID NO 80
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Trp Ile Asp Tyr Glu Glu Glu Gly Val Ile Gly Glu Ala Ile Tyr Leu
            35                  40                  45

His Val Pro Gly Ser Glu Arg Ser Tyr Asp Leu Thr Gly Leu Lys Pro
        50                  55                  60
```

Gly Thr Glu Tyr Val Val Lys Ile His Gly Val Lys Gly Gly His Pro
65                  70                  75                  80

Ser His Pro Leu Val Ala Val Phe Thr Thr
                85                  90

<210> SEQ ID NO 81
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Leu Pro Ala Pro Lys Asn Leu Val Val Ser Arg Val Thr Glu Asp
1               5                   10                  15

Ser Ala Arg Leu Ser Trp Gln Gly Val Ala Arg Ala Phe Asp Ser Phe
                20                  25                  30

Leu Ile Thr Tyr Val Glu Leu Arg His Leu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Val Trp Ile Gln Gly Val Lys Gly Gly Ser Pro
65                  70                  75                  80

Ser Ala Pro Leu Ser Ala Glu Phe Thr Thr
                85                  90

<210> SEQ ID NO 82
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Leu Ile Pro Tyr Ala Glu Thr Ser Pro Ser Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Asp Tyr
65                  70                  75                  80

Ser Ser Pro Leu Ser Ala Ile Phe Thr Thr
                85                  90

<210> SEQ ID NO 83
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Leu Pro Ala Pro Lys Asn Leu Val Val Ser Arg Val Thr Glu Asp
1               5                   10                  15

```
Ser Ala Arg Leu Ser Trp Thr Ala Pro Asp Ala Ala Phe Asp Ser Phe
                20                  25                  30

Pro Ile Ala Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Ser Ala Ile Ser Thr Thr
                85                  90

<210> SEQ ID NO 84
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Leu Pro Ala Pro Lys Asn Leu Val Val Ser Arg Val Thr Glu Asp
1               5                   10                  15

Ser Ala Arg Leu Ser Trp Gln Gly Val Ala Arg Ala Phe Asp Ser Phe
                20                  25                  30

Ser Ile Leu Tyr Leu Glu Leu Thr Pro Lys Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Val Trp Ile Gln Gly Val Lys Gly Gly Ser Pro
65                  70                  75                  80

Ser Ala Pro Leu Ser Ala Glu Phe Thr Thr
                85                  90

<210> SEQ ID NO 85
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ile Ile Glu Tyr Phe Glu Pro Ile Pro Ile Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ala Val Asn Ile Tyr Gly Val Lys Gly Gly Tyr Leu
65                  70                  75                  80

Ser His Pro Leu Ser Ala Ile Phe Thr Thr
                85                  90

<210> SEQ ID NO 86
<211> LENGTH: 90
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 86

Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Leu
        35                  40                  45

Thr Val Pro Gly Ser Glu Cys Ser Tyr Asp Leu Thr Gly Leu Lys Pro
    50                  55                  60

Gly Thr Glu Tyr Pro Val Trp Ile Gln Gly Val Lys Gly Ser Pro
65                  70                  75                  80

Ser Ala Pro Leu Ser Ala Glu Phe Thr Thr
                85                  90

<210> SEQ ID NO 87
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Thr Glu Phe Leu Tyr Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Pro Ile Asn Gly Val Lys Gly Gly Phe Val
65                  70                  75                  80

Ser Pro Pro Leu Ser Ala Ile Val Thr Thr
                85                  90

<210> SEQ ID NO 88
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Lys Tyr Arg Glu Val Leu Arg Cys Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Pro Ile Thr Gly Val Lys Gly Gly Phe Gly
65                  70                  75                  80

Ser Ser Pro Leu Ser Ala Ile Phe Thr Thr
```

<210> SEQ ID NO 89
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Leu Pro Ala Pro Glu Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Glu Tyr Tyr Glu Gly Val Ile Gln Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Ala Ile Trp Gly Val Lys Gly Gly Lys Trp
65                  70                  75                  80

Ser Val Pro Leu Ser Ala Ile Phe Thr Thr
                85                  90

<210> SEQ ID NO 90
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Leu Pro Ala Pro Lys Asn Leu Val Val Ser Arg Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Trp Ile Gln Gly Val Lys Gly Gly Ser Pro
65                  70                  75                  80

Ser Ala Glu Phe Thr Thr
                85

<210> SEQ ID NO 91
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gln Ile His Tyr Trp Glu Thr Gln Gly Phe Gly Glu Ala Ile Val Leu
        35                  40                  45

```
Thr Val Pro Gly Ser Glu Arg Ser Tyr Asp Leu Thr Gly Leu Lys Pro
        50                  55                  60

Gly Thr Glu Tyr Pro Val Leu Ile Pro Gly Val Lys Gly Gly Pro Ser
 65                  70                  75                  80

Ser Leu Pro Leu Ser Ala Ile Phe Thr Thr
                85                  90
```

<210> SEQ ID NO 92
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Phe Ile Pro Tyr Ala Glu Pro Ser Pro Thr Gly Glu Ala Ile Val Leu
                35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly His Leu
 65                  70                  75                  80

Ser Asp Pro Leu Ser Ala Ile Phe Thr Thr
                85                  90
```

<210> SEQ ID NO 93
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Ala Ile Glu Tyr Tyr Glu Pro Val Pro Ala Gly Glu Ala Ile Tyr Leu
                35                  40                  45

Asp Val Pro Gly Ser Glu Arg Ser Tyr Asp Leu Thr Gly Leu Lys Pro
        50                  55                  60

Gly Thr Glu Tyr Asp Val Thr Ile Tyr Gly Val Lys Gly Gly Tyr Tyr
 65                  70                  75                  80

Ser His Pro Leu Phe Ala Ser Phe Thr Thr
                85                  90
```

<210> SEQ ID NO 94
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Leu
                35                  40                  45

Thr Val Pro Gly Ser Glu Arg Ser Tyr Asp Leu Thr Gly Leu Lys Pro
        50                  55                  60

Gly Thr Glu Tyr Pro Val Trp Ile Gln Gly Val Lys Gly Gly Ser Pro
65                  70                  75                  80

Ser Ala Pro Leu Ser Ala Ile Phe Thr Thr
                85                  90
```

<210> SEQ ID NO 95
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Leu
                35                  40                  45

Thr Val Pro Gly Ser Glu Arg Ser Tyr Asp Leu Thr Gly Leu Lys Pro
        50                  55                  60

Gly Thr Glu Tyr Pro Val Trp Ile Gln Gly Val Lys Gly Gly Ser Pro
65                  70                  75                  80

Ser Ala Pro Leu Ser Ala Glu Phe Thr Thr
                85                  90
```

<210> SEQ ID NO 96
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Met Ser Leu Pro Ala Pro Lys Asn Leu Val Val Ser Arg Val Thr Glu
1               5                   10                  15

Asp Ser Ala Arg Leu Ser Trp Thr Ala Pro Asp Ala Ala Phe Asp Ser
            20                  25                  30

Phe Pro Ile Ala Tyr Leu Glu Val Phe Tyr Glu Gly Glu Ala Ile Val
                35                  40                  45

Leu Thr Val Pro Gly Ser Glu Arg Ser Tyr Asp Leu Thr Gly Leu Lys
        50                  55                  60

Pro Gly Thr Glu Tyr Gln Val Pro Ile Glu Gly Val Lys Gly Gly Ala
65                  70                  75                  80

Met Ser Leu Pro Leu Ser Ala Ile Phe Thr Thr
                85                  90
```

<210> SEQ ID NO 97
<211> LENGTH: 90

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Trp Tyr Glu Glu Thr Thr Ile Gly Glu Ala Ile Tyr Leu
        35                  40                  45

His Val Pro Gly Ser Glu Arg Ser Tyr Asp Leu Thr Gly Leu Lys Pro
    50                  55                  60

Gly Thr Glu Tyr Glu Val His Ile Thr Gly Val Lys Gly Gly Pro Tyr
65                  70                  75                  80

Ser Arg Pro Leu Phe Ala Asn Phe Thr Thr
                85                  90

<210> SEQ ID NO 98
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gly Ile Ala Tyr Asp Glu Trp Pro Glu Phe Gly Glu Ala Ile Val Leu
        35                  40                  45

Thr Val Pro Gly Ser Glu Arg Ser Tyr Asp Leu Thr Gly Leu Lys Pro
    50                  55                  60

Asp Thr Glu Tyr Ile Val Glu Ile Tyr Gly Val Lys Gly Gly Trp Phe
65                  70                  75                  80

Ser Trp Pro Leu Ser Ala Ile Phe Thr Thr
                85                  90

<210> SEQ ID NO 99
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Pro Tyr Ala Glu Pro Ser Pro Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly His Leu
```

```
65                  70                  75                  80

Ser Asp Pro Leu Ser Val Ile Phe Thr Thr
                85                  90

<210> SEQ ID NO 100
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Trp Tyr Glu Glu Val Met Tyr Leu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Pro Ile Pro Gly Val Lys Gly Gly His Ser
65                  70                  75                  80

Ser Pro Pro Leu Ser Ala Ile Phe Thr Thr
                85                  90

<210> SEQ ID NO 101
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

His Ile Leu Tyr Glu Glu Leu Phe Leu Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Lys Val Pro Ile Ser Gly Val Lys Gly Gly Pro Val
65                  70                  75                  80

Ser Arg Pro Leu Ser Ala Ile Phe Thr Thr
                85                  90

<210> SEQ ID NO 102
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Met Leu Pro Ala Pro Lys Asn Leu Val Val Ser Arg Val Thr Glu Asp
1               5                   10                  15

Ser Ala Arg Leu Ser Trp Gln Gly Val Ala Arg Ala Phe Asp Ser Phe
                20                  25                  30
```

```
Leu Ile Thr Tyr Arg Glu Gln Ile Phe Ala Gly Glu Val Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Pro Val Trp Ile Gln Gly Val Lys Gly Gly Ser Pro
 65                  70                  75                  80

Ser Ala Pro Leu Ser Ala Glu Phe Thr Thr
                85                  90

<210> SEQ ID NO 103
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

His Ile Val Tyr His Glu Pro Arg Pro Ser Gly Glu Ala Ile Trp Leu
            35                  40                  45

His Val Pro Gly Ser Glu Arg Ser Tyr Asp Leu Thr Gly Leu Lys Pro
 50                  55                  60

Gly Thr Glu Tyr Glu Val Gly Ile Val Ser Val Lys Gly Gly Asp Leu
 65                  70                  75                  80

Ser Val Pro Leu Val Ala Phe Phe Thr Thr
                85                  90

<210> SEQ ID NO 104
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Ser Leu
            35                  40                  45

Leu Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Tyr Ala Val Phe Thr Thr
                85                  90

<210> SEQ ID NO 105
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 105

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Phe Leu
        35                  40                  45

Val Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu His Ala Asn Phe Thr Thr
                85                  90

<210> SEQ ID NO 106
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
        35                  40                  45

Asp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Tyr Ala Ser Phe Thr Thr
                85                  90

<210> SEQ ID NO 107
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Ser Leu Pro Ala Pro Lys Asn Leu Val Val Ser Arg Val Thr Glu
1               5                   10                  15

Asp Ser Ala Arg Leu Ser Trp Thr Ala Pro Asp Ala Ala Phe Asp Ser
            20                  25                  30

Phe Tyr Ile Ala Tyr Ala Glu Pro Arg Pro Asp Gly Glu Ala Ile Ser
        35                  40                  45

Leu Tyr Val Pro Gly Ser Glu Arg Ser Tyr Asp Leu Thr Gly Leu Lys
    50                  55                  60

Pro Gly Thr Glu Tyr Ser Val Leu Ile His Gly Val Lys Gly Gly Leu
65                  70                  75                  80

Leu Ser Ser Pro Leu Ser Ala Ile Ser Thr Thr
                85                  90

<210> SEQ ID NO 108
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Gln Leu
        35                  40                  45

Arg Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 109
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ser Tyr Glu Glu Asp Tyr Thr Phe Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Arg Val Val Ile Gly Gly Val Lys Gly Gly Trp Phe
65                  70                  75                  80

Ser Glu Pro Leu Leu Ala Ala Phe Thr Thr
                85                  90

<210> SEQ ID NO 110
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Tyr Leu
        35                  40                  45

Thr Val Pro Gly Ser Glu Arg Ser Tyr Asp Leu Thr Gly Leu Lys Pro

```
                 50                  55                  60
Gly Thr Glu Tyr Asn Val Thr Ile Gln Gly Val Lys Gly Gly Phe Pro
 65                  70                  75                  80

Ser Tyr Pro Leu Asp Ala Ser Phe Thr Thr
                 85                  90

<210> SEQ ID NO 111
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Phe Ile Gly Tyr Leu Glu Pro Gln Pro Pro Gly Glu Ala Ile Asp Leu
                 35                  40                  45

Gly Val Pro Gly Ser Glu Arg Ser Tyr Asp Leu Thr Gly Leu Lys Pro
 50                  55                  60

Gly Thr Glu Tyr Asn Val Thr Ile Gln Gly Val Lys Gly Gly Phe Pro
 65                  70                  75                  80

Ser Met Pro Leu Asp Pro Leu Glu Ala Tyr Phe Thr Thr
                 85                  90

<210> SEQ ID NO 112
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Leu Leu
                 35                  40                  45

Leu Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Ser Ala Ile Phe Thr Thr
                 85                  90

<210> SEQ ID NO 113
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Leu Pro Ala Pro Lys Asn Leu Val Val Ser Arg Val Thr Glu Asp
  1               5                  10                  15
```

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Asn Leu
        35                  40                  45

Gln Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Val Ala Phe Phe Thr Thr
                85                  90

<210> SEQ ID NO 114
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Leu Pro Ala Pro Lys Asn Leu Val Val Ser Arg Val Thr Glu Asp
1               5                   10                  15

Ser Ala Arg Leu Ser Trp Thr Thr Pro Asp Ala Ala Phe Asp Ser Phe
            20                  25                  30

Phe Ile Gly Tyr Leu Glu Pro Gln Pro Gly Glu Ala Ile Ser Leu
        35                  40                  45

Gln Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Ser Pro Leu Phe Ala Val Phe Thr Thr
                85                  90

<210> SEQ ID NO 115
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Glu Leu
        35                  40                  45

His Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Phe Thr Thr
                85

<210> SEQ ID NO 116
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Val Val Pro Gly Ser Glu Arg Ser Tyr Asp Leu Thr Gly Leu Lys Pro
50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 117
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Thr Leu
        35                  40                  45

Asp Val Pro Gly Ser Glu Arg Ser Tyr Asp Leu Thr Gly Leu Lys Pro
50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 118
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Trp Leu
        35                  40                  45

Val Val Pro Gly Ser Glu Arg Ser Tyr Asp Leu Thr Gly Leu Lys Pro
50                  55                  60

Gly Thr Glu Tyr Ser Val Leu Ile His Gly Val Lys Gly Gly Leu Leu
65                  70                  75                  80

Ser Ser Pro Leu Val Ala Ser Phe Thr Thr
            85                  90

<210> SEQ ID NO 119
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Asn Leu
        35                  40                  45

Asp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Val Ala Glu Phe Thr Thr
            85                  90

<210> SEQ ID NO 120
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile His Leu
        35                  40                  45

Ser Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Val Ala Ile Phe Thr Thr
            85                  90

<210> SEQ ID NO 121
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Ala Leu

```
                35                  40                  45
Trp Val Pro Gly Ser Glu Arg Ser Tyr Asp Leu Thr Gly Leu Lys Pro
 50                  55                  60

Gly Thr Glu Tyr Asn Val Thr Ile Gln Gly Val Lys Gly Gly Phe Pro
 65                  70                  75                  80

Ser Met Pro Leu Ser Ala Ile Phe Thr Thr
                 85                  90
```

<210> SEQ ID NO 122
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

```
Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Ile Leu
             35                  40                  45

Val Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Ser Ala His Phe Thr Thr
                 85                  90
```

<210> SEQ ID NO 123
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Phe Ile Gly Tyr Leu Glu Pro Gln Pro Gly Glu Ala Ile Gln Leu
             35                  40                  45

Trp Val Pro Gly Ser Glu Arg Ser Tyr Asp Leu Thr Gly Leu Lys Pro
 50                  55                  60

Gly Thr Glu Tyr Asn Val Thr Ile Gln Gly Val Lys Gly Gly Phe Pro
 65                  70                  75                  80

Ser His Pro Leu Gly Ala Val Phe Thr Thr
                 85                  90
```

<210> SEQ ID NO 124
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Gln Leu
            35                  40                  45

His Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Leu Ala Ser Phe Thr Thr
                85                  90

<210> SEQ ID NO 125
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Ala Leu
            35                  40                  45

His Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Val Ala Phe Phe Thr Thr
                85                  90

<210> SEQ ID NO 126
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Gly Glu Ala Ile His Leu
            35                  40                  45

His Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
65                  70                  75                  80

Ser Ile Pro Leu His Ala Asn Phe Thr Thr
                85                  90

<210> SEQ ID NO 127

```
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Phe Leu
        35                  40                  45

Gly Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 128
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Arg Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ile Ala Ser Phe Thr Thr
                85                  90

<210> SEQ ID NO 129
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Asn Leu
        35                  40                  45

Trp Val Pro Gly Ser Glu Arg Ser Tyr Asp Leu Thr Gly Leu Lys Pro
    50                  55                  60
```

```
Gly Thr Glu Tyr Ser Val Leu Ile His Gly Val Lys Gly Gly Leu Leu
 65                  70                  75                  80

Ser Ser Pro Leu Asp Ala Ser Phe Thr Thr
                 85                  90

<210> SEQ ID NO 130
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Val Ile Glu Tyr Phe Glu Trp Thr Leu Asn Gly Glu Ala Ile Val Leu
                35                  40                  45

Thr Val Pro Gly Ser Glu Arg Ser Tyr Asp Leu Thr Gly Leu Lys Pro
         50                  55                  60

Gly Thr Glu Tyr Ser Val Gln Ile Tyr Gly Val Lys Gly Gly Cys Leu
 65                  70                  75                  80

Ser Arg Pro Leu Ser Ala Ile Phe Thr Thr
                 85                  90

<210> SEQ ID NO 131
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile His Leu
                35                  40                  45

Trp Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Leu Leu
 65                  70                  75                  80

Ser Ser Pro Leu Ile Ala His Phe Thr Thr
                 85                  90

<210> SEQ ID NO 132
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
```

```
                    20                  25                  30

Phe Ile Pro Tyr Ala Glu Pro Ser Pro Thr Gly Glu Ala Ile Val Leu
                35                  40                  45

Thr Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Leu Leu
65                  70                  75                  80

Ser Ser Pro Leu Ser Ala His Phe Thr Thr
                85                  90

<210> SEQ ID NO 133
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Tyr Leu
            35                  40                  45

Tyr Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Leu Leu
65                  70                  75                  80

Ser Ser Pro Leu Asp Ala Phe Phe Thr Thr
                85                  90

<210> SEQ ID NO 134
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Gly Leu
            35                  40                  45

Gln Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 135
<211> LENGTH: 90
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 135

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Ala Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu His Ala Phe Phe Thr Thr
                85                  90

<210> SEQ ID NO 136
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Trp Leu
        35                  40                  45

His Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Ile Pro Leu Ile Ala Ile Phe Thr Thr
                85                  90

<210> SEQ ID NO 137
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Asp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Val Ala Glu Phe Thr Thr
                85                  90

<210> SEQ ID NO 138
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Leu Pro Thr Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Arg Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu His Ala Ser Phe Thr Thr
                85                  90

<210> SEQ ID NO 139
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Gln Leu
        35                  40                  45

Gly Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser His Pro Leu Asn Ala Asn Phe Thr Thr
                85                  90

<210> SEQ ID NO 140
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Gln Leu
        35                  40                  45

Glu Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
 65                  70                  75                  80

Ser Met Pro Leu Ser Ala Ile Phe Thr Thr
                85                  90

<210> SEQ ID NO 141
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Phe Leu
            35                  40                  45

Gly Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
 65                  70                  75                  80

Ser Ser Pro Leu Ile Ala Phe Phe Thr Thr
                85                  90

<210> SEQ ID NO 142
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Gly Glu Ala Ile Gly Leu
            35                  40                  45

Gln Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
 65                  70                  75                  80

Ser His Pro Leu Lys Ala Gln Phe Thr Thr
                85                  90

<210> SEQ ID NO 143
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Leu Pro Ala Pro Lys Asn Leu Val Val Ser Arg Val Thr Glu Asp

```
                1               5                  10                  15
Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Leu Leu
             35                  40                  45

Phe Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Leu Leu
 65                  70                  75                  80

Ser Ser Pro Leu Val Ala His Phe Thr Thr
                 85                  90
```

<210> SEQ ID NO 144
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Gly Leu
             35                  40                  45

Tyr Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Leu Leu
 65                  70                  75                  80

Ser Ser Pro Leu Gly Ala Phe Phe Thr Thr
                 85                  90
```

<210> SEQ ID NO 145
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Leu Leu
             35                  40                  45

Gln Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Leu Leu
 65                  70                  75                  80

Ser Ser Pro Leu Thr Ala Ile Phe Thr Thr
                 85                  90
```

<210> SEQ ID NO 146
<211> LENGTH: 90
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 146

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Thr Leu
        35                  40                  45

His Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 147
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Glu Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Asp Ala His Phe Thr Thr
                85                  90

<210> SEQ ID NO 148
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ala Leu
        35                  40                  45

His Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

```
Ser Ser Pro Leu Arg Ala Val Phe Thr Thr
            85                  90
```

<210> SEQ ID NO 149
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Trp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
            85                  90
```

<210> SEQ ID NO 150
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Met Leu Pro Ala Pro Lys Asn Leu Val Val Ser Arg Val Thr Glu Asp
1               5                   10                  15

Ser Ala Arg Leu Ser Arg Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Ile Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
            85                  90
```

<210> SEQ ID NO 151
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30
```

-continued

Phe Ile Gly Tyr Leu Glu Pro Gln Pro Pro Gly Glu Ala Ile Gln Leu
            35                  40                  45

Trp Val Pro Gly Ser Glu Arg Ser Tyr Asp Leu Thr Gly Leu Lys Pro
 50                  55                  60

Gly Thr Glu Tyr Asn Val Thr Ile Gln Gly Val Lys Gly Gly Phe Pro
 65                  70                  75                  80

Ser Arg Pro Leu Gln Ala His Phe Thr Thr
                 85                  90

<210> SEQ ID NO 152
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Thr Leu
            35                  40                  45

Asp Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Tyr Ala Phe Phe Thr Thr
                 85                  90

<210> SEQ ID NO 153
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Ala Leu
            35                  40                  45

His Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Ser Ala Ile Phe Thr Thr
                 85                  90

<210> SEQ ID NO 154
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gly Leu
        35                  40                  45

Trp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ile Ala His Phe Thr Thr
                85                  90

<210> SEQ ID NO 155
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Trp Leu
        35                  40                  45

Val Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu His Ala Arg Phe Thr Thr
                85                  90

<210> SEQ ID NO 156
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Phe Leu
        35                  40                  45

Gln Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ala Ala Val Phe Thr Thr
                85                  90

```
<210> SEQ ID NO 157
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
        35                  40                  45

His Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Ser Thr Thr
                85                  90

<210> SEQ ID NO 158
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ile Leu
        35                  40                  45

Gln Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Val Phe Thr Thr
                85                  90

<210> SEQ ID NO 159
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Tyr Leu
        35                  40                  45

Lys Val Pro Gly Ser Glu Arg Ser Tyr Asp Leu Thr Gly Leu Lys Pro
    50                  55                  60
```

Gly Thr Glu Tyr Ser Val Leu Ile His Gly Val Lys Gly Gly Leu Leu
65                  70                  75                  80

Ser Ser Pro Leu Val Ala His Phe Thr Thr
                85                  90

<210> SEQ ID NO 160
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Leu Ala Tyr Phe Thr Thr
                85                  90

<210> SEQ ID NO 161
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Ile Leu
            35                  40                  45

His Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Glu Ala Lys Phe Thr Thr
                85                  90

<210> SEQ ID NO 162
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Leu Pro Ala Pro Lys Asn Leu Val Val Ser Arg Val Thr Glu Asp
1               5                   10                  15

-continued

```
Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Lys Leu
        35                  40                  45

Glu Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ala Ile Phe Thr Thr
                85

<210> SEQ ID NO 163
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Tyr Leu
        35                  40                  45

Glu Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Phe Pro Leu Lys Ala Ala Phe Thr Thr
                85                  90

<210> SEQ ID NO 164
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ile Leu
        35                  40                  45

Arg Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Val Ala Ile Phe Thr Thr
                85                  90

<210> SEQ ID NO 165
<211> LENGTH: 90
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 165

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Gln Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ala Ala Trp Phe Thr Thr
                85                  90

<210> SEQ ID NO 166
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Phe Leu
        35                  40                  45

Gln Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Asn Ala Phe Phe Thr Thr
                85                  90

<210> SEQ ID NO 167
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Ile Leu
        35                  40                  45

Gly Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu His Ala Tyr Ser Thr Thr

```
                        85                  90

<210> SEQ ID NO 168
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
        35                  40                  45

Asp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 169
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
        35                  40                  45

Leu Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Val Phe Thr Thr
                85                  90

<210> SEQ ID NO 170
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile His Leu
        35                  40                  45
```

```
Leu Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
 65                  70                  75                  80

Ser Ser Pro Leu Leu Ala His Phe Thr Thr
                85                  90

<210> SEQ ID NO 171
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Gln Leu
            35                  40                  45

Trp Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
 65                  70                  75                  80

Ser Ser Pro Leu Asp Ala Tyr Phe Thr Thr
                85                  90

<210> SEQ ID NO 172
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
 65                  70                  75                  80

Ser Met Pro Leu Ala Ser Phe Thr Thr
                85

<210> SEQ ID NO 173
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173
```

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

His Ile Val Tyr His Glu Pro Arg Pro Ser Gly Glu Ala Ile His Leu
                35                  40                  45

Gln Val Pro Gly Ser Glu Arg Ser Tyr Asp Leu Thr Gly Leu Lys Pro
            50                  55                  60

Gly Thr Glu Tyr Asn Val Thr Ile Gln Gly Val Lys Gly Gly Phe Pro
65                  70                  75                  80

Ser Tyr Pro Leu Ser Ala Phe Phe Thr Thr
                85                  90

<210> SEQ ID NO 174
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Pro Gly Glu Ala Ile Gln Leu
                35                  40                  45

Trp Val Pro Gly Ser Glu Arg Ser Tyr Asp Leu Thr Gly Leu Lys Pro
            50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 175
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Arg Ile Ser Tyr Cys Glu Thr Phe Tyr His Gly Glu Ala Ile Val Leu
                35                  40                  45

Thr Val Pro Gly Ser Glu Arg Ser Tyr Asp Leu Thr Gly Leu Lys Pro
            50                  55                  60

Gly Thr Glu Tyr Ser Val Leu Ile His Gly Val Lys Gly Gly Leu Leu
65                  70                  75                  80

Ser Ser Pro Leu Ile Ala Lys Phe Thr Thr
                85                  90

<210> SEQ ID NO 176
<211> LENGTH: 90

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Trp Leu
        35                  40                  45

Lys Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Gln Ala Asn Phe Thr Thr
                85                  90

<210> SEQ ID NO 177
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Trp Leu
        35                  40                  45

Lys Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Gln Ala Asn Phe Thr Thr
                85                  90

<210> SEQ ID NO 178
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Gln Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
```

```
65                  70                  75                  80

Ser Ser Pro Leu Ser Ala Ile Val Thr Thr
                85                  90

<210> SEQ ID NO 179
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Ala Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Ser Ala Phe Phe Thr Thr
                85                  90

<210> SEQ ID NO 180
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Ala Leu
            35                  40                  45

Leu Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Val Ala Gln Phe Thr Thr
                85                  90

<210> SEQ ID NO 181
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30
```

Tyr Ile Ala Tyr Ala Glu Pro Arg Pro Asp Gly Glu Ala Ile Ile Leu
            35                  40                  45

His Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Glu Ala Lys Phe Thr Thr
                85                  90

<210> SEQ ID NO 182
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Asp Leu
            35                  40                  45

His Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu His Ala Leu Phe Thr Thr
                85                  90

<210> SEQ ID NO 183
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
            35                  40                  45

Asp Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Phe Pro
65                  70                  75                  80

Ser Met Pro Leu Ser Ala Ile Phe Thr Thr
                85                  90

<210> SEQ ID NO 184
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Asp Leu
        35                  40                  45

Ala Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Phe Thr Thr
                85

<210> SEQ ID NO 185
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Tyr Leu
        35                  40                  45

Gly Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Arg Ala Lys Phe Thr Thr
                85                  90

<210> SEQ ID NO 186
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Gly Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 187
<211> LENGTH: 88
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Ser Leu
        35                  40                  45

Leu Val Pro Asp Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Lys Phe Thr Thr
                85

<210> SEQ ID NO 188
<211> LENGTH: 90
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 188

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gly Leu
        35                  40                  45

Gly Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Asp Ala Ser Phe Thr Thr
                85                  90

<210> SEQ ID NO 189
<211> LENGTH: 90
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 189

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Thr Val Pro Gly Ser Glu Arg Ser Tyr Asp Leu Thr Gly Pro Lys Pro

```
Gly Thr Glu Tyr Trp Val Leu Ile Gln Gly Val Lys Gly Gly Gly Ser
 65                  70                  75                  80

Ser Val Pro Leu Val Ala Tyr Phe Thr Thr
                 85                  90

<210> SEQ ID NO 190
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Ser Leu
             35                  40                  45

Asp Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Glu Ala Ser Phe Thr Thr
                 85                  90

<210> SEQ ID NO 191
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Phe Ile Gly Tyr Leu Glu Pro Gln Pro Gly Glu Ala Ile Ile Leu
             35                  40                  45

Ala Val Pro Gly Ser Glu Arg Ser Tyr Asp Leu Thr Gly Leu Lys Pro
 50                  55                  60

Gly Thr Glu Tyr Asn Val Thr Ile Gln Gly Val Lys Gly Gly Phe Pro
 65                  70                  75                  80

Ser Leu Pro Leu Val Ala Ser Phe Thr Thr
                 85                  90

<210> SEQ ID NO 192
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Met Leu Pro Ala Pro Lys Asn Leu Val Val Ser Arg Val Thr Glu Asp
  1               5                  10                  15
```

```
Ser Ala Arg Leu Ser Trp Thr Ala Pro Asp Ala Ala Phe Asp Ser Phe
                20                  25                  30

Asp Ile Gly Tyr Thr Glu Tyr Gly Gly Tyr Gly Glu Ala Ile Tyr Leu
            35                  40                  45

Ser Val Pro Gly Ser Glu Arg Ser Tyr Asp Leu Thr Gly Leu Lys Pro
    50                  55                  60

Gly Thr Glu Tyr Trp Val Leu Ile Gln Gly Val Lys Gly Gly Gly Ser
65                  70                  75                  80

Ser Val Pro Leu Ser Ala Ile Phe Thr Thr
                85                  90
```

<210> SEQ ID NO 193
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Ser Leu
            35                  40                  45

Ser Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ile Ala Asn Phe Thr Thr
                85                  90
```

<210> SEQ ID NO 194
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Ala Leu
            35                  40                  45

Leu Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Val Thr Thr
                85                  90
```

<210> SEQ ID NO 195
<211> LENGTH: 90
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 195

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ile Leu
        35                  40                  45

Asp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ser Ile Phe Thr Thr
                85                  90

<210> SEQ ID NO 196
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Trp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Arg Ala Ser Phe Thr Thr
                85                  90

<210> SEQ ID NO 197
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Lys Leu
        35                  40                  45

Asp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80
```

Ser Ser Pro Leu Val Ala Phe Phe Thr Thr
                85                  90

<210> SEQ ID NO 198
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Ile Leu
                35                  40                  45

Glu Val Pro Gly Ser Gly Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Val Ala Tyr Phe Thr Thr
                85                  90

<210> SEQ ID NO 199
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile His Leu
                35                  40                  45

Trp Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu His Ala Asp Phe Thr Thr
                85                  90

<210> SEQ ID NO 200
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Trp Leu

```
            35                  40                  45

Glu Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Val Ala Asp Phe Thr Thr
                 85                  90

<210> SEQ ID NO 201
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Ser Leu
             35                  40                  45

Trp Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Leu Ala His Phe Thr Thr
                 85                  90

<210> SEQ ID NO 202
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Asp Ile Gly Tyr Thr Glu Tyr Gly Gly Tyr Gly Glu Ala Ile Leu His
             35                  40                  45

Val Pro Gly Ser Glu Arg Ser Tyr Asp Leu Thr Gly Leu Lys Pro Gly
 50                  55                  60

Thr Glu Tyr Trp Val Leu Ile Gln Gly Val Lys Gly Gly Gly Ser Ser
 65                  70                  75                  80

Val Pro Leu Ser Ala Ile Phe Thr Thr
                 85

<210> SEQ ID NO 203
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203
```

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Val Leu
        35                  40                  45

Leu Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Val Pro Leu Ala Ala Phe Phe Thr Thr
            85                  90

<210> SEQ ID NO 204
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Leu Leu
        35                  40                  45

Trp Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Gln Phe Thr Thr
            85

<210> SEQ ID NO 205
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Leu Leu
        35                  40                  45

Gly Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu His Pro Leu Val Ala Leu Phe Thr Thr
            85                  90

<210> SEQ ID NO 206

```
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gly Leu
        35                  40                  45

Asp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 207
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile His Leu
        35                  40                  45

Ser Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ala Ala Tyr Phe Thr Thr
                85                  90

<210> SEQ ID NO 208
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Val Leu
        35                  40                  45

Ala Val Pro Gly Ser Glu Arg Ser Tyr Asp Leu Thr Gly Leu Lys Pro
    50                  55                  60
```

Gly Thr Glu Tyr Asn Val Thr Ile Gln Gly Val Lys Gly Gly Phe Pro
65                  70                  75                  80

Ser Tyr Pro Leu Val Ala Ala Phe Thr Thr
                85                  90

<210> SEQ ID NO 209
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
        35                  40                  45

Gln Val Pro Gly Ser Cys Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Thr Ala Ile Phe Thr Thr
                85                  90

<210> SEQ ID NO 210
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Asn Leu
        35                  40                  45

Gln Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Phe Pro Leu Ser Ala Val Phe Thr Thr
                85                  90

<210> SEQ ID NO 211
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe

```
               20                  25                  30

Tyr Ile Ala Tyr Ala Glu Pro Arg Pro Asp Gly Glu Ala Ile Gln Leu
            35                  40                  45

His Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Val Ala Ile Phe Thr Thr
                85                  90

<210> SEQ ID NO 212
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Trp Leu
        35                  40                  45

Ala Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu His Ala Gln Phe Thr Thr
                85                  90

<210> SEQ ID NO 213
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
        35                  40                  45

Gly Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Phe Thr Thr
                85

<210> SEQ ID NO 214
<211> LENGTH: 90
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 214

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gly Leu
        35                  40                  45

Gln Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Cys Ala Glu Phe Thr Thr
                85                  90

<210> SEQ ID NO 215
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Trp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ile Ala Glu Phe Thr Thr
                85                  90

<210> SEQ ID NO 216
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ser Leu
        35                  40                  45

Ser Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Pro Lys Phe Thr Thr
                85

<210> SEQ ID NO 217
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ile Leu
        35                  40                  45

Glu Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Arg Ala Val Phe Thr Thr
                85                  90

<210> SEQ ID NO 218
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile His Leu
        35                  40                  45

Val Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 219
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ser Leu
        35                  40                  45

Lys Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Glu Ala Ile Phe Thr Thr
                 85                  90

<210> SEQ ID NO 220
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Met Leu Pro Ala Pro Lys Asn Pro Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile His Leu
             35                  40                  45

Leu Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Lys Arg Leu Ser Pro Val Val Thr Ile Thr Ile
                 85                  90                  95

Thr Met Ala Val Cys Arg Lys Pro Val Ala Glu Asn Leu Ser Gln Thr
            100                 105                 110

Leu Ser

<210> SEQ ID NO 221
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Phe Ile Gly Tyr Leu Glu Pro Gln Pro Pro Gly Glu Ala Ile Phe Leu
             35                  40                  45

Asp Val Pro Gly Ser Glu Arg Ser Tyr Asp Leu Thr Gly Leu Lys Pro
 50                  55                  60

Gly Thr Glu Tyr Asn Val Thr Ile Gln Gly Val Lys Gly Gly Phe Pro
 65                  70                  75                  80

Ser Pro Leu Thr Ala Phe Phe Thr Thr
                 85

<210> SEQ ID NO 222
<211> LENGTH: 90
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 222

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Val Leu
        35                  40                  45

Asp Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser His Pro Leu Ala Ala Ala Phe Thr Thr
                85                  90

<210> SEQ ID NO 223
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Gly Leu
        35                  40                  45

Ala Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Val Pro Leu Gln Ala Asn Phe Thr Thr
                85                  90

<210> SEQ ID NO 224
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
        35                  40                  45

Arg Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Val Ala Glu Phe Thr Thr
                85                  90

<210> SEQ ID NO 225
<211> LENGTH: 90
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 225

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Leu Leu
            35                  40                  45

Gln Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Ser Ala Ser Phe Thr Thr
                85                  90

<210> SEQ ID NO 226
<211> LENGTH: 90
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 226

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Gly Leu
            35                  40                  45

His Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Thr Ala Ser Phe Thr Thr
                85                  90

<210> SEQ ID NO 227
<211> LENGTH: 90
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 227

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Gly Leu
            35                  40                  45

Arg Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
 65                  70                  75                  80

Ser Ser Pro Leu Ser Ala Ile Phe Thr Thr
                85                  90

<210> SEQ ID NO 228
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Val Leu
            35                  40                  45

Arg Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
 65                  70                  75                  80

Ser Ser Pro Leu Ala Ala Ser Phe Thr Thr
                85                  90

<210> SEQ ID NO 229
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Gln Leu
            35                  40                  45

Leu Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
 65                  70                  75                  80

Ser Ser Pro Leu Val Ala His Phe Thr Thr
                85                  90

<210> SEQ ID NO 230
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Met Leu Pro Ala Pro Lys Asn Leu Val Val Ser Arg Val Thr Glu Asp

```
                1               5                   10                  15
Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Trp Leu
                35                  40                  45

Leu Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Val Ala Phe Phe Thr Thr
                85                  90
```

<210> SEQ ID NO 231
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Pro Gly Glu Ala Ile His Leu
                35                  40                  45

Tyr Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
65                  70                  75                  80

Ser Asp Pro Leu Asp Ala Val Phe Thr Thr
                85                  90
```

<210> SEQ ID NO 232
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Pro Gly Glu Ala Ile Tyr Leu
                35                  40                  45

Asp Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
65                  70                  75                  80

Ser Thr Phe Thr Thr
                85
```

<210> SEQ ID NO 233
<211> LENGTH: 90
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 233

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Phe Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Lys Ala Tyr Phe Thr Thr
                85                  90

<210> SEQ ID NO 234
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Val Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 235
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Gln Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80
```

```
Ser Leu Pro Leu Ser Ala Asp Phe Thr Thr
                85                  90
```

<210> SEQ ID NO 236
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Leu Leu
            35                  40                  45

Gln Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Asp Ala Glu Phe Thr Thr
                85                  90
```

<210> SEQ ID NO 237
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Val Leu
            35                  40                  45

Ala Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Tyr Ala Ser Phe Thr Thr
                85                  90
```

<210> SEQ ID NO 238
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

```
Met Leu Pro Ala Pro Lys Asn Leu Val Val Ser Arg Val Thr Glu Asp
1               5                   10                  15

Ser Ala Arg Leu Ser Trp Thr Thr Pro Asp Ala Ala Phe Asp Ser Phe
                20                  25                  30
```

-continued

Tyr Ile Ala Tyr Ala Glu Pro Arg Pro Asp Gly Glu Ala Ile Arg Leu
         35                  40                  45

Gln Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Gly Phe Thr Thr
                 85

<210> SEQ ID NO 239
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Gln Leu
         35                  40                  45

Val Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu Tyr Ala Ile Phe Thr Thr
                 85                  90

<210> SEQ ID NO 240
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Ser Leu
         35                  40                  45

Ser Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
 65                  70                  75                  80

Ser Ser Pro Leu His Ala Lys Phe Thr Thr
                 85                  90

<210> SEQ ID NO 241
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile His Leu
        35                  40                  45

Gly Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Ile Pro Leu Phe Ala Ser Phe Thr Thr
                85                  90

<210> SEQ ID NO 242
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Leu Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Tyr Ala Ala Phe Thr Thr
                85                  90

<210> SEQ ID NO 243
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile His Leu
        35                  40                  45

Ala Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Val Pro Leu Ala Ala Val Phe Thr Thr
                85                  90

```
<210> SEQ ID NO 244
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ser Leu
        35                  40                  45

Gln Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Gly Ala His Phe Thr Thr
                85                  90

<210> SEQ ID NO 245
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ala Leu
        35                  40                  45

Trp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Val Ala Ser Phe Thr Thr
                85                  90

<210> SEQ ID NO 246
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

His Val Pro Gly Ser Glu Arg Ser Tyr Asp Leu Thr Gly Leu Lys Pro
    50                  55                  60
```

```
Gly Thr Glu Tyr Ser Val Leu Ile His Gly Val Lys Gly Gly Leu Leu
 65                  70                  75                  80

Ser Ser Pro Leu Tyr Ala Phe Phe Thr Thr
                 85                  90

<210> SEQ ID NO 247
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Leu Leu
             35                  40                  45

His Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Leu Leu
 65                  70                  75                  80

Ser Ser Pro Leu Arg Ala Ser Phe Thr Thr
                 85                  90

<210> SEQ ID NO 248
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Trp Leu
             35                  40                  45

Gly Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Leu Leu
 65                  70                  75                  80

Ser Ser Pro Leu His Ala Thr Phe Thr Thr
                 85                  90

<210> SEQ ID NO 249
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Met Leu Pro Ala Pro Lys Asn Leu Val Val Ser Arg Val Thr Glu Asp
  1               5                  10                  15
```

```
Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Glu Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu His Ala Asn Phe Thr Thr
                85                  90

<210> SEQ ID NO 250
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
        35                  40                  45

Arg Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Tyr Ala Lys Phe Thr Thr
                85                  90

<210> SEQ ID NO 251
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Gly Leu
        35                  40                  45

Trp Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Asp Pro Leu Gln Ala Val Phe Thr Thr
                85                  90

<210> SEQ ID NO 252
<211> LENGTH: 90
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 252

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

His Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Asp Ala Phe Phe Thr Thr
                85                  90

<210> SEQ ID NO 253
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ile Leu
        35                  40                  45

His Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Asp Ala Tyr Phe Thr Thr
                85                  90

<210> SEQ ID NO 254
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
        35                  40                  45

Ala Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Lys Phe Thr Thr

```
                            85                  90

<210> SEQ ID NO 255
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Leu Leu
        35                  40                  45

Phe Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Thr Pro Leu Ser Ala Ser Phe Thr Thr
                85                  90

<210> SEQ ID NO 256
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu His Ala Tyr Phe Thr Thr
                85                  90

<210> SEQ ID NO 257
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45
```

Gly Val Pro Gly Ser Glu Arg Ser Tyr Asp Leu Thr Gly Leu Lys Pro
            50                  55                  60

Gly Thr Glu Tyr Ser Val Leu Ile His Gly Val Lys Gly Gly Leu Leu
65                  70                  75                  80

Ser Ser Pro Leu Arg Ala Tyr Phe Thr Thr
                85                  90

<210> SEQ ID NO 258
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Leu Leu
        35                  40                  45

Glu Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Val Ala Phe Phe Thr Thr
                85                  90

<210> SEQ ID NO 259
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gln Leu
        35                  40                  45

Gly Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Leu Ala Val Phe Thr Thr
                85                  90

<210> SEQ ID NO 260
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile His Leu
            35                  40                  45

Arg Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 261
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Leu Leu
            35                  40                  45

Gln Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Ile Ala Lys Phe Thr Thr
                85                  90

<210> SEQ ID NO 262
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Val Leu
            35                  40                  45

His Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Gln Ala Ile Phe Thr Thr
                85                  90

<210> SEQ ID NO 263
<211> LENGTH: 90
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Ala Leu
        35                  40                  45

Val Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ala Ala Asn Phe Thr Thr
                85                  90

<210> SEQ ID NO 264
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Asn Leu
        35                  40                  45

Ser Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Asp Ala Tyr Phe Thr Thr
                85                  90

<210> SEQ ID NO 265
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Glu Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
```

```
                65                   70                  75                  80
Ser Ser Pro Leu Thr Ala Ser Phe Thr Thr
                    85                  90

<210> SEQ ID NO 266
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Arg Leu
        35                  40                  45

Gln Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Gly Ala Ser Phe Thr Thr
                    85                  90

<210> SEQ ID NO 267
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Gly Leu
        35                  40                  45

Trp Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Val Ala Tyr Phe Thr Thr
                    85                  90

<210> SEQ ID NO 268
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30
```

Tyr Ile Ala Tyr Ala Glu Pro Arg Pro Asp Gly Glu Ala Ile Tyr Leu
            35                  40                  45

Glu Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
65                   70                  75                  80

Ser Ser Pro Leu Phe Thr Thr
                85

<210> SEQ ID NO 269
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Ala Tyr Ala Glu Pro Arg Pro Asp Gly Glu Ala Ile Trp Leu
            35                  40                  45

Asp Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Leu Leu
65                   70                  75                  80

Ser Ser Pro Leu Asp Ala Tyr Phe Thr Thr
                85                  90

<210> SEQ ID NO 270
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Glu Tyr Cys Glu Thr Lys Met Cys Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Arg Val Pro Ile Pro Gly Val Lys Gly Gly Thr Ala
65                   70                  75                  80

Ser Leu Pro Leu Ser Ala Ile Phe Thr Thr
                85                  90

<210> SEQ ID NO 271
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Tyr Tyr Ile Glu Ser Tyr Pro Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Gly Ile Asp Gly Val Lys Gly Gly Arg Trp
65                  70                  75                  80

Ser Thr Pro Leu Ser Ala Ile Phe Thr Thr
            85                  90

<210> SEQ ID NO 272
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Tyr Tyr Ile Glu Ser Tyr Pro Ala Gly Glu Ala Ile Val Leu
        35                  40                  45

Thr Val Pro Gly Ser Cys Arg Ser Tyr Asp Leu Thr Gly Leu Lys Pro
    50                  55                  60

Gly Thr Glu Tyr Trp Val Gly Ile Asp Gly Val Lys Gly Gly Arg Trp
65                  70                  75                  80

Ser Thr Pro Leu Ser Ala Ile Phe Thr Thr
            85                  90

<210> SEQ ID NO 273
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: D, F, Y, or H
<220> FEATURE:
<221> NAME/KEY: MOD_RES
<222> LOCATION: (35)..(35)
<223> OTHER INFORMATION: Y, G, A, or V
<220> FEATURE:
<221> NAME/KEY: MOD_RES
<222> LOCATION: (37)..(37)
<223> OTHER INFORMATION: I, T, L, A, or H
<220> FEATURE:
<221> NAME/KEY: MOD_RES
<222> LOCATION: (39)..(39)
<223> OTHER INFORMATION: S, Y or P
<220> FEATURE:
<221> NAME/KEY: MOD_RES
<222> LOCATION: (40)..(40)
<223> OTHER INFORMATION: Y, G, Q, or R
<220> FEATURE:

```
<221> NAME/KEY: MOD_RES
<222> LOCATION: (41)..(41)
<223> OTHER INFORMATION: G or P
<220> FEATURE:
<221> NAME/KEY: MOD_RES
<222> LOCATION: (42)..(42)
<223> OTHER INFORMATION: A, Y, P, D, or S
<220> FEATURE:
<221> NAME/KEY: MOD_RES
<222> LOCATION: (47)..(47)
<223> OTHER INFORMATION: A, C, D, E, F, G, H, I, K, L, N, Q, R, S, T, V,
     W, or Y
<220> FEATURE:
<221> NAME/KEY: MOD_RES
<222> LOCATION: (49)..(49)
<223> OTHER INFORMATION: A, C, D, E, F, G, H, I, K, L, N, Q, R, S, T, V,
     W, or Y
<220> FEATURE:
<221> NAME/KEY: MOD_RES
<222> LOCATION: (69)..(69)
<223> OTHER INFORMATION: W, N, S, or E
<220> FEATURE:
<221> NAME/KEY: MOD_RES
<222> LOCATION: (71)..(71)
<223> OTHER INFORMATION: L, Y, or G
<220> FEATURE:
<221> NAME/KEY: MOD_RES
<222> LOCATION: (73)..(73)
<223> OTHER INFORMATION: D, Q, H, or V
<220> FEATURE:
<221> NAME/KEY: MOD_RES
<222> LOCATION: (74)..(74)
<223> OTHER INFORMATION: G or S
<220> FEATURE:
<221> NAME/KEY: MOD_RES
<222> LOCATION: (79)..(79)
<223> OTHER INFORMATION: R, G, F, L, or D
<220> FEATURE:
<221> NAME/KEY: MOD_RES
<222> LOCATION: (80)..(80)
<223> OTHER INFORMATION: W, S, P, or L
<220> FEATURE:
<221> NAME/KEY: MOD_RES
<222> LOCATION: (82)..(82)
<223> OTHER INFORMATION: T, V, M, or S
<220> FEATURE:
<221> NAME/KEY: MOD_RES
<222> LOCATION: (85)..(85)
<223> OTHER INFORMATION: A, C, D, E, F, G, H, I, K, L, N, Q, R, S, T, V,
     W, or Y
<220> FEATURE:
<221> NAME/KEY: MOD_RES
<222> LOCATION: (87)..(87)
<223> OTHER INFORMATION: A, C, D, E, F, G, H, I, K, L, N, Q, R, S, T, V,
     W, or Y

<400> SEQUENCE: 273

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Xaa Ile Xaa Tyr Xaa Glu Xaa Xaa Xaa Gly Glu Ala Ile Xaa Leu
            35                  40                  45

Xaa Val Pro Gly Ser Glu Arg Ser Tyr Asp Leu Thr Gly Leu Lys Pro
    50                  55                  60

Gly Thr Glu Tyr Xaa Val Xaa Ile Xaa Xaa Val Lys Gly Gly Xaa Xaa
65                  70                  75                  80

Ser Xaa Pro Leu Xaa Ala Xaa Phe Thr Thr
                85                  90

<210> SEQ ID NO 274
<211> LENGTH: 291
```

<212> TYPE: PRT
<213> ORGANISM: Homo sapiens

<400> SEQUENCE: 274

Met Thr Lys Glu Tyr Gln Asp Leu Gln His Leu Asp Asn Glu Glu Ser
1               5                   10                  15

Asp His His Gln Leu Arg Lys Gly Pro Pro Pro Gln Pro Leu Leu
            20                  25                  30

Gln Arg Leu Cys Ser Gly Pro Arg Leu Leu Leu Ser Leu Gly Leu
        35                  40                  45

Ser Leu Leu Leu Leu Val Val Cys Val Ile Gly Ser Gln Asn Ser
50                  55                  60

Gln Leu Gln Glu Glu Leu Arg Gly Leu Arg Glu Thr Phe Ser Asn Phe
65                  70                  75                  80

Thr Ala Ser Thr Glu Ala Gln Val Lys Gly Leu Ser Thr Gln Gly Gly
                85                  90                  95

Asn Val Gly Arg Lys Met Lys Ser Leu Glu Ser Gln Leu Glu Lys Gln
            100                 105                 110

Gln Lys Asp Leu Ser Glu Asp His Ser Ser Leu Leu Leu His Val Lys
        115                 120                 125

Gln Phe Val Ser Asp Leu Arg Ser Leu Ser Cys Gln Met Ala Ala Leu
130                 135                 140

Gln Gly Asn Gly Ser Glu Arg Thr Cys Cys Pro Val Asn Trp Val Glu
145                 150                 155                 160

His Glu Arg Ser Cys Tyr Trp Phe Ser Arg Ser Gly Lys Ala Trp Ala
                165                 170                 175

Asp Ala Asp Asn Tyr Cys Arg Leu Glu Asp Ala His Leu Val Val Val
            180                 185                 190

Thr Ser Trp Glu Glu Gln Lys Phe Val Gln His Ile Gly Pro Val
        195                 200                 205

Asn Thr Trp Met Gly Leu His Asp Gln Asn Gly Pro Trp Lys Trp Val
210                 215                 220

Asp Gly Thr Asp Tyr Glu Thr Gly Phe Lys Asn Trp Arg Pro Glu Gln
225                 230                 235                 240

Pro Asp Asp Trp Tyr Gly His Gly Leu Gly Gly Gly Glu Asp Cys Ala
                245                 250                 255

His Phe Thr Asp Asp Gly Arg Trp Asn Asp Asp Val Cys Gln Arg Pro
            260                 265                 270

Tyr Arg Trp Val Cys Glu Thr Glu Leu Asp Lys Ala Ser Gln Glu Pro
        275                 280                 285

Pro Leu Leu
    290

<210> SEQ ID NO 275
<211> LENGTH: 230
<212> TYPE: PRT
<213> ORGANISM: Homo sapiens

<400> SEQUENCE: 275

Gln Asn Ser Gln Leu Gln Glu Glu Leu Arg Gly Leu Arg Glu Thr Phe
1               5                   10                  15

Ser Asn Phe Thr Ala Ser Thr Glu Ala Gln Val Lys Gly Leu Ser Thr
            20                  25                  30

Gln Gly Gly Asn Val Gly Arg Lys Met Lys Ser Leu Glu Ser Gln Leu
        35                  40                  45

```
Glu Lys Gln Gln Lys Asp Leu Ser Glu Asp His Ser Ser Leu Leu Leu
 50                  55                  60

His Val Lys Gln Phe Val Ser Asp Leu Arg Ser Leu Ser Cys Gln Met
 65                  70                  75                  80

Ala Ala Leu Gln Gly Asn Gly Ser Glu Arg Thr Cys Cys Pro Val Asn
                 85                  90                  95

Trp Val Glu His Glu Arg Ser Cys Tyr Trp Phe Ser Arg Ser Gly Lys
            100                 105                 110

Ala Trp Ala Asp Ala Asp Asn Tyr Cys Arg Leu Glu Asp Ala His Leu
        115                 120                 125

Val Val Val Thr Ser Trp Glu Glu Gln Lys Phe Val Gln His His Ile
130                 135                 140

Gly Pro Val Asn Thr Trp Met Gly Leu His Asp Gln Asn Gly Pro Trp
145                 150                 155                 160

Lys Trp Val Asp Gly Thr Asp Tyr Glu Thr Gly Phe Lys Asn Trp Arg
                165                 170                 175

Pro Glu Gln Pro Asp Asp Trp Tyr Gly His Gly Leu Gly Gly Gly Glu
            180                 185                 190

Asp Cys Ala His Phe Thr Asp Asp Gly Arg Trp Asn Asp Asp Val Cys
        195                 200                 205

Gln Arg Pro Tyr Arg Trp Val Cys Glu Thr Glu Leu Asp Lys Ala Ser
    210                 215                 220

Gln Glu Pro Pro Leu Leu
225                 230

<210> SEQ ID NO 276
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Leu Pro Ala Pro Lys Asn Leu Val Val Ser Glu Val Thr Glu Asp Ser
1               5                  10                  15

Leu Arg Leu Ser Trp Thr Ala Pro Asp Ala Ala Phe Asp Ser Phe Leu
             20                  25                  30

Ile Gln Tyr Gln Glu Ser Glu Lys Val Gly Glu Ala Ile Asn Leu Thr
         35                  40                  45

Val Pro Gly Ser Glu Arg Ser Tyr Asp Leu Thr Gly Leu Lys Pro Gly
     50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                 85

<210> SEQ ID NO 277
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Leu Pro Ala Pro Lys Asn Leu Val Val Ser Arg Val Thr Glu Asp Ser
1               5                  10                  15
```

-continued

```
Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Lys Gly His Arg Ser
 65                  70                  75                  80

Asn Pro Leu Ser Ala Ile Phe Thr Thr
                 85

<210> SEQ ID NO 278
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gly Ser Gly Ser
1

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Gly Gly Ser Gly Gly Gly Ser
1               5

<210> SEQ ID NO 280
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(25)
<223> OTHER INFORMATION: This sequence may encompass 1-5 "Gly Gly Gly
      Gly Ser" repeating units

<400> SEQUENCE: 280

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 281
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ala Pro Ala Pro
1
```

<210> SEQ ID NO 282
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ala Pro Ala Pro Ala Pro Ala Pro Ala Pro
1               5                   10

<210> SEQ ID NO 283
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ala Pro Ala Pro Ala Pro Ala Pro Ala Pro Ala Pro Ala Pro Ala Pro
1               5                   10                  15

Ala Pro Ala Pro
            20

<210> SEQ ID NO 284
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40

<210> SEQ ID NO 285
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Glu Ala Ala Ala Lys Glu Ala Ala Ala Lys Glu Ala Ala Ala Lys
1               5                   10                  15

Glu Ala Ala Ala Lys Glu Ala Ala Lys Ala Ala Ala
            20                  25

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ucucguggcc uuaaugaaa                                                  19

<210> SEQ ID NO 287
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
uucauuaagg ccacgagauu                                                 20

<210> SEQ ID NO 288
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 289
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 290
<211> LENGTH: 90
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 290

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Val Tyr His Glu Pro Arg Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Glu Val Gly Ile Val Ser Val Lys Gly Gly Asp Leu
65                  70                  75                  80

Ser Val Pro Leu Ser Ala Ile Phe Thr Thr
            85                  90

<210> SEQ ID NO 291
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asp Ile Gly Tyr Thr Glu Tyr Gly Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Leu Ile Gln Gly Val Lys Gly Gly Gly Ser
65                  70                  75                  80

Ser Val Pro Leu Ser Ala Ile Phe Thr Thr
            85                  90

<210> SEQ ID NO 292
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Val Tyr His Glu Pro Arg Pro Asp Gly Glu Ala Ile Val Leu
        35                  40                  45

Thr Val Pro Gly Ser Cys Arg Ser Tyr Asp Leu Thr Gly Leu Lys Pro
    50                  55                  60

Gly Thr Glu Tyr Glu Val Val Ile Leu Gly Val Lys Gly Gly Val His
65                  70                  75                  80

Ser Tyr Pro Leu Ser Ala Ile Phe Thr Thr Ala Pro Ala Pro Ala Pro

```
                    85                  90                  95
Ala Pro Ala Pro Leu Pro Ala Pro Lys Asn Leu Val Val Ser Arg Val
                100                 105                 110

Thr Glu Asp Ser Ala Arg Leu Ser Trp Thr Ala Pro Asp Ala Ala Phe
            115                 120                 125

Asp Ser Phe Ala Ile Val Tyr His Glu Pro Arg Pro Asp Gly Glu Ala
        130                 135                 140

Ile Val Leu Thr Val Pro Gly Ser Glu Arg Ser Tyr Asp Leu Thr Gly
145                 150                 155                 160

Leu Lys Pro Gly Thr Glu Tyr Glu Val Val Ile Leu Gly Val Lys Gly
                165                 170                 175

Gly Val His Ser Tyr Pro Leu Ser Ala Ile Phe Thr Thr
            180                 185
```

<210> SEQ ID NO 293
<211> LENGTH: 199
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 293

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Val Tyr His Glu Pro Arg Pro Asp Gly Glu Ala Ile Val Leu
        35                  40                  45

Thr Val Pro Gly Ser Cys Arg Ser Tyr Asp Leu Thr Gly Leu Lys Pro
    50                  55                  60

Gly Thr Glu Tyr Glu Val Val Ile Leu Gly Val Lys Gly Gly Val His
65                  70                  75                  80

Ser Tyr Pro Leu Ser Ala Ile Phe Thr Thr Gly Gly Gly Gly Ser Gly
                85                  90                  95

Gly Gly Gly Ser Gly Gly Gly Ser Gly Gly Gly Gly Ser Leu Pro
                100                 105                 110

Ala Pro Lys Asn Leu Val Val Ser Arg Val Thr Glu Asp Ser Ala Arg
            115                 120                 125

Leu Ser Trp Thr Ala Pro Asp Ala Ala Phe Asp Ser Phe Ala Ile Val
        130                 135                 140

Tyr His Glu Pro Arg Pro Asp Gly Glu Ala Ile Val Leu Thr Val Pro
145                 150                 155                 160

Gly Ser Glu Arg Ser Tyr Asp Leu Thr Gly Leu Lys Pro Gly Thr Glu
                165                 170                 175

Tyr Glu Val Val Ile Leu Gly Val Lys Gly Val His Ser Tyr Pro
            180                 185                 190

Leu Ser Ala Ile Phe Thr Thr
        195
```

<210> SEQ ID NO 294
<211> LENGTH: 199
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 294

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Val Tyr His Glu Pro Arg Pro Asp Gly Glu Ala Ile Val Leu
        35                  40                  45

Thr Val Pro Gly Ser Cys Arg Ser Tyr Asp Leu Thr Gly Leu Lys Pro
    50                  55                  60

Gly Thr Glu Tyr Glu Val Val Ile Leu Gly Val Lys Gly Val His
65                  70                  75                  80

Ser Tyr Pro Leu Ser Ala Ile Phe Thr Thr Glu Ala Ala Lys Glu
                85                  90                  95

Ala Ala Lys Glu Ala Ala Lys Glu Ala Ala Lys Leu Pro
            100                 105                 110

Ala Pro Lys Asn Leu Val Val Ser Arg Val Thr Glu Asp Ser Ala Arg
        115                 120                 125

Leu Ser Trp Thr Ala Pro Asp Ala Ala Phe Asp Ser Phe Ala Ile Val
    130                 135                 140

Tyr His Glu Pro Arg Pro Asp Gly Glu Ala Ile Val Leu Thr Val Pro
145                 150                 155                 160

Gly Ser Glu Arg Ser Tyr Asp Leu Thr Gly Leu Lys Pro Gly Thr Glu
                165                 170                 175

Tyr Glu Val Val Ile Leu Gly Val Lys Gly Val His Ser Tyr Pro
            180                 185                 190

Leu Ser Ala Ile Phe Thr Thr
        195

<210> SEQ ID NO 295
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Val Tyr His Glu Pro Arg Pro Asp Gly Glu Ala Ile Val Leu
        35                  40                  45

Thr Val Pro Gly Ser Cys Arg Ser Tyr Asp Leu Thr Gly Leu Lys Pro
    50                  55                  60

Gly Thr Glu Tyr Glu Val Val Ile Leu Gly Val Lys Gly Val His
65                  70                  75                  80

Ser Tyr Pro Leu Ser Ala Ile Phe Thr Thr Glu Ala Ala Lys Leu
                85                  90                  95

Pro Ala Pro Lys Asn Leu Val Val Ser Arg Val Thr Glu Asp Ser Ala
            100                 105                 110

Arg Leu Ser Trp Thr Ala Pro Asp Ala Ala Phe Asp Ser Phe Ala Ile
        115                 120                 125

Val Tyr His Glu Pro Arg Pro Asp Gly Glu Ala Ile Val Leu Thr Val
    130                 135                 140

```
Pro Gly Ser Glu Arg Ser Tyr Asp Leu Thr Gly Leu Lys Pro Gly Thr
145                 150                 155                 160

Glu Tyr Glu Val Val Ile Leu Gly Val Lys Gly Gly Val His Ser Tyr
                165                 170                 175

Pro Leu Ser Ala Ile Phe Thr Thr
            180
```

<210> SEQ ID NO 296
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Lys Ile Glu Tyr Phe Glu Tyr Val Gly Tyr Gly Glu Ala Ile Val Leu
            35                  40                  45

Thr Val Pro Gly Ser Cys Arg Ser Tyr Asp Leu Thr Gly Leu Lys Pro
    50                  55                  60

Gly Thr Glu Tyr Tyr Val Ala Ile Tyr Gly Val Lys Gly Gly Trp Tyr
65                  70                  75                  80

Ser Arg Pro Leu Ser Ala Ile Phe Thr Thr Ala Pro Ala Pro Ala Pro
                85                  90                  95

Ala Pro Ala Pro Leu Pro Ala Pro Lys Asn Leu Val Val Ser Arg Val
                100                 105                 110

Thr Glu Asp Ser Ala Arg Leu Ser Trp Thr Ala Pro Asp Ala Ala Phe
            115                 120                 125

Asp Ser Phe Lys Ile Glu Tyr Phe Glu Tyr Val Gly Tyr Gly Glu Ala
130                 135                 140

Ile Val Leu Thr Val Pro Gly Ser Glu Arg Ser Tyr Asp Leu Thr Gly
145                 150                 155                 160

Leu Lys Pro Gly Thr Glu Tyr Tyr Val Ala Ile Tyr Gly Val Lys Gly
                165                 170                 175

Gly Trp Tyr Ser Arg Pro Leu Ser Ala Ile Phe Thr Thr
            180                 185
```

<210> SEQ ID NO 297
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Lys Ile Glu Tyr Phe Glu Tyr Val Gly Tyr Gly Glu Ala Ile Val Leu
            35                  40                  45

Thr Val Pro Gly Ser Cys Arg Ser Tyr Asp Leu Thr Gly Leu Lys Pro
    50                  55                  60
```

Gly Thr Glu Tyr Tyr Val Ala Ile Tyr Gly Val Lys Gly Gly Trp Tyr
65                  70                  75                  80

Ser Arg Pro Leu Ser Ala Ile Phe Thr Thr Gly Gly Gly Ser Gly
                85                  90                  95

Gly Gly Gly Ser Gly Gly Gly Ser Gly Gly Gly Ser Leu Pro
            100                 105                 110

Ala Pro Lys Asn Leu Val Val Ser Arg Val Thr Glu Asp Ser Ala Arg
            115                 120                 125

Leu Ser Trp Thr Ala Pro Asp Ala Ala Phe Asp Ser Phe Lys Ile Glu
            130                 135                 140

Tyr Phe Glu Tyr Val Gly Tyr Gly Glu Ala Ile Val Leu Thr Val Pro
145                 150                 155                 160

Gly Ser Glu Arg Ser Tyr Asp Leu Thr Gly Leu Lys Pro Gly Thr Glu
                165                 170                 175

Tyr Tyr Val Ala Ile Tyr Gly Val Lys Gly Gly Trp Tyr Ser Arg Pro
                180                 185                 190

Leu Ser Ala Ile Phe Thr Thr
                195

<210> SEQ ID NO 298
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Lys Ile Glu Tyr Phe Glu Tyr Val Gly Tyr Gly Glu Ala Ile Val Leu
            35                  40                  45

Thr Val Pro Gly Ser Cys Arg Ser Tyr Asp Leu Thr Gly Leu Lys Pro
50                  55                  60

Gly Thr Glu Tyr Tyr Val Ala Ile Tyr Gly Val Lys Gly Gly Trp Tyr
65                  70                  75                  80

Ser Arg Pro Leu Ser Ala Ile Phe Thr Thr Glu Ala Ala Lys Glu
                85                  90                  95

Ala Ala Ala Lys Glu Ala Ala Ala Lys Glu Ala Ala Ala Lys Leu Pro
            100                 105                 110

Ala Pro Lys Asn Leu Val Val Ser Arg Val Thr Glu Asp Ser Ala Arg
            115                 120                 125

Leu Ser Trp Thr Ala Pro Asp Ala Ala Phe Asp Ser Phe Lys Ile Glu
            130                 135                 140

Tyr Phe Glu Tyr Val Gly Tyr Gly Glu Ala Ile Val Leu Thr Val Pro
145                 150                 155                 160

Gly Ser Glu Arg Ser Tyr Asp Leu Thr Gly Leu Lys Pro Gly Thr Glu
                165                 170                 175

Tyr Tyr Val Ala Ile Tyr Gly Val Lys Gly Gly Trp Tyr Ser Arg Pro
                180                 185                 190

Leu Ser Ala Ile Phe Thr Thr
                195

<210> SEQ ID NO 299

```
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Lys Ile Glu Tyr Phe Glu Tyr Val Gly Tyr Gly Glu Ala Ile Val Leu
        35                  40                  45

Thr Val Pro Gly Ser Cys Arg Ser Tyr Asp Leu Thr Gly Leu Lys Pro
    50                  55                  60

Gly Thr Glu Tyr Tyr Val Ala Ile Tyr Gly Val Lys Gly Gly Trp Tyr
65                  70                  75                  80

Ser Arg Pro Leu Ser Ala Ile Phe Thr Thr Glu Ala Ala Ala Lys Leu
                85                  90                  95

Pro Ala Pro Lys Asn Leu Val Val Ser Arg Val Thr Glu Asp Ser Ala
            100                 105                 110

Arg Leu Ser Trp Thr Ala Pro Asp Ala Ala Phe Asp Ser Phe Lys Ile
        115                 120                 125

Glu Tyr Phe Glu Tyr Val Gly Tyr Gly Glu Ala Ile Val Leu Thr Val
    130                 135                 140

Pro Gly Ser Glu Arg Ser Tyr Asp Leu Thr Gly Leu Lys Pro Gly Thr
145                 150                 155                 160

Glu Tyr Tyr Val Ala Ile Tyr Gly Val Lys Gly Gly Trp Tyr Ser Arg
                165                 170                 175

Pro Leu Ser Ala Ile Phe Thr Thr
            180

<210> SEQ ID NO 300
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Glu Ala Ala Ala Lys Glu Ala Ala Ala Lys Glu Ala Ala Ala Lys Glu
1               5                   10                  15

Ala Ala Ala Lys
            20

<210> SEQ ID NO 301
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gly Gly Gly Gly Ser Gly Gly Gly Ser Gly Gly Gly Gly Ser Gly
1               5                   10                  15

Gly Gly Gly Ser
            20
```

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Ala Pro Ala Pro Ala Pro Ala Pro Ala Pro
1               5                   10

<210> SEQ ID NO 303
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Glu Ala Ala Ala Lys
1               5

<210> SEQ ID NO 304
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Val Tyr His Glu Pro Arg Pro Asp Gly Glu Ala Ile Val Leu
        35                  40                  45

Thr Val Pro Gly Ser Cys Arg Ser Tyr Asp Leu Thr Gly Leu Lys Pro
    50                  55                  60

Gly Thr Glu Tyr Glu Val Val Ile Leu Gly Val Lys Gly Val His
65                  70                  75                  80

Ser Tyr Pro Leu Ser Ala Ile Phe Thr Thr
                85                  90

<210> SEQ ID NO 305
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Val Tyr His Glu Pro Arg Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60

```
Gly Thr Glu Tyr Glu Val Val Ile Leu Gly Val Lys Gly Gly Val His
 65                  70                  75                  80

Ser Tyr Pro Leu Ser Ala Ile Phe Thr Thr
                 85                  90

<210> SEQ ID NO 306
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Phe Ile Gly Tyr Leu Glu Pro Gln Pro Pro Gly Glu Ala Ile His Leu
                 35                  40                  45

Gly Val Pro Gly Ser Cys Arg Ser Tyr Asp Leu Thr Gly Leu Lys Pro
 50                  55                  60

Gly Thr Glu Tyr Asn Val Thr Ile Gln Gly Val Lys Gly Gly Phe Pro
 65                  70                  75                  80

Ser Ile Pro Leu Phe Ala Ser Phe Thr Thr
                 85                  90

<210> SEQ ID NO 307
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(25)
<223> OTHER INFORMATION: This sequence may encompass 1-5 "Glu Ala Ala
      Ala Lys" repeating units

<400> SEQUENCE: 307

Glu Ala Ala Ala Lys Glu Ala Ala Ala Lys Glu Ala Ala Ala Lys Glu
  1               5                  10                  15

Ala Ala Ala Lys Glu Ala Ala Ala Lys
                 20                  25

<210> SEQ ID NO 308
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gly Gly Gly Gly Ser
  1               5

<210> SEQ ID NO 309
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                        6xHis tag

<400> SEQUENCE: 309

His His His His His His
1               5

<210> SEQ ID NO 310
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline

<400> SEQUENCE: 310

Gly Gly Val Xaa
1

<210> SEQ ID NO 311
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-20 "Ala Pro"
      repeating units

<400> SEQUENCE: 311

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40
```